United States Patent
Bienayme et al.

(10) Patent No.: US 8,426,437 B2
(45) Date of Patent: Apr. 23, 2013

(54) PYRROLOQUINOLINE DERIVATIVES AND THEIR USE AS PROTEIN KINASES INHIBITORS

(75) Inventors: Hugues Bienayme, Saint Symphorien d'Ozon (FR); Antoine Dumoulin, Castres (FR); Serge Grisoni, Portet sur Garonne (FR); Bachir Kaloun El, Roquettes (FR); Stephane Poigny, Saubens (FR); Remi Rabot, Toulouse (FR); Rachid Rahali, St Laurent des Arbres (FR); Eric Tam, Singapour (SG); Pascaline Klein, Toulouse (FR); Karim Bedjeguelal, Toulouse (FR); Houcine Rahali, St Laurent des Arbres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 1432 days.

(21) Appl. No.: 11/988,142

(22) PCT Filed: Jun. 30, 2006

(86) PCT No.: PCT/EP2006/063768
§ 371 (c)(1),
(2), (4) Date: Feb. 20, 2008

(87) PCT Pub. No.: WO2007/003611
PCT Pub. Date: Jan. 11, 2007

(65) Prior Publication Data
US 2009/0042876 A1    Feb. 12, 2009

(30) Foreign Application Priority Data
Jul. 1, 2005   (FR) ..................... 05 07009

(51) Int. Cl.
*A61K 31/437* (2006.01)
*C07D 487/04* (2006.01)
*C07D 471/04* (2006.01)

(52) U.S. Cl.
USPC .......................... 514/290; 546/80

(58) Field of Classification Search ............... 546/80; 514/290
See application file for complete search history.

(56) References Cited

FOREIGN PATENT DOCUMENTS
WO   WO-01/98299 A1   12/2001
WO   WO-03/082868 A1  10/2003

OTHER PUBLICATIONS

Dorwald F. A. Side Reactions in Organic Synthesis, 2005, Wiley: VCH, Weinheim p. IX of Preface.*
Bergman J et al: "Synthesis of 4-oxo-4,5-dihydro-3H-pyrrolo[2,3-c]quinoli ne-1-carboxylic acid ethyl ester and its isomer 1-oxo-2,9-dihydro-1H-beta-carboline-4 carboxylic acid ethyl ester" Nov. 4, 2002, pp. 9179-9185.
Arighi E et al: "RET tyrosine kinase signaling in development and cancer" vol. 16, No. 4-5, Jun. 27, 2005, pp. 441-467.

* cited by examiner

*Primary Examiner* — Rita Desai
(74) *Attorney, Agent, or Firm* — Birch, Stewart, Kolasch & Birch, LLP

(57) ABSTRACT

The present invention relates to inhibitors of protein kinases of formula I:

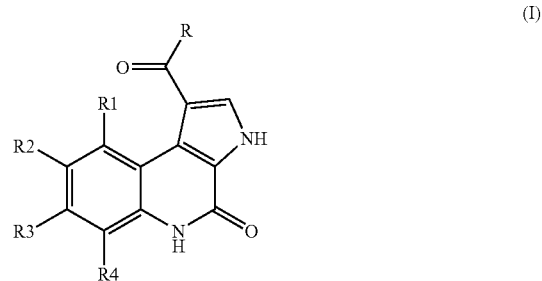

which can be used in the treatment of various diseases, notably cancer, inflammation or disorders of the central nervous system. It also relates to pharmaceutical compositions containing the compounds according to the invention and their use in therapy.

10 Claims, 5 Drawing Sheets

PYRROLOQUINOLINE DERIVATIVES AND THEIR USE AS PROTEIN KINASES INHIBITORS

The present invention relates to novel compounds which inhibit or modulate the enzymatic activity of protein kinases, and which can be used in the treatment of various diseases, notably cancer, inflammation or disorders of the central nervous system. The present invention also relates to pharmaceutical compositions containing the compounds according to the invention and their use in therapy.

The protein kinases are enzymes that are known to catalyze the transfer of the terminal phosphate of adenosine triphosphate (ATP) to a tyrosine, a serine or a threonine of their substrate proteins. There are two major classes of protein kinases: the tyrosine kinases (receptor and non-receptor), which transfer a phosphate group to a tyrosine residue and which are membrane or cytoplasmic enzymes, and the serine/threonine kinases, which transfer the phosphate to a serine or a threonine and which are essentially cytoplasmic enzymes.

The tyrosine kinases are divided into two categories: the "receptor" tyrosine kinases, which are transmembrane, and possess an extracellular portion capable of recognizing a ligand, and the "non-receptor" tyrosine kinases, which are cytoplasmic. These enzymes play a key role in cellular signal transduction, and consequently are regarded as important in physiological processes such as cell proliferation, mitosis, differentiation, invasion and cellular mobility, apoptosis, etc. These enzymes are considered to play an important role in the various stages of tumor development, and consequently are regarded as important pharmaceutical targets for the treatment of cancers in particular.

Among the receptor tyrosine kinases (RTK), we may mention: ALK, EGFR, VEGFR, IGFR, FGFR, Trk, MET and RET. In this family, RET has been described as a protooncogene involved in the survival and proliferation of certain cells. In particular, it has been shown that phosphorylation of RET induces the activation of other kinases such as JAK-STAT, PKC, ERK5, p38MAPK, PI3K-AKT, RAS-ERK or JNK. All these metabolic pathways contribute to cellular transformation when they are overactivated, whereas they participate in cell survival in normal conditions. It has been shown that RET can be activated by mutations or rearrangements of the gene, leading to multiple endocrine neoplasias of type II A (MEN 2A) and II B (MEN 2B), Hirschsprung disease (HSCR) or medullary thyroid carcinomas (MTC). Some oncogene mutations can cause autoactivation of the kinase function of RET (Salvatore et al. 2000, *J. Clin. Endocr. Metab.* 85: 3898-3907). This activation leads to autophosphorylation of tyrosines and induction of the RET-dependent signal.

Several works describe the effects of RET inhibition on cellular metabolism (see the review: Pützer and Drosten, 2004, *Trends in Mol. Med.* Vol. 10, No 7: 351-357). In particular, the use of a dominant negative mutant of RET in TT cells has the effect of inducing strong inhibition of the viability of these cells, an effect which leads both to inhibition of cell growth, as well as possible induction of apoptosis (Drosten et al. 2002, *Surgery* 132:991-7). In addition, it has been shown that certain kinase inhibitors have an action on RET; for example, STI571 (Gleevec), genistein and allyl-geldanamycin produce dose-dependent inhibition of RET activity (Cohen et al. 2002, *Surgery* 132:960-7). The kinase inhibitor of the family Src, PP1, is also able to inhibit RET (Carlomagno et al. 2002, *Cancer Research* 62: 1077-1082). These authors have shown that PP1 strongly inhibits tumorigenicity of NIH3T3 fibroblasts expressing the RET/PTC3 oncogene in nude mice.

The function of RET has been described particularly well in the thyroid, a tissue where this receptor is strongly expressed, notably in the presence of tumors. More generally, these are tumors arising from neural crests which express RET most strongly (neuroblastomas, pheochromocytomas or medullary thyroid carcinomas) (Ikeda et al. 1990, *Oncogene* 5: 1291-1296; Santoro et al. 1990, *Oncogene* 5: 1595-1598). In non-tumoral tissues, RET is expressed in the neurons of the peripheral, sympathetic and sensory enteric systems as well as in the central nervous system (dopamine neurons and norepinephrine neurons). Moreover, expression of RET has been described in the kidney during embryonic development (Avantaggiato et al. 1994, Cell Growth Differ. 5: 305-311; Attie-Bitach et al. 1998, *Am. J. Med. Genet.* 80: 481-486).

These studies demonstrate the use of an inhibitor of the RET protein in cancers (Takahashi et al. 1991 Oncogene 6:297-301), in particular but not limited to solid tumors (Jhiang S M, 2000 *Oncogene* 19(49):5590-5597), and in various types of tissues overexpressing RET (thyroid, lung, prostate, breast, kidney, colon, pancreas). An RET inhibitor may also be indicated for inflammatory diseases (Russell et al. 2004 *J. Immunol.* 172(7):4059-4067) and for the treatment of diabetes (Harada et al. 2002 *Diabetes Care* 25(6): 1060-1065).

The present invention relates to compounds of formula I:

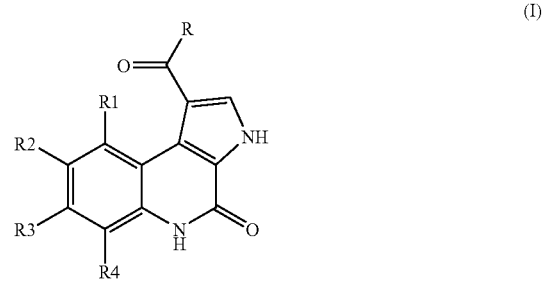

in which:

R represents a hydrogen atom or a group selected from the alkyl, alkenyl, alkynyl, cycloalkyl, aralkyl, aryl, heteroaryl —O—R5, or —NR5-R6 radicals, optionally substituted with one or more substituents, R1 and R4 represent, independently, a hydrogen atom, a halogen or a group selected from the nitro, alkyl, alkenyl, alkynyl, alkoxy or cycloalkyl radicals, optionally substituted with one or more substituents, R2 and R3 represent a hydrogen atom, a halogen or a group selected from the alkyl, alkenyl, alkynyl, alkoxy, aryl, heteroaryl, aryloxy, aralkyloxy radicals, optionally substituted with one or more substituents, and the hydroxy, cyano, —Y—(NR7)n-R8, —SOm-R8, —NR7-(Y)n-R8, —NO2, COOR9 radicals, n=0 or 1 m=0 or 1

Y=—CO— or —SO$_2$

R2 and R3 not being the following groups simultaneously on the same compound: aryl, heteroaryl, aryloxy, aralkyloxy, —Y—(NR7)n-R8, —SOm-R8, —NR7-(Y)n-R8, —NO2, COOR9, R5 represents a hydrogen atom or an alkyl or alkenyl radical of at least 3 carbon atoms not directly branched on the unsaturation, alkynyl of at least 3 carbon atoms not directly branched on the unsaturation, cycloalkyl, cycloalkylalkyl, aralkyl, heteroaralkyl, saturated non-nitrated alkyl heterocycle optionally substituted with one or more substituents, R6 represents a hydrogen atom or an alkyl or alkenyl radical of at least 3 carbon atoms not directly branched on the unsaturation, alkynyl of at least 3 carbon atoms not directly branched on the unsaturation, cycloalkyl, cycloalkylalkyl, aryl, heteroaryl, aralkyl, heteroaralkyl, saturated non-nitrated alkyl heterocycle optionally substituted with one or more substituents, R7 represents a hydrogen atom or an alkyl or alkenyl radical of at least 3 carbon atoms not directly branched on the unsaturation, alkynyl of at least 3 carbon atoms not directly branched on the unsaturation, cycloalkyl, cycloalkylalkyl, optionally substituted with one or more substituents, R8 represents a hydrogen atom or a group selected from the radicals alkyl, alkenyl, alkynyl, alkoxy, cycloalkyl, cycloalkylalkyl, aralkyl, aryl, heteroaryl, heteroaralkyl, saturated heterocycle or saturated alkyl heterocycle, optionally substituted with one or more substituents, R9 represents a hydrogen atom or a group selected from the radicals alkyl, alkenyl, alkynyl, cycloalkyl, cycloalkylalkyl, aralkyl, aryl, heteroaralkyl, saturated heterocycle or saturated alkyl heterocycle, optionally substituted with one or more substituents, R7 and R8 can form, together, a ring or a double ring containing 1 or more heteroatoms with the nitrogen to which they are attached, said heterocycle being optionally substituted with one or more alkyl, alkenyl, alkynyl, amino, NR10R11, hydroxy, alkoxy, alcoyl, carbamoyl, sulfamoyl, sulfonyl, sulfenyl, sulfanyl, cyano groups or an oxo radical, R10 represents a hydrogen atom or an alkyl or alkenyl radical of at least 3 carbon atoms not directly branched on the unsaturation, alkynyl of at least 3 carbon atoms not directly branched on the unsaturation, cycloalkyl, cycloalkylalkyl, optionally substituted with one or more substituents, R11 represents independently a hydrogen atom or a group selected from the radicals alkyl, alkenyl, alkynyl, cycloalkyl, cycloalkylalkyl, aralkyl, aryl, heteroaryl, heteroaralkyl, saturated heterocycle or saturated alkyl heterocycle, alcoyl, alkoxycarbonyl, carbamoyl, sulfamoyl, optionally substituted with one or more substituents, where R10 and R11 can form, together, a ring containing 1 or more heteroatoms with the nitrogen to which they are attached, said heterocycle being optionally substituted and physiologically acceptable salts thereof.

The invention relates more particularly to compounds of general formula I':

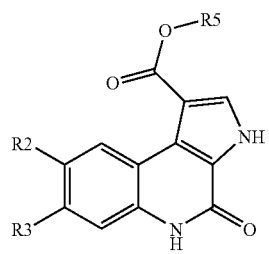

(I')

in which R2, R3 and R5 are as defined previously and below.

According to a particular embodiment of the invention, R2 is selected from the aryl, alkyl, alkenyl, alkynyl, heteroaryl —SOm-R8, —SO2-(NR7)n-R8 or —NR7-(Y)n-R8 radicals, optionally substituted with one or more substituents, R7 and R8 being as defined previously and below.

Advantageously,

R3 is a hydrogen atom, a halogen, or a hydroxy or alkoxy group.

R5 is an alkyl, alkenyl, alkynyl, cycloalkyl, cycloalkylalkyl, aralkyl radical, saturated non-nitrated alkyl heterocycle, and/or R7 is a hydrogen or an alkyl, alkenyl, alkynyl, cycloalkyl, cycloalkylalkyl, optionally substituted with one or more substituents, and/or R8 is selected from the radicals alkyl, cycloalkyl, aryl, heteroaryl, aralkyl, heteroaralkyl, saturated heterocycle or saturated alkyl heterocycle, optionally substituted with one or more substituents; for n=1, R8 can also be a hydrogen atom.

R7 and R8 can form, together, a ring or a double ring containing 1 or more heteroatoms with the nitrogen to which they are attached, said heterocycle being optionally substituted with one or more alkyl, alkenyl, alkynyl, amino, NR10R11, hydroxy, alkoxy, alcoyl, carbamoyl, sulfamoyl, sulfonyl, sulfenyl, sulfanyl, cyano, alkoxycarbonyl groups or an oxo radical, R10 and R11 being as defined previously.

More advantageously,

R5 is selected from the groups methyl, ethyl, propyl, isopropyl, butyl, iso-butyl, iso-pentyl, allyl, isoprenyl, propargyl, cyclopentyl, cyclohexyl, cyclopropylmethyl, cyclopentylmethyl, cyclohexyl methyl, tetrahydropyran-4-yl-methyl or tetrahydrofuran-3-yl-methyl, and/or R7 is a hydrogen atom or is selected from the groups methyl, ethyl, propyl, iso-propyl, butyl, iso-butyl, allyl, isoprenyl, propargyl cyclopropyl, cyclopentyl, cyclohexyl, cyclopropylmethyl, cyclopentylmethyl, cyclohexylmethyl, tetrahydropyran-4-yl-methyl, tetrahydrofuran-3-yl-methyl, hydroxy-2-ethyl, and/or R8 is selected from the groups methyl, hydroxy-2-ethyl, amino-2-ethyl, methylamino-2-ethyl, dimethylamino-2-ethyl, cyanomethyl, carbamoylmethyl, 2-cyanoethyl, cyclohexyl, cycloheptyl, cyclopropylmethyl, cyclopentylmethyl, cyclohexylmethyl, piperidin-4-yl, piperidin-3-yl, piperidin-2-yl, piperidine-4-methyl, piperidine-3-methyl, piperidine-2-methyl, pyrrolidin-3-yl-methyl, pyrrolidin-2-yl-methyl, pyrrolidin-3-yl, azetidin-3-yl-methyl, tetrahydro-thiopyran-4-yl, tetrahydropyran-4-yl, imidazol-4-yl-methyl, phenyl, o-tolyl, m-tolyl, p-tolyl, 2-fluorophenyl, 3-fluorophenyl, 4-fluorophenyl, 2-chlorophenyl, 3-chlorophenyl, 4-chlorophenyl, 3-hydroxy-phenyl, 2-methoxy-phenyl, 3-methoxy-phenyl, 4-methoxy-phenyl, 4-aminophenyl, 4-nitrophenyl, 4-fluoro-2-methyl-phenyl, 3-fluoro-2-methyl-phenyl, 3,4-difluorophenyl, 3,5-difluorophenyl, 2,6-dichlorophenyl, pyridyl, thiophene, 5-chloro-thiophene or benzyl, R7 and R8 can form, with the nitrogen to which they are attached, a 2,3-dihydro-indolyl, piperidinyl, piperazinyl, pyrrolidinyl or morpholinyl ring.

According to the invention, the substituents are advantageously selected from the halogens, the groups hydroxyl, amino (primary, secondary or tertiary amine), nitro, the C1-C4 alkyl radicals, the C1-C4 perfluoroalkyl radicals, alkoxy, perfluoroalkoxy, alkoxycarbonyl, cycloalkyl, carbamoyl, sulfamoyl, sulfonyl, sulfenyl, sulfanyl, carbonylamino, aryl, heteroaryl, cyano or an oxo radical.

By halogen, we mean in particular according to the present invention the following halogens: F, Cl, Br and I.

By alkyl, we mean in particular according to the present invention the linear or branched alkyl radicals, in particular the C1, C2, C3, C4, C5 or C6 alkyl radicals, in particular the methyl, ethyl, n-propyl, i-propyl, n-butyl, i-butyl or t-butyl radicals. This definition also applies to the alkyl portions of the alkoxy, alkoxy-carbonyl, carbonylamino, carbonyl, aralkyl or alkoxycarbonyl-alkyl radicals.

By alkenyl, preferably we mean, according to the invention, a hydrocarbon chain, monovalent, unsaturated and containing at least one double bond, linear or branched, with from 2 to 6 carbon atoms, representative elements of which are for example the groups vinyl, 1-propenyl, 2-propenyl, isoprenyl, butenyl, pentenyl, hexenyl.

By alkynyl, preferably we mean, according to the invention, a hydrocarbon chain, monovalent, unsaturated and containing at least one triple bond, linear or branched, with from 2 to 6 carbon atoms, representative elements of which are in particular the radicals ethynyl, propargyl.

By cycloalkyl, we mean advantageously according to the invention the C3-C7 cycloalkyls, more particularly the cyclopropyl, cyclobutyl, cyclopentyl, cyclohexyl and cycloheptyl radicals.

By aryl, we mean preferably according to the invention one or more aromatic rings having 6 to 10 carbon atoms, which may be joined or fused, in particular the radicals phenyl, naphthyl. This definition also applies to the aryl portion of the aralkyl and aryloxy radicals.

By heteroaryl, we mean according to the invention one or more aromatic rings having 5 to 10 atoms, which may be joined or fused, containing in its ring at least one heteroatom selected from nitrogen, oxygen or sulphur, in particular the benzimidazolyl, benzofuranyl, isobenzofuranyl, benzoxazolyl, benzothiazolyl, benzothienyl, chromenyl, isochromenyl, chromanyl, isochromanyl, cinnolinyl, furanyl, imidazolyl, indazolyl, indolyl, isoquinolinyl, isoxazolyl, benzisoxazolyl, isothiazolyl, benzisothiazolyl, oxazolyl, pyrazolyl, pyrazinyl, pyridazinyl, pyridinyl, pyrimidinyl, pyrrolyl, quinazolinyl, quinolinyl, quinoxalinyl, thiazolyl, thiadiazolyl, thienyl, triazolyl radicals. This definition also applies to the aryl portion of the aralkyl radicals.

The aryl or heteroaryl radicals preferably correspond to the following groups of formulas,

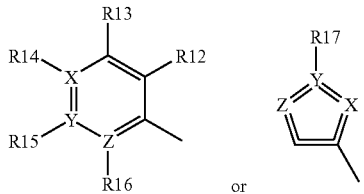

in which

X, Y or Z represent independently of one another a carbon atom, a nitrogen atom, a sulfur atom or an oxygen atom, it being understood that when X, Y or Z are a nitrogen, sulfur or oxygen atom, the presence of a radical R14, R15, R16 or R117 depends on observance of the valence of said nitrogen or sulfur atom, preserving the aromaticity of the ring, R12 represents a hydrogen atom, a halogen or an alkyl group R13 to R16 represent, independently of one another, a hydrogen atom, a halogen atom, a hydroxy group, a cyano group, a radical selected from the linear or branched alkyl groups, alkoxy, alkylsulfonyl, alkoxycarbonyl, carbamoyl, cycloalkyl, aryl, optionally substituted with one or more substituents, and the radical —NR7-(Y)n-R8, R7 and R8 being as defined previously, R13 and R14, R14 and R15 or R15 and R16 can form an aliphatic or aromatic ring, with one or more heteroatoms selected from oxygen or nitrogen, optionally substituted with one or more substituents, R17 represents a hydrogen atom, an alkyl, cycloalkyl or aryl radical, optionally substituted with one or more substituents, radical —NR7-(Y)n-R8 or —NR7-NH—R8, R7 and R8 being as defined previously.

By saturated heterocycle, we mean advantageously according to the invention a C3-C7 ring containing at least one heteroatom selected from nitrogen, oxygen or sulphur, in particular the pyrrolidinyl, pyrrolinyl, piperidinyl, tetrahydropyridinyl, azepinyl, azetidinyl, indolinyl, isoindolinyl, piperazinyl, morpholinyl, thiomorpholinyl, tetrahydropyranyl, tetrahydrothiopyranyl, tetrahydrofuranyl, tetrahydrothienyl, perhydropyrrolopyrolyl, quinuclidinyl radicals.

By pharmaceutically acceptable salt we preferably mean according to the invention a salt of a pharmaceutically acceptable acid, i.e. with any non-toxic acid, including the organic and inorganic acids. Such acids include acetic, benzenesulfonic, benzoic, citric, ethanesulfonic, fumaric, gluconic, glutamic, hydrobromic, hydrochloric, lactic, maleic, malic, mandelic, methanesulfonic, mucic, nitric, pamoic, pantothenic, phosphoric, succinic, sulfuric, tartaric and paratoluenesulfonic acid.

Advantageously, the compounds according to the invention are selected from the compounds of the formulas II to IX below.

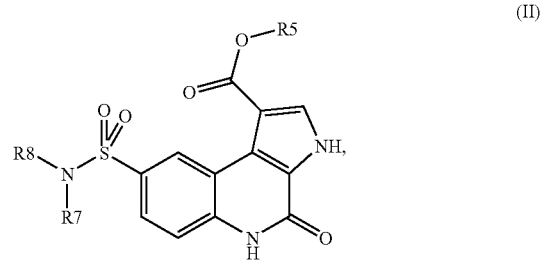

(II)

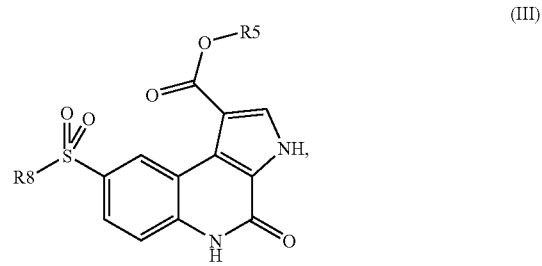

(III)

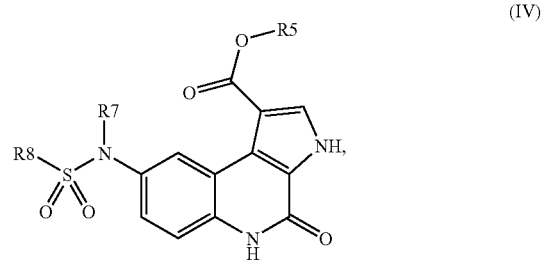

(IV)

-continued

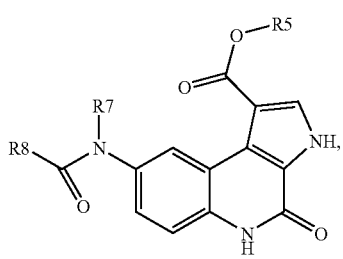

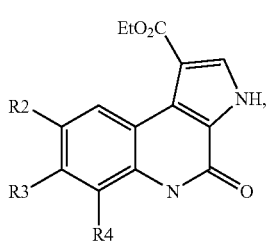

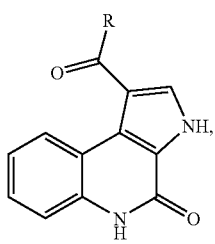

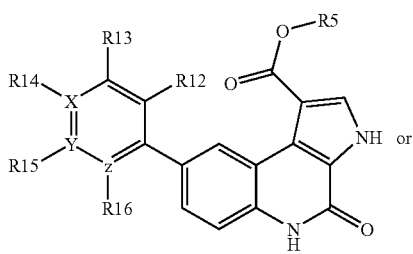

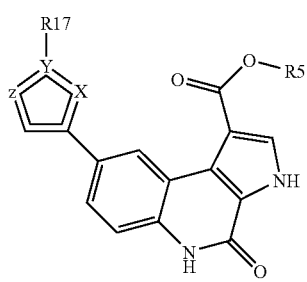

R, R2, R3, R4, R5, R7, R8, R12, R13, R14, R15, R16, R17, X, Y and Z being as defined previously.

The compounds shown below are described as synthetic intermediates in the literature (Jan Bergman* and Stanley Rehn, Tetrahedron 58 (2002) 9179-9185) without any RET inhibitory property being described or even suggested.

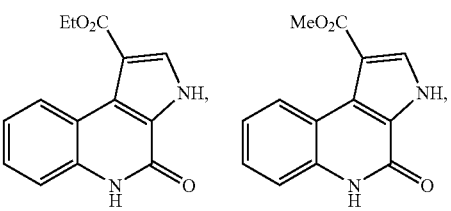

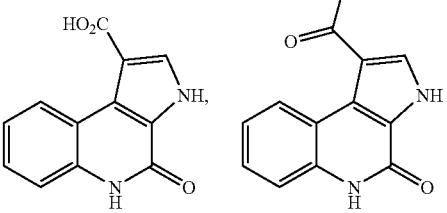

It is to be understood that these compounds do not form part of the compounds according to the invention. However, the pharmaceutical compositions containing them and their use in therapy are part of the present invention.

The present invention also relates to the compounds defined above and below for use in therapy, in particular for the treatment of cancers, inflammatory diseases or of disorders of the central nervous system.

It also relates to the use of such a compound for the preparation of a medicinal product intended for the treatment of cancers, inflammatory diseases or diseases of the central nervous system.

The invention relates to a pharmaceutical composition containing a compound as defined above and below and a suitable pharmaceutical vehicle.

These compositions can be formulated for administration to mammals, including humans. The posology varies depending on the treatment and depending on the particular disorder. These compositions are prepared so that they can be administered by the alimentary or parenteral route.

In the pharmaceutical compositions of the present invention for oral, sublingual, subcutaneous, intramuscular, intravenous, transdermal, local or rectal administration, the active ingredient can be administered in unit forms of administration, mixed with conventional excipients, to animals or to humans. The appropriate unit forms of administration comprise the forms by the oral route such as tablets, capsules, powders, granules and oral solutions or suspensions, sublingual and buccal forms of administration, subcutaneous, intramuscular, intravenous, intranasal or intraocular forms of administration and rectal forms of administration.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other suitable materials or they can be treated in such a way that they have sustained or delayed activity and release a predetermined quantity of active principle continuously.

A preparation in capsules is obtained by mixing the active ingredient with a diluent and pouring the mixture obtained into soft or hard capsules.

A preparation in the form of syrup or elixir can contain the active ingredient together with a sweetener, an antiseptic, as well as a flavoring agent and a suitable colorant.

Water-dispersible powders or granules can contain the active ingredient mixed with dispersants or wetting agents, or suspending agents, as well as with taste-correcting agents or sweeteners.

The compounds according to the invention can be used in therapy on their own, or in combination with at least one other active agent. These other active agents are in particular selected from active substances suitable for the treatment of cancers, inflammatory diseases or of disorders of the central nervous system. They may be adjuvants for improving the activity of the compounds according to the invention, or other active substances known for their use in the treatment of said disorders. Such active agents are familiar to a person skilled in the art, and are commercially available or are described in works of reference such as Le Dictionnaire Vidal, published with annual updates, in particular the active agents in the pharmacotherapeutic groups "Anti-inflammatories", "Cancerology Hematology" and "Neurology".

The present invention therefore also relates to a product containing a compound according to the invention and another active agent as a compound product for therapeutic use, simultaneously, separately or spread over time, and in particular in the treatment of cancers, inflammatory diseases or of disorders of the central nervous system.

The invention also relates to the use of a compound as defined above and below as kinase inhibitor. This use can be effected in vitro, in cellulo or in vivo. This use can notably be effected in particular in methods of screening for evaluating the properties of the compounds according to the invention in different biological contexts.

The compounds according to the invention can be prepared according to the various methods of preparation presented below and in the examples. The reaction schemes are given in an appendix.

Figure 1:
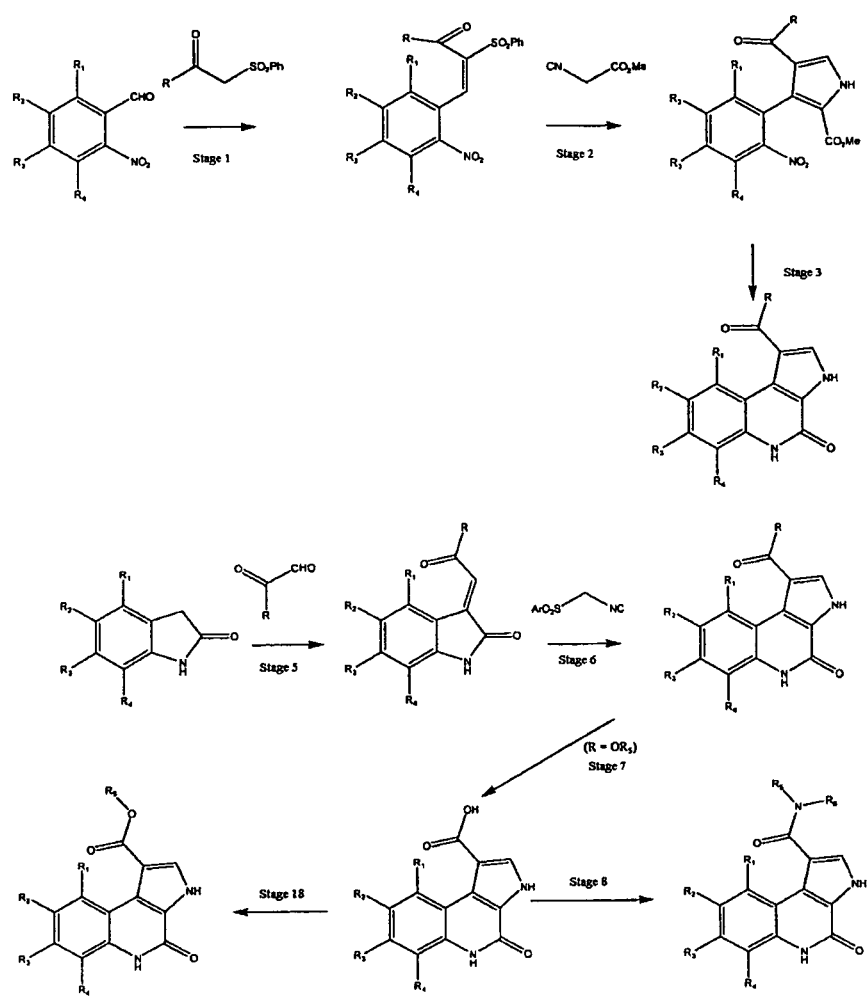
FIG. 1 shows the scheme for synthesis of the tricyclic nucleus and access to compounds of type VII.
Figure 2:
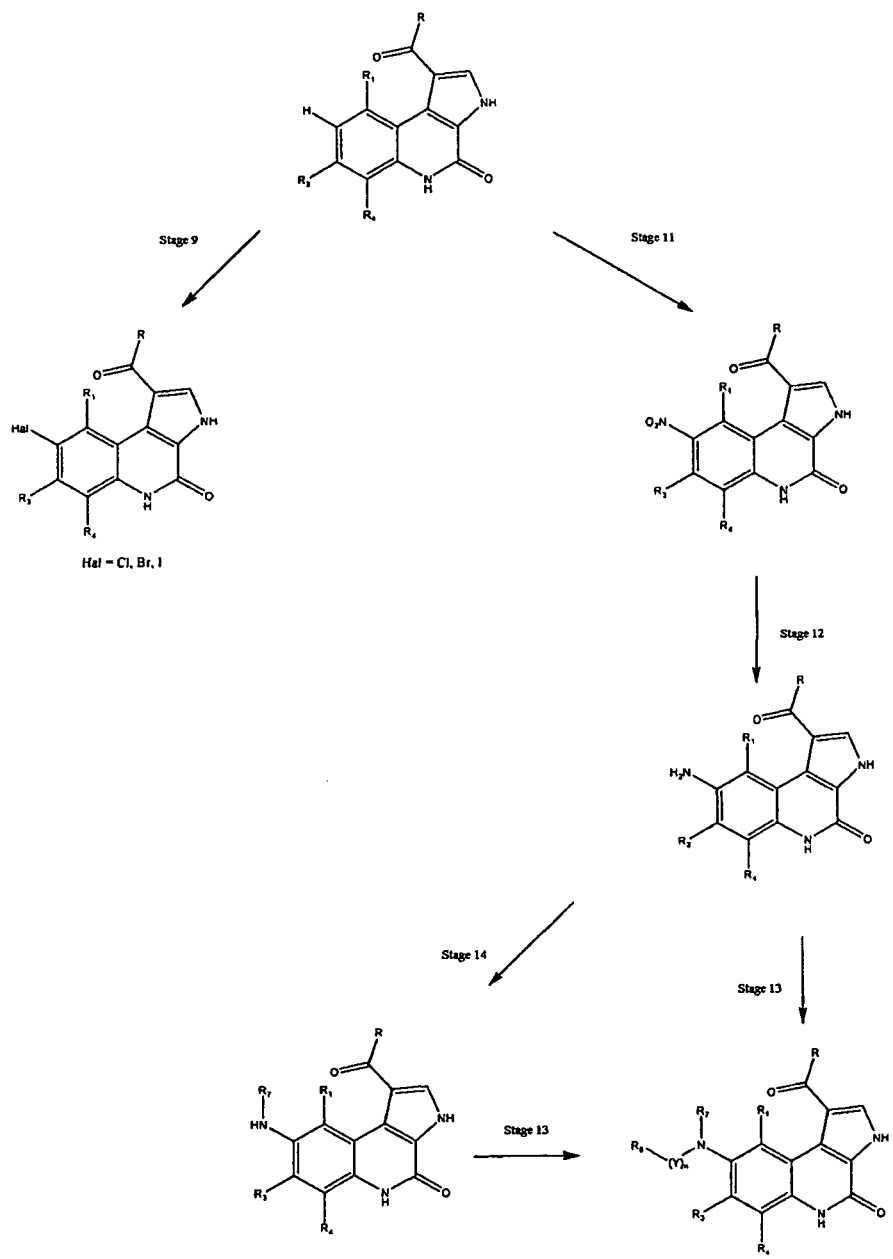
FIG. 2 shows the scheme for access to compounds of type IV, V and VI.
Figure 3:
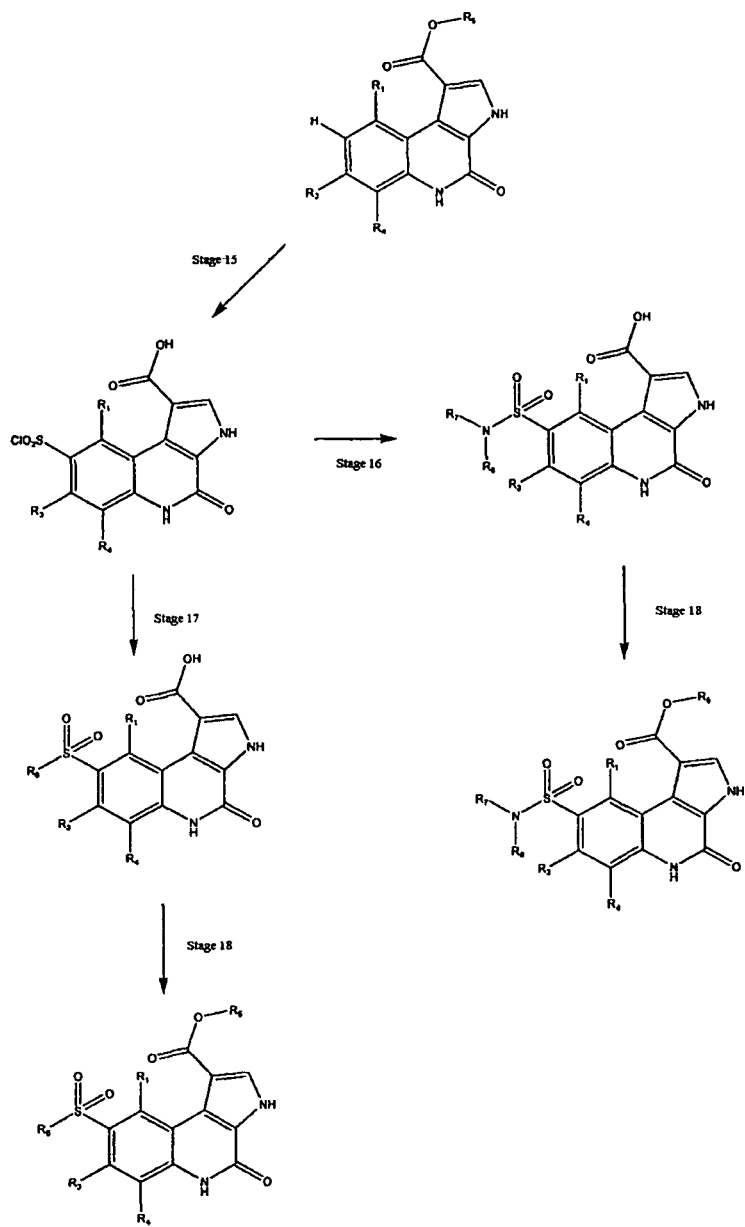
FIG. 3 shows the scheme for access to compounds of type III as well as to certain compounds of type II.
Figure 4:
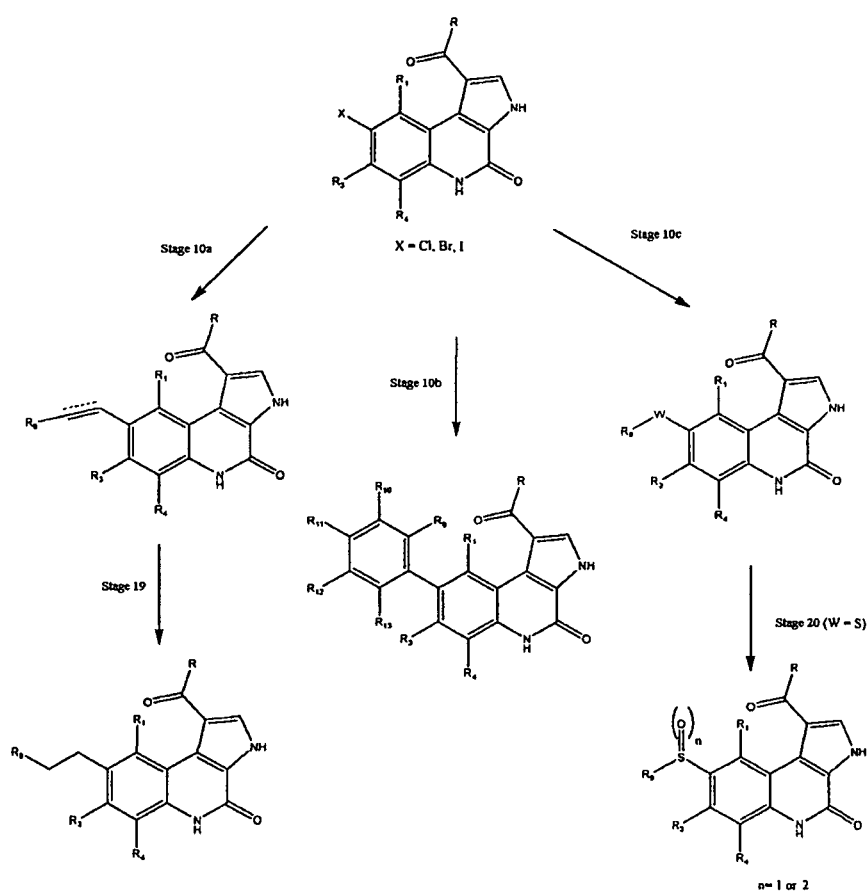
FIG. 4 shows the scheme for access to certain compounds of type II and VI and VIII.
Figure 5:
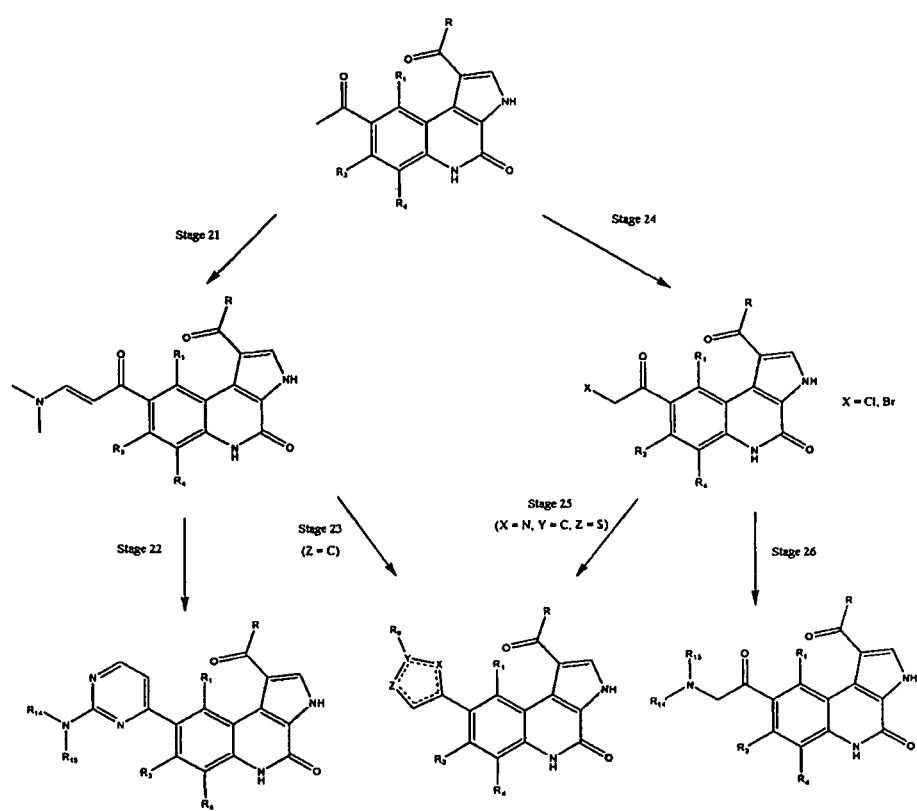
FIG. 5 shows the scheme for access to compounds of type IX as well as to certain compounds of type VI and VIII.

Stage 1 is carried out in the presence of a base of the di- or tri-alkylamine type (typically piperidine) or of anionic type such as lithium diisopropylamide or butyllithium or of inorganic type such as sodium hydroxide or potassium carbonate depending on the nature of group R1. The reaction is carried out in an aprotic solvent in the case of anionic bases and any type of solvent in other cases, at a temperature between −78° C., for the anionic bases, and the boiling point of the solvent principally for the other bases. The reaction mixture is often acidified to permit the removal of water and to give the desired intermediate.

Stage 2 is carried out with an isonitrile derived from glycine in the presence of a base of the trialkylamine type (more generally DBU) or of an anionic base of the potassium tert-butylate or butyllithium type in an aprotic solvent such as tetrahydrofuran, dioxan or an ether, at a temperature between −78° C. and the boiling point of the solvent.

Stage 3 is carried out using a reducing agent of the nitro function such as zinc, iron, or tin for example, in the presence of an acid or hydrogen (or hydrogen donor such as ammonium formate, cyclohexene, cyclohexadiene) in the presence of a hydrogenation catalyst (palladium, platinum), in any type of solvent and at a temperature between −30° C. and the boiling point of the solvent.

Stage 5 is carried out with a glyoxal, in the presence of a base of the di- or tri-alkylamine type, or of the inorganic type such as potassium carbonate. The reaction is carried out in any type of solvent, at a temperature between 0° C. and the boiling point of the solvent. The reaction mixture is often acidified to permit the removal of water and to give the desired intermediate.

The starting products can in particular be prepared according to the methods described in the following patents (Peng Cho Tang et al. US2003/0069451, McNutt Robert Walton Jr et al. WO99/10325, Lanzi Chinzia et al. WO2004/009083).

Stage 6 is carried out with a sulfonylmethylisonitrile derivative (typically tosylmethylisonitrile) optionally substituted with a group $R_2$ corresponding to the definition of the general formula in the presence of an anionic base of the potassium tert-butylate type, an inorganic base of the sodium amide type, or a base of the trialkylamine type (typically DBU) in an inert solvent such as tetrahydrofuran, dioxan or an ether at a temperature between −20° C. and the boiling point of the solvent.

Stage 7 is carried out in the presence of an inorganic base such as sodium hydroxide or lithium hydroxide in a solvent mixture comprising water and a polar solvent more generally an alcohol or a solvent of the ketone type (acetone), at a temperature between 0° C. and the boiling point of the solvent.

Stage 8 is carried out with an amine HNR5R6 in all the conditions of coupling of the peptide type known by a person skilled in the art. More generally, the reaction can be carried out in the presence of coupling agents such as 1-hydroxybenzotriazole/1-(3-dimethylaminopropyl)-3-ethylcarbodiimide hydrochloride, or benzotriazole-1-yl-oxy-trispyrrolidino-phosphonium hexafluorophosphate in an inert solvent such as dimethylformamide or a chlorinated solvent (methylene chloride, chloroform for example) at a temperature between −20° C. and the boiling point of the solvent.

Stage 9 is carried out with an alkylating agent of the N—X-succinimide type in which X is the halogen that is to be introduced, in an inert solvent such as dimethylformamide or a chlorinated solvent (chloroform or carbon tetrachloride for example) at a temperature between −20° C. and the boiling point of the solvent.

Stage 9a can also be carried out with a dihalogen $Hal_2$ in the presence of an acid (generally acetic acid) used as solvent or diluted in an inert solvent at a temperature between −40° C. and the boiling point of the solvent.

Stage 10 can comprise any organometallic coupling known by a person skilled in the art (typically coupling of the Heck, Sonogashira, Stille and Suzuki type) and is carried out in the usual conditions employed by a person skilled in the art.

Typically for stage 10a, it is carried out with an ethylenic compound $R_1$—$CR_2$=$CHR_3$ in which $R_1$ is either an electron-accepting group (more generally an ester, or an amide) or an aromatic group and $R_2$ and $R_3$ can be any group beginning with H in the presence of a base of the trialkylamine type (generally triethylamine) or inorganic base (generally potassium carbonate) and a palladium compound of order 0 (palladium tetrakis) or of the palladium compound of order II (generally palladium acetate)/triarylphosphine couple in an inert solvent such as toluene or dimethylformamide at a temperature between −20° and the boiling point of the solvent. It can also be carried out with a true alkyne compound in the presence of a palladium compound of order 0 (palladium tetrakis) or of the palladium compound of order II (generally palladium acetate)/triarylphosphine couple, an organic base (typically triethylamine) or inorganic base (typically potassium carbonate) and copper(I) iodide in an inert solvent such as toluene, ethereal solvents (dioxan, dimethoxyethane, tetrahydrofuran) or dimethylformamide at a temperature between −20° and the boiling point of the solvent.

Stage 10b is carried out with a boronic acid (or boronic ester), a borane or a stannane in the presence of a palladium compound of order 0 (palladium tetrakis) or of the palladium compound of order II (generally palladium acetate)/triarylphosphine couple in the presence of an inorganic base (potassium carbonate for example) or organic (typically triethylamine) in an inert solvent such as toluene, ethereal solvents (dioxan, dimethoxyethane, tetrahydrofuran) or dimethylformamide at a temperature between −20° and the boiling point of the solvent.

Stage 10c is carried out with an aromatic or aliphatic thiol or the corresponding thiolate anion in the presence of a palladium or copper catalyst (generally copper(I) iodide), an inorganic base (potassium carbonate for example), or organic base (typically triethylamine) and generally of various co-ligands in an inert solvent such as toluene, ethereal solvents (dioxan, dimethoxyethane, tetrahydrofuran) or dimethylformamide at a temperature between −20° and the boiling point of the solvent.

Stage 11 is carried out with a nitrating agent (typically nitric acid or sodium nitrate) in a moderate acid (typically acetic acid) at a temperature between −40° C. and the boiling point of the solvent.

Stage 12 is carried out using a reducing agent of the nitro function such as zinc, iron, or tin for example, in the presence of an acid or hydrogen (or hydrogen donor of the ammonium formate type) in the presence of a catalyst (palladium, platinum), in any type of solvent and at a temperature between −30° C. and the boiling point of the solvent.

Stage 13 is carried out in the presence either of a sulfonyl chloride $R8SO_2Cl$ or of an acid chloride R8COCl in the presence of a base of the trialkylamine type (typically triethylamine), pyridine or an inorganic base such as potassium carbonate in an inert solvent such as dimethylformamide, acetone or chlorinated solvent (methylene chloride, chloroform for example) at a temperature between −20° C. and the boiling point of the solvent.

Stage 14 is carried out with an aldehyde or a ketone in the presence of a reducing agent of the sodium borohydride or sodium cyanoborohydride type in an alcohol or an ether (typically tetrahydrofuran) at a temperature between −20° C. and the boiling point of the solvent.

Alternatively, stage 14 can be carried out in two substages, the first comprises a condensation of an acylating agent (typically acid chloride, ethyl formate) in a solvent such as dimethylformamide, toluene or a halogenated solvent at a temperature between −30° C. and the boiling point of the solvent; the second substage comprises a reduction of this amide intermediate by a reducing agent of the borane type in an inert solvent such as tetrahydrofuran or ether at a temperature between −30° C. and the boiling point of the solvent.

Stage 15 is carried out with a chlorosulfonylating agent (typically chlorosulfonic acid but which can also be oleum followed by a chlorinating agent of the thionyl chloride or phosphorus oxychloride type) without solvent or in a chlorinated solvent (methylene chloride or chloroform for example) at a temperature between −20° C. and the boiling point of the reactants.

Stage 16 is carried out with an amine HNR7R8 in the presence of a base of the trialkylamine type (typically triethylamine), pyridine or an inorganic base of the potassium carbonate type in an inert solvent such as dimethylformamide, acetone or chlorinated solvent (methylene chloride, chloroform for example) at a temperature between −20° C. and the boiling point of the solvent.

Stage 17 is carried out in the presence either of a reducing system of the inorganic type (typically the sodium sulfite, potassium hydrogensulfate couple) in water or of a reducing metal such as zinc in an inert solvent such as tetrahydrofuran or ether at a temperature between 0° C. and the boiling point of the solvent. The sulfinate obtained is then condensed with an alkyl halide in a mixture composed of water and an inert solvent of the ether, ketone or dimethylformamide type at a temperature between 0° C. and the boiling point of the solvent.

The conditions employed during some of the stages cause hydrolysis of the ester. Esterification (stage 18) is carried out in the presence of sulfonyl chloride or of an anhydrous acid (typically HCl) in an alcohol R5OH where R5 is an alkyl at a temperature between 0° C. and the boiling point of the solvent. Stage 18 (R5=Me) can also be carried out in the presence of a precursor of diazomethane (typically trimethylsilyldiazomethane) in a mixture of solvents in which the compounds are soluble such as alcohol, dimethylformamide, ether at a temperature between 0° C. and 50° C. Stage 18 can also be carried out by condensation on an alkyl halide or an alkylating agent (methyl sulfate for example) in the presence of an organic base of the tertiary amine type (typically triethylamine) or inorganic base (typically potassium carbonate or cesium fluoride) in a polar solvent such as ketone, ether or dimethylformamide at a temperature between 0° C. and 100° C.

Stage 19 is carried out in the presence of hydrogen (or hydrogen donor such as ammonium formate, cyclohexene, cyclohexadiene) and a hydrogenation catalyst (palladium, platinum), in any type of solvents (generally alcohols) in the presence or absence of a mineral acid (hydrochloric acid) or organic acid and at a temperature between 0° C. and the boiling point of the solvent and at a pressure varying from atmospheric pressure to several bars.

Stage 20 is carried out using an oxidizing agent of the type Oxone, hydrogen peroxide in solvents such as water, alcohols, acetonitrile, or using an oxidizing agent of the metachloroperbenzoic acid type in chlorinated solvents (of the dichloromethane type) or inert solvents of the tetrahydrofuran or dioxan type at a temperature between 0° C. and the boiling point of the solvent.

Stage 21 is carried out using reactants such as tert-butoxybis(dimethylamino)methane or the dimethyl acetal of N,N-dimethylformamide in solvents such as dioxan, tetrahydrofuran, dimethylformamide or without solvent at a temperature between 0° C. and the boiling point of the solvent.

Stage 22 is carried out in the presence of a guanidine in a solvent of the dioxan type or ethanol, dimethylformamide or dimethylacetamide at a temperature between 20° C. and the boiling point of the solvent.

Stage 23 is carried out in the presence of a hydroxylamine or a hydrazine in a solvent such as dioxan, ethanol, dimethylformamide or dimethylacetamide at a temperature between 20° C. and the boiling point of the solvent.

Stage 24 is carried out in the presence of a halogenating agent such as dibromine, tetrabutylammonium tribromide or benzyltrimethylammonium dichloroiodate in a solvent such as dioxan, tetrahydrofuran or acetic acid at a temperature between 0° C. and the boiling point of the solvent.

Stage 25 is carried out in the presence of a thioacetamide or a thiourea in a solvent such as dioxan, ethanol, dimethylformamide or dimethylacetamide at a temperature between 20° C. and the boiling point of the solvent.

Stage 26 is carried out in the presence of any nucleophile of the primary or secondary amine, alcohol, or thiol type in the presence of a base typically a tertiary amine using as solvent either the nucleophile itself or an inert solvent such as dimethylformamide, acetone, acetonitrile or chlorinated solvent (methylene chloride, chloroform for example) at a temperature between −20° C. and the boiling point of the solvent.

Methods of Esterification

A stage of esterification is sometimes necessary during synthesis of the various compounds. This has been carried out in various ways in the course of time and depending on the nature of the compounds and desired ester. The various experimental conditions are summarized below:

Method A:

In a sealed tube, a solution of thionyl chloride (10 equivalents) in the corresponding anhydrous alcohol is added at 0° C. to the carboxylic acid (1 equivalent) suspended in the corresponding anhydrous alcohol (0.3 mol/l, or more dilute). The solution is stirred under reflux for 1 to 5 days then cooled to room temperature. The solid, composed mainly of the unreacted acid, is filtered and the filtrate is evaporated, then purified by column chromatography to give the desired ester.

Method B:

A 2M solution of trimethylsilyldiazomethane in diethyl ether (1 equivalent) is added to the carboxylic acid (1 equivalent) dissolved in a suitable solvent mixture (generally a mixture of dimethylformamide and methanol). The reaction mixture is stirred at room temperature with very regular monitoring by LC/MS. 2M solution of trimethylsilyldiazomethane in diethyl ether (generally as additional 0.5 to 2 equivalents) is added until the starting acid has disappeared. Acetic acid (5 equivalents) is then added and the solvents are evaporated. The residue is then purified by trituration in water or by silica column chromatography to give the desired methyl ester.

Method C

The triethylamine (5 to 10 equivalents) and the appropriate dialkylsulfate (2 equivalents) are added to the carboxylic acid (1 equivalent) dissolved in dimethylformamide. The solution is stirred at room temperature for 12 hours. The dialkylsulfate (generally 3 to 5 equivalents in total) is added, monitoring the reaction with LC/MS. Ammonia is added and stirring is continued for a further 15 minutes. Water is added and the product is extracted with ethyl acetate. The organic phases are dried over magnesium sulfate, filtered and evaporated and the residue is purified by column chromatography to give the desired ester.

The dialkylsulfates are either commercially available or are prepared by the method used by SoonY Ko et al., J. Org. Chem., 1994, 59, 2570-6.

EXAMPLE 1

Synthesis of the Compounds

4-Oxo-4,5-dihydro-3H-pyrrolo[2,3-c]quinoline-1-ethyl carboxylate (1)

The synthesis of this compound is described by J. Bergman (Tetrahedron, 2002, 58, pp 9179-9185).

18.3 g (93.6 mmol) of p-toluenesulfonylmethyl isonitrile followed by a solution of 54 mL (93.6 mmol) of a 20% solution of potassium tert-butoxide in tetrahydrofuran in 700 mL of anhydrous tetrahydrofuran are added to a solution of 20.3 g (93.6 mmol) of (2-oxo-1,2-dihydro-indol-3-ylidene)-ethyl ethanoate dissolved in 340 mL of anhydrous tetrahydrofuran (time of addition 90 minutes). The reaction mixture is refluxed for 1 hour then the solid is filtered. The filtrate is poured into a mixture of ice and water (about 1 L) and the solution is acidified with acetic acid until the pH is 4. The solvents are concentrated by evaporation under vacuum then the solid is filtered and then recrystallized from acetic acid to give 11.05 g (37%) of 4-oxo-4,5-dihydro-3H-pyrrolo[2,3-c]quinoline-1-ethyl carboxylate cocrystallized with one equivalent of acetic acid in the form of a white solid.

LCMS (IE, m/z): (M+1) 256.89

$^1$H-NMR: $\delta_H$ ppm 250 MHz, DMSO 12.97 (1H, bs, NH), 11.66 (1H, s, NH), 9.22 (1H, d, $CH_{arom}$), 7.98 (1H, s, $CH_{arom}$), 7.43-7.35 (2H, m, 2×$CH_{arom}$), 7.26-7.17 (1H, m, $CH_{arom}$), 4.30 (2H, q, $CH_2$), 1.34 (3H, t, $CH_3$).

73.5 mL (360 mmol) of a 50% solution of ethyl glyoxalate in toluene then 3.6 ml, (36 mmol) of piperidine and 4.2 mL (72 mmol) of acetic acid are added to a solution of 24 g (180 mmol) of 1,3-dihydro-indol-2-one dissolved in 350 mL of ethanol. The reaction mixture is stirred at 70° C. for 20 hours then concentrated to a quarter by evaporation of the solvents under vacuum. The solid is filtered to give 18.3 g (47%) of (2-oxo-1,2-dihydro-indol-3-ylidene)-ethyl ethanoate in the form of an orange solid. The filtrate is evaporated, then recrystallized from ethanol to give an additional 2.7 g (7%) of (2-oxo-1,2-dihydro-indol-3-ylidene)-ethyl ethanoate in the form of an orange solid.

4-Oxo-8-phenylsulfamoyl-4,5-dihydro-3H-pyrrolo[2,3-c]quinoline-1-ethyl carboxylate (2)

A solution of 20 μL (0.28 mmol) of thionyl chloride diluted in 0.5 mL of anhydrous ethanol is added dropwise to 27 mg (0.07 mmol) of 4-oxo-8-phenylsulfamoyl-4,5-dihydro-3H-pyrrolo[2,3-c]quinoline-1-carboxylic acid suspended in 0.5 mL of anhydrous ethanol. The solution is stirred under reflux for 72 hours then cooled to room temperature. The solid is filtered to give 3.5 mg (12%) of 4-oxo-8-phenylsulfamoyl-4,5-dihydro-3H-pyrrolo[2,3-c]quinoline-1-ethyl carboxylate in the form of a white solid.

LCMS (IE, m/z): (M+1) 411.91

$^1$H-NMR: $\delta_H$ ppm 250 MHz, DMSO 13.18 (1H, bs, NH), 12.05 (1H, s, NH), 10.26 (1H, s, NH), 9.85 (1H, d, $CH_{arom}$), 8.04 (1H, d, $CH_{arom}$), 7.73 (1H, dd, $CH_{arom}$), 7.47 (1H, d, $CH_{arom}$), 7.22-7.10 (4H, m, 4×$CH_{arom}$), 7.00-6.92 (1H, m, $CH_{arom}$), 4.35 (2H, q, $CH_2$), 1.34 (3H, t, $CH_3$).

30 μL (0.37 mmol) of pyridine and 20 μL (0.22 mmol) of aniline are added to 60 mg (0.18 mmol) of 8-chlorosulfonyl-4-oxo-4,5-dihydro-3H-pyrrolo[2,3-c]quinoline-1-carboxylic acid suspended in 4 mL of anhydrous dichloromethane and 1 mL of anhydrous dimethylformamide. The reaction mixture is stirred for 5 hours at room temperature then diluted with a 10% aqueous solution of potassium carbonate and dichloromethane. The phases are separated and the aqueous phase is acidified with acetic acid to pH of 4. The product is extracted with dichloromethane. The organic phase is dried over magnesium sulfate, filtered then evaporated. The residue is diluted with water (5 mL) then the solid is filtered and dried under vacuum to give 30 mg (42%) of 4-oxo-8-phenylsulfamoyl-4,5-dihydro-3H-pyrrolo[2,3-c]quinoline-1-carboxylic acid in the form of a beige solid.

85 mg (0.33 mmol) of 4-oxo-4,5-dihydro-3H-pyrrolo[2,3-c]quinoline-1-ethyl carboxylate as prepared in the preceding synthesis 1 is added in the space of 90 minutes to 106 μL (1.65 mmol) of chlorosulfonic acid cooled to 0° C. on an ice bath.

On completion of addition, the solution is stirred for 1 hour at room temperature then 3 hours at 70° C. The reaction mixture is cooled to room temperature then poured into ice water (20 mL). The mixture is stirred for 15 minutes then the solid is filtered, and taken up in methanol/toluene mixture. The solvents are evaporated to give 64 mg (60%) of 8-chlorosulfonyl-4-oxo-4,5-dihydro-3H-pyrrolo[2,3-c]quinoline-1-carboxylic acid in the form of a beige solid.

8-(Methyl-phenylsulfamoyl)-4-oxo-4,5-dihydro-3H-pyrrolo[2,3-c]quinoline-1-ethyl carboxylate (3)

This compound was synthesized according to synthesis 1, from 265 mg (0.88 mmol) of 5-(methylphenylsulfamoyl)-1,3-dihydro-indol-2-one to give, after recrystallization from acetic acid, 15 mg (2% in two stages) of 8-(methyl-phenylsulfamoyl)-4-oxo-4,5-dihydro-3H-pyrrolo[2,3-c]quinoline-1-ethyl carboxylate in the form of a gray solid.

LCMS (IE, m/z): (M+1) 426.28

$^1$H-NMR: $\delta_H$ ppm 250 MHz, DMSO 13.21 (1H, bs, NH), 12.10 (1H, s, NH), 9.64 (1H, s, $CH_{arom}$), 8.05 (1H, s, $CH_{arom}$), 7.51-7.19 (5H, m, 5×$CH_{arom}$), 7.18-7.06 (2H, m, 2×$CH_{arom}$), 4.26 (2H, q, $CH_2$), 3.17 (3H, s, $CH_3$), 1.32 (3H, t, $CH_3$).

350 μL (4.32 mmol) of pyridine and 270 μL (2.48 mmol) of N-methylaniline are added to 500 mg (2.16 mmol) of 2-oxo-2,3-dihydro-1H-indole sulfonyl chloride suspended in 7 mL of anhydrous dichloromethane. The reaction mixture is stirred for 4 hours at room temperature then diluted in water (20 mL). The product is extracted in dichloromethane (3×20 mL). The organic phases are combined, dried over magnesium sulfate, filtered then evaporated. The residue is purified by chromatography on silica (eluent dichloromethane/ethyl acetate 8/2) to give 273 mg (42%) of 5-(methyl-phenylsulfamoyl)-1,3-dihydro-indol-2-one in the form of a slightly pink solid.

2-Oxo-2,3-dihydro-1H-indole sulfonyl chloride was synthesized by Peng Cho Tang (US 2003/0069421). The compound was prepared according to this procedure from 2.5 g (18.8 mmol) of 1,3-dihydro-indol-2-one to give 3.1 g (71%) of 2-oxo-2,3-dihydro-1H-indole sulfonyl chloride in the form of a beige solid.

4-Oxo-8-o-tolylsulfamoyl-4,5-dihydro-3H-pyrrolo[2,3-c]quinoline-1-ethyl carboxylate (4)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 59 μL (0.55 mmol) of 2-methylaniline. After purification by chromatography on silica (eluent dichloromethane/methanol 96/4) then trituration in methanol, 17 mg (9%) of 4-oxo-8-O— tolylsulfamoyl-4,5-dihydro-3H-pyrrolo[2,3-c]quinoline-1-ethyl carboxylate is obtained in the form of a white solid.

LCMS (IE, m/z): (M+1) 425.82

$^1$H-NMR: $\delta_H$ ppm 400 MHz, DMSO 13.17 (1H, bs, NH), 12.04 (1H, s, NH), 9.71 (1H, d, $CH_{arom}$), 9.47 (1H, s, NH), 8.03 (1H, s, $CH_{arom}$), 7.61 (1H, dd, $CH_{arom}$), 7.47 (1H, d, $CH_{arom}$), 7.12-7.00 (4H, m, 4×$CH_{arom}$), 4.30 (2H, q, $CH_2$), 2.00 (3H, s, $CH_3$), 1.33 (3H, 1, $CH_3$).

4-Oxo-8-m-tolylsulfamoyl-4,5-dihydro-3H-pyrrolo[2,3-c]quinoline-1-ethyl carboxylate (5)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 59 μL (0.55 mmol) of 3-methylaniline. After purification by chromatography on silica (eluent dichloromethane/methanol 96/4) then trituration in diethyl ether, 45 mg (23%) of 4-oxo-8-m-tolylsulfamoyl-4,5-dihydro-3H-pyrrolo[2,3-c]quinoline-1-ethyl carboxylate is obtained in the form of a white solid.

LCMS (IE, m/z): (M+1) 425.83

$^1$H-NMR: $\delta_H$ ppm 400 MHz, DMSO 13.17 (1H, bs, NH), 12.03 (1H, s, NH), 10.17 (1H, bs, NH), 9.87 (1H, d, $CH_{arom}$), 8.05 (1H, s, $CH_{arom}$), 7.75 (1H, dd, $CH_{arom}$), 7.49 (1H, d, $CH_{arom}$), 7.07-7.00 (2H, m, 2×$CH_{arom}$), 6.92 (1H, dl, $CH_{arom}$), 6.77 (1H, dl, $CH_{arom}$), 4.36 (2H, q, $CH_2$), 2.17 (3H, s, $CH_3$), 1.37 (3H, t, $CH_3$).

4-Oxo-8-p-tolylsulfamoyl-4,5-dihydro-3H-pyrrolo[2,3-c]quinoline-1-ethyl carboxylate (6)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 62 μL (0.55 mmol) of 4-methylaniline. After purification by chromatography on silica (eluent dichloromethane/methanol 95/5) then trituration in diethyl ether, 40 mg (20%) of 4-oxo-8-p-tolylsulfamoyl-4,5-dihydro-3H-pyrrolo[2,3-c]quinoline-1-ethyl carboxylate is obtained in the form of a white solid.

LCMS (IE, m/z): (M+1) 425.78

$^1$H-NMR: $\delta_H$ ppm 400 MHz, DMSO 13.13 (1H, bs, NH), 12.01 (1H, s, NH), 10.06 (1H, bs, NH), 9.79 (1H, d, $CH_{arom}$), 8.03 (1H, s, $CH_{arom}$), 7.70 (1H, dd, $CH_{arom}$), 7.46 (1H, d, $CH_{arom}$), 7.02 (2H, d, 2×$CH_{arom}$), 6.98 (2H, d, 2×$CH_{arom}$), 4.35 (2H, q, $CH_2$), 2.14 (3H, s, $CH_3$), 1.36 (3H, t, $CH_3$).

8-(2-Methoxy-phenylsulfamoyl)-4-oxo-4,5-dihydro-3H-pyrrolo[2,3-c]quinoline-1-ethyl carboxylate (7)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 62 μL (0.55 mmol) of 2-methoxyaniline. After purification by chromatography on silica (eluent dichloromethane/methanol 95/5) then trituration in diethyl ether, 22 mg (11%) of 8-(2-methoxy-phenylsulfamoyl)-4-oxo-4,5-dihydro-3H-pyrrolo[2,3-c]quinoline-1-ethyl carboxylate is obtained in the form of a white solid.

LCMS (IE, t/z): (M+1) 441.75

$^1$H-NMR: $\delta_H$ ppm 400 MHz, DMSO 13.16 (1H, bs, NH), 12.01 (1H, s, NH), 9.72 (1H, d, $CH_{arom}$), 9.24 (1H, bs, NH), 8.03 (1H, s, $CH_{arom}$), 7.70 (1H, dd, $CH_{arom}$), 7.46 (1H, d, $CH_{arom}$), 7.29 (1H, dd, $CH_{arom}$), 7.06 (1H, dt, $CH_{arom}$), 6.86-6.81 (2H, m, 2×$CH_{arom}$), 4.32 (2H, q, $CH_2$), 3.44 (3H, s, $CH_3$), 1.35 (3H, t, $CH_3$).

8-(3-Methoxy-phenylsulfamoyl)-4-oxo-4,5-dihydro-3H-pyrrolo[2,3-c]quinoline-1-ethyl carboxylate (8)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 62 μL (0.55 mmol) of 3-methoxyaniline. After purification by chromatography on silica (eluent dichloromethane/methanol 95/5) then trituration in diethyl ether, 29 mg (14%) of 8-(3-methoxy-phenylsulfamoyl)-4-oxo-4,5-dihydro-3H-pyrrolo[2,3-c]quinoline-1-ethyl carboxylate is obtained in the form of a white solid.

LCMS (IE, t/z): (M+1) 441.77
$^1$H-NMR: $\delta_H$ ppm 400 MHz, DMSO
13.17 (1H, bs, NH), 12.04 (1H, s, NH), 10.26 (1H, bs, NH), 9.87 (1H, d, CH$_{arom}$), 8.05 (1H, d, CH$_{arom}$), 7.76 (1H, dd, CH$_{arom}$), 7.50 (1H, d, CH$_{arom}$), 7.07 (1H, t, CH$_{arom}$), 6.75 (1H, t, CH$_{arom}$), 6.72-6.66 (1H, m, CH$_{arom}$), 6.53 (1H, dd, CH$_{arom}$), 4.35 (2H, q, CH$_2$), 3.64 (3H, s, CH$_3$), 1.37 (3H, 1, CH$_3$).

8-(4-Methoxy-phenylsulfamoyl)-4-oxo-4,5-dihydro-3H-pyrrolo[2,3-c]quinoline-1-ethyl carboxylate (9)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 64 µL (0.55 mmol) of 4-methoxyaniline. After purification by chromatography on silica (eluent dichloromethane/methanol/acetonitrile 95/3/2) then trituration in diethyl ether, 21 mg (10%) of 8-(4-methoxy-phenylsulfamoyl)-4-oxo-4,5-dihydro-3H-pyrrolo[2,3-c]quinoline-1-ethyl carboxylate is obtained in the form of a white solid.
LCMS (IE, m/z): (M+1) 441.83
$^1$H-NMR: $\delta_H$ ppm 400 MHz, DMSO
13.16 (1H, bs, NH), 12.02 (1H, s, NH), 9.85 (1H, bs, NH), 9.73 (1H, d, CH$_{arom}$), 8.03 (1H, s, CH$_{arom}$), 7.66 (1H, dd, CH$_{arom}$), 7.47 (1H, d, CH$_{arom}$), 7.02 (2H, d, 2×CH$_{arom}$), 6.76 (2H, d, 2×CH$_{arom}$), 4.33 (2H, q, CH$_2$), 3.63 (3H, s, CH$_3$), 1.36 (3H, t, CH$_3$).

8-(3-Chlorophenylsulfamoyl)-4-oxo-4,5-dihydro-3H-pyrrolo[2,3-c]quinoline-1-ethyl carboxylate (10)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 59 µL (0.55 mmol) of 3-chloro-aniline. After purification by chromatography on silica (eluent dichloromethane/methanol 95/5) then trituration in diethyl ether, 15 mg (7%) of 8-(3-chlorophenylsulfamoyl)-4-oxo-4,5-dihydro-3H-pyrrolo[2,3-c]quinoline-1-ethyl carboxylate is obtained in the form of a white solid.
LCMS (IE, m/z): (M+1) 445.73-447.74
$^1$H-NMR: $\delta_H$ ppm 400 MHz, DMSO
13.18 (1H, bs, NH), 12.05 (1H, s, NH), 10.52 (1H, bs, NH), 9.88 (1H, d, CH$_{arom}$), 8.04 (1H, s, CH$_{arom}$), 7.76 (1H, dd, CH$_{arom}$), 7.51 (1H, d, CH$_{arom}$), 7.23-7.18 (2H, m, 2×CH$_{arom}$), 7.08 (1H, dl, CH$_{arom}$), 7.01 (1H, dl, CH$_{arom}$), 4.36 (2H, q, CH$_2$), 1.37 (3H, t, CH$_3$).

8-(4-Chlorophenylsulfamoyl)-4-oxo-4,5-dihydro-3H-pyrrolo[2,3-c]quinoline-1-ethyl carboxylate (11)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 70 mg (0.55 mmol) of 4-chloro-aniline. After purification by chromatography on silica (eluent dichloromethane/methanol 96/4) then trituration in diethyl ether, 15 mg (7%) of 8-(4-chlorophenylsulfamoyl)-4-oxo-4,5-dihydro-3H-pyrrolo[2,3-c]quinoline-1-ethyl carboxylate is obtained in the form of a white solid.
LCMS (IE, m/z): (M+1) 445.72-447.61
$^1$H-NMR: $\delta_H$ ppm 400 MHz, DMSO
13.18 (1H, bs, NH), 12.04 (1H, s, NH), 10.39 (1H, bs, NH), 9.82 (1H, d, CH$_{arom}$), 8.04 (1H, s, CH$_{arom}$), 7.73 (1H, dd, CH$_{arom}$), 7.49 (1H, d, CH$_{arom}$), 7.25 (2H, d, 2×CH$_{arom}$), 7.14 (2H, d, 2×CH$_{arom}$), 4.35 (2H, q, CH$_2$), 1.36 (3H, t, CH$_3$).

8-(4-Fluorophenylsulfamoyl)-4-oxo-4,5-dihydro-3H-pyrrolo[2,3-c]quinoline-1-ethyl carboxylate (12)

This compound is prepared according to synthesis 25, from 300 mg (0.92 mmol) of 8-chlorosulfonyl-4-oxo-4,5-dihydro-3H-pyrrolo[2,3-c]quinoline-1-carboxylic acid (synthesis 2) and 112 µL (1.1 mmol) of 4-fluoro-aniline. After purification by chromatography on silica (eluent dichloromethane/methanol 95/5) then trituration in water then diethyl ether, 45 mg (12%) of 8-(4-fluorophenylsulfamoyl)-4-oxo-4,5-dihydro-3H-pyrrolo[2,3-c]quinoline-1-ethyl carboxylate is obtained in the form of a white solid.
LCMS (IE, m/z): (M+1) 429.66
$^1$H-NMR: $\delta_H$ ppm 400 MHz, DMSO
13.17 (1H, bs, NH), 12.04 (1H, s, NH), 10.16 (1H, bs, NH), 9.77 (1H, d, CH$_{arom}$), 8.04 (1H, s, CH$_{arom}$), 7.70 (1H, dd, CH$_{arom}$), 7.48 (1H, d, CH$_{arom}$), 7.16-7.08 (2H, m, 2×CH$_{arom}$), 7.08-7.00 (2H, m, 2×CH$_{arom}$), 4.33 (2H, q, CH$_2$), 1.36 (3H, t, CH$_3$).

8-[(4-Fluorophenyl)-N-methyl-sulfamoyl]-4-oxo-4,5-dihydro-3H-pyrrolo[2,3-c]quinoline-1-ethyl carboxylate (13)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 62 µL (0.55 mmol) of (4-fluoro)-N-methyl-aniline. After purification by chromatography on silica (eluent dichloromethane/methanol 95/5) then trituration in methanol, 25 mg (12%) of 8-[(4-fluorophenyl)-methyl-sulfamoyl]-4-oxo-4,5-dihydro-3H-pyrrolo[2,3-c]quinoline-1-ethyl carboxylate is obtained in the form of a white solid.
LCMS (IE, m/z): (M+1) 443.78
$^1$H-NMR: $\delta_H$ ppm 400 MHz, DMSO
13.20 (1H, bs, NH), 12.10 (1H, s, NH), 9.59 (1H, d, CH$_{arom}$), 8.04 (1H, s, CH$_{arom}$), 7.51 (1H, d, CH$_{arom}$), 7.46 (1H, dd, CH$_{arom}$), 7.14 (4H, d, 4×CH$_{arom}$), 4.28 (2H, q, CH$_2$), 3.14 (3H, s, CH$_3$), 1.32 (3H, t, CH$_3$).

8-(4-Ethoxycarbonyl-phenylsulfamoyl)-4-oxo-4,5-dihydro-3H-pyrrolo[2,3-c]quinoline-1-ethyl carboxylate (14)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 91 mg (0.55 mmol) of ethyl 4-amino-benzoate. After purification by chromatography on silica (eluent dichloromethane/methanol 96/4) then trituration in methanol, 4 mg (2%) of 8-(4-ethoxycarbonyl-phenylsulfamoyl)-4-oxo-4,5-dihydro-3H-pyrrolo[2,3-c]quinoline-1-ethyl carboxylate is obtained in the form of a white solid.
LCMS (IE, m/z): (M+1) 483.91
$^1$H-NMR: $\delta_H$ ppm 400 MHz, DMSO
13.19 (1H, bs, NH), 12.06 (1H, s, NH), 10.82 (1H, bs, NH), 9.93 (1H, d, CH$_{arom}$), 8.05 (1H, d, CH$_{arom}$), 7.84-7.76 (3H, m, 3×CH$_{arom}$), 7.51 (1H, d, CH$_{arom}$), 7.28 (2H, d, 2×CH$_{arom}$), 4.37 (2H, q, CH$_2$), 4.22 (2H, q, CH$_2$), 1.38 (3H, t, CH$_3$), 1.25 (3H, t, CH$_3$).

8-(3-Hydroxy-phenylsulfamoyl)-4-oxo-4,5-dihydro-3H-pyrrolo[2,3-c]quinoline-1-ethyl carboxylate (15)

This compound is prepared according to synthesis 25, from 150 mg (0.46 mmol) of 8-chlorosulfonyl-4-oxo-4,5-dihydro- 3H-pyrrolo[2,3-c]quinoline-1-carboxylic acid (synthesis 2) and 60 mg (0.55 mmol) of 3-hydroxy-aniline. After purification by chromatography on silica (eluent dichloromethane/methanol 95/5) then trituration in diethyl ether, 22 mg (12%) of 8-(3-hydroxy-phenylsulfamoyl)-4-oxo-4,5-dihydro-3H-pyrrolo[2,3-c]quinoline-1-ethyl carboxylate is obtained in the form of a yellow solid.

LCMS (IE, m/z): (M+1) 427.77

$^1$H-NMR: $\delta_H$ ppm 400 MHz, DMSO 13.17 (1H, bs, NH), 12.03 (1H, s, NH), 10.12 (1H, bs, NH), 9.84 (1H, d, $CH_{arom}$), 9.36 (1H, s, OH), 8.04 (1H, d, $CH_{arom}$), 7.73 (1H, dd, $CH_{arom}$), 7.48 (1H, d, $CH_{arom}$), 6.94 (1H, t, $CH_{arom}$) 6.61-6.55 (2H, m, 2×$CH_{arom}$), 636 (1H, dd, $CH_{arom}$), 4.36 (2H, q, $CH_2$), 1.37 (3H, t, $CH_3$).

8-(3-Fluoro-2-methyl-phenylsulfamoyl)-4-oxo-4,5-dihydro-3H-pyrrolo[2,3-c]quinoline-1-ethyl carboxylate (16)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 63 µL (0.55 mmol) of 3-fluoro-2-methylaniline. After purification by chromatography on silica (eluent dichloromethane/methanol 96/4) then trituration in diethyl ether, 3.5 mg (2%) of 8-(3-fluoro-2-methyl-phenylsulfamoyl)-4-oxo-4,5-dihydro-3H-pyrrolo[2,3-c]quinoline-1-ethyl carboxylate is obtained in the form of a beige solid.

LCMS (IE, m/z): (M+1) 443.74

$^1$H-NMR: $\delta_H$ ppm 400 MHz, DMSO 13.18 (1H, bs, NH), 12.06 (1H, s, NH), 9.70 (2H, m, $CH_{arom}$ and NH), 8.03 (1H, s, $CH_{arom}$), 7.64 (1H, dd, $CH_{arom}$), 7.49 (1H, d, $CH_{arom}$), 7.13-7.06 (1H, m, $CH_{arom}$), 6.98 (1H, t, $CH_{arom}$), 6.88 (1H, d, $CH_{arom}$), 4.29 (2H, q, $CH_2$), 1.93 (3H, d, $CH_3$), 1.33 (3H, t, $CH_3$).

8-(4-Fluoro-2-methyl-phenylsulfamoyl)-4-oxo-4,5-dihydro-3H-pyrrolo[2,3-c]quinoline-1-ethyl carboxylate (17)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 61 µL (0.55 mmol) of 4-fluoro-2-methyl-aniline. After purification by chromatography on silica gel (dichloromethane/methanol 95/5) then trituration in diethyl ether, 19 mg (9%) of 8-(4-fluoro-2-methyl-phenylsulfamoyl)-4-oxo-4,5-dihydro-3H-pyrrolo[2,3-c]quinoline-1-ethyl carboxylate is obtained in the form of a white solid.

LCMS (IE, m/z): (M+1) 443.72

$^1$H-NMR: $\delta_H$ ppm 400 MHz, DMSO 13.17 (1H, bs, NH), 12.06 (1H, s, NH), 9.64 (1H, d, $CH_{arom}$), 9.47 (1H, bs, NH), 8.03 (1H, s, $CH_{arom}$), 7.61 (1H, dd, $CH_{arom}$), 7.49 (1H, d, $CH_{arom}$), 7.04-6.87 (3H, m, 3×$CH_{arom}$), 4.28 (2H, q, $CH_2$), 1.96 (3H, s, $CH_3$), 1.32 (3H, t, $CH_3$).

8-(3,4-Difluorophenylsulfamoyl)-4-oxo-4,5-dihydro-3H-pyrrolo[2,3-c]quinoline-1-ethyl carboxylate (18)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 55 µL (0.55 mmol) of 3,4-difluoro-aniline. After purification by chromatography on silica gel (dichloromethane/methanol 95/5) then trituration in diethyl ether, 24 mg (12%) of 8-(3,4-difluorophenylsulfamoyl)-4-oxo-4,5-dihydro-3H-pyrrolo[2,3-c]quinoline-1-ethyl carboxylate is obtained in the form of a white solid.

LCMS (IE, m/z): (M+1) 447.72

$^1$H-NMR: $\delta_H$ ppm 400 MHz, DMSO 13.19 (1H, bs, NH), 12.06 (1H, s, NH), 10.42 (1H, bs, NH), 9.80 (1H, d, $CH_{arom}$), 8.04 (1H, s, $CH_{arom}$), 7.76 (1H, dd, $CH_{arom}$), 7.51 (1H, d, $CH_{arom}$), 7.32-7.17 (2H, m, 2×$CH_{arom}$), 6.91-6.85 (1H, m, $CH_{arom}$), 4.34 (2H, q, $CH_2$), 1.36 (3H, t, $CH_3$).

8-(3,5-Difluorophenylsulfamoyl)-4-oxo-4,5-dihydro-3H-pyrrolo[2,3-c]quinoline-1-ethyl carboxylate (19)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 55 µL (0.55 mmol) of 3,5-difluoro-aniline. After purification by chromatography on silica gel (dichloromethane/methanol 95/5) then trituration in diethyl ether, 3 mg (2%) of 8-(3,5-difluorophenylsulfamoyl)-4-oxo-4,5-dihydro-3H-pyrrolo[2,3-c]quinoline-1-ethyl carboxylate is obtained in the form of a white solid.

LCMS (IE, m/z): (M+1) 447.72

$^1$H-NMR: $\delta_H$ ppm 400 MHz, DMSO 13.19 (1H, s flattened, NH), 12.08 (1H, bs, NH), 10.80 (1H, s flattened, NH), 9.94 (1H, d, $CH_{arom}$), 8.05 (1H, s, $CH_{arom}$), 7.82 (1H, dd, $CH_{arom}$), 7.54 (1H, d, $CH_{arom}$), 6.86-6.77 (3H, m, 3×$CH_{arom}$), 4.36 (2H, q, $CH_2$), 1.37 (3H, t, $CH_3$).

8-(4-Aminophenylsulfamoyl)-4-oxo-4,5-dihydro-3H-pyrrolo[2,3-c]quinoline-1-ethyl carboxylate (20)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 115 mg (0.55 mmol) of N-tert-butoxycarbonyl-para-phenylenediamine. After purification by chromatography on silica gel (chloroform/methanol/ammonia 90/25/4) then trituration in diethyl ether, 5 mg (3%) of 8-(4-aminophenylsulfamoyl)-4-oxo-4,5-dihydro-3H-pyrrolo[2,3-c]quinoline-1-ethyl carboxylate is obtained in the form of a white solid.

LCMS (IE, m/z): (M+1) 426.77

$^1$H-NMR: $\delta_H$ ppm 400 MHz, DMSO 13.14 (1H, bs, NH), 12.00 (1H, s, NH), 9.71 (1H, d, $CH_{arom}$), 9.43 (1H, s, NH), 8.03 (1H, s, $CH_{arom}$), 7.60 (1H, dd, $CH_{arom}$), 7.45 (1H, d, $CH_{arom}$), 6.72 (2H, d, 2×$CH_{arom}$), 6.36 (2H, d, 2×$CH_{arom}$), 4.90 (2H, bs, $NH_2$), 4.33 (2H, q, $CH_2$), 1.36 (3H, t, $CH_3$).

8-(2,3-Dihydro-indole-1-sulfonyl)-4-oxo-4,5-dihydro-3H-pyrrolo[2,3-c]quinoline-1-ethyl carboxylate (21)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 62 µL (0.55 mmol) of 2,3-dihydro-1H-indole. After purification by chromatography on silica (eluent dichloromethane/methanol 96/4) then trituration in methanol, 40 mg (20%) of 8-(2,3-dihydro-indole-1-sulfonyl)-4-oxo-4,5-dihydro-3H-pyrrolo[2,3-c]quinoline-1-ethyl carboxylate is obtained in the form of a white solid.

LCMS (IE, m/z): (M+1) 437.77

$^1$H-NMR: $\delta_H$ ppm 400 MHz, DMSO 13.18 (1H, bs, NH), 12.06 (1H, s, NH), 9.94 (1H, d, $CH_{arom}$), 8.05 (1H, s, $CH_{arom}$), 7.80 (1H, dd, $CH_{arom}$), 7.57

(1H, d, CH$_{arom}$), 7.49 (1H, d, CH$_{arom}$), 7.15-7.08 (2H, m, 2×CH$_{arom}$), 6.91 (1H, td, CH$_{arom}$), 4.39 (2H, q, CH$_2$), 3.96 (2H, t, CH$_2$), 2.93 (2H, t, CH$_2$), 1.39 (3H, t, CH$_3$).

8-(4-Morpholin-4-yl-phenylsulfamoyl)-4-oxo-4,5-dihydro-3H-pyrrolo[2,3-c]quinoline-1-ethyl carboxylate (22)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 98 mg (0.55 mmol) of 4-morpholin-4-yl-aniline. After purification by chromatography on silica (eluent dichloromethane/methanol 95/5) then trituration in methanol, 57 mg (25%) of 8-(4-morpholin-4-yl-phenylsulfamoyl)-4-oxo-4,5-dihydro-3H-pyrrolo[2,3-c]quinoline-1-ethyl carboxylate is obtained in the form of a gray solid.

LCMS (IE, m/z): (M+1) 496.93
$^1$H-NMR: δ$_H$ ppm 400 MHz, DMSO
13.16 (1H, bs, NH), 12.02 (1H, s, NH), 9.78 (1H, bs, NH), 9.73 (1H, d, CH$_{arom}$), 8.03 (1H, s, CH$_{arom}$), 7.67 (1H, dd, CH$_{arom}$), 7.47 (1H, d, CH$_{arom}$), 6.96 (2H, d, 2×CH$_{arom}$), 6.76 (2H, d, 2×CH$_{arom}$), 4.34 (2H, q, CH$_2$), 3.68-3.64 (4H, m, 4×CH$_{morp}$), 2.98-2.94 (4H, m, 4×CH$_{morp}$), 1.36 (3H, t, CH$_3$).

4-Oxo-8-(pyridin-3-ylsulfamoyl)-4,5-dihydro-3H-pyrrolo[2,3-c]quinoline-1-ethyl carboxylate (23)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 52 mg (0.55 mmol) of 3-aminopyridine. After purification by chromatography on silica (eluent dichloromethane/methanol 9/1 then chloroform/methanol/ammonia 90/25/4) then trituration in diethyl ether, 5 mg (3%) of 4-oxo-8-(pyridin-3-ylsulfamoyl)-4,5-dihydro-3H-pyrrolo[2,3-c]quinoline-1-ethyl carboxylate is obtained in the form of a yellow solid.

LCMS (IE, m/z): (M+1) 412.80
$^1$H-NMR: δ$_H$ ppm 400 MHz, DMSO
13.18 (1H, bs, NH), 12.06 (1H, s, NH), 10.58 (1H, bs, NH), 9.83 (1H, d, CH$_{arom}$), 8.32 (1H, d, CH$_{arom}$), 8.22 (1H, d, CH$_{arom}$), 8.03 (1H, d, CH$_{arom}$), 7.76 (1H, dd, CH$_{arom}$), 7.64-7.58 (1H, m, CH$_{arom}$), 7.51 (1H, d, CH$_{arom}$), 7.32-7.26 (1H, m, CH$_{arom}$), 4.34 (2H, q, CH$_2$), 1.36 (3H, t, CH$_3$).

8-(Benzyl-methyl-sulfamoyl)-4-oxo-4,5-dihydro-3H-pyrrolo[2,3-c]quinoline-1-ethyl carboxylate (24)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 71 μL (0.55 mmol) of benzyl-methylamine. After purification by chromatography on silica (eluent dichloromethane/methanol 95/5) then trituration in methanol, 35 mg (17%) of 8-(benzyl-methyl-sulfamoyl)-4-oxo-4,5-dihydro-3H-pyrrolo[2,3-c]quinoline-1-ethyl carboxylate is obtained in the form of a white solid.

LCMS (IE, m/z): (M+1) 439.71
$^1$H-NMR: δ$_H$ ppm 400 MHz, DMSO
13.22 (1H, bs, NH), 12.10 (1H, s, NH), 9.86 (1H, d, CH$_{arom}$), 8.07 (1H, s, CH$_{arom}$), 7.85 (1H, dd, CH$_{arom}$), 7.61 (1H, d, CH$_{arom}$), 7.39-7.27 (5H, m, 5×CH$_{arom}$), 4.32 (2H, q, CH$_2$), 4.15 (2H, s, CH$_2$), 2.58 (3H, s, CH$_3$), 1.33 (3H, t, CH$_3$).

8-(Methyl-phenethyl-sulfamoyl)-4-oxo-4,5-dihydro-3H-pyrrolo[2,3-c]quinoline-1-ethyl carboxylate (25)

97 μL (0.70 mmol) of triethylamine and 61 μL (0.42 mmol) of N-methylphenethylamine are added to 115 mg (0.35 mmol) of 8-chlorosulfonyl-4-oxo-4,5-dihydro-3H-pyrrolo[2,3-c]quinoline-1-carboxylic acid (synthesis 2) suspended in 2 mL of anhydrous dichloromethane and 0.5 mL of anhydrous dimethylformamide. The reaction mixture is stirred for 5 hours at room temperature. The solvents are evaporated then the residue is taken up in 2 mL of anhydrous ethanol. A solution of 255 μL (3.5 mmol) of thionyl chloride in 1 mL of anhydrous ethanol is then added slowly. The reaction mixture is stirred at 70° C. for 5 days then cooled to room temperature. The solid is filtered then the filtrate is evaporated. The residue is purified by chromatography on silica (eluent dichloromethane/methanol 96/4) to give 63 mg (40%) of 8-(methyl-phenethyl-sulfamoyl)-4-oxo-4,5-dihydro-3H-pyrrolo[2,3-c]quinoline-1-ethyl carboxylate in the form of a beige solid.

LCMS (IE, m/z): (M+1) 453.94
$^1$H-NMR: δ$_H$ ppm 400 MHz, DMSO
13.20 (1H, bs, NH), 12.07 (1H, s, NH), 9.80 (1H, d, CH$_{arom}$), 8.05 (1H, d, CH$_{arom}$), 7.76 (1H, dd, CH$_{arom}$), 7.56 (1H, d, CH$_{arom}$), 7.28-7.16 (5H, m, 5×CH$_{arom}$), 4.29 (2H, q, CH$_2$), 3.24 (2H, t, CH$_2$), 2.78 (2H, t, CH$_2$), 2.74 (3H, s, CH$_3$), 1.32 (3H, t, CH$_3$).

8-Dimethylsulfamoyl-4-oxo-4,5-dihydro-3H-pyrrolo[2,3-c]quinoline-1-ethyl carboxylate (26)

This compound is prepared according to synthesis 25, from 115 mg (0.35 mmol) of 8-chlorosulfonyl-4-oxo-4,5-dihydro-3H-pyrrolo[2,3-c]quinoline-1-carboxylic acid (synthesis 2), 147 μL (1.05 mmol) of triethylamine and 35 mg (0.42 mmol) of dimethylamine hydrochloride. After purification by chromatography on silica (eluent dichloromethane/methanol 95/5) then trituration in methanol, 30 mg (24%) of 8-dimethylsulfamoyl-4-oxo-4,5-dihydro-3H-pyrrolo[2,3-c]quinoline-1-ethyl carboxylate is obtained in the form of a white solid.

LCMS (IE, m/z): (M+1) 363.95
$^1$H-NMR: δ$_H$ ppm 400 MHz, DMSO
13.25 (1H, bs, NH), 12.10 (1H, s, NH), 9.76 (1H, d, CH$_{arom}$), 8.07 (1H, s, CH$_{arom}$), 7.75 (1H, dd, CH$_{arom}$), 7.60 (1H, d, CH$_{arom}$), 4.33 (2H, q, CH$_2$), 2.64 (6H, s, 2×CH$_3$), 1.35 (3H, t, CH$_3$).

8-Methylsulfamoyl-4-oxo-4,5-dihydro-3H-pyrrolo[2,3-c]quinoline-1-ethyl carboxylate (27)

This compound is prepared according to synthesis 25, from 115 mg (0.35 mmol) of 8-chlorosulfonyl-4-oxo-4,5-dihydro-3H-pyrrolo[2,3-c]quinoline-1-carboxylic acid (synthesis 2), 147 μL (1.05 mmol) of triethylamine and 28 mg (0.42 mmol) of methylamine hydrochloride. After purification by chromatography on silica (eluent dichloromethane/methanol 9/1), 13 mg (11%) of 8-methylsulfamoyl-4-oxo-4,5-dihydro-3H-pyrrolo[2,3-c]quinoline-1-ethyl carboxylate is obtained in the form of a white solid.

LCMS (IE, m/z): (M+1) 349.93
$^1$H-NMR: δ$_H$ ppm 400 MHz, DMSO
13.18 (1H, bs, NH), 12.05 (1H, s, NH), 9.79 (1H, d, CH$_{arom}$), 8.05 (1H, d, CH$_{arom}$), 7.77 (1H, dd, CH$_{arom}$), 7.56 (1H, d, CH$_{arom}$), 7.32 (1H, q, NH), 4.33 (2H, q, CH$_2$), 2.45 (3H, d, CH$_3$), 1.35 (3H, t, CH$_3$).

8-(Morpholine-4-sulfonyl)-4-oxo-4,5-dihydro-3H-pyrrolo[2,3-c]quinoline-1-ethyl carboxylate (28)

This compound is prepared according to synthesis 25, from 115 mg (0.30 mmol) of 8-chlorosulfonyl-4-oxo-4,5-dihydro-3H-pyrrolo[2,3-c]quinoline-1-carboxylic acid (synthesis 2)

and 32 µL (0.36 mmol) of morpholine. After trituration in hot methanol, 5 mg (4%) of 8-(morpholine-4-sulfonyl)-4-oxo-4,5-dihydro-3H-pyrrolo[2,3-c]quinoline-1-ethyl carboxylate is obtained in the form of a gray solid.

LCMS (IE, m/z): (M+1) 405.99

$^1$H-NMR: $\delta_H$ ppm 400 MHz, DMSO 13.22 (1H, bs, NH), 12.11 (1H, s, NH), 9.77 (1H, d, $CH_{arom}$), 8.07 (1H, d, $CH_{arom}$), 7.74 (1H, dd, $CH_{arom}$), 7.60 (1H, d, $CH_{arom}$), 4.33 (2H, q, $CH_2$), 3.65-3.62 (4H, m, $4 \times CH_{morp}$), 2.91-2.88 (4H, m, $4 \times CH_{morp}$), 1.35 (3H, t, $CH_3$).

8-(2-Ethoxycarbonyl-ethylsulfamoyl)-4-oxo-4,5-dihydro-3H-pyrrolo[2,3-c]quinoline-1-ethyl carboxylate (29)

This compound is prepared according to synthesis 25, from 115 mg (0.35 mmol) of 8-chlorosulfonyl-4-oxo-4,5-dihydro-3H-pyrrolo[2,3-c]quinoline-1-carboxylic acid (synthesis 2), 147 µL (1.05 mmol) of triethylamine and 59 mg (0.42 mmol) of methyl 3-aminopropanoate hydrochloride. After purification by chromatography on silica (eluent dichloromethane/methanol 96/4), 25 mg (18%) of 8-(2-ethoxycarbonyl-ethylsulfamoyl)-4-oxo-4,5-dihydro-3H-pyrrolo[2,3-c]quinoline-1-ethyl carboxylate is obtained in the form of a gray solid.

LCMS (IE, m/z): (M+1) 435.91

$^1$H-NMR: $\delta_H$ ppm 400 MHz, DMSO 13.19 (1H, bs, NH), 12.05 (1H, s, NH), 9.79 (1H, d, $CH_{arom}$), 8.06 (1H, s, $CH_{arom}$), 7.78 (1H, dd, $CH_{arom}$), 7.60 (1H, t, NH), 7.55 (1H, d, $CH_{arom}$), 4.33 (2H, q, $CH_2$), 3.99 (2H, q, $CH_2$), 3.06-3.00 (2H, m, $CH_2$), 2.44 (2H, t, $CH_2$), 1.35 (3H, t, $CH_3$), 1.12 (3H, t, $CH_3$).

8-Cyclohexylsulfamoyl-4-oxo-4,5-dihydro-3H-pyrrolo[2,3-c]quinoline-1-ethyl carboxylate (30)

This compound is prepared according to synthesis 25, from 115 mg (0.35 mmol) of 8-chlorosulfonyl-4-oxo-4,5-dihydro-3H-pyrrolo[2,3-c]quinoline-1-carboxylic acid (synthesis 2) and 48 µL (0.42 mmol) of cyclohexylamine. After purification by chromatography on silica (eluent dichloromethane/methanol 95/5), 20 mg (14%) of 8-cyclohexylsulfamoyl-4-oxo-4,5-dihydro-3H-pyrrolo[2,3-c]quinoline-1-ethyl carboxylate is obtained in the form of a white solid.

LCMS (IE, m/z): (M+1) 418.00

$^1$H-NMR: $\delta_H$ ppm 400 MHz, DMSO 13.17 (1H, bs, NH), 12.03 (1H, s, NH), 9.80 (1H, s, $CH_{arom}$), 8.05 (1H, s, $CH_{arom}$), 7.80 (1H, d, $CH_{arom}$), 7.55-7.49 (2H, m, $CH_{arom}$ and NH), 4.33 (2H, q, $CH_2$), 3.08-2.98 (1H, m, $CH_{cyclo}$) 1.64-1.54 (4H, m, $4 \times CH_{cyclo}$), 1.45-0.96 (9H, m, $6 \times CH_{cyclo}$ and $CH_3$).

8-Cycloheptylsulfamoyl-4-oxo-4,5-dihydro-3H-pyrrolo[2,3-c]quinoline-1-ethyl carboxylate (31)

This compound is prepared according to synthesis 25, from 150 mg (0.46 mmol) of 8-chlorosulfonyl-4-oxo-4,5-dihydro-3H-pyrrolo[2,3-c]quinoline-1-carboxylic acid (synthesis 2) and 70 µL (0.55 mmol) of cycloheptylamine. After purification by chromatography on silica gel (dichloromethane/methanol 96/4) then trituration in diethyl ether, 15 mg (8%) of 8-cycloheptylsulfamoyl-4-oxo-4,5-dihydro-3H-pyrrolo[2,3-c]quinoline-1-ethyl carboxylate is obtained in the form of a white solid.

LCMS (IE, m/z): (M+1) 431.80

$^1$H-NMR: $\delta_H$ ppm 400 MHz, DMSO 13.16 (1H, bs, NH), 12.02 (1H, s, NH), 9.81 (1H, d, $CH_{arom}$), 8.05 (1H, s, $CH_{arom}$), 7.80 (1H, dd, $CH_{arom}$), 7.53 (1H, d, $CH_{arom}$), 7.50 (1H, d, NH), 4.34 (2H, q, $CH_2$), 3.30-3.18 (1H, nm, CH), 1.68-1.59 (2H, m, $2 \times CH_{cyclohep}$), 1.52-1.32 (11H, m, $CH_3$ and $8 \times CH_{cyclohep}$), 1.29-1.18 (2H, m, $2 \times CH_{cyclohep}$).

8-(3-Dimethylamino-propylsulfamoyl)-4-oxo-4,5-dihydro-3H-pyrrolo[2,3-c]quinoline-1-ethyl carboxylate (32)

This compound is prepared according to synthesis 25, from 115 mg (0.35 mmol) of 8-chlorosulfonyl-4-oxo-4,5-dihydro-3H-pyrrolo[2,3-c]quinoline-1-carboxylic acid (synthesis 2) and 53 µL (0.42 mmol) of 3-dimethylaminopropylamine. After purification by chromatography on silica (eluent chloroform/methanol/ammonia 160/25/4), 15 mg (10%) of 8-(3-dimethylamino-propylsulfamoyl)-4-oxo-4,5-dihydro-3H-pyrrolo[2,3-c]quinoline-1-ethyl carboxylate is obtained in the form of a white solid.

LCMS (IE, m/z): (M+1) 420.92

$^1$H-NMR: $\delta_H$ ppm 250 MHz, DMSO 13.17 (1H, bs, NH), 12.04 (1H, s, NH), 9.79 (1H, d, $CH_{arom}$), 8.05 (1H, s, $CH_{arom}$), 7.79 (1H, dd, $CH_{arom}$), 7.55 (1H, d, $CH_{arom}$), 7.50 (1H, bs, NH), 4.33 (2H, q, $CH_2$), 2.81 (2H, t, $CH_2$), 2.24-2.15 (2H, m, $CH_2$), 2.06 (6H, s, $2 \times CH_3$), 1.50 (2H, quint, $CH_2$), 1.36 (3H, t, $CH_3$).

8-(4-Amino-butylsulfamoyl)-4-oxo-4,5-dihydro-3H-pyrrolo[2,3-c]quinoline-1-ethyl carboxylate (33)

This compound is prepared according to synthesis 25, from 115 mg (0.35 mmol) of 8-chlorosulfonyl-4-oxo-4,5-dihydro-3H-pyrrolo[2,3-c]quinoline-1-carboxylic acid (synthesis 2) and 71 mg (0.42 mmol) of N-(tert-butoxycarbonyl)-diaminobutane. After purification by chromatography on silica (eluent chloroform/methanol/ammonia 90/25/4 then 65/25/4), 26 mg (18%) of 8-(4-amino-butylsulfamoyl)-4-oxo-4,5-dihydro-3H-pyrrolo[2,3-c]quinoline-1-ethyl carboxylate is obtained in the form of a white solid.

LCMS (IE, m/z): (M+1) 406.99

$^1$H-NMR: $\delta_H$ ppm 400 MHz, DMSO 13.22 (1H, bs, NH), 12.05 (1H, bs, NH), 9.80 (1H, d, $CH_{arom}$), 8.07 (1H, s, $CH_{arom}$), 7.79 (1H, dd, $CH_{arom}$), 7.56 (1H, d, $CH_{arom}$), 7.50 (3H, bs, NH and $NH_2$), 4.34 (2H, q, $CH_2$), 2.81 (2H, t, $CH_2$), 2.75 (2H, t, $CH_2$), 1.59-1.33 (4H, m, $2 \times CH_2$), 1.36 (3H, t, $CH_3$).

8-[(3-Chlorophenyl)-methyl-sulfamoyl)-4-oxo-4,5-dihydro-3H-pyrrolo[2,3-c]quinoline-1-ethyl carboxylate (34)

This compound is prepared according to synthesis 3, from 88 mg (0.21 mmol) of 5-(3-chlorophenyl-methyl-sulfamoyl)-1,3-dihydro-indol-2-one to give, after purification by preparative LC/MS, 13 mg (6% in two stages) of 8-[(3-chlorophenyl)-methyl-sulfamoyl]-4-oxo-4,5-dihydro-3H-pyrrolo[2,3-c]quinoline-1-ethyl carboxylate in the form of a white solid.

LCMS (IE, m/z): (M+1) 459.07

$^1$H-NMR: $\delta_H$ ppm 200 MHz, DMSO/$CDCl_3$ 13.0 (1H, bs, NH), 11.96 (1H, s, NH), 9.78 (1H, s, $CH_{arom}$), 7.97 (1H, s, $CH_{arom}$), 7.54 (1H, d, $CH_{arom}$), 7.41 (1H, dd, $CH_{arom}$), 7.27 (3H, m, $3 \times CH_{arom}$), 7.03 (1H, m, $CH_{arom}$), 4.34 (2H, q, $CH_2$), 3.22 (3H, s, $CH_3$), 1.40 (3H, t, $CH_3$).

4-Oxo-8-phenylmethanesulfonyl-4,5-dihydro-3H-pyrrolo[2,3-c]quinoline-1-ethyl carboxylate (35)

This compound is prepared according to synthesis 1, from 1.08 g (3.76 mmol) of 5-phenylmethanesulfonyl-1,3-dihydro-indol-2-one, giving, after recrystallization from acetic acid, 0.41 g (27% in two stages) of 4-oxo-8-phenylmethanesulfonyl-4,5-dihydro-3H-pyrrolo[2,3-c]quinoline-1-ethyl carboxylate in the form of a white solid.

LCMS (IE, m/z): (M+1) 410.75

$^1$H-NMR: $\delta_H$ ppm 400 MHz, DMSO 13.21 (1H, bs, NH), 12.10 (1H, s, NH), 9.69 (1H, d, $CH_{arom}$), 8.05 (1H, x, $CH_{arom}$), 7.64 (1H, dd, $CH_{arom}$), 7.50 (1H, d, $CH_{arom}$), 7.31-7.24 (3H, m, $3\times CH_{arom}$), 7.19-7.15 (2H, m, $2\times CH_{arom}$), 4.61 (2H, x, $CH_2$), 4.33 (2H, q, $CH_2$), 1.36 (3H, t, $CH_3$).

5-Phenylmethanesulfonyl-1,3-dihydro-indol-2-one was prepared according to the method described by Jiong Jack Chen et al. (Organic Process Research and Development, 2003, 7, 313-317) from 1 g (4.32 mmol) of 2-oxo-2,3-dihydro-1H-indole-5-sulfonyl chloride and 0.51 mL (4.32 mmol) of bromomethyl-benzene. After filtration and washing with acetone, 1.08 g (87%) of 5-phenylmethanesulfonyl-1,3-dihydro-indol-2-one is obtained in the form of a white solid.

8-(2,6-Dichlorophenylmethanesulfonyl)-4-oxo-4,5-dihydro-3H-pyrrolo[2,3-c]quinoline-1-ethyl carboxylate (36)

This compound is prepared according to synthesis 35, from 0.75 g (3.24 mmol) of 2-oxo-2,3-dihydro-1H-indole-5-sulfonyl chloride (synthesized as in synthesis 35) and 0.78 g (3.24 mmol) of 2-bromomethyl-1,3-dichloro-benzene to give, after recrystallization from acetic acid, 82 mg (6% after three stages) of 8-(2,6-dichlorophenylmethanesulfonyl)-4-oxo-4,5-dihydro-3H-pyrrolo[2,3-c]quinoline-1-ethyl carboxylate in the form of a pink solid.

LCMS (IE, m/z): (M+1) 478.72-482.73

$^1$H-NMR: $\delta_H$ ppm 400 MHz, DMSO 13.13 (1H, s flattened, NH), 12.16 (1H, s, NH), 9.74 (1H, d, $CH_{arom}$), 8.06 (1H, s, $CH_{arom}$), 7.73 (1H, dd, $CH_{arom}$), 7.56 (1H, d, $CH_{arom}$), 7.49-7.43 (2H, m, $2\times CH_{arom}$), 7.37 (1H, dd, $CH_{arom}$), 4.88 (2H, s, $CH_2$), 4.30 (2H, q, $CH_2$), 1.34 (3H, t, $CH_3$).

8-Benzenesulfonylamino-4-oxo-4,5-dihydro-3H-pyrrolo[2,3-c]quinoline-1-ethyl carboxylate (37)

62 µL (0.44 mmol) of triethylamine and then 31 µL (0.24 mmol) of benzenesulfonyl chloride are added to 60 mg (0.22 mmol) of 8-amino-4-oxo-4,5-dihydro-3H-pyrrolo[2,3-c]quinoline-1-ethyl carboxylate (synthesis 64) suspended in anhydrous dimethylformamide (1 mL). The solution is stirred for 1 h at 40° C. The solvent is evaporated and the raw product obtained is purified by recrystallization from methanol to give 51 mg (57%) of 8-benzenesulfonylamino-4-oxo-4,5-dihydro-3H-pyrrolo[2,3-c]quinoline-1-ethyl carboxylate in the form of a white solid.

LCMS (IE, m/z): (M+1) 412.26

$^1$H-NMR: $\delta_H$ ppm 250 MHz, DMSO 12.99 (1H, bs, NH), 11.62 (1H, s, NH), 10.15 (1H, s, NH), 8.96 (1H, d, $CH_{arom}$), 7.94 (1H, d, $CH_{arom}$), 7.76 (2H, d, $2\times CH_{arom}$), 7.60-7.46 (3H, m, $3\times CH_{arom}$), 7.24 (1H, d, $CH_{arom}$), 7.06 (1H, dd, $CH_{arom}$), 4.32 (2H, q, $CH_2$), 1.34 (3H, t, $CH_3$).

8-Methanesulfonylamino-4-oxo-4,5-dihydro-3H-pyrrolo[2,3-c]quinoline-1-ethyl carboxylate (38)

This compound is prepared according to synthesis 37, from 50 mg (0.18 mmol) of 8-amino-4-oxo-4,5-dihydro-3H-pyrrolo[2,3-c]quinoline-1-ethyl carboxylate (synthesis 64) and 17 µL (0.20 mmol) of methanesulfonyl chloride. After recrystallization from methanol, 29 mg (45%) of 8-methanesulfonylamino-4-oxo-4,5-dihydro-3H-pyrrolo[2,3-c]quinoline-1-ethyl carboxylate is obtained in the form of a white solid.

LCMS (IE, m/z): (M+1) 350.22

$^1$H-NMR: $\delta_H$ ppm 250 MHz, DMSO 13.02 (1H, bs, NH), 11.70 (1H, s, NH), 9.64 (1H, s, NH), 9.08 (1H, s, $CH_{arom}$), 7.98 (1H, d, $CH_{arom}$), 7.38 (1H, d, $CH_{arom}$), 7.26 (1H, dd, $CH_{arom}$), 4.32 (2H, q, $CH_2$), 3.01 (3H, s, $CH_3$), 1.34 (3H, t, $CH_3$).

4-Oxo-8-phenylmethanesulfonylamino-4,5-dihydro-3H-pyrrolo[2,3-c]quinoline-1-ethyl carboxylate (39)

This compound is prepared according to synthesis 37, from 50 mg (0.18 mmol) of 8-amino-4-oxo-4,5-dihydro-3H-pyrrolo[2,3-c]quinoline-1-ethyl carboxylate (synthesis 64) and 39 mg (0.20 mmol) of phenylmethanesulfonyl chloride. After recrystallization from methanol, 9 mg (11%) of 8-phenylmethanesulfonylamino-4-oxo-4,5-dihydro-3H-pyrrolo[2,3-e]quinoline-1-ethyl carboxylate is obtained in the form of a beige solid.

LCMS (IE, m/z): (M+1) 426.46

$^1$H-NMR: $\delta_H$ ppm 250 MHz, DMSO 13.03 (1H, bs, NH), 11.68 (1H, s, NH), 9.79 (1H, s, NH), 9.17 (1H, d, $CH_{arom}$), 8.00 (1H, d, $CH_{arom}$), 7.45-7.32 (6H, m, $6\times CH_{arom}$), 7.21 (1H, dd, $CH_{arom}$), 4.50 (2H, s, $CH_2$), 4.34 (2H, q, $CH_2$), 1.35 (3H, t, $CH_3$).

8-(4-Chloro-benzenesulfonylamino)-4-oxo-4,5-dihydro-3H-pyrrolo[2,3-c]quinoline-1-ethyl carboxylate (40)

This compound is prepared according to synthesis 37, from 60 mg (0.22 mmol) of 8-amino-4-oxo-4,5-dihydro-3H-pyrrolo[2,3-c]quinoline-1-ethyl carboxylate (synthesis 64) and 51 mg (0.24 mmol) of 4-chloro-benzenesulfonyl chloride. After recrystallization from methanol, 25 mg (25%) of 8-(4-chloro-benzenesulfonylamino)-4-oxo-4,5-dihydro-3H-pyrrolo[2,3-e]quinoline-1-ethyl carboxylate is obtained in the form of a white solid.

LCMS (IE, m/z): (M+1) 446.24-448.23

$^1$H-NMR: $\delta_H$ ppm 250 MHz, DMSO 13.00 (1H, bs, NH), 11.66 (1H, s, NH), 10.20 (1H, s, NH), 8.92 (1H, d, $CH_{arom}$), 7.95 (1H, s, $CH_{arom}$), 7.73 (2H, d, $2\times CH_{arom}$), 7.59 (2H, d, $2\times CH_{arom}$), 7.28 (1H, d, $CH_{arom}$), 7.08 (1H, dd, $CH_{arom}$), 4.31 (2H, q, $CH_2$), 1.34 (3H, t, $CH_3$).

8-(3-Chloro-benzenesulfonylamino)-4-oxo-4,5-dihydro-3H-pyrrolo[2,3-c]quinoline-1-ethyl carboxylate (41)

This compound is prepared according to synthesis 37, from 60 mg (0.22 mmol) of 8-amino-4-oxo-4,5-dihydro-3H-pyrrolo[2,3-c]quinoline-1-ethyl carboxylate (synthesis 64) and 34 µL (0.24 mmol) of 3-chloro-benzenesulfonyl chloride. After recrystallization from methanol then trituration in hot methanol, 27 mg (27%) of 8-(3-chloro-benzenesulfonylamino)-4-oxo-4,5-dihydro-3H-pyrrolo[2,3-c]quinoline-1-ethyl carboxylate is obtained in the form of a white solid.

LCMS (IE, m/z): (M+1) 445.86-447.88

$^1$H-NMR: $\delta_H$ ppm 250 MHz, DMSO 12.99 (1H, bs, NH), 11.64 (1H, s, NH), 10.26 (1H, s, NH), 8.95 (1H, s, $CH_{arom}$), 7.95 (1H, d, $CH_{arom}$), 7.84 (1H, s, $CH_{arom}$), 7.78-7.62 (2H, m, $2\times CH_{arom}$), 7.57-7.48 (1H, m, CH$_{arom}$), 7.29 (1H, d, CH$_{arom}$), 7.09 (1H, dd, CH$_{arom}$), 4.32 (2H, q, CH$_2$), 1.34 (3H, t, CH$_3$).

8-(2-Chloro-benzenesulfonylamino)-4-oxo-4,5-dihydro-3H-pyrrolo[2,3-c]quinoline-1-ethyl carboxylate (42)

This compound is prepared according to synthesis 37, from 60 mg (0.22 mmol) of 8-amino-4-oxo-4,5-dihydro-3H-pyrrolo[2,3-c]quinoline-1-ethyl carboxylate (synthesis 64) and 33 µL (0.24 mmol) of 2-chloro-benzenesulfonyl chloride. After trituration in methanol, 46 mg (46%) of 8-(2-chloro-benzenesulfonylamino)-4-oxo-4,5-dihydro-3H-pyrrolo[2,3-e]quinoline-1-ethyl carboxylate is obtained in the form of a white solid.

LCMS (IE, m/z): (M+1) 446.24-448.23
$^1$H-NMR: δ$_H$ ppm 250 MHz, DMSO
12.98 (1H, bs, NH), 11.61 (1H, s, NH), 10.43 (1H, s, NH), 8.98 (1H, d, CH$_{arom}$), 8.02 (1H, d, CH$_{arom}$), 7.93 (1H, d, CH$_{arom}$), 7.65-7.52 (2H, m, 2×CH$_{arom}$), 7.47-7.38 (1H, m, CH$_{arom}$), 7.25 (1H, d, CH$_{arom}$), 7.12 (1H, dd, CH$_{arom}$), 4.33 (2H, q, CH$_2$), 1.36 (3H, t, CH$_3$).

8-(4-Fluoro-benzenesulfonylamino)-4-oxo-4,5-dihydro-3H-pyrrolo[2,3-c]quinoline-1-ethyl carboxylate (43)

82 µL (0.59 mmol) of triethylamine is added to 60 mg (0.20 mmol) of 8-amino-4-oxo-4,5-dihydro-3H-pyrrolo[2,3-c]quinoline-1-ethyl carboxylate hydrochloride (synthesis 64) suspended in anhydrous dimethylformamide (1 mL). The mixture is cooled to 0° C., then 42 mg (0.21 mmol) of 4-fluoro-benzenesulfonyl chloride is added. The solution is stirred for 1 h at 0° C. The solvent is evaporated and the raw product obtained is purified by recrystallization from methanol to give 32 mg (38%) of 8-(4-fluoro-benzenesulfonylamino)-4-oxo-4,5-dihydro-3H-pyrrolo[2,3-c]quinoline-1-ethyl carboxylate in the form of a light brown solid.

LCMS (IE, m/z): (M+1) 429.88
$^1$H-NMR: δ$_H$ ppm 250 MHz, DMSO
12.98 (1H, bs, NH), 11.63 (1H, s, NH), 10.12 (1H, s, NH), 8.92 (1H, d, CH$_{arom}$), 7.94 (1H, d, CH$_{arom}$), 7.84-7.74 (2H, m, 2×CH$_{arom}$), 7.40-7.30 (2H, m, 2×CH$_{arom}$), 7.27 (1H, d, CH$_{arom}$), 707 (1H, dd, CH$_{arom}$), 4.31 (2H, q, CH$_2$), 1.34 (3H, t, CH$_3$).

8-(3-Fluoro-benzenesulfonylamino)-4-oxo-4,5-dihydro-3H-pyrrolo[2,3-c]quinoline-1-ethyl carboxylate (44)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 29 µL (0.21 mmol) of 3-fluoro-benzenesulfonyl chloride. After recrystallization from methanol then trituration in hot methanol, 20 mg (24%) of 8-(3-fluoro-benzenesulfonylamino)-4-oxo-4,5-dihydro-3H-pyrrolo[2,3-c]quinoline-1-ethyl carboxylate is obtained in the form of a beige solid.

LCMS (IE, m/z): (M+1) 429.92
$^1$H-NMR: δ$_H$ ppm 400 MHz, DMSO
12.98 (1H, bs, NH), 11.64 (1H, s, NH), 10.25 (1H, s, NH), 8.94 (1H, d, CH$_{arom}$), 7.94 (1H, d, CH$_{arom}$), 7.64-7.52 (3H, m, 3×CH$_{arom}$), 745-7.42 (1H, m, CH$_{arom}$), 7.28 (1H, d, CH$_{arom}$), 7.09 (1H, dd, CH$_{arom}$), 4.31 (2H, q, CH$_2$), 1.34 (3H, t, CH$_3$).

8-(2-Fluoro-benzenesulfonylamino)-4-oxo-4,5-dihydro-3H-pyrrolo[2,3-c]quinoline-1-ethyl carboxylate (45)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 28 µL (0.21 mmol) of 2-fluoro-benzenesulfonyl chloride. After recrystallization from methanol, 38 mg (45%) of 8-(2-fluoro-benzenesulfonylamino)-4-oxo-4,5-dihydro-3H-pyrrolo[2,3-c]quinoline-1-ethyl carboxylate is obtained in the form of a light brown solid.

LCMS (IE, m/z): (M+1) 429.88
$^1$H-NMR: δ$_H$ ppm 400 MHz, DMSO
12.97 (1H, bs, NH), 11.62 (1H, s, NH), 10.41 (1H, s, NH), 8.97 (1H, d, CH$_{arom}$), 7.93 (1H, d, CH$_{arom}$), 7.79 (1H, ddd, CH$_{arom}$), 7.67-7.60 (1H, m, CH$_{arom}$), 7.41-7.36 (1H, m, CH$_{arom}$), 7.30-7.24 (2H, m, 2×CH$_{arom}$), 7.12 (1H, dd, CH$_{arom}$), 4.32 (2H, q, CH$_2$), 1.35 (3H, t, CH$_3$).

8-(4-Bromo-benzenesulfonylamino)-4-oxo-4,5-dihydro-3H-pyrrolo[2,3-c]quinoline-1-ethyl carboxylate (46)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 52 mg (0.21 mmol) of 4-bromo-benzenesulfonyl chloride. After recrystallization from methanol, 40 mg (42%) of 8-(4-bromo-benzenesulfonylamino)-4-oxo-4,5-dihydro-3H-pyrrolo[2,3-c]quinoline-1-ethyl carboxylate is obtained in the form of a light brown solid.

LCMS (IE, m/z): (M+1) 489.85-491.84
$^1$H-NMR: δ$_H$ ppm 250 MHz, DMSO
12.98 (1H, bs, NH), 11.64 (1H, s, NH), 10.19 (1H, s, NH), 8.92 (1H, d, CH$_{arom}$), 7.94 (1H, d, CH$_{arom}$), 7.73 (2H, d, 2×CH$_{arom}$), 7.65 (2H, d, 2×CH$_{arom}$), 7.28 (1H, d, CH$_{arom}$), 7.08 (1H, dd, CH$_{arom}$), 4.31 (2H, q, CH$_2$), 1.34 (3H, t, CH$_3$).

4-Oxo-8-(4-toluenesulfonylamino)-4,5-dihydro-3H-pyrrolo[2,3-c]quinoline-1-ethyl carboxylate (47)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 41 mg (0.21 mmol) of 4-toluenesulfonyl chloride. After recrystallization from methanol, 23 mg (28%) of 4-oxo-8-(4-toluenesulfonylamino)-4,5-dihydro-3H-pyrrolo[2,3-c]quinoline-1-ethyl carboxylate is obtained in the form of a brown solid.

LCMS (IE, m/z): (M+1) 425.88
$^1$H-NMR: δ$_H$ ppm 400 MHz, DMSO
12.97 (1H, bs, NH), 11.60 (1H, s, NH), 10.06 (1H, s, NH), 8.95 (1H, d, CH$_{arom}$), 7.94 (1H, d, CH$_{arom}$), 7.64 (2H, d, 2×CH$_{arom}$), 7.29 (2H, d, 2×CH$_{arom}$), 7.24 (1H, d, CH$_{arom}$), 7.06 (1H, dd, CH$_{arom}$), 4.32 (2H, q, CH$_2$), 2.30 (3H, s, CH$_3$), 1.35 (3H, t, CH$_3$).

4-Oxo-8-(3-toluenesulfonylamino)-4,5-dihydro-3H-pyrrolo[2,3-c]quinoline-1-ethyl carboxylate (48)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 31 mg (0.21 mmol) of 3-toluenesulfonyl chloride. After recrystallization from methanol, 33 mg (40%)

of 4-oxo-8-(3-toluenesulfonylamino)-4,5-dihydro-3H-pyrrolo[2,3-c]quinoline-1-ethyl carboxylate is obtained in the form of a beige solid.

LCMS (IE, m/z): (M+1) 425.88

$^1$H-NMR: $\delta_H$ ppm 400 MHz, DMSO 12.97 (1H, bs, NH), 11.60 (1H, s, NH), 10.10 (1H, s, NH), 8.95 (1H, d, $CH_{arom}$), 7.94 (1H, d, $CH_{arom}$), 7.65 (1H, s, $CH_{arom}$), 7.55-7.50 (1H, m, $CH_{arom}$), 7.39-7.34 (2H, m, 2×$CH_{arom}$), 7.25 (1H, d, $CH_{arom}$), 7.08 (1H, dd, $CH_{arom}$), 4.32 (2H, q, $CH_2$), 2.32 (3H, s, $CH_3$), 1.35 (3H, t, $CH_3$).

8-(4-tert-Butyl-benzenesulfonylamino)-4-oxo-4,5-dihydro-3H-pyrrolo[2,3-c]quinoline-1-ethyl carboxylate (49)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 55 mg (0.23 mmol) of 4-tert-butyl-benzenesulfonyl chloride. After recrystallization from acetonitrile/dichloromethane mixture, 36 mg (40%) of 8-(4-tert-butyl-benzenesulfonylamino)-4-oxo-4,5-dihydro-3H-pyrrolo[2,3-c]quinoline-1-ethyl carboxylate is obtained in the form of a light brown solid.

LCMS (IE, m/z): (M+1) 468.03

$^1$H-NMR: $\delta_H$ ppm 400 MHz, DMSO 12.96 (1H, bs, NH), 11.60 (1H, s, NH), 10.01 (1H, s, NH), 8.94 (1H, d, $CH_{arom}$), 7.94 (11H, d, $CH_{arom}$), 7.69 (2H, d, 2×$CH_{arom}$), 7.52 (2H, d, 2×$CH_{arom}$), 7.25 (1H, d, $CH_{arom}$), 7.11 (1H, dd, $CH_{arom}$), 4.32 (2H, q, $CH_2$), 1.34 (3H, t, $CH_3$), 1.23 (9H, s, 3×$CH_3$).

8-(4-Methoxy-benzenesulfonylamino)-4-oxo-4,5-dihydro-3H-pyrrolo[2,3-c]quinoline-1-ethyl carboxylate (50)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 44 mg (0.21 mmol) of 4-methoxy-benzenesulfonyl chloride. After recrystallization from methanol, 45 mg (53%) of 8-(4-methoxy-benzenesulfonylamino)-4-oxo-4,5-dihydro-3H-pyrrolo[2,3-c]quinoline-1-ethyl carboxylate is obtained in the form of a light brown solid.

LCMS (IE, m/z): (M+1) 441.91

$^1$H-NMR: $\delta_H$ ppm 400 MHz, DMSO 12.98 (1H, bs, NH), 11.60 (1H, s, NH), 9.98 (1H, s, NH), 8.94 (1H, d, $CH_{arom}$), 7.94 (1H, d, $CH_{arom}$), 7.68 (2H, d, 2×$CH_{arom}$), 7.24 (1H, d, $CH_{arom}$), 7.06 (1H, dd, $CH_{arom}$), 7.01 (2H, d, 2×$CH_{arom}$), 4.32 (2H, q, $CH_2$), 3.76 (3H, s, $CH_3$), 1.34 (3H, t, $CH_3$).

8-(3-Methoxy-benzenesulfonylamino)-4-oxo-4,5-dihydro-3H-pyrrolo[2,3-c]quinoline-1-ethyl carboxylate (51)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 30 µL (0.21 mmol) of 3-methoxy-benzenesulfonyl chloride. After recrystallization from methanol then trituration in hot methanol, 21 mg (25%) of 8-(3-methoxy-benzenesulfonylamino)-4-oxo-4,5-dihydro-3H-pyrrolo[2,3-c]quinoline-1-ethyl carboxylate is obtained in the form of a beige solid.

LCMS (IE, m/z): (M+1) 441.91

$^1$H-NMR: $\delta_H$ ppm 400 MHz, DMSO 12.98 (1H, bs, NH), 11.61 (1H, s, NH), 10.14 (1H, s, NH), 8.97 (1H, s, $CH_{arom}$), 7.94 (1H, s, $CH_{arom}$), 7.42-7.21 (4H, m, 4×$CH_{arom}$), 7.16-7.06 (2H, m, 2×$CH_{arom}$), 4.31 (2H, q, $CH_2$), 3.75 (3H, s, $CH_3$), 1.34 (3H, t, $CH_3$).

8-(4-Acetylamino-benzenesulfonylamino)-4-oxo-4,5-dihydro-3H-pyrrolo[2,3-c]quinoline-1-ethyl carboxylate (52)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 50 mg (0.21 mmol) of 4-acetylamino-benzenesulfonyl chloride. After trituration in hot methanol, 35 mg (38%) of 8-(4-acetylamino-benzenesulfonylamino)-4-oxo-4,5-dihydro-3H-pyrrolo[2,3-c]quinoline-1-ethyl carboxylate is obtained in the form of an orange-brown solid.

LCMS (IE, m/z): (M+1) 468.93

$^1$H-NMR: $\delta_H$ ppm 400 MHz, DMSO 12.97 (1H, bs, NH), 11.60 (1H, s, NH), 10.24 (1H, s, NH), 10.00 (1H, s, NH), 8.93 (1H, d, $CH_{arom}$), 7.94 (1H, d, $CH_{arom}$), 7.70-7.63 (4H, m, 4×$CH_{arom}$), 7.24 (1H, d, $CH_{arom}$), 7.05 (1H, dd, $CH_{arom}$), 4.31 (2H, q, $CH_2$), 2.03 (3H, s, $CH_3$), 1.34 (3H, t, $CH_3$).

8-(4-Nitro-benzenesulfonylamino)-4-oxo-4,5-dihydro-3H-pyrrolo[2,3-c]quinoline-1-ethyl carboxylate (53)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 45 mg (0.21 mmol) of 4-nitro-benzenesulfonyl chloride. After purification by preparative LCMS, 5 mg (6%) of 8-(4-nitro-benzenesulfonylamino)-4-oxo-4,5-dihydro-3H-pyrrolo[2,3-c]quinoline-1-ethyl carboxylate is obtained in the form of a light brown solid.

LCMS (IE, m/z): (M+1) 456.85

$^1$H-NMR: $\delta_H$ ppm 400 MHz, DMSO 12.99 (1H, bs, NH), 11.66 (1H, s, NH), 10.43 (1H, bs, NH), 8.88 (1H, d, $CH_{arom}$), 8.35 (2H, d, 2×$CH_{arom}$), 7.98 (2H, d, 2×$CH_{arom}$), 7.94 (1H, s, $CH_{arom}$), 7.30 (1H, d, $CH_{arom}$), 7.11 (1H, dd, $CH_{arom}$), 4.26 (2H, q, $CH_2$), 1.32 (3H, t, $CH_3$).

8-(Naphthalene-2-sulfonylamino)-4-oxo-4,5-dihydro-3H-pyrrolo[2,3-c]quinoline-1-ethyl carboxylate (54)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 46 mg (0.21 mmol) of naphthalene-2-sulfonyl chloride. After recrystallization from methanol, 36 mg (40%) of 8-(naphthalene-2-sulfonylamino)-4-oxo-4,5-dihydro-3H-pyrrolo[2,3-c]quinoline-1-ethyl carboxylate is obtained in the form of a brown solid.

LCMS (IE, m/z): (M+1) 461.92

$^1$H-NMR: $\delta_H$ ppm 250 MHz, DMSO 12.94 (1H, bs, NH), 11.58 (1H, s, NH), 10.26 (1H, s, NH), 8.98 (1H, d, $CH_{arom}$), 8.45 (1H, s, $CH_{arom}$), 8.05 (2H, d, 2×$CH_{arom}$), 7.97 (1H, d, $CH_{arom}$), 7.91 (1H, d, $CH_{arom}$), 7.80 (1H, dd, $CH_{arom}$), 7.69-7.56 (2H, m, 2×$CH_{arom}$), 7.23 (1H, d, $CH_{arom}$), 7.10 (1H, dd, $CH_{arom}$), 4.26 (2H, q, $CH_2$), 1.31 (3H, t, $CH_3$).

8-(4-Acetyl-benzenesulfonylamino)-4-oxo-4,5-dihydro-3H-pyrrolo[2,3-c]quinoline-1-ethyl carboxylate (55)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 45 mg (0.21 mmol) f 4-acetyl-benzenesulfonyl chloride. After recrystallization from methanol and trituration in hot methanol, 44 mg (49%) of 8-(4-acetyl-benzenesulfonylamino)-4-oxo-4,5-dihydro-3H-pyrrolo[2,3-c]quinoline-1-ethyl carboxylate is obtained in the form of a brown solid.

LCMS (IE, m/z): (M+1) 453.89
$^1$H-NMR: $\delta_H$ ppm 250 MHz, DMSO
12.97 (1H, bs, NH), 11.63 (1H, s, NH), 10.30 (1H, s, NH), 8.95 (1H, d, $CH_{arom}$), 8.05 (2H, d, $2\times CH_{arom}$), 7.94 (1H, d, $CH_{arom}$), 7.88 (2H, d, $2\times CH_{arom}$), 7.26 (1H, d, $CH_{arom}$), 7.08 (1H, dd, $CH_{arom}$), 4.29 (2H, q, $CH_2$), 2.56 (3H, s, $CH_3$), 1.33 (3H, t, $CH_3$).

4-Oxo-8-(thiophene-2-sulfonylamino)-4,5-dihydro-3H-pyrrolo[2,3-c]quinoline-1-ethyl carboxylate (56)

This compound is prepared according to synthesis 43, from 60 mg (0.20 mmol) of 8-amino-4-oxo-4,5-dihydro-3H-pyrrolo[2,3-c]quinoline-1-ethyl carboxylate hydrochloride (synthesis 64) and 39 mg (0.21 mmol) of thiophene-2-sulfonyl chloride. After recrystallization from methanol, 17 mg (21%) of 4-oxo-8-(thiophene-2-sulfonylamino)-4,5-dihydro-3H-pyrrolo[2,3-c]quinoline-1-ethyl carboxylate is obtained in the form of a light brown solid.

LCMS (IE, m/z): (M+1) 417.84
$^1$H-NMR: $\delta_H$ ppm 250 MHz, DMSO
12.98 (1H, bs, NH), 11.64 (1H, s, NH), 10.27 (1H, s, NH), 9.01 (1H, bs, $CH_{arom}$), 8.00-7.91 (1H, m, $CH_{arom}$), 7.90-7.80 (1H, m, $CH_{arom}$), 7.60-7.45 (1H, m, $CH_{arom}$), 7.34-7.23 (1H, m, $CH_{arom}$), 7.16-7.02 (2H, m, $2\times CH_{arom}$), 4.40-4.23 (2H, m, $CH_2$), 1.41-1.26 (3H, m, $CH_3$).

8-(5-Chloro-thiophene-2-sulfonylamino)-4-oxo-4,5-dihydro-3H-pyrrolo[2,3-c]quinoline-1-ethyl carboxylate (57)

This compound is prepared according to synthesis 45, from 60 mg (0.20 mmol) of 8-amino-4-oxo-4,5-dihydro-3H-pyrrolo[2,3-c]quinoline-1-ethyl carboxylate hydrochloride (synthesis 64) and 29 µL (0.21 mmol) of 5-chloro-thiophene-2-sulfonyl chloride. After recrystallization from methanol and trituration in hot methanol, 4 mg (3%) of 8-(5-chloro-thiophene-2-sulfonylamino)-4-oxo-4,5-dihydro-3H-pyrrolo[2,3-c]quinoline-1-ethyl carboxylate is obtained in the form of a white solid.

LCMS (IE, m/z): (M+1) 451.84-453.85
$^1$H-NMR: $\delta_H$ ppm 400 MHz, DMSO
12.99 (1H, bs, NH), 11.66 (1H, s, NH), 10.40 (1H, bs, NH), 8.98 (1H, s, $CH_{arom}$), 7.96 (1H, s, $CH_{arom}$), 7.38-7.28 (2H, m, $2\times CH_{arom}$), 7.17-7.12 (2H, m, $2\times CH_{arom}$), 4.31 (2H, q, $CH_2$), 1.34 (3H, t, $CH_3$).

8-(Benzenesulfonyl-methyl-amino)-4-oxo-4,5-dihydro-3H-pyrrolo[2,3-c]quinoline-1-ethyl carboxylate (58)

177 µL (1.27 mmol) of triethylamine is added to 135 mg of 8-methylamino-4-oxo-4,5-dihydro-3H-pyrrolo[2,3-c]quinoline-1-ethyl carboxylate hydrochloride (synthesis 63) contaminated with 30% of 8-amino-4-oxo-4,5-dihydro-3H-pyrrolo[2,3-c]quinoline-1-ethyl carboxylate suspended in anhydrous dimethylformamide (2 mL) and the mixture is cooled to 0° C., then 56 µL (0.44 mmol) of benzenesulfonyl chloride is added. The solution is stirred for 1 h at 0° C. The solvent is evaporated and the raw product obtained is purified by chromatography on silica (eluent dichloromethane/methanol/acetonitrile 96/2/2) to give, after trituration in diethyl ether, 47 mg (37%) of 8-(benzenesulfonyl-methyl-amino)-4-oxo-4,5-dihydro-3H-pyrrolo[2,3-c]quinoline-1-ethyl carboxylate in the form of a white solid.

LCMS (IE, m/z): (M+1) 425.88
$^1$H-NMR: $\delta_H$ ppm 400 MHz, DMSO
13.04 (1H, bs, NH), 11.77 (1H, s, NH), 8.95 (1H, d, $CH_{arom}$), 7.96 (1H, s, $CH_{arom}$), 7.71-7.65 (1H, m, $CH_{arom}$), 7.61-7.51 (4H, m, $4\times CH_{arom}$), 7.35 (1H, d, $CH_{arom}$), 7.15 (1H, dd, $CH_{arom}$), 4.23 (2H, q, $CH_2$), 3.19 (3H, s, $CH_3$), 1.31 (3H, t, $CH_3$).

8-(Methanesulfonyl-methyl-amino)-4-oxo-4,5-dihydro-3H-pyrrolo[2,3-c]quinoline-1-ethyl carboxylate (59)

This compound is prepared according to synthesis 58, from 130 mg of 8-methylamino-4-oxo-4,5-dihydro-3H-pyrrolo[2,3-c]quinoline-1-ethyl carboxylate hydrochloride (synthesis 63) contaminated with 30% of 8-amino-4-oxo-4,5-dihydro-3H-pyrrolo[2,3-c]quinoline-1-ethyl carboxylate to which 33 µL (0.42 mmol) of methanesulfonyl chloride is added. After purification by chromatography on silica (eluent dichloromethane/methanol/acetonitrile 94/3/3), 32 mg (31%) of 8-(methanesulfonyl-methyl-amino)-4-oxo-4,5-dihydro-3H-pyrrolo[2,3-c]quinoline-1-ethyl carboxylate is obtained in the form of a white solid.

LCMS (IE, m/z): (M+1) 363.79
$^1$H-NMR: $\delta_H$ ppm 400 MHz, DMSO
13.07 (1H, bs, NH), 11.77 (1H, bs, NH), 9.31 (1H, d, $CH_{arom}$), 8.02 (1H, s, $CH_{arom}$), 7.47 (1H, dd, $CH_{arom}$), 7.42 (1H, d, $CH_{arom}$), 4.32 (2H, q, $CH_2$), 3.28 (3H, s, $CH_3$), 3.02 (3H, s, $CH_3$), 1.35 (3H, t, $CH_3$).

8-Benzoylamino-4-oxo-4,5-dihydro-3H-pyrrolo[2,3-c]quinoline-1-ethyl carboxylate (60)

52 µL (0.37 mmol) of triethylamine and then 24 µL (0.20 mmol) of benzoyl chloride are added to 50 mg (0.18 mmol) of 8-amino-4-oxo-4,5-dihydro-3H-pyrrolo[2,3-c]quinoline-1-ethyl carboxylate (synthesis 64) suspended in anhydrous dimethylformamide (1 mL). The solution is stirred for 2.5 h at 40° C. The solvent is evaporated and the residue obtained is purified by recrystallization from methanol to give 36 mg (52%) of 8-benzoylamino-4-oxo-4,5-dihydro-3H-pyrrolo[2,3-c]quinoline-1-ethyl carboxylate in the form of a white solid.

LCMS (IE, m/z): (M+1) 376.29
$^1$H-NMR: $\delta_H$ ppm 250 MHz, DMSO
13.02 (1H, bs, NH), 11.70 (1H, s, NH), 10.37 (1H, s, NH), 9.39 (1H, d, $CH_{arom}$), 8.06-7.95 (3H, m, $3\times CH_{arom}$), 7.73-7.49 (4H, m, $4\times CH_{arom}$), 7.40 (1H, d, $CH_{arom}$), 4.32 (2H, q, $CH_2$), 1.34 (3H, t, $CH_3$).

8-Acetylamino-4-oxo-4,5-dihydro-3H-pyrrolo[2,3-c]quinoline-1 ethyl carboxylate (61)

134 mg (2.4 mmol) of iron is added to 72 mg (0.24 mmol) of 8-nitro-4-oxo-4,5-dihydro-3H-pyrrolo[2,3-c]quinoline-1-ethyl carboxylate (synthesis 66) dissolved in 4 mL of acetic acid. The mixture is refluxed for 1 h. The solution is filtered while hot and the solid is rinsed with a minimum of hot acetic acid. The filtrate is evaporated, then the residue (mixture of 8-acetylamino-4-oxo-4,5-dihydro-3H-pyrrolo[2,3-c]quinoline-1-ethyl carboxylate and 8-amino-4-oxo-4,5-dihydro-3H-pyrrolo[2,3-c]quinoline-1-ethyl carboxylate 85/15) is purified by preparative LCMS to give 4 mg (5%) of 8-acetylamino-4-oxo-4,5-dihydro-3H-pyrrolo[2,3-c]quinoline-1-ethyl carboxylate in the form of a gray solid.

LCMS (IE, m/z): (M+1) 314.29

$^1$H-NMR: $\delta_H$ ppm 250 MHz, DMSO 12.96 (1H, bs, NH), 11.62 (1H, s, NH), 9.98 (1H, s, NH), 9.15 (1H, d, $CH_{arom}$), 796 (1H, s, $CH_{arom}$), 7.71 (1H, dd, $CH_{arom}$), 7.32 (1H, d, $CH_{arom}$), 4.32 (2H, q, $CH_2$), 2.05 (3H, s, $CH_3$), 1.34 (3H, t, $CH_3$).

8-Dimethylamino-4-oxo-4,5-dihydro-3H-pyrrolo[2,3-c]quinoline-1-ethyl carboxylate (62)

33 μL (0.41 mmol) of a 37% aqueous solution of formaldehyde, 20 μL (0.35 mmol) of acetic acid and 26 mg (0.41 mmol) of sodium cyanoborohydride are added to 100 mg (0.37 mmol) of 8-amino-4-oxo-4,5-dihydro-3H-pyrrolo[2,3-c]quinoline-1-ethyl carboxylate (synthesis 64) suspended in 1.2 ml of ethanol. The mixture is stirred for 6 hours at room temperature then 33 μL (0.41 mmol) of a 37% aqueous solution of formaldehyde, 20 μL (0.35 mmol) of acetic acid and 7 mg (0.11 mmol) of sodium cyanoborohydride are added again. The reaction mixture is stirred overnight at room temperature. The solvents are evaporated and the residue obtained is purified by preparative LCMS to give 5 mg (5%) of 8-dimethylamino-4-oxo-4,5-dihydro-3H-pyrrolo[2,3-c]quinoline-1-ethyl carboxylate in the form of a white solid.

LCMS (IE, m/z): (M+1) 299.95

$^1$H-NMR: $\delta_H$ ppm 400 MHz, DMSO 12.85 (1H, bs, NH), 11.37 (1H, s, NH), 8.72 (1H, d, $CH_{arom}$), 7.93 (1H, s, $CH_{arom}$), 7.26 (1H, d, $CH_{arom}$), 6.96 (1H, dd, $CH_{arom}$), 4.29 (2H, q, $CH_2$), 2.92 (6H, s, $2 \times CH_3$), 1.33 (3H, t, $CH_3$).

8-Methylamino-4-oxo-4,5-dihydro-3H-pyrrolo[2,3-c]quinoline-1-ethyl carboxylate hydrochloride (63)

0.41 mL (0.41 mmol) of a 1M solution of a borane-tetrahydrofuran complex in tetrahydrofuran is added to a solution of 45 mg (0.15 mmol) of 8-formylamino-4-oxo-4,5-dihydro-3H-pyrrolo[2,3-c]quinoline-1-ethyl carboxylate in 0.5 mL of anhydrous tetrahydrofuran. The reaction mixture is stirred overnight at room temperature then for 8 hours under reflux before further addition of 0.3 mL of a 1M solution of a borane-tetrahydrofuran complex in tetrahydrofuran. The reaction mixture is then stirred for 3 hours under reflux. The solvent is evaporated under reduced pressure, and the residue is taken up in 1 mL of anhydrous ethanol and 0.76 mL (1.52 mmol) of 2M hydrochloric acid in diethyl ether. The solution is stirred at 70° C. for 3 hours. The precipitate is filtered, washed with ethanol then with diethyl ether to give 24 mg (50%) of 8-methylamino-4-oxo-4,5-dihydro-3H-pyrrolo[2,3-c]quinoline-1-ethyl carboxylate hydrochloride in the form of a white solid.

LCMS (IE, m/z): (M+1) 285.92

$^1$H-NMR: $\delta_H$ ppm 400 MHz, DMSO 13.12 (1H, bs, NH), 11.82 (1H, s, NH), 10.53 (1H, bs, NH), 9.22 (1H, s, $CH_{arom}$), 8.03 (1H, s, $CH_{arom}$), 7.56-7.36 (2H, m, $2 \times CH_{arom}$), 4.42-4.24 (2H, m, $CH_2$), 2.93 (3H, s, $CH_3$), 1.48-1.22 (3H, m, $CH_3$).

74 μL (1.95 mmol) of formic acid is added slowly to 153 μL (1.63 mmol) of acetic anhydride cooled on an ice bath, then the reaction mixture is stirred for 2 hours at 60° C. The mixture is cooled to room temperature then added to a solution of 500 mg (1.63 mmol) of 8-amino-4-oxo-4,5-dihydro-3H-pyrrolo[2,3-c]quinoline-1-ethyl carboxylate hydrochloride (synthesis 64) dissolved in 5 mL of anhydrous dimethylformamide and 460 μL (3.25 mmol) of triethylamine. The reaction mixture is stirred for 2 hours at 60° C. The solvent is evaporated and the residue is triturated in hot methanol to give 359 mg (74%) of 8-formylamino-4-oxo-4,5-dihydro-3H -pyrrolo[2,3-c]quinoline-1-ethyl carboxylate in the form of a pale pink solid.

8-Amino-4-oxo-4,5-dihydro-3H-pyrrolo[2,3-c]quinoline-1-ethyl carboxylate (64)

30 mg of palladium on charcoal (10 wt. %) and 530 mg (8.30 mmol) of ammonium formate are added to 500 mg (1.66 mmol) of 8-nitro-4-oxo-4,5-dihydro-3H-pyrrolo[2,3-c]quinoline-1-ethyl carboxylate (synthesis 66) suspended in 10 mL of anhydrous dimethylformamide. The reaction mixture is stirred for 2 hours at 60° C. The mixture is then diluted in ethyl acetate and filtered on celite. The filtrate is evaporated and the residue is triturated in diethyl ether to give, after filtration, 360 mg (80%) of 8-amino-4-oxo-4,5-dihydro-3H-pyrrolo[2,3-c]quinoline-1-ethyl carboxylate in the form of a beige solid.

LCMS (IE, m/z): (M+1) 272.29

$^1$H-NMR: $\delta_H$ ppm 250 MHz, DMSO 12.81 (1H, bs, NH), 11.30 (1H, s, NH), 8.37 (1H, d, $CH_{arom}$), 7.90 (1H, s, $CH_{arom}$), 7.12 (1H, d, $CH_{arom}$), 6.72 (1H, dd, $CH_{arom}$), 5.04 (2H, bs, $NH_2$), 4.29 (2H, q, $CH_2$), 1.33 (3H, t, $CH_3$).

8-Amino-4-oxo-4,5-dihydro-3H-pyrrolo[2,3-c]quinoline-1-ethyl carboxylate hydrochloride (64 HCl)

0.22 g of palladium on charcoal (10 wt. %) and 3.74 g (59.25 mmol) of ammonium formate are added to 3.57 g (11.65 mmol) of 8-nitro-4-oxo-4,5-dihydro-3H-pyrrolo[2,3-c]quinoline-1-ethyl carboxylate (synthesis 66) suspended in 80 mL of anhydrous dimethylformamide. The reaction mixture is stirred overnight at 60° C. then 0.50 g of palladium on charcoal (10 wt. %) and 0.75 g (11.89 mmol) of ammonium formate are added. Stirring is continued for 4 h. The mixture is then diluted in ethyl acetate and filtered on celite. The filtrate is evaporated and triturated in ether to give, after filtration, 3.16 g of a mixture of 8-amino-4-oxo-4,5-dihydro-3H-pyrrolo[2,3-c]quinoline-1-ethyl carboxylate and 8-formylamino-4-oxo-4,5-dihydro-3H-pyrrolo[2,3-c]quinoline-1-ethyl carboxylate. The beige residue is suspended in 40 mL of anhydrous ethanol before adding 11.7 mL (23.29 mmol) of 2M hydrochloric acid in diethyl ether. The solution is stirred for 90 minutes then filtered to give 3.34 g (92%) of 8-amino-4-oxo-4,5-dihydro-3H-pyrrolo[2,3-c]quinoline-1-ethyl carboxylate hydrochloride in the form of a light violet solid.

LCMS (IE, m/z): (M+1) 272.29

$^1$H-NMR: $\delta_H$ ppm 250 MHz, DMSO 13.17 (1H, bs, NH), 11.91 (1H, s, NH), 10.38 (3H, bs, $3 \times NH$), 9.29 (1H, d, $CH_{arom}$), 8.04 (1H, d, $CH_{arom}$), 7.53 (1H, d, $CH_{arom}$), 7.46 (1H, dd, $CH_{arom}$), 4.33 (2H, q, $CH_2$), 1.35 (3H, t, $CH_3$).

8-(2-Ethoxycarbonyl-vinyl)-4-oxo-4,5-dihydro-3H-pyrrolo[2,3-c]quinoline-1-ethyl carboxylate (65)

This compound is prepared according to synthesis 68, from 114 mg (0.3 mmol) of 8-iodo-4-oxo-4,5-dihydro-3H-pyrrolo[2,3-c]quinoline-1-ethyl carboxylate and 36 µL (0.33 mmol) of ethyl acrylate. After purification by chromatography on silica (eluent dichloromethane/methanol 98/2) then trituration in ethanol, 23 mg (22%) of 8-(2-ethoxycarbonyl-vinyl)-4-oxo-4,5-dihydro-3H-pyrrolo[2,3-c]quinoline-1-ethyl carboxylate is obtained in the form of a white solid.

LC/MS (IE, m/z): (M+1) 355.25
$^1$H-NMR: $\delta_H$ ppm 400 MHz, DMSO 13.09 (1H, bs, NH), 11.88 (1H, bs, NH), 9.56 (1H, s, $CH_{arom}$), 8.03 (1H, s, $CH_{arom}$), 7.80 (1H, d, $CH_{arom}$), 7.68 (1H, d, CH), 7.43 (1H, d, $CH_{arom}$), 6.54 (1H, d, CH), 4.35 (2H, q, $CH_2$), 4.22 (2H, q, $CH_2$), 1.36 (3H, t, $CH_3$), 1.29 (3H, t, $CH_3$).

8-Nitro-4-oxo-4,5-dihydro-3H-pyrrolo[2,3-c]quinoline-1-ethyl carboxylate (66)

1 g (3.90 mmol) of 4-oxo-4,5-dihydro-3H-pyrrolo[2,3-c]quinoline-1-ethyl carboxylate (synthesis 1) suspended in 15 mL of acetic anhydride is stirred on an ice bath. A solution of 0.27 mL (5.85 mmol) of nitric acid in 2 mL of acetic acid is added dropwise and the suspension is stirred for 2 hours at 0° C. 270 µL of nitric acid is then added to this mixture and stirring is continued for 1 h at 0° C. The yellowish-white solid is filtered and washed with acetic acid to give a mixture of 8-nitro-4-oxo-4,5-dihydro-3H-pyrrolo[2,3-c]quinoline-1-ethyl carboxylate and 6-nitro-4-oxo-4,5-dihydro-3H-pyrrolo[2,3-c]quinoline-1-ethyl carboxylate. The solid is stirred in acetic acid (20 mL) at 110° C. for 1 h then filtered while hot to give 0.55 g (47%) of 8-nitro-4-oxo-4,5-dihydro-3H-pyrrolo[2,3-c]quinoline-1-ethyl carboxylate in the form of a white solid.

LCMS (IE, m/z): (M+1) 302.24
$^1$H-NMR: $\delta_H$ ppm 250 MHz, DMSO
13.29 (1H, bs, NH), 12.28 (1H, s, NH), 10.30 (1H, d, $CH_{arom}$), 8.26 (1H, dd, $CH_{arom}$), 8.08 (1H, d, $CH_{arom}$), 7.54 (1H, d, $CH_{arom}$), 4.35 (2H, q, $CH_2$), 1.36 (3H, t, $CH_3$).

6-Nitro-4-oxo-4,5-dihydro-3H-pyrrolo[2,3-c]quinoline-1-ethyl carboxylate (67)

This compound is formed during synthesis of 8-nitro-4-oxo-4,5-dihydro-3H-pyrrolo[2,3-c]quinoline-1-ethyl carboxylate (synthesis 66). The filtrate recovered during hot filtration is evaporated. The yellow solid thus obtained is recrystallized from methanol to give 8 mg (1%) of 6-nitro-4-oxo-4,5-dihydro-3H-pyrrolo[2,3-c]quinoline-1-ethyl carboxylate in the form of a yellow solid.

LCMS (IE, m/z): (M+1) 302.26
$^1$H-NMR: $\delta_H$ ppm 250 MHz, DMSO
13.41 (1H, bs, NH), 11.24 (1H, s, NH), 9.72 (1H, dd, $CH_{arom}$), 8.34 (1H, dd, $CH_{arom}$), 8.12 (1H, s, $CH_{arom}$), 7.45 (1H, t, $CH_{arom}$), 4.32 (2H, q, $CH_2$), 1.35 (3H, t, $CH_3$).

8-(2-Benzylcarbamoyl-vinyl)-4-oxo-4,5-dihydro-3H-pyrrolo[2,3-c]quinoline-1-ethyl carboxylate (68)

Under an argon atmosphere, 53 mg (0.33 mmol) of N-benzyl-acrylamide, 29 mg (0.10 mmol) of tri-o-tolyl-phosphine, 83 µL (0.60 mmol) of triethylamine and 6 mg (0.02 mmol) of palladium acetate are added to 100 mg (0.30 mmol) of 8-bromo-4-oxo-4,5-dihydro-3H-pyrrolo[2,3-c]quinoline-1-ethyl carboxylate (synthesis 71) dissolved in 0.6 ml of anhydrous dimethylformamide. The reaction mixture is stirred overnight at 80° C. The mixture is diluted with ethyl acetate (20 mL) and a saturated solution of sodium chloride (20 mL). The two phases are separated and the aqueous phase is extracted with ethyl acetate. The organic phases are combined, washed with a saturated solution of sodium chloride, dried over magnesium sulfate then evaporated. The residue obtained is triturated in a dichloromethane/methanol mixture (1.8 mL/0.2 mL) to give 87 mg of a solid. After purification by preparative LCMS, 1 mg (1%) of 8-(2-benzylcarbamoyl-vinyl)-4-oxo-4,5-dihydro-3H-pyrrolo[2,3-c]quinoline-1-ethyl carboxylate is obtained in the form of a white solid.

LCMS (IE, m/z): (M+1) 416.41
$^1$H-NMR: $\delta_H$ ppm 250 MHz, CD$_3$OD
9.73 (1H, s, $CH_{arom}$), 8.06 (1H, s, $CH_{arom}$), 7.70 (1H, d, $CH_{ethyl}$) 7.68-7.60 (1H, m, $CH_{arom}$), 7.41 (1H, d, $CH_{arom}$), 7.38-7.18 (5H, m, 5×$CH_{arom}$), 6.73 (1H, d, $CH_{ethyl}$), 4.51 (2H, s, $CH_2$), 4.40 (2H, q, $CH_2$), 1.42 (3H, t, $CH_3$).

8-[2-(2-Methoxycarbonyl-ethylcarbamoyl)-vinyl]-4-oxo-4,5-dihydro-3H-pyrrolo[2,3-c]quinoline-1-ethyl carboxylate (69)

This compound is prepared according to synthesis 68, from 70 mg (0.21 mmol) of 8-bromo-4-oxo-4,5-dihydro-3H-pyrrolo[2,3-c]quinoline-1-ethyl carboxylate (synthesis 71) and 36 mg (0.23 mmol) of methyl 3-acryloylamino-propionate. After trituration in dichloromethane, 10 mg (12%) of 8-[2-(2-methoxycarbonyl-ethylcarbamoyl)-vinyl]-4-oxo-4,5-dihydro-3H-pyrrolo[2,3-c]quinoline-1-ethyl carboxylate is obtained in the form of a light brown solid.

LCMS (IE, m/z): (M+1) 412.39
$^1$H-NMR: $\delta_H$ ppm 250 MHz, DMSO
13.08 (1H, bs, NH), 11.85 (1H, s, NH), 9.45 (1H, s, $CH_{arom}$), 8.37-8.23 (1H, m, NH), 8.02 (1H, s, $CH_{arom}$), 7.62 (1H, d, $CH_{arom}$), 7.53-7.36 (2H, m, $CH_{arom}$ and $CH_{ethyl}$), 6.56 (1H, d, $CH_{ethyl}$), 4.34 (2H, q, $CH_2$), 3.62 (3H, s, $CH_3$), 3.47-3.34 (2H, m, $CH_2$), 2.55 (2H, t, $CH_2$), 1.36 (3H, t, $CH_3$).

4-Oxo-8-styryl-4,5-dihydro-3H-pyrrolo[2,3-c]quinoline-1-ethyl carboxylate (70)

This compound is prepared according to synthesis 68, from 70 mg (0.21 mmol) of 8-bromo-4-oxo-4,5-dihydro-3H-pyrrolo[2,3-c]quinoline-1-ethyl carboxylate (synthesis 71) and 26 µL (0.23 mmol) of styrene. After filtration and trituration in diethyl ether, 10 mg (14%) of 4-oxo-8-styryl-4,5-dihydro-3H-pyrrolo[2,3-c]quinoline-1-ethyl carboxylate is obtained in the form of a light brown solid.

LCMS (IE, m/z): (M+1) 359.35
$^1$H-NMR: $\delta_H$ ppm 250 MHz, DMSO
13.04 (1H, bs, NH), 11.77 (1H, s, NH), 9.43 (1H, d, $CH_{arom}$), 8.01 (1H, s, $CH_{arom}$), 7.72 (1H, dd, $CH_{arom}$), 7.60 (2H, d, 2×$CH_{arom}$), 7.45-7.14 (6H, m, 4×$CH_{arom}$ and 2× $CH_{ethyl}$), 4.36 (2H, q, $CH_2$), 1.36 (3H, t, $CH_3$).

8-Bromo-4-oxo-4,5-dihydro-3H-pyrrolo[2,3-c]quinoline-1-ethyl carboxylate (71)

434 mg (2.44 mmol) of N-bromosuccinimide is added to 500 mg (1.95 mmol) of 4-oxo-4,5-dihydro-3H-pyrrolo[2,3-c]quinoline-1-ethyl carboxylate (synthesis 1) dissolved in 10 ml of anhydrous dimethylformamide and the reaction mixture is stirred for 1 h at room temperature. The mixture is then diluted in 10 mL of ethyl acetate, the solid is filtered, rinsed with diethyl ether then recrystallized from acetic acid to give 360 mg (55%) of 8-bromo-4-oxo-4,5-dihydro-3H-pyrrolo[2, 3-c]quinoline-1-ethyl carboxylate cocrystallized with one equivalent of acetic acid in the form of a white solid.

LCMS (IE, m/z): (M+1) 334.77-336.77

$^1$H-NMR: $\delta_H$ ppm 250 MHz, DMSO 13.10 (1H, bs, NH), 11.80 (1H, s, NH), 9.49 (1H, d, $CH_{arom}$), 8.01 (1H, s, $CH_{arom}$), 7.56 (1H, dd, $CH_{arom}$), 7.36 (1H, d, $CH_{arom}$), 4.32 (2H, q, $CH_2$), 1.35 (3H, t, $CH_3$).

7,8-Dimethoxy-4-oxo-4,5-dihydro-3H-pyrrolo[2,3-c]quinoline-1-ethyl carboxylate (72)

This compound was synthesized according to synthesis 1, from 0.8 g (4.14 mmol) of 5,6-dimethoxy-1,3-dihydro-indol-2-one to give, after recrystallization from acetic acid, 0.19 g (14% in two stages) of 7,8-dimethoxy-4-oxo-4,5-dihydro-3H-pyrrolo[2,3-c]quinoline-1-ethyl carboxylate cocrystallized with one equivalent of acetic acid in the form of a gray solid.

LCMS (IE, m/z): (M+1) 316.90

$^1$H-NMR: H ppm 250 MHz, DMSO 12.84 (1H, bs, NH), 11.43 (1H, s, NH), 8.94 (1H, s, $CH_{arom}$), 7.94 (1H, s, $CH_{arom}$), 7.00 (1H, s, $CH_{arom}$), 4.30 (2H, q, $CH_2$), 3.83 (3H, s, $CH_3$), 3.80 (3H, s, $CH_3$), 1.33 (3H, t, $CH_3$).

Synthesis of the 5,6-dimethoxy-1,3-dihydro-indol-2-one is described by C. Lanzi (WO2004/009083 A1). This compound was prepared according to this procedure from 4.34 g (22.13 mmol) of (3,4-dimethoxy-phenyl)-acetic acid to give, after trituration in diethyl ether, 2.87 g (67% in two stages) of 5,6-dimethoxy-1,3-dihydro-indol-2-one in the form of a beige solid.

4-Oxo-4,5-dihydro-3H-pyrrolo[2,3-c]quinoline-1-methyl carboxylate (73)

A solution of 55 µL (0.75 mmol) of thionyl chloride in 1.5 mL of anhydrous methanol is added dropwise to 68 mg (0.3 mmol) of 4-oxo-4,5-dihydro-3H-pyrrolo[2,3-c]quinoline-1-carboxylic acid (synthesis 75) suspended in 2 mL of anhydrous methanol. The solution is stirred under reflux for 48 hours then cooled to room temperature. The solid is filtered to give 15 mg (20%) of 4-oxo-4,5-dihydro-3H-pyrrolo[2,3-c]quinoline-1-methyl carboxylate in the form of a beige solid.

LCMS (IE, m/z): (M+1) 243.30

$^1$H-NMR: $\delta_H$ ppm 250 MHz, DMSO 12.98 (1H, bs, NH), 11.65 (1H, s, NH), 9.22 (1H, d, $CH_{arom}$), 7.99 (1H, s, $CH_{arom}$), 7.44-7.38 (2H, m, 2×$CH_{arom}$), 7.27-7.17 (1H, m, $CH_{arom}$), 3.83 (3H, s, $CH_3$).

4-Oxo-4,5-dihydro-3H-pyrrolo[2,3-c]quinoline-1-carboxylate benzyl (74)

124 µL (0.88 mmol) of triethylamine and 79 µL (0.66 mmol) of benzyl bromide are added in portions (over 3 days) to 50 mg (0.22 mmol) of 4-oxo-4,5-dihydro-3H-pyrrolo[2,3-c]quinoline-1-carboxylic acid (synthesis 75) in 0.5 mL of anhydrous dimethylformamide, until the starting product has disappeared completely. The residue is purified by chromatography on silica gel (eluent dichloromethane/methanol 94/6) to give 56 mg of an impure product. After recrystallization from methanol, 4 mg (6%) of 4-oxo-4,5-dihydro-3H-pyrrolo[2,3-c]quinoline-1-carboxylate benzyl is obtained in the form of a white solid.

LCMS (IE, m/z): (M+1) 319.25

$^1$H-NMR: $\delta_H$ ppm 250 MHz, DMSO 13.03 (1H, bs, NH), 11.66 (1H, s, NH), 9.21 (1H, d, $CH_{arom}$), 8.05 (1H, s, $CH_{arom}$), 7.55-7.47 (2H, m, 2×$CH_{arom}$), 7.46-7.27 (5H, m, 5×$CH_{arom}$), 7.24-7.14 (1H, m, $CH_{arom}$), 5.36 (2H, s, $CH_2$).

4-oxo-4,5-dihydro-3H-pyrrolo[2,3-c]quinoline-1-carboxylic acid (75)

1.64 g (39 mmol) of lithium hydroxide monohydrate is added to 1 g (3.9 mmol) of 4-oxo-4,5-dihydro-3H-pyrrolo[2,3-c]quinoline-1-ethyl carboxylate (synthesis 1) suspended in 45 mL of ethanol and 45 mL of water, and the solution is stirred for 17 h at 70° C. then 5 h at 100° C. The ethanol is evaporated under vacuum and distilled water is added. The aqueous solution is washed with ethyl acetate then acidified with acetic acid to pH 4-5. The precipitate that forms is filtered then dried under vacuum at 55° C. to give 0.9 g (100%) of 4-oxo-4,5-dihydro-3H-pyrrolo[2,3-c]quinoline-1-carboxylic acid in the form of a beige solid.

LCMS (IE, m/z): (M+1) 229.25

$^1$H-NMR: $\delta_H$ ppm 250 MHz, DMSO 13.31-11.76 (2H, flattened signal, NH and COOH), 11.55 (1H, s, NH), 9.66 (1H, dd, $CH_{arom}$), 7.78 (1H, s, $CH_{arom}$), 7.38 (1H, dd, $CH_{arom}$), 7.35-7.27 (1H, m, $CH_{arom}$), 7.18-7.10 (1H, m, $CH_{arom}$).

1-Benzoyl-3,5-dihydro-pyrrolo[2,3-c]quinolin-4-one (76)

The synthesis of this compound is described by J. Bergman (*Tetrahedron*, 2002, 58, pp 9179-9185). The compound was prepared according to this procedure from 0.8 g (6 mmol) of 1,3-dihydro-indol-2-one to give, after trituration in dichloromethane, 190 mg (11% in two stages) of 1-benzoyl-3,5-dihydro-pyrrolo[2,3-c]quinolin-4-one in the form of a beige solid.

LCMS (IE, t/z): (M+1) 289.32

$^1$H-NMR: $\delta_H$ ppm 250 MHz, DMSO 13.04 (1H, bs, NH), 11.72 (1H, s, NH), 8.84 (1H, d, $CH_{arom}$), 7.87-7.80 (2H, m, 2×$CH_{arom}$), 7.70-7.51 (4H, m, 4×$CH_{arom}$), 7.47-7.35 (2H, m, 2×$CH_{arom}$), 7.23-7.14 (1H, m, $CH_{arom}$).

1-Acetyl-3,5-dihydro-pyrrolo[2,3-c]quinolin-4-one (77)

This compound is prepared according to synthesis 76, from 930 mg (7 mmol) of 1,3-dihydro-indol-2-one and 1.9 mL (about 10.5 mmol) of a 40% aqueous solution of pyruvic aldehyde. After trituration in ethyl acetate, 63 mg (4% in two stages) of 1-acetyl-3,5-dihydro-pyrrolo[2,3-c]quinolin-4-one is obtained in the form of a beige solid.

LCMS (IE, m/z): (M+1) 227.27

$^1$H-NMR: $\delta_H$ ppm 250 MHz, DMSO 13.02 (1H, bs, NH), 11.70 (1H, s, NH), 9.31 (1H, d, $CH_{arom}$), 8.35 (1H, d, $CH_{arom}$), 740-7.37 (2H, m, 2×$CH_{arom}$), 7.24-7.16 (1H, m, $CH_{arom}$), 2.58 (3H, s, $CH_3$).

4-Oxo-4,5-dihydro-3H-pyrrolo[2,3-c]quinoline-1-carboxylate isopropyl (78)

58 mg (0.42 mmol) of isopropyl bromide and 66 µL (0.7 mmol) of potassium carbonate are added to a solution of 120 mg (0.47 mmol) of 4-oxo-4,5-dihydro-3H-pyrrolo[2,3-c]quinoline-1-carboxylic acid dissolved in 2 mL of dimethylformamide. The reaction mixture is stirred for 48 hours at 70° C. The reaction is monitored by LC/MS over 7 days with regular addition of additional isopropyl bromide (300 mg, 2.17 mmol) and potassium carbonate (132 µL, 1.4 mmol) so that the starting product disappears completely. The solvents are evaporated and the residue is purified by chromatography on silica (eluent dichloromethane/methanol 95/5) to give 20 mg (15%) of 4-oxo-4,5-dihydro-3H-pyrrolo[2,3-c]quinoline-1-carboxylate isopropyl in the form of a white solid.

LCMS (IE, m/z): (M+1) 270.76

$^1$H-NMR: $\delta_H$ ppm 400 MHz, DMSO 12.94 (1H, bs, NH), 11.65 (1H, s, NH), 9.22 (1H, d, $CH_{arom}$), 7.94 (1H, s, $CH_{arom}$), 7.43-7.37 (2H, m, 2×$CH_{arom}$), 7.21 (1H, ddd, $CH_{arom}$), 5.14 (1H, sept, CH), 1.34 (6l, d, 2×$CH_3$).

N-(2-Dimethylamino-ethyl)-4-oxo-4,5-dihydro-3H-pyrrolo[2,3-c]quinoline-1-carboxamide (79)

49 mg (0.36 mmol) of 1-hydroxybenzotriazole, 69 mg (0.36 mmol) of 1-ethyl-3-(3-dimethylaminopropyl)carbodiimide hydrochloride, 73 µL (0.66 mmol) of N-methylmorpholine and 40 µL (0.36 mmol) of N,N-dimethylethylenediamine are added to 75 mg (0.33 mmol) of 4-oxo-4,5-dihydro-3H-pyrrolo[2,3-c]quinoline-1-carboxylic acid (synthesis 75) suspended in 0.7 ml of anhydrous dimethylformamide. The reaction mixture is stirred overnight at room temperature. The mixture is diluted with ethyl acetate (20 mL) and a saturated solution of sodium chloride (20 mL). The two phases are separated and the aqueous phase is extracted with ethyl acetate (3×20 mL). The organic phases are combined, washed with n aqueous solution of potassium carbonate (10%) (3×40 mL), water (40 mL) and a saturated solution of sodium chloride (50 mL), dried over magnesium sulfate and evaporated. The residue obtained is triturated in diethyl ether to give 13 mg (13%) of N-(2-dimethylamino-ethyl)-4-oxo-4,5-dihydro-3H-pyrrolo[2,3-c]quinoline-1-carboxamide in the form of a light brown solid.

LCMS (IE, m/z): (M+1) 299.36

$^1$H-NMR: $\delta_H$ ppm 250 MHz, CD$_3$OD 8.79 (1H, d, $CH_{arom}$), 7.82 (1H, s, $CH_{arom}$), 7.43-7.34 (2H, m, 2×$CH_{arom}$), 7.30-7.18 (1H, m, $CH_{arom}$), 3.58 (2H, t, $CH_2$), 2.65 (2H, t, $CH_2$), 2.36 (6H, s, 2×$CH_3$).

N-(3-Dimethylamino-propyl)-4-oxo-4,5-dihydro-3H-pyrrolo[2,3-c]quinoline-1-carboxamide (80)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 46 µL (0.36 mmol) of 3-dimethylaminopropylamine. After trituration in diethyl ether, 37 mg (36%) of N-(3-dimethylamino-propyl)-4-oxo-4,5-dihydro-3H-pyrrolo[2,3-c]quinoline-1-carboxamide is obtained in the form of a white solid.

LCMS (IE, m/z): (M+1) 313.37

$^1$H-NMR: $\delta_H$ ppm 250 MHz, CD$_3$OD 8.76 (1H, d, $CH_{arom}$), 7.76 (1H, s, $CH_{arom}$), 7.43-7.35 (2H, m, 2×$CH_{arom}$), 7.28-7.19 (1H, nm, $CH_{arom}$), 3.46 (2H, t, $CH_2$), 2.61-2.51 (2H, m, $CH_2$), 2.35 (6H, s, 2×$CH_3$), 1.97-1.81 (2H, m, $CH_{12}$).

3-[(4-Oxo-4,5-dihydro-3H-pyrrolo[2,3-c]quinoline-1-carbonyl)-amino]-methyl propanoate (81)

This compound is prepared according to synthesis 79 from 75 mg (0.33 mmol) of 4-oxo-4,5-dihydro-3H-pyrrolo[2,3-c]quinoline-1-carboxylic acid (synthesis 75), 108 µL (0.99 mmol) of N-methylmorpholine and 51 mg (0.36 mmol) of methyl 3-aminopropanoate hydrochloride. After trituration in methanol, 9 mg (9%) of 3-[(4-oxo-4,5-dihydro-3H-pyrrolo[2,3-c]quinoline-1-carbonyl)-amino]-methyl propanoate is obtained in the form of a white solid.

LCMS (IE, m/z): (M+1) 314.34

$^1$H-NMR: $\delta_H$ ppm 250 MHz, DMSO 12.60 (1H, bs, NH), 11.54 (1H, s, NH), 8.99 (1H, d, $CH_{arom}$), 8.37-8.27 (1H, m, NH), 7.79 (1H, s, $CH_{arom}$), 7.42-7.28 (2H, m, 2×$CH_{arom}$), 7.22-7.09 (1H, m, $CH_{arom}$), 3.62 (3H, s, $CH_3$), 3.58-3.44 (2H, m, $CH_2$), 2.62 (2H, t, $CH_2$).

N-(Cyclohexylmethyl)-4-oxo-4,5-dihydro-3H-pyrrolo[2,3-c]quinoline-1-carboxamide (82)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 47 µL (0.36 mmol) of C-cyclohexyl-methylamine. After recrystallization from methanol, 8 mg (8%) of N-(cyclohexylmethyl)-4-oxo-4,5-dihydro-3H-pyrrolo[2,3-c]quinoline-1-carboxamide is obtained in the form of a white solid.

LCMS (IE, m/z): (M+1) 324.41

$^1$H-NMR. $\delta_H$ ppm 250 MHz, CD$_3$OD 8.71 (1H, d, $CH_{arom}$), 7.73 (1H, s, $CH_{arom}$), 7.42-7.37 (2H, m, 2×$CH_{arom}$), 7.28-7.18 (1H, m, $CH_{arom}$), 3.26 (2H, d, $CH_2$), 1.94-1.57 (6H, m, 6×$CH_{cyclo}$) 1.43-1.17 (3H, m, 3×$CH_{cyclo}$) 1.15-0.96 (2H, m, 2×$CH_{cyclo}$).

N-(Benzyl)-4-oxo-4,5-dihydro-3H-pyrrolo[2,3-c]quinoline-1-carboxamide (83)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 40 µL (0.36 mmol) of benzylamine. After recrystallization from methanol, 8 mg (8%) of N-(benzyl)-4-oxo-4,5-dihydro-3H-pyrrolo[2,3-c]quinoline-1-carboxamide is obtained in the form of a white solid.

LCMS (IE, m/z): (M+1) 318.37

$^1$H-NMR: $\delta_H$ ppm 250 MHz, CD$_3$OD 8.72 (1H, d, $CH_{arom}$), 7.79 (1H, s, $CH_{arom}$), 7.46-7.16 (8H, m, 8×$CH_{arom}$), 4.62 (2H, s, $CH_2$).

N-[2-(1H-Indol-3-yl)-ethyl]-4-oxo-4,5-dihydro-3H-pyrrolo[2,3-c]quinoline-1-carboxamide (84)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 58 mg (0.36 mmol) of tryptamine. After trituration in diethyl ether, 48 mg (40%) of N-[2-(1H-indol-3-yl)-ethyl]-4-oxo-4,5-dihydro-3H-pyrrolo[2,3-c]quinoline-1-carboxamide is obtained in the form of a light brown solid.

LCMS (IE, m/z): (M+1) 371.37

$^1$H-NMR: $\delta_H$ ppm 250 MHz, CD$_3$OD 8.68 (1H, d, $CH_{arom}$), 7.64 (1H, d, $CH_{arom}$), 7.59 (1H, s, $CH_{arom}$), 7.42-7.30 (3H, m, 3×$CH_{arom}$), 7.22-6.95 (4H, m, 4×$CH_{arom}$), 3.73 (2H, t, $CH_2$), 3.13 (2H, t, $CH_2$).

N-(3-Hydroxy-propyl)-4-oxo-4,5-dihydro-3H-pyrrolo[2,3-c]quinoline-1-carboxamide (85)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 28 µL (0.36 mmol) of 3-hydroxy-propylamine. The aqueous phase is evaporated, the residue is taken up in methanol and then filtered. The filtrate is evaporated and the residue is purified by preparative LCMS to give 8 mg (9%) of N-(3-hydroxypropyl)-4-oxo-4,5-dihydro-3H-pyrrolo[2,3-c]quinoline-1-carboxamide in the form of a white solid.

LCMS (IE, m/z): (M+1) 286.34

$^1$H-NMR: $\delta_H$ ppm 250 MHz, DMSO 12.57 (1H, s, NH), 11.53 (1H, s, NH), 9.00 (1H, d, $CH_{arom}$), 8.19 (1H, t, NH), 7.79 (1H, s, $CH_{arom}$), 7.40-7.28 (2H, m, 2×$CH_{arom}$), 7.18-7.10 (1H, m, $CH_{arom}$), 4.49 (1H, t, OH), 3.54-3.45 (2H, m, $CH_2$), 3.37-3.27 (2H, m, $CH_2$), 1.70 (2H, quint., $CH_2$).

N-(Pyridin-4-ylmethyl)-4-oxo-4,5-dihydro-3H-pyrrolo[2,3-c]quinoline-1-carboxamide (86)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 37 μL (0.36 mmol) of pyridin-4-ylmethylamine. The precipitate that forms during the reaction is filtered then washed with dimethylformamide and diethyl ether to give 46 mg (44%) of N-(pyridin-4-ylmethyl)-4-oxo-4,5-dihydro-3H-pyrrolo[2,3-c]quinoline-1-carboxamide in the form of a white solid.

LCMS (IE, m/z): (M+1) 319.37

$^1$H-NMR: $\delta_H$ ppm 250 MHz, DMSO 12.68 (1H, bs, NH), 11.57 (1H, bs, NH), 9.07-8.81 (2H, m, NH and $CH_{arom}$), 8.67-8.35 (2H, m, 2×$CH_{arom}$), 7.99 (1H, s, $CH_{arom}$), 7.54-7.23 (4H, m, 4×$CH_{arom}$), 7.17-7.02 (1H, m, $CH_{arom}$), 4.50 (2H, s, $CH_2$).

N-(Phenyl)-4-oxo-4,5-dihydro-3H-pyrrolo[2,3-c]quinoline-1-carboxamide (87)

This compound is prepared according to synthesis 79 from 75 mg (0.33 mmol) of 4-oxo-4,5-dihydro-3H-pyrrolo[2,3-c]quinoline-1-carboxylic acid (synthesis 75) and 33 μL (0.36 mmol) of aniline. After trituration in diethyl ether, 45 mg (45%) of N-(phenyl)-4-oxo-4,5-dihydro-3H-pyrrolo[2,3-c]quinoline-1-carboxamide is obtained in the form of a light brown solid.

LCMS (IE, m/z): (M+1) 304.33

$^1$H-NMR: $\delta_H$ ppm 250 MHz, DMSO 12.78 (1H, bs, NH), 11.61 (1H, s, NH), 10.15 (1H, s, NH), 8.87 (1H, d, $CH_{arom}$), 8.03 (1H, s, $CH_{arom}$), 7.79 (2H, d, 2×$CH_{arom}$), 744-7.30 (4H, m, 4×$CH_{arom}$), 7.21-7.03 (2H, m, 2×$CH_{arom}$).

N-(Methyl)-4-oxo-4,5-dihydro-3H-pyrrolo[2,3-c]quinoline-1-carboxamide (88)

This compound is prepared according to synthesis 79 from 37 mg (0.17 mmol) of 4-oxo-4,5-dihydro-3H-pyrrolo[2,3-c]quinoline-1-carboxylic acid (synthesis 75), 108 μL (0.99 mmol) of N-methylmorpholine and 17 mg (0.25 mmol) of methylamine hydrochloride. After trituration in diethyl ether, 3 mg (7%) of N-(methyl)-4-oxo-4,5-dihydro-3H-pyrrolo[2,3-c]quinoline-1-carboxamide are obtained in the form of a light brown solid.

LCMS (IE, m/z): (M+1) 242.29

$^1$H-NMR: $\delta_H$ ppm 250 MHz, $CD_3OD$ 8.77 (1H, d, $CH_{arom}$), 7.74 (1H, s, $CH_{arom}$), 7.43-7.36 (2H, m, 2×$CH_{arom}$), 7.29-7.19 (1H, m, $CH_{arom}$), 2.96 (3H, s, $CH_3$).

N,N-(Dimethyl)-4-oxo-4,5-dihydro-3H-pyrrolo[2,3-c]quinoline-1-carboxamide (89)

This compound is prepared according to synthesis 79 from 41 mg (0.18 mmol) of 4-oxo-4,5-dihydro-3H-pyrrolo[2,3-c]quinoline-1-carboxylic acid (synthesis 75), 108 μL (0.99 mmol) of N-methylmorpholine and 22 mg (0.25 mmol) of dimethylamine hydrochloride. After filtration of the reaction mixture, 10 mg (22%) of N,N-(dimethyl)-4-oxo-4,5-dihydro-3H-pyrrolo[2,3-c]quinoline-1-carboxamide are obtained in the form of a white solid.

LCMS (IE, m/z): (M+1) 256.26

$^1$H-NMR: $\delta_H$ ppm 250 MHz, DMSO 12.54 (1H, bs, NH), 11.48 (1H, s, NH), 7.84 (1H, d, $CH_{arom}$), 7.51 (1H, s, $CH_{arom}$), 7.42-7.29 (2H, m, 2×$CH_{arom}$), 7.19-7.11 (1H, m, $CH_{arom}$), 3.02 (6H, bs, 2×$CH_3$).

4-Oxo-4,5-dihydro-3H-pyrrolo[2,3-c]quinoline-1-carboxamide (90)

A suspension of 84 mg (0.4 mmol) of 4-oxo-4,5-dihydro-3H-pyrrolo[2,3-c]quinoline-1-carbonitrile in 1 mL of polyphosphoric acid is heated at 130° C. for 2 h. The reaction mixture is cooled to room temperature then poured into ice. The mixture is stirred for 30 min and the solid thus formed is filtered then taken up in a methanol/toluene mixture. After evaporation of the solvents, the residue (mixture of 4-oxo-4,5-dihydro-3H-pyrrolo[2,3-c]quinoline-1-carboxamide and 4-oxo-4,5-dihydro-3H-pyrrolo[2,3-c]quinoline-1-carboxylic acid 2/1) is purified by preparative LCMS to give 4 mg (4%) of 4-oxo-4,5-dihydro-3H-pyrrolo[2,3-c]quinoline-1-carboxamide in the form of a white solid.

LCMS (IE, m/z): (M+1) 228.24

$^1$H-NMR: $\delta_H$ ppm 250 MHz, DMSO 12.60 (1H, bs, NH), 11.53 (1H, s, NH), 9.57 (1H, d, $CH_{arom}$), 7.90 (1H, s, $CH_{arom}$), 7.69 (1H, bs, NH), 7.40-7.29 (2H, m, 2×$CH_{arom}$), 7.19-7.02 (2H, m, NH and $CH_{arom}$).

The synthesis of 4-oxo-4,5-dihydro-3H-pyrrolo[2,3-c]quinoline-1-carbonitrile was described by J. Bergman (Tetrahedron, 2002, 58, pp 9179-9185). The compound was prepared according to this procedure from 1.2 g (7.96 mmol) of 2-nitrobenzaldehyde to give, after recrystallization from acetic acid, 283 mg (17% in three stages) of 4-oxo-4,5-dihydro-3H-pyrrolo[2,3-c]quinoline-1-carbonitrile in the form of a white solid.

4-oxo-8-(piperidin-4-ylsulfamoyl)-4,5-dihydro-3H-pyrrolo[2,3-c]quinoline-1-ethyl carboxylate (91)

This compound is prepared according to synthesis 25, from 326 mg (1 mmol) of 8-chlorosulfonyl-4-oxo-4,5-dihydro-3H-pyrrolo[2,3-c]quinoline-1-carboxylic acid (synthesis 2) and 236 mg (1 mmol) of 4-amino-1-tert-butoxycarbonyl piperidine hydrochloride and 700 μL (5 mmol) of triethylamine. After purification by chromatography on silica (eluent chloroform/methanol/ammonia 65/25/4) then trituration in methanol, 16 mg (4%) of 4-oxo-8-(piperidin-4-ylsulfamoyl)-4,5-dihydro-3H-pyrrolo[2,3-c]quinoline-1-ethyl carboxylate is obtained in the form of a white solid.

LCMS (IE, m/z): (M+1) 419.10

$^1$H-NMR: $\delta_H$ ppm 400 MHz, DMSO 12.08 (1H, s, NH), 9.84 (1H, d, $CH_{arom}$), 8.07 (1H, s, $CH_{arom}$), 7.87 (1H, dd, $CH_{arom}$), 7.56 (1H, d, $CH_{arom}$), 4.34 (2H, q, $CH_2$), 3.40-3.30 (1H, m, $CH_{pip}$), 3.20-3.11 (2H, m, 2×$CH_{pip}$), 3.00-2.92 (1H, m, NH), 2.91-2.81 (2H, m, 2×$CH_{pip}$), 1.84-1.75 (2H, m, 2×$CH_{pip}$), 1.61-1.52 (2H, m, 2×$CH_{pip}$), 1.36 (3H, t, $CH_3$).

8-Cyclopentylsulfamoyl-4-oxo-4,5-dihydro-3H-pyrrolo[2,3-c]quinoline-1-methyl carboxylate (92)

146 μL (1.04 mmol) of triethylamine and 57 μL (0.57 mmol) of cyclopentylamine are added to 170 mg (0.5 mmol)

of 8-chlorosulfonyl-4-oxo-4,5-dihydro-3H-pyrrolo[2,3-c]quinoline-1-carboxylic acid (synthesis 2) suspended in 2 mL of anhydrous dichloromethane and 0.5 mL of anhydrous dimethylformamide. The reaction mixture is stirred for 5 hours at room temperature. The solvents are evaporated then the residue is taken up in 2 mL of anhydrous methanol. A solution of 380 μL (5.2 mmol) of thionyl chloride in 2.5 mL of anhydrous methanol is then added slowly. The reaction mixture is stirred at 70° C. for 24 hours then cooled to room temperature. The solid is filtered then the filtrate is evaporated. The residue is purified by chromatography on silica (eluent dichloromethane/methanol/acetonitrile 94/3/3) to give 10 mg (5%) of 8-cyclopentylsulfamoyl-4-oxo-4,5-dihydro-3H-pyrrolo[2,3-c]quinoline-1-methyl carboxylate in the form of a beige solid contaminated with 20% of its ethyl carboxylate analog.

LCMS (IE, m/z): (M+1) 389.92

$^1$H-NMR: $\delta_H$ ppm 400 MHz, DMSO 13.19 (1H, s, NH), 12.05 (1H, s, NH), 9.83 (1H, d, $CH_{arom}$), 8.07 (1H, s, $CH_{arom}$), 7.56-7.51 (2H, m, $CH_{arom}$ and NH), 7.54 (1H, d, $CH_{arom}$), 3.86 (3H, s, $CH_3$), 3.53-3.45 (1H, m, $CH_{pen}$) 1.55-1.48 (4H, m, 4×$CH_{pen}$), 1.40-1.22 (6H, m, 6×$CH_{pen}$).

8-(Octahydro-pyrrolo[3,4-c]pyrrole-2-sulfonyl)-4-oxo-4,5-dihydro-3H-pyrrolo[2,3-c]quinoline-1-ethyl carboxylate (93)

250 μL (1.83 mmol) of triethylamine and 175 μL (0.57 mmol) of 2-benzyl-octahydro-pyrrolo[3,4-c]pyrrole hydrochloride (compound obtained according to the procedure described by A. Madin, US 006107321) are added to 200 mg (0.61 mmol) of 8-chlorosulfonyl-4-oxo-4,5-dihydro-3H-pyrrolo[2,3-c]quinoline-1-carboxylic acid (synthesis 2) suspended in 3.5 mL of anhydrous dichloromethane and 1 mL of anhydrous dimethylformamide. The reaction mixture is stirred for 5 hours at room temperature. The solvents are evaporated then the residue is taken up in 2 mL of anhydrous ethanol. A solution of 450 μL (6.1 mmol) of thionyl chloride in 2.5 mL of anhydrous ethanol is then added slowly. The reaction mixture is stirred at 70° C. for 24 hours then cooled to room temperature. The solid is filtered then the filtrate is evaporated. The residue is purified by chromatography on silica (eluent chloroform/methanol/ammonia 80/5/2) to give 70 mg of a yellow solid. The solid is dissolved in 5 mL of ethanol. The reaction mixture is stirred under a hydrogen atmosphere with regular addition of palladium 10% on charcoal and a 1M aqueous solution of hydrochloric acid until the starting product has disappeared completely. The reaction mixture is filtered on celite and the filtrate is evaporated. The residue is purified by chromatography on silica (eluent chloroform/methanol/ammonia 65/25/4) to give 18 mg (7% in three stages) of 8-(octahydro-pyrrolo[3,4-c]pyrrole-2-sulfonyl)-4-oxo-4,5-dihydro-3H-pyrrolo[2,3-c]quinoline-1-ethyl carboxylate in the form of a white solid.

LCMS (IE, m/z): (M+1) 431.13

$^1$H-NMR: $\delta_H$ ppm 400 MHz, DMSO 12.15 (1H, s, NH), 9.80 (1H, d, $CH_{arom}$), 8.08 (1H, s, $CH_{arom}$), 7.78 (1H, dd, $CH_{arom}$), 7.62 (1H, d, $CH_{arom}$), 4.34 (2H, q, $CH_2$), 3.22-3.17 (2H, m, 2×$CH_{pyr}$), 3.08-3.01 (2H, m, 2×$CH_{pyr}$), 2.95-2.80 (6H, m, 6×$CH_{pyr}$), 1.36 (3H, 1, $CH_3$).

8-(1-Azabicyclo[2.2.2]oct-3-ylsulfamoyl)-4-oxo-4,5-dihydro-3H-pyrrolo[2,3-c]quinoline-1-ethyl carboxylate (94)

This compound is prepared according to synthesis 25, from 200 mg (0.6 mmol) of 8-chlorosulfonyl-4-oxo-4,5-dihydro-3H-pyrrolo[2,3-c]quinoline-1-carboxylic acid (synthesis 2), 100 mg (0.8 mmol) of 3-aminoquinuclidine (in free form) and 170 μL (1.22 mmol) of triethylamine. After purification by chromatography on silica (eluent chloroform/methanol/ammonia 85/13/2), 11 mg (4%) of 8-(1-azabicyclo[2.2.2]oct-3-ylsulfamoyl)-4-oxo-4,5-dihydro-3H-pyrrolo[2,3-c]quinoline-1-ethyl carboxylate is obtained in the form of a brown solid.

LCMS (IE, m/z): (M+1) 444.83

$^1$H-NMR: $\delta_H$ ppm 400 MHz, DMSO 13.10 (1H, s, NH), 12.07 (1H, s, NH), 9.81 (1H, d, $CH_{arom}$), 8.06 (1H, s, $CH_{arom}$), 7.81 (1H, dd, $CH_{arom}$), 7.75 (1H, d, NH), 7.53 (1H, d, $CH_{arom}$), 4.33 (2H, q, $CH_2$), 3.27-3.22 (1H, m, $CH_{qui}$), 2.91-2.82 (1H, m, $CH_{qui}$), 2.80-2.65 (1H, m, $CH_{qui}$), 2.60-2.36 (3H, m, 3×$CH_{qui}$), 1.79-1.69 (1H, m, $CH_{qui}$), 1.68-1.61 (1H, m, $CH_{qui}$), 1.49-1.32 (5H, m, 2×$CH_{qui}$ and $CH_3$), 1.24-1.15 (1H, m, $CH_{qui}$).

8-(4-Methyl-piperazine-1-sulfonyl)-4-oxo-4,5-dihydro-3H-pyrrolo[2,3-c]quinoline-1-methyl carboxylate (95)

60 μL (0.12 mmol) of a 2M solution of trimethylsilyldiazomethane in diethyl ether is added to a suspension of 38 mg (0.1 mmol) of 8-(4-methyl-piperazine-1-sulfonyl)-4-oxo-4,5-dihydro-3H-pyrrolo[2,3-c]quinoline-1-carboxylic acid dissolved in 1 mL of dimethylformamide and 1 mL of methanol. After monitoring by LC/MS analysis, 60 μL (0.12 mmol) of the 2M solution of trimethylsilyldiazomethane in diethyl ether is added again, then the reaction mixture is stirred for one hour. The precipitate is then collected by filtration, then washed with water, with diisopropyl ether then dried in the stove under vacuum, obtaining 10 mg (17%) of 8-(4-methyl-piperazine-1-sulfonyl)-4-oxo-4,5-dihydro-3H-pyrrolo[2,3-c]quinoline-1-methyl carboxylate in the form of a white solid.

LCMS (IE, m/z): (M+1) 404.87

$^1$H-NMR: $\delta_H$ ppm 400 MHz, DMSO 13.25 (1H, bs, NH), 12.12 (1H, s, NH), 9.80 (1H, s, $CH_{arom}$), 8.11 (1H, s, $CH_{arom}$), 7.76 (1H, dd, $CH_{arom}$), 7.61 (1H, d, $CH_{arom}$), 3.86 (3H, s, $CH_3$), 2.95 (4H, m, 2×$CH_2$), 2.39 (4H, m, 2×$CH_2$).

8-(4-Methyl-piperazine-1-sulfonyl)-4-oxo-4,5-dihydro-3H-pyrrolo[2,3-c]quinoline-1-carboxylic acid is prepared according to synthesis 25, from 440 mg (0.75 mmol) of 8-chlorosulfonyl-4-oxo-4,5-dihydro-3H-pyrrolo[2,3-c]quinoline-1-carboxylic acid (synthesis 2) and 164 μl (1.48 mmol) of 1-methyl-piperazine to give, after washing with water, 340 mg (65%) of 8-(4-methyl-piperazine-1-sulfonyl)-4-oxo-4,5-dihydro-3H-pyrrolo[2,3-c]quinoline-1-carboxylic acid in the form of a white solid.

4-Oxo-8-sulfamoyl-4,5-dihydro-3H-pyrrolo[2,3-c]quinoline-1-ethyl carboxylate (96)

In a sealed tube, 490 mg (1.5 mmol) of 8-chlorosulfonyl-4-oxo-4,5-dihydro-3H-pyrrolo[2,3-c]quinoline-1-carboxylic acid (synthesis 2) is dissolved in 1.5 mL of an aqueous solution of ammonia at 28%. The mixture is stirred at 100° C. for 4 hours. The solution is cooled then the solvents are evaporated. The residue is taken up in 10 mL of anhydrous ethanol. A solution of 1.1 mL (15 mmol) of thionyl chloride in 4.5 mL of anhydrous ethanol is then added slowly. The reaction mixture is stirred at 70° C. for 48 hours then cooled to room temperature. The solvents are evaporated and the residue is purified by chromatography on silica (eluent chloroform/methanol/ammonia 85/13/2) to give 18 mg (3%) of 4-oxo-8-sulfamoyl-4,5-dihydro-3H-pyrrolo[2,3-c]quinoline-1-ethyl carboxylate in the form of a beige solid.

LCMS (IE, m/z): (M+1) 335.98

$^1$H-NMR. $\delta_H$ ppm 400 MHz, DMSO 13.08 (1H, s, NH), 12.01 (1H, s, NH), 9.82 (1H, d, $CH_{arom}$), 8.05 (1H, s, $CH_{arom}$), 7.84 (1H, dd, $CH_{arom}$), 7.53 (1H d, $CH_{arom}$), 7.26 (2H, s, $NH_2$), 4.34 (2H, q, $CH_2$), 1.36 (3H, t, $CH_3$).

(S)-4-Oxo-8-[(pyrrolidin-3-methyl)-sulfamoyl]-4,5-dihydro-3H-pyrrolo[2,3-c]quinoline-1-ethyl carboxylate (97)

This compound is prepared according to synthesis 25, from 392 mg (1.2 mmol) of 8-chlorosulfonyl-4-oxo-4,5-dihydro-3H-pyrrolo[2,3-c]quinoline-1-carboxylic acid (synthesis 2), 252 mg (1.26 mmol) of (R)-2-(aminomethyl)-1-tert-butoxycarbonyl-pyrrolidine and 200 μL (1.44 mmol) of triethylamine. After purification by chromatography on silica (eluent chloroform/methanol/ammonia 80/16/4), 25 mg (4%) of (S)-4-oxo-8-[(pyrrolidin-3-methyl)-sulfamoyl]-4,5-dihydro-3H-pyrrolo[2,3-c]quinoline-1-ethyl carboxylate is obtained in the form of a white solid.

LCMS (IE, m/z): (M+1) 418.93

$^1$H-NMR: $\delta_H$ ppm 400 MHz, DMSO 13.19 (1H, s, NH), 12.10 (1H, s, NH), 9.84 (1H, d, $CH_{arom}$), 8.87 (1H, bs, NH), 8.07 (1H, s, $CH_{arom}$), 7.95 (1H, s, NH), 7.84 (1H, dd, $CH_{arom}$), 7.59 (1H, d, $CH_{arom}$), 4.34 (2H, q, $CH_2$), 3.60-3.50 (1H, m, CH), 3.21-2.98 (4H, m, 4×CH), 2.21-1.95 (1H, m, CH), 1.94-1.78 (2H, m, 2×CH), 1.66-1.55 (1H, m, CH), 1.36 (3H, t, $CH_3$).

8-(4-Hydroxy-phenylsulfamoyl)-4-oxo-4,5-dihydro-3H-pyrrolo[2,3-c]quinoline-1-ethyl carboxylate (98)

This compound is prepared according to synthesis 25, from 440 mg (0.75 mmol) of 8-chlorosulfonyl-4-oxo-4,5-dihydro-3H-pyrrolo[2,3-c]quinoline-1-carboxylic acid (synthesis 2) and 161 mg (1.48 mmol) of 4-hydroxyaniline. After trituration in ethanol/diisopropyl ether mixture, then washing with water and drying, 33 mg (11%) of 8-(4-hydroxy-phenylsulfamoyl)-4-oxo-4,5-dihydro-3H-pyrrolo[2,3-c]quinoline-1-ethyl carboxylate is obtained in the form of a white solid.

LCMS (IE, m/z): (M+1) 427.77

$^1$H-NMR: $\delta_H$ ppm 400 MHz, DMSO 13.15 (1H, bs, NH), 12.01 (1H, s, NH), 9.71 (1H, s, $CH_{arom}$), 9.67 (1H, s, OH), 9.20 (1H, s, NH), 8.03 (1H, s, $CH_{arom}$), 7.63 (1H, dd, $CH_{arom}$), 7.47 (1H, d, $CH_{arom}$), 6.88 (2H, d, 2×$CH_{arom}$), 6.56 (2H, d, 2×$CH_{arom}$), 4.33 (2H, q, $CH_2$), 1.35 (3H, t, $CH_3$).

8-Fluoro-4-oxo-4,5-dihydro-3H-pyrrolo[2,3-c]quinoline-1-ethyl carboxylate (99)

This compound was synthesized according to synthesis 1, from 5.8 g (38 mmol) of 5-fluoro-1,3-dihydro-indol-2-one to give, after recrystallization from acetic acid, 805 mg (7% in two stages) of 8-fluoro-4-oxo-4,5-dihydro-3H-pyrrolo[2,3-c]quinoline-1-ethyl carboxylate cocrystallized with one equivalent of acetic acid in the form of a gray solid.

LCMS (IE, m/z): (M+1) 275.05

$^1$H-NMR. $\delta_H$ ppm 400 MHz, DMSO 13.12 (1H, s, NH), 11.78 (1H, s, NH), 9.12-9.07 (1H, m, $CH_{arom}$), 8.02 (1H, s, $CH_{arom}$), 7.45-740 (1H, m, $CH_{arom}$), 7.34-7.25 (1H, m, $CH_{arom}$), 4.32 (2H, q, $CH_2$), 1.34 (3H, t, $CH_3$).

8-Fluoro-4-oxo-4,5-dihydro-3H-pyrrolo[2,3-c]quinoline-1-carboxylate of 2-diethylaminoethyl (100)

104 mg (0.4 mmol) of 2-bromoethyl-diethylamine hydrobromide and 163 mg (0.5 mmol) of cesium carbonate are added to a solution of 123 mg (0.5 mmol) of 8-fluoro-4-oxo-4,5-dihydro-3H-pyrrolo[2,3-c]quinoline-1-carboxylic acid dissolved in 0.5 mL of dimethylformamide. The reaction mixture is stirred for 2 hours at room temperature then water is added and the solid is filtered. The latter is purified by chromatography on silica (eluent dichloromethane/methanol/triethylamine 95/5/0.1) then triturated in methanol to give 13 mg (7%) of 8-fluoro-4-oxo-4,5-dihydro-3H-pyrrolo[2,3-c]quinoline-1-2-diethylaminoethyl carboxylate in the form of a white solid.

LCMS (IE, m/z): (M+1) 345.97

$^1$H-NMR: $\delta_H$ ppm 400 MHz, DMSO 13.12 (1H, bs, NH), 11.77 (1H, s, NH), 9.08 (1H, d, $CH_{arom}$), 8.05-7.97 (1H, m, $CH_{arom}$), 7.47-7.41 (1H, m, $CH_{arom}$), 7.33-7.27 (1H, m, $CH_{arom}$), 4.42-4.28 (2H, m, $CH_2$), 2.87-2.70 (2H, m, $CH_2$), 2.66-2.45 (4H, m, 2×$CH_2$), 1.15-0.91 (6H, m, 2×$CH_3$).

8-Fluoro-4-oxo-4,5-dihydro-3H-pyrrolo[2,3-c]quinoline-1-carboxylic acid is prepared according to synthesis 75 from 403 mg (1.47 mmol) of 8-fluoro-4-oxo-4,5-dihydro-3H-pyrrolo[2,3-c]quinoline-1-ethyl carboxylate and 616 mg (14.7 mmol) of lithium hydroxide monohydrate to give, after acid-basic treatment, 365 mg (quantitative) of 8-fluoro-4-oxo-4,5-dihydro-3H-pyrrolo[2,3-c]quinoline-1-carboxylic acid in the form of a pale pink solid.

8-Acetyl-4-oxo-4,5-dihydro-3H-pyrrolo[2,3-c]quinoline-1-ethyl carboxylate (101)

This compound was synthesized according to synthesis 1, from 5-acetyl-1,3-dihydro-indol-2-one to give, after precipitation in 1N HCl and washing with water and with diisopropyl ether, 1.8 g (22% in two stages) of 8-acetyl-4-oxo-4,5-dihydro-3H-pyrrolo[2,3-c]quinoline-1-ethyl carboxylate in the form of a brown solid.

LCMS (IE, m/z): (M+1) 298.94

$^1$H-NMR: $\delta_H$ ppm 400 MHz, DMSO 13.13 (1H, bs, NH), 11.99 (1H, s, NH), 10.01 (1H, s, $CH_{arom}$), 8.04 (1H, s, $CH_{arom}$), 7.96 (1H, d, $CH_{arom}$), 7.47 (1H, d, $CH_{arom}$), 4.34 (2H, q, $CH_2$), 2.62 (3H, s, $CH_3$), 1.35 (3H, t, $CH_3$).

Synthesis of 5-acetyl-1,3-dihydro-indol-2-one is described by Peng Cho Tang (US2003/0069421 A1). This compound was prepared according to this procedure from 6.65 g (50 mmol) of 1,3-dihydro-indol-2-one, aluminium trichloride (150 mmol) and acetyl chloride (100 mmol) to give, after trituration in water and drying, 7.32 g (83%) of 5-acetyl-1,3-dihydro-indol-2-one in the form of a beige solid.

8-Benzoyl-4-oxo-4,5-dihydro-3H-pyrrolo[2,3-c]quinoline-1-ethyl carboxylate (102)

This compound was synthesized according to synthesis 1, from 5-benzoyl-1,3-dihydro-indol-2-one to give, after precipitation in 1N HCl and washing with water and with diisopropyl ether, 7 mg (3% in two stages) of 8-benzoyl-4-oxo-4,5-dihydro-3H-pyrrolo[2,3-c]quinoline-1-ethyl carboxylate in the form of a brown solid.

LCMS (IE, m/z): (M+1) 361.06

$^1$H-NMR: $\delta_H$ ppm 400 MHz, DMSO 13.14 (1H, bs, NH), 12.04 (1H, s, NH), 9.76 (1H, s, $CH_{arom}$), 8.02 (1H, s, $CH_{arom}$), 7.83-7.38 (7H, m, 7×$CH_{arom}$), 4.18 (2H, q, $CH_2$), 1.24 (3H, t, $CH_3$).

Synthesis of 5-benzoyl-1,3-dihydro-indol-2-one is described by McNutt (WO99/10325). This compound was prepared according to this procedure from 665 g (5 mmol) of 1,3-dihydro-indol-2-one, aluminium trichloride (15 mmol) and benzoyl chloride (10 mmol) to give, after trituration in water and drying, 880 mg (74%) of 5-benzoyl-1,3-dihydro-indol-2-one in the form of a beige solid.

8-[(4-Fluorophenyl)-methyl-sulfamoyl]-4-oxo-4,5-dihydro-3H-pyrrolo[2,3-c]quinoline-1-carboxylic acid (103)

This compound is prepared according to synthesis 75 from 412 mg (0.93 mmol) of 8-[(4-fluorophenyl)-methyl-sulfamoyl]-4-oxo-4,5-dihydro-3H-pyrrolo[2,3-c]quinoline-1-ethyl carboxylate and 360 mg (13.95 mmol) of lithium hydroxide monohydrate to give, after acid-basic treatment and precipitation in an acid aqueous phase (pH 5), 200 mg (52%) of 8-[(4-fluorophenyl)-methyl-sulfamoyl]-4-oxo-4,5-dihydro-3H-pyrrolo[2,3-c]quinoline-1-carboxylic acid in the form of a pale pink solid.

LCMS (IE, m/z): (M+1) 415.98

$^1$H-NMR: $\delta_H$ ppm 400 MHz, $CD_3OD$ 10.03 (1H, s, $CH_{arom}$), 8.08 (1H, s, $CH_{arom}$), 7.44 (2H, s, 2×$CH_{arom}$), 7.17-7.14 (2H, m, 2×$CH_{arom}$), 7.03 (2H, t, 2×$CH_{arom}$), 3.28 (3H, t, $NCH_3$).

8-[(4-Fluorophenyl)-methyl-sulfamoyl]-4-oxo-4,5-dihydro-3H-pyrrolo[2,3-c]quinoline-1-2-hydroxyethyl carboxylate (104)

5 μL of a 2M solution of hydrochloric acid in diethyl ether is added to a solution of 62 mg (0.15 mmol) of 8-[(4-fluorophenyl)-methyl-sulfamoyl]-4-oxo-4,5-dihydro-3H-pyrrolo[2,3-c]quinoline-1-carboxylic acid dissolved in 2 mL of ethylene glycol. The reaction mixture is stirred at 80° C. for 20 hours. Water is added and the compound is extracted with dichloromethane/methanol mixture (95/5). The organic phases are dried over magnesium sulfate, filtered and evaporated and the residue is purified by chromatography on silica (eluent dichloromethane/methanol 95/5) to give 25 mg (36%) of 8-[(4-fluorophenyl)-methyl-sulfamoyl]-4-oxo-4,5-dihydro-3H-pyrrolo[2,3-c]quinoline-1-2-hydroxyethyl carboxylate in the form of a brown product.

LCMS (IE, m/z): (M+1) 460.14

$^1$H-NMR: $\delta_H$ ppm 400 MHz, $CD_3OD$ 9.87 (1H, s, $CH_{arom}$), 8.23 (1H, s, $CH_{arom}$), 7.52-7.48 (2H, m, 2×$CH_{arom}$), 7.17-7.14 (2H, m, 2×$CH_{arom}$), 7.05-7.01 (2H, m, 2×$CH_{arom}$), 4.40 (2H, t, $OCH_2$), 3.91 (2H, t, $CH_2$), 3.26 (3H, t, $NCH_3$).

8-[(4-Fluorophenyl)-methyl-sulfamoyl]-4-oxo-4,5-dihydro-3H-pyrrolo[2,3-c]quinoline-1-2-aminoethyl trifluoroacetate carboxylate (105)

10 μL of trifluoroacetic acid is added to a solution of 5 mg (0.01 mmol) of 8-[(4-fluorophenyl)-methyl-sulfamoyl]-4-oxo-4,5-dihydro-3H-pyrrolo[2,3-c]quinoline-1-2-tert-butoxycarbonylaminoethyl carboxylate dissolved in 1 mL of dichloroethane. The solution is stirred for 18 hours at room temperature then the residue is recrystallized from dichloromethane/diethyl ether mixture to give 4 mg (80%) of 8-[(4-fluorophenyl)-methyl-sulfamoyl]-4-oxo-4,5-dihydro-3H-pyrrolo[2,3-c]quinoline-1-carboxylate of 2-aminoethyl trifluoroacetate in the form of a beige solid.

LCMS (IE, m/z): (M+1) 459.26

$^1$H-NMR: $\delta_H$ ppm 400 MHz, $CD_3OD$ 9.77 (1H, s, $CH_{arom}$), 8.29 (1H, s, $CH_{arom}$), 7.52-7.50 (2H, m, 2×$CH_{arom}$), 7.15-7.13 (2H, m, 2×$CH_{arom}$), 7.06-7.04 (2H, m, 2×$CH_{arom}$), 4.56 (2H, t, $OCH_2$), 3.61-3.59 (2H, m, $NCH_2$), 3.24 (3H, t, $NCH_3$).

2-tert-Butoxycarbonylaminoethyl 8-[(4-fluorophenyl)-methyl-sulfamoyl]-4-oxo-4,5-dihydro-3H-pyrrolo[2,3-c]quinoline-1-carboxylate (106)

7 mg (0.03 mmol) of 2-bromo-N-tert-butoxycarbonylethylamine and 19 mg (0.06 mmol) of cesium carbonate are added to a solution of 20 mg (0.05 mmol) of 8-[(4-fluorophenyl)-methyl-sulfamoyl]-4-oxo-4,5-dihydro-3H-pyrrolo[2,3-c]quinoline-1-carboxylic acid dissolved in 0.5 mL of dimethylformamide. The reaction mixture is stirred for 18 hours at room temperature then the solvents are evaporated. The residue is purified by chromatography on silica (eluent cyclohexane/ethyl acetate 2/8) then triturated in diethyl ether to give 5 mg (18%) of 3-tert-butoxycarbonylaminoethyl 8-[(4-fluorophenyl)-methyl-sulfamoyl]-4-oxo-4,5-dihydro-3H-pyrrolo[2,3-c]quinoline-1-carboxylate in the form of a white solid.

LCMS (IE, m/z): (M+1) 559.19

$^1$H-NMR: $\delta_H$ ppm 400 MHz, $CD_3OD$ 9.84 (1H, s, $CH_{arom}$), 8.16 (1H, s, $CH_{arom}$), 7.46-7.44 (2H, m, 2×$CH_{arom}$), 7.14-7.03 (2H, m, 2×$CH_{arom}$), 7.00-6.98 (2H, m, 2×$CH_{arom}$), 4.42 (2H, t, $OCH_2$), 3.60-3.45 (2H, m, NCH), 3.23 (3H, t, $NCH_3$), 1.41 (9H, s, t-Bu).

Trifluoroacetate of 8-[(4-fluorophenyl)-methyl-sulfamoyl]-4-oxo-4,5-dihydro-3H-pyrrolo[2,3-c]quinoline-1-3-aminopropyl carboxylate (107)

100 μL of trifluoroacetic acid is added to a solution of 45 mg (0.08 mmol) of 2-tert-butoxycarbonylaminopropyl 8-[(4-fluorophenyl)-methyl-sulfamoyl]-4-oxo-4,5-dihydro-3H-pyrrolo[2,3-c]quinoline-1-carboxylate dissolved in 1 mL of dichloroethane. The solution is stirred for 18 hours at room temperature then the residue is recrystallized in dichloromethane/diethyl ether mixture to give 12 mg (26%) of 8-[(4-fluorophenyl)-methyl-sulfamoyl]-4-oxo-4,5-dihydro-3H-pyrrolo[2,3-c]quinoline-1-carboxylate of 2-aminopropyl trifluoroacetate in the form of a beige solid.

LCMS (IE, m/z): (M+1) 473.21

$^1$H-NMR: $\delta_H$ ppm 400 MHz, $CD_3OD$ 9.71 (1H, s, $CH_{arom}$), 8.08 (1H, s, $CH_{arom}$), 7.45 (2H, dd, 2×$CH_{arom}$), 7.09-7.06 (2H, m, 2×$CH_{arom}$), 699-697 (2H, m, 2×$CH_{arom}$), 4.37 (2H, t, $OCH_2$), 3.17 (3H, t, $NCH_3$), 3.10-3.07 (2H, m, $NCH_2$), 2.11-2.09 (2H, m, $CH_2$).

3-tert-Butoxycarbonylamino-propyl 8-[(4-fluorophenyl)-methyl-sulfamoyl]-4-oxo-4,5-dihydro-3H-pyrrolo[2,3-c]quinoline-1-carboxylate (108)

9 mg (0.04 mmol) of 3-bromo-N-tert-butoxycarbonyl-propylamine and 8 mg (0.06 mmol) of potassium carbonate are added to a solution of 21 mg (0.05 mmol) of 8-[(4-fluorophenyl)-methyl-sulfamoyl]-4-oxo-4,5-dihydro-3H-pyrrolo[2,3-c]quinoline-1-carboxylic acid dissolved in 0.5 mL of dimethylformamide. The reaction mixture is stirred for 18 hours at room temperature then the solvents are evaporated. The residue is purified by chromatography on silica (eluent cyclohexane/ethyl acetate 2/8) then triturated in diethyl ether to give 6 mg (21%) of 3-tert-butoxycarbonylamino-propyl 8-[(4-fluorophenyl)-methyl-sulfamoyl]-4-oxo-4,5-dihydro-3H-pyrrolo[2,3-c]quinoline-1-carboxylate in the form of a white solid.

LCMS (IE, m/z): (M+1) 573.26

$^1$H-NMR: $\delta_H$ ppm 400 MHz, CD$_3$OD 9.72 (1H, s, CH$_{arom}$), 8.04 (1H, s, CH$_{arom}$), 7.39-7.36 (2H, m, 2×CH$_{arom}$), 7.05-7.02 (2H, m, 2×CH$_{arom}$), 693-6.91 (2H, m, 2×CH$_{arom}$), 4.25 (2H, t, OCH$_2$), 3.25 (2H, m, NCH$_2$), 3.14 (3H, t, NCH$_3$), 1.86-1.83 (2H, m, CH$_2$) 1.33 (9H, s, t-Bu).

N-Propyl-8-dimethylsulfamoyl-4-oxo-4,5-dihydro-3H-pyrrolo[2,3-c]quinoline-1-carboxamide (109)

This compound is prepared according to synthesis 79 from 100 mg (0.3 mmol) of 8-dimethylsulfamoyl-4-oxo-4,5-dihydro-3H-pyrrolo[2,3-c]quinoline-1-carboxylic acid and 27 µL (0.33 mmol) of propylamine to give, after purification by column chromatography (eluent dichloromethane/methanol/acetonitrile 90/5/5), 45 mg (40%) of N-propyl-8-dimethylsulfamoyl-4-oxo-4,5-dihydro-3H-pyrrolo[2,3-c]quinoline-1-carboxamide in the form of a white solid.

LCMS (IE, m/z): (M+1) 377.16

$^1$H-NMR: $\delta_H$ ppm 400 MHz, DMSO 12.79 (1H, bs, NH), 11.94 (1H, bs, NH), 9.62 (1H, d, CH$_{arom}$), 8.25 (1H, t, NH), 7.92 (1H, s, CH$_{arom}$), 7.69 (1H, dd, CH$_{arom}$), 7.54 (1H, d, CH$_{arom}$), 3.24 (2H, q, CH$_2$), 2.63 (6H, s, 2×CH$_3$), 1.56 (2H, sext, CH$_2$), 0.92 (3H, t, CH$_3$).

8-Dimethylsulfamoyl-4-oxo-4,5-dihydro-3H-pyrrolo[2,3-c]quinoline-1-carboxylic acid is prepared according to synthesis 178, from 326 mg (1 mmol) of 8-chlorosulfonyl-4-oxo-4,5-dihydro-3H-pyrrolo[2,3-c]quinoline-1-carboxylic acid and 85 mg (1.05 mmol) of dimethylamine hydrochloride to give, after purification by precipitation and trituration in water, 210 mg (62%) of 8-dimethylsulfamoyl-4-oxo-4,5-dihydro-3H-pyrrolo[2,3-c]quinoline-1-carboxylic acid in the form of a gray solid.

N-Methyl-N-propyl-8-dimethylsulfamoyl-4-oxo-4,5-dihydro-3H-pyrrolo[2,3-c]quinoline-1-carboxamide (110)

This compound is prepared according to synthesis 79 from 100 mg (0.3 mmol) of 8-dimethylsulfamoyl-4-oxo-4,5-dihydro-3H-pyrrolo[2,3-c]quinoline-1-carboxylic acid and 34 µL (0.33 mmol) of N-methyl-propylamine to give, after purification by column chromatography (eluent dichloromethane/methanol/acetonitrile 90/5/5), 46 mg (40%) of N-methyl-N-propyl-8-dimethylsulfamoyl-4-oxo-4,5-dihydro-3H-pyrrolo[2,3-c]quinoline-1-carboxamide in the form of a beige solid.

LCMS (IE, m/z): (M+1) 391.35

$^1$H-NMR: 4H ppm 400 MHz, DMSO 12.77 (1H, bs, NH), 11.93 (1H, bs, NH), 8.37-8.19 (1H, m, CH$_{arom}$), 7.69 (1H, dd, CH$_{arom}$), 7.65-7.56 (1H, m, CH$_{arom}$), 7.57 (1H, d, CH$_{arom}$), 3.50-3.34 (2H, m, CH$_2$), 3.01 (3H, tb, CH$_3$), 2.60 (6H, s, 2×CH$_3$), 1.75-1.37 (2H, m, CH$_2$), 1.01-0.53 (3H, m, CH$_3$).

8-Cyclohexylsulfamoyl-4-oxo-4,5-dihydro-3H-pyrrolo[2,3-c]quinoline-1-methyl carboxylate (111)

This compound was obtained by general method of esterification B from 258 mg (0.66 mmol) of 8-cyclohexylsulfamoyl-4-oxo-4,5-dihydro-3H-pyrrolo[2,3-c]quinoline-1-carboxylic acid and 995 µL (1.99 mmol) of a 2M solution of trimethylsilyldiazomethane in diethyl ether to give, after purification by chromatography on silica (eluent dichloromethane/methanol 98/2), 57 mg (21%) of 8-cyclohexylsulfamoyl-4-oxo-4,5-dihydro-3H-pyrrolo[2,3-c]quinoline-1-methyl carboxylate in the form of a white solid.

LC/MS (IE, m/z): (M+1) 404.05

$^1$H-NMR: $\delta_H$ ppm 400 MHz, DMSO 13.19 (1H, bs, NH), 12.04 (1H, bs, NH), 9.83 (1H, s, CH$_{arom}$), 8.07 (1H, s, CH$_{arom}$), 7.80 (1H, dd, CH$_{arom}$), 7.54-7.51 (2H, m, CH$_{arom}$, NH), 3.86 (3H, s, CH$_3$), 3.02 (1H, m, CH), 1.62-1.56 (4H, m, 2×CH$_2$), 1.42 (2H, m, CH), 1.14-0.99 (5H, m, CH$_2$ and CH$_3$).

314 µL (2.25 mmol) of triethylamine and 189 µL (1.65 mmol) of cyclohexylamine are added to 490 mg (1.5 mmol) of 8-chlorosulfonyl-4-oxo-4,5-dihydro-3H-pyrrolo[2,3-c]quinoline-1-carboxylic acid suspended in 4 mL of anhydrous dichloromethane and 1 mL of anhydrous dimethylformamide. The reaction mixture is stirred for 2 days at room temperature. The solvents are evaporated, and the residue is taken up in water. The solid is filtered, rinsed with water then diisopropyl ether and dried under vacuum to give 258 mg (44%) of 8-cyclohexylsulfamoyl-4-oxo-4,5-dihydro-3H-pyrrolo[2,3-c]quinoline-1-carboxylic acid in the form of a cream-coloured solid.

In a sealed tube, 1.42 g (4.5 mmol) of 4-oxo-4,5-dihydro-3H-pyrrolo[2,3-c]quinoline-1-ethyl carboxylate cocrystallized with one equivalent of acetic acid (synthesis 1) is dissolved in 6 mL (90 mmol) of chlorosulfonic acid. The reaction mixture is placed on an oil bath heated beforehand to 85° C. for 20 minutes, cooled on an ice bath then poured slowly onto crushed ice. The solid is filtered, rinsed with water, diisopropyl ether and pentane then dried under vacuum to give 1.47 g (quantitative) of 8-chlorosulfonyl-4-oxo-4,5-dihydro-3H-pyrrolo[2,3-c]quinoline-1-carboxylic acid in the form of a brown solid.

4-Oxo-8-(piperidin-3-ylsulfamoyl)-4,5-dihydro-3H-pyrrolo[2,3-c]quinoline-1-methyl carboxylate (112)

A 1M solution of hydrochloric acid in methanol (510 µL, 0.64 mmol) and 17 mg of palladium 10% on charcoal are added to a solution of 172 mg (0.32 mmol) of 8-(1-benzyloxycarbonyl-piperidin-3-ylsulfamoyl)-4-oxo-4,5-dihydro-3H-pyrrolo[2,3-c]quinoline-1-methyl carboxylate in 10 mL of methanol. The solution is stirred at room temperature for 5 days then filtered on celite. The filtrate is evaporated, the residue is taken up in dichloromethane and triethylamine is added to release the amine in the form of free base. The solvents are evaporated then the residue is purified by chromatography on silica (eluent chloroform/methanol/ammonia 150/25/4) to give 56 mg (43%) of 4-oxo-8-(piperidin-3-ylsulfamoyl)-4,5-dihydro-3H-pyrrolo[2,3-c]quinoline-1-methyl carboxylate in the form of a white solid.

LCMS (IE, m/z): (M+1) 405.05

$^1$H-NMR: $\delta_H$ ppm 400 MHz, DMSO 12.05 (1H, bs, NH), 9.84 (1H, d, CH$_{arom}$), 8.07 (1H, s, CH$_{arom}$), 7.81 (1H, dd, CH$_{arom}$), 7.63 (1H, bs, NH), 7.54 (1H, d, CH$_{arom}$), 3.86 (3H, s, CH$_3$), 3.09-3.00 (1H, m, CH$_{arom}$), 2.81 (1H, dd, CH$_{piper}$), 2.71 (1H, dd, CH$_{piper}$), 2.37-2.31 (1H, m, CH$_{piper}$), 2.28 (1H, dd, CH$_{piper}$), 1.68-1.60 (1H, m, CH$_{piper}$), 1.55-1.49 (1H, m, CH$_{piper}$), 1.28-1.21 (2H, m, 2×CH$_{piper}$).

8-(1-Benzyloxycarbonyl-piperidin-3-ylsulfamoyl)-4-oxo-4,5-dihydro-3H-pyrrolo[2,3-c]quinoline-1-methyl carboxylate is prepared according to synthesis 111, from 326 mg (1 mmol) of 8-chlorosulfonyl-4-oxo-4,5-dihydro-3H-pyrrolo[2,3-c]quinoline-1-carboxylic acid and 246 mg (1.05 mmol) of 3-amino-1-benzyloxycarbonyl-piperidine to give, after esterification according to general method B and purification by trituration in water, 172 mg (32% in two stages) of 8-(1-benzyloxycarbonyl-piperidin-3-ylsulfamoyl)-4-oxo-4,5-dihydro-3H-pyrrolo[2,3-c]quinoline-1-methyl carboxylate in the form of a white solid.

4-Oxo-8-(piperidin-4-ylsulfamoyl)-4,5-dihydro-3H-pyrrolo[2,3-c]quinoline-1-methyl carboxylate (113)

This compound is prepared according to synthesis 111, from 294 mg (0.9 mmol) of 8-chlorosulfonyl-4-oxo-4,5-dihydro-3H-pyrrolo[2,3-c]quinoline-1-carboxylic acid, 276 µL (1.99 mmol) of triethylamine and 224 mg (0.95 mmol) of 4-amino-1-tert-butoxycarbonyl-piperidine hydrochloride to give, after esterification according to general method A (using methanol as the alcohol) and purification by chromatography on silica (eluent chloroform/methanol/ammonia 90/25/4), 205 mg (52% in two stages) of 4-oxo-8-(piperidin-4-ylsulfamoyl)-4,5-dihydro-3H-pyrrolo[2,3-c]quinoline-1-methyl carboxylate in the form of a light yellow solid.

LCMS (IE, t/z): (M+1) 419.05
$^1$H-NMR: $\delta_H$ ppm 400 MHz, DMSO
13.21 (1H, bs, NH), 12.10 (1H, bs, NH), 9.84 (1H, d, $CH_{arom}$), 8.08 (1H, s, $CH_{arom}$), 7.92 (1H, d, NH), 7.83 (1H, dd, $CH_{arom}$), 7.57 (1H, d, $CH_{arom}$), 3.86 (3H, s, $CH_3$), 3.40-3.31 (1H, m, $CH_{piper}$), 3.19-3.10 (2H, m, 2×$CH_{piper}$), 2.91-2.80 (2H, m, 2×$CH_{piper}$), 1.84-1.74 (2H, m, 2×$CH_{piper}$), 1.65-1.54 (2H, m, 2×$CH_{piper}$).

4-Oxo-8-(piperidin-4-ylsulfamoyl)-4,5-dihydro-3H-pyrrolo[2,3-c]quinoline-1-propyl carboxylate (114)

107 µL (0.76 mmol) of triethylamine and 100 µL (0.61 mmol) of di-n-propylsulfate are added to a solution of 150 mg (0.3 mmol) of 8-(1-tert-butoxycarbonyl-piperidin-4-ylsulfamoyl)-4-oxo-4,5-dihydro-3H-pyrrolo[2,3-c]quinoline-1-carboxylic acid dissolved in 2 mL of anhydrous dimethylformamide. The solution is stirred at room temperature for 20 hours then 43 µL (0.3 mmol) of triethylamine and 51 µL (0.3 mmol) of di-n-propylsulfate are added again. Stirring is continued for a further 24 hours and 3 mL of ammonia is added. After stirring for a further 15 minutes, water is added and the product is extracted with dichloromethane. The organic phases are dried over magnesium sulfate, filtered then evaporated. The residue is dissolved in 2 mL of dichloroethane and 1 mL of trifluoroacetic acid. The solution is stirred at room temperature for 1 hour then the solvents are evaporated. The solid is taken up in dichloromethane then triethylamine is added to release the amine. The solvents are evaporated again and the residue is purified by chromatography on silica (eluent chloroform/methanol/ammonia 160/25/4) to give 44 mg (33% in two stages) of 4-oxo-8-(piperidin-4-ylsulfamoyl)-4,5-dihydro-3H-pyrrolo[2,3-c]quinoline-1-propyl carboxylate in the form of a white solid.

LCMS (IE, m/z): (M+1) 433.20
$^1$H-NMR: $\delta_H$ ppm 400 MHz, DMSO
9.82 (1H, d, $CH_{arom}$), 8.05 (1H, s, $CH_{arom}$), 7.80 (1H, dd, $CH_{arom}$), 7.58 (1H, dl, NH), 7.52 (1H, d, $CH_{arom}$), 4.25 (2H, t, $CH_2$), 3.13-3.04 (1H, m, $CH_{piper}$), 2.82-2.75 (2H, m, 2×$CH_{piper}$), 2.35-2.26 (2H, m, 2×$CH_{piper}$), 1.81-1.72 (2H, m, $CH_2$), 1.56-1.48 (2H, m, 2×$CH_{piper}$), 1.27-1.14 (2H, m, 2×$CH_{piper}$), 0.99 (3H, t, $CH_3$).

8-(1-tert-Butoxycarbonyl-piperidin-4-ylsulfamoyl)-4-oxo-4,5-dihydro-3H-pyrrolo[2,3-c]quinoline-1-carboxylic acid is prepared according to synthesis 178, from 2.1 g (6.45 mmol) of 8-chlorosulfonyl-4-oxo-4,5-dihydro-3H-pyrrolo[2,3-c]quinoline-1-carboxylic acid, 1.8 mL (12.9 mmol) of triethylamine and 1.29 g (6.45 mmol) of 4-amino-1-tert-butoxycarbonyl-piperidine to give, after purification by precipitation and trituration in water, 1.86 g (59%) of 8-(1-tert-butoxycarbonyl-piperidin-4-ylsulfamoyl)-4-oxo-4,5-dihydro-3H-pyrrolo[2,3-c]quinoline-1-carboxylic acid in the form of a beige solid.

4-Oxo-8-(piperidin-4-ylsulfamoyl)-4,5-dihydro-3H-pyrrolo[2,3-c]quinoline-1-carboxylate of butyl (115)

This compound is prepared according to synthesis 114, from 100 mg (0.2 mmol) of 8-(1-tert-butoxycarbonyl-piperidin-4-ylsulfamoyl)-4-oxo-4,5-dihydro-3H-pyrrolo[2,3-c]quinoline-1-carboxylic acid, 85 µL (0.61 mmol) of triethylamine and 102 µL (0.51 mmol) of di-n-butylsulfate to give, after purification by chromatography on silica (eluent chloroform/methanol/ammonia 160/25/4), 31 mg (34% in two stages) of 4-oxo-8-(piperidin-4-ylsulfamoyl)-4,5-dihydro-3H-pyrrolo[2,3-c]quinoline-1-butyl carboxylate in the form of a white solid.

LCMS (IE, m/z): (M+1) 447.01
$^1$H-NMR: $\delta_H$ ppm 400 MHz, DMSO
9.82 (1H, d, $CH_{arom}$), 8.04 (1H, s, $CH_{arom}$), 7.80 (1H, dd, $CH_{arom}$), 7.58 (1H, dl, NH), 7.52 (1H, d, $CH_{arom}$), 4.29 (2H, t, $CH_2$), 3.15-3.04 (1H, m, $CH_{piper}$), 2.83-2.75 (2H, m, 2×$CH_{piper}$), 2.35-2.26 (2H, m, 2×$CH_{piper}$), 1.77-1.69 (2H, m, $CH_2$), 1.56-1.49 (2H, m, 2×$CH_{piper}$), 1.48-1.40 (2H, m, $CH_2$), 1.27-1.15 (2H, m, 2×$CH_{piper}$), 0.95 (3H, t, $CH_3$).

4-Oxo-8-(piperidin-4-ylsulfamoyl)-4,5-dihydro-3H-pyrrolo[2,3-c]quinoline-1-cyclopentyl carboxylate (116)

This compound is prepared according to synthesis 114, from 150 mg (0.3 mmol) of 8-(1-tert-butoxycarbonyl-piperidin-4-ylsulfamoyl)-4-oxo-4,5-dihydro-3H-pyrrolo[2,3-c]quinoline-1-carboxylic acid, 322 µL (2.31 mmol) of triethylamine and 500 mg (2.13 mmol) of dicyclopentylsulfate to give, after purification by chromatography on silica (eluent chloroform/methanol/ammonia 160/25/4), 80 mg (42% in two stages) of 4-oxo-8-(piperidin-4-ylsulfamoyl)-4,5-dihydro-3H-pyrrolo[2,3-c]quinoline-1-cyclopentyl carboxylate in the form of a white solid.

LCMS (IE, m/z): (M+1) 459.19
$^1$H-NMR: $\delta_H$ ppm 400 MHz, DMSO
9.83 (1H, d, $CH_{arom}$), 8.02 (1H, s, $CH_{arom}$), 7.80 (1H, dd, $CH_{arom}$), 7.58 (1H, bs, NH), 7.52 (1H, d, $CH_{arom}$), 5.37-5.32 (1H, m, CH), 3.14-3.05 (1H, m, CH), 2.82-2.75 (2H, m, 2×CH), 2.35-2.26 (2H, m, 2×CH), 1.99-1.89 (2H, m, 2×CH), 1.86-1.72 (4H, m, 4×CH), 1.67-1.49 (4H, m, 4×CH), 1.27-1.15 (2H, m, 2×CH).

4-Oxo-8-(piperidin-4-ylsulfamoyl)-4,5-dihydro-3H-pyrrolo[2,3-c]quinoline-1-methylcyclohexyl carboxylate (117)

This compound is prepared according to synthesis 114, from 150 mg (0.3 mmol) of 8-(1-tert-butoxycarbonyl-piperidin-4-ylsulfamoyl)-4-oxo-4,5-dihydro-3H-pyrrolo[2,3-c]quinoline-1-carboxylic acid, 496 µL (3.56 mmol) of triethylamine and 975 mg (3.35 mmol) of dicyclohexylmethylsulfate to give, after purification by chromatography on silica (eluent chloroform/methanol/ammonia 160/25/4) then recrystallization from methanol, 11 mg (7% in two stages) of 4-oxo-8-(piperidin-4-ylsulfamoyl)-4,5-dihydro-3H-pyrrolo[2,3-c]quinoline-1-methylcyclohexyl carboxylate in the form of a white solid.

LCMS (IE, m/z): (M+1) 487.19

$^1$H-NMR: δ ppm 400 MHz, DMSO 12.01 (1H, bs, NH), 9.83 (1H, d, $CH_{arom}$), 8.05 (1H, s, $CH_{arom}$), 7.80 (1H, dd, $CH_{arom}$), 7.57 (1H, dl, NH), 7.52 (1H, d, $CH_{arom}$), 4.11 (2H, d, $CH_2$), 3.14-3.04 (1H, m, CH), 2.82-2.75 (2H, m, 2×CH), 2.35-2.26 (2H, m, 2×CH), 1.84-1.60 (6H, m, 6×CH), 1.55-1.47 (2H, m, 2×CH), 1.33-0.98 (7H, m, 7×CH).

4-Oxo-8-(piperidin-4-ylsulfamoyl)-4,5-dihydro-3H-pyrrolo[2,3-c]quinoline-1-methyltetrahydrofuran-3-yl carboxylate (118)

This compound is prepared according to synthesis 114, from 152 mg (0.31 mmol) of 8-(1-tert-butoxycarbonyl-piperidin-4-ylsulfamoyl)-4-oxo-4,5-dihydro-3H-pyrrolo[2,3-c]quinoline-1-carboxylic acid, 216 μL (1.55 mmol) of triethylamine and 372 mg (1.4 mmol) of di-(tetrahydrofuran-3-yl)-methylsulfate to give, after purification by chromatography on silica (eluent chloroform/methanol/ammonia 100/25/4), 19 mg (13% in two stages) of 4-oxo-8-(piperidin-4-ylsulfamoyl)-4,5-dihydro-3H-pyrrolo[2,3-c]quinoline-1-methyltetrahydrofuran-3-yl carboxylate in the form of a white solid.

LCMS (IE, m/z): (M+1) 475.13

$^1$H-NMR: $δ_H$ ppm 400 MHz, DMSO 12.02 (1H, bs, NH), 9.82 (1H, d, $CH_{arom}$), 8.08 (1H, s, $CH_{arom}$), 7.81 (1H, dd, $CH_{arom}$), 7.65 (1H, d, NH), 7.53 (1H, d, $CH_{arom}$), 4.28 (1H, dd, $CH_{ali}$), 4.20 (1H, dd, $CH_{ali}$), 3.84-3.75 (2H, m, 2×$CH_{ali}$), 3.70-3.63 (1H, m, $CH_{ali}$), 3.61-3.55 (1H, m, $CH_{ali}$), 3.17-3.07 (1H, m, $CH_{ali}$), 2.88-2.80 (2H, m, 2×$CH_{ali}$), 2.73-2.63 (1H, m, $CH_{ali}$), 2.44-2.33 (2H, m, 2×$CH_{ali}$), 2.10-2.00 (1H, m, $CH_{ali}$), 1.74-1.65 (1H, m, $CH_{ali}$), 1.60-1.50 (2H, m, 2×$CH_{ali}$), 1.31-1.18 (2H, m, 2×$CH_{ali}$).

8-(q-Methyl-piperidin-4-ylsulfamoyl)-4-oxo-4,5-dihydro-3H-pyrrolo[2,3-c]quinoline-1-cyclopentyl carboxylate (119)

83 μL (0.6 mmol) of triethylamine and 22 μL (0.24 mmol) of dimethylsulfate are added to a solution of 55 mg (0.12 mmol) of 4-oxo-8-(piperidin-4-ylsulfamoyl)-4-oxo-4,5-dihydro-3H-pyrrolo[2,3-c]quinoline-1-cyclopentyl carboxylate dissolved in 5 mL of anhydrous dimethylformamide. The solution is stirred at room temperature for 3 hours before adding 2 mL of ammonia. After stirring for a further 10 minutes, water is added and the product is extracted with ethyl acetate. The organic phases are dried over magnesium sulfate, filtered and evaporated. The residue is purified by chromatography on silica (eluent chloroform/methanol/ammonia 300/24/4) to give 22 mg (39%) of 8-(1-methyl-piperidin-4-ylsulfamoyl)-4-oxo-4,5-dihydro-3H-pyrrolo[2,3-c]quinoline-1-cyclopentyl carboxylate in the form of a white solid.

LCMS (IE, m/z): (M+1) 473.26

$^1$H-NMR: $δ_H$ ppm 400 MHz, $CD_3OD$ 10.04 (1H, d, $CH_{arom}$), 8.05 (1H, s, $CH_{arom}$), 7.90 (1H, dd, $CH_{arom}$), 7.55 (1H, d, $CH_{arom}$) 5.47-5.42 (1H, m, $CH_{ali}$), 3.55-3.47 (1H, m, $CH_{ali}$), 3.44-3.35 (2H, m, 2×$CH_{ali}$), 3.13-2.94 (2H, nm, 2×$CH_{ali}$), 2.80 (3H, s, $CH_3$), 2.15-1.97 (4H, m, 4×$CH_{ali}$), 1.96-1.65 (8H, m, 8×$CH_{ali}$).

8-(Methyl-piperidin-4-yl-sulfamoyl)-4-oxo-4,5-dihydro-3H-pyrrolo[2,3-c]quinoline-1-propyl carboxylate (120)

This compound is prepared according to synthesis 114, from 294 mg (0.6 mmol) of 8-[(4-tert-butoxycarbonyl-cyclohexyl)-methyl-sulfamoyl]-4-oxo-4,5-dihydro-3H-pyrrolo[2, 3-c]quinoline-1-carboxylic acid, 418 μL (3 mmol) of triethylamine and 345 μL (2.1 mmol) of di-n-propylsulfate to give, after purification by chromatography on silica (eluent chloroform/methanol/ammonia 220/25/4), 80 mg (30% in two stages) of 8-(methyl-piperidin-4-yl-sulfamoyl)-4-oxo-4,5-dihydro-3H-pyrrolo[2,3-c]quinoline-1-propyl carboxylate in the form of a white solid.

LCMS (IE, m/z): (M+1) 447.08

$^1$H-NMR: $δ_H$ ppm 400 MHz, DMSO 9.83 (1H, d, $CH_{arom}$), 8.06 (1H, s, $CH_{arom}$), 7.78 (1H, dd, $CH_{arom}$), 7.53 (1H, d, $CH_{arom}$), 4.25 (2H, t, $CH_2$), 3.86-3.75 (1H, m, $CH_{piper}$), 2.85 (2H, d, 2×$CH_{piper}$), 2.69 (3H, s, $CH_3$), 2.41 (2H, t, 2×$CH_{piper}$), 1.75 (2H, sex, $CH_2$), 1.45-1.33 (2H, m, 2×$CH_{piper}$), 1.22 (2H, d, 2×$CH_{piper}$), 0.99 (3H, 1, $CH_3$).

8-[(4-tert-Butoxycarbonyl-cyclohexyl)-methyl-sulfamoyl]-4-oxo-4,5-dihydro-3H-pyrrolo[2,3-c]quinoline-1-carboxylic acid is prepared according to synthesis 178, from 653 mg (2 mmol) of 8-chlorosulfonyl-4-oxo-4,5-dihydro-3H-pyrrolo[2,3-c]quinoline-1-carboxylic acid, 334 mL (2.4 mmol) of triethylamine and 557 mg (2.6 mmol) of 4-methylamino-1-tert-butoxycarbonyl-piperidine to give, after purification by precipitation and trituration in water, 770 mg (76%) of 8-[(4-tert-butoxycarbonyl-cyclohexyl)-methyl-sulfamoyl]-4-oxo-4,5-dihydro-3H-pyrrolo[2,3-c]quinoline-1-carboxylic acid in the form of a beige solid.

3.8 mL (13 mmol) of titanium isopropoxide and 2 g (10 mmol) of 1-tert-butoxycarbonyl-piperidine-4-one are added to 3.7 mL (30 mmol) of a 33% solution of methylamine in ethanol. The solution is stirred for 5 hours at room temperature then 378 mg (10 mmol) of sodium borohydride is added. Stirring is continued for a further 2 hours then 2 mL of water is added. The reaction mixture is filtered then the solvents are evaporated to give 1.18 g (55%) of 4-methylamino-1-tert-butoxycarbonyl-piperidine in the form of an oil.

4-Oxo-8-[(piperidin-4-ylmethyl)-sulfamoyl]-4,5-dihydro-3H-pyrrolo[2,3-c]quinoline-1-ethyl carboxylate (121)

This compound is prepared according to synthesis 25, from 433 mg (1.32 mmol) of 8-chlorosulfonyl-4-oxo-4,5-dihydro-3H-pyrrolo[2,3-c]quinoline-1-carboxylic acid, 276 μL (1.99 mmol) of triethylamine and 313 mg (1.46 mmol) of 4-aminomethyl-1-tert-butoxycarbonyl-piperidine to give, after purification by chromatography on silica (eluent chloroform/methanol/ammonia 65/25/4) then by preparative LC, 13 mg (2% in two stages) of 4-oxo-8-[(piperidin-4-ylmethyl)-sulfamoyl]-4,5-dihydro-3H-pyrrolo[2,3-c]quinoline-1-ethyl carboxylate in the form of a beige solid.

LCMS (IE, m/z): (M+1) 433.09

$^1$H-NMR: $δ_H$ ppm 400 MHz, DMSO 13.21 (1H, bs, NH), 12.06 (1H, bs, NH), 9.79 (1H, d, $CH_{arom}$), 8.45 (1H, m, NH), 8.10 (1H, bs, NH), 8.06 (1H, d, $CH_{arom}$), 7.79 (1H, dd, $CH_{arom}$), 7.65 (1H, t, NH), 7.55 (1H, d, $CH_{arom}$), 4.33 (2H, q, $CH_2$), 3.28-3.20 (2H, m, 2×$CH_{piper}$), 2.87-2.75 (2H, m, 2×$CH_{piper}$), 2.72 (2H, t, $CH_2$), 1.83-1.75 (2H, m, 2×$CH_{piper}$), 1.73-1.63 (1H, m, $CH_{piper}$), 1.36 (3H, t, $CH_3$), 1.28-1.16 (2H, m, 2×$CH_{piper}$).

8-(8-Aza-bicyclo[3.2.1]oct-3-ylsulfamoyl)-4-oxo-4,5-dihydro-3H-pyrrolo[2,3-c]quinoline-1-ethyl carboxylate (122)

4 mg of activated Pd 10% on charcoal is added to a solution of 75 mg (0.14 mmol) of 8-(8-benzyl-8-aza-bicyclo[3.2.1]oct-3-ylsulfamoyl)-4-oxo-4,5-dihydro-3H-pyrrolo[2,3-c]quinoline 1-ethyl carboxylate dissolved in 15 mL of ethanol.

The solution is stirred under a hydrogen atmosphere at room temperature for 18 hours then filtered on celite. The filtrate is evaporated and the residue is purified by chromatography on silica (eluent dichloromethane/methanol/ammonia 200/25/4) to give 20 mg (32%) of 8-(8-aza-bicyclo[3.2.1]oct-3-ylsulfamoyl)-4-oxo-4,5-dihydro-3H-pyrrolo[2,3-c]quinoline-1-ethyl carboxylate in the form of a brown solid.

LCMS (IE, m/z): (M+1) 444.97

$^1$H-NMR: $\delta_H$ ppm 400 MHz, DMSO 9.85 (1H, s, $CH_{arom}$), 8.06 (1H, s, $CH_{arom}$), 7.77 (1H, dd, $CH_{arom}$), 7.52 (1H, d, $CH_{arom}$), 7.42 (1H, d, NH), 4.33 (2H, dd, $OCH_2$), 2.41-2.51 (3H, m, 3×CH), 3.14 (3H, t, $CH_3$), 1.52-1.24 (8H, m, 8×CH) 0.92 (3H, t, $CH_3$).

8-(8-Benzyl-8-aza-bicyclo[3.2.1]oct-3-ylsulfamoyl)-4-oxo-4,5-dihydro-3H-pyrrolo[2,3-c]quinoline-1-ethyl carboxylate is prepared according to synthesis 111, from 360 mg (1.1 mmol) of 8-chlorosulfonyl-4-oxo-4,5-dihydro-3H-pyrrolo[2,3-c]quinoline-1-carboxylic acid and 238 mg (1.1 mmol) of 8-benzyl-8-aza-bicyclo[3.2.1]oct-3-ylamine to give, after esterification according to general method C (using diethylsulfate as the dialkylsulfate) and precipitation in water, 411 mg (69% in two stages) of 8-(8-benzyl-8-aza-bicyclo[3.2.1]oct-3-ylsulfamoyl)-4-oxo-4,5-dihydro-3H-pyrrolo[2,3-c]quinoline-1-ethyl carboxylate in the form of a brown solid.

8-Cyclopropylsulfamoyl-4-oxo-4,5-dihydro-3H-pyrrolo[2,3-c]quinoline-1-ethyl carboxylate (123)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 73 µL (1.05 mmol) of cyclopropylamine to give, after esterification according to general method C (using diethylsulfate as the dialkylsulfate) and purification by chromatography on silica (eluent dichloromethane/methanol 97/3), 85 mg (23% in two stages) of 8-cyclopropylsulfamoyl-4-oxo-4,5-dihydro-3H-pyrrolo[2,3-c]quinoline-1-ethyl carboxylate in the form of a light yellow solid.

LCMS (IE, m/z): (M+1) 376.07

$^1$H-NMR: $\delta_S$ ppm 400 MHz, DMSO 13.16 (1H, bs, NH), 12.06 (1H, bs, NH), 9.83 (1H, d, $CH_{arom}$), 8.05 (1H, s, $CH_{arom}$), 7.83-7.78 (2H, m, NH and $CH_{arom}$), 7.56 (1H, d, $CH_{arom}$), 4.33 (2H, q, $CH_2$), 2.20-2.12 (1H, m, $CH_{cyclopro}$), 1.36 (3H, t, $CH_3$), 0.51-0.44 (2H, m, 2×$CH_{cyclopro}$), 0.41-0.36 (2H, m, 2×$CH_{cyclopro}$).

8-Cyclopropylsulfamoyl-4-oxo-4,5-dihydro-3H-pyrrolo[2,3-c]quinoline-1-propyl carboxylate (124)

This compound is prepared according to synthesis 111, from 1.47 g (4.5 mmol) of 8-chlorosulfonyl-4-oxo-4,5-dihydro-3H-pyrrolo[2,3-c]quinoline-1-carboxylic acid and 624 µL (9 mmol) of cyclopropylamine to give, after esterification according to general method C (using di-n-propylsulfate as the dialkylsulfate) and purification by chromatography on silica (eluent dichloromethane/methanol 98/2 then 90/10), 99 mg (6% in two stages) of 8-cyclopropylsulfamoyl-4-oxo-4,5-dihydro-3H-pyrrolo[2,3-c]quinoline-1-propyl carboxylate in the form of a white solid.

LC/MS (IE, m/z): (M+1) 390.12

$^1$H-NMR: $\delta_H$ ppm 400 MHz, DMSO 13.21 (1H, bs, NH), 12.07 (1H, bs, NH), 9.85 (1H, s, $CH_{arom}$), 8.06 (1H, s, $CH_{arom}$), 7.80 (2H, m, NH and $CH_{arom}$), 7.56 (1H, d, $CH_{arom}$), 4.24 (2H, q, $CH_2$), 2.20-2.05 (1H, m, $CH_{cycloprop}$), 1.87-1.67 (2H, m, $CH_2$), 0.99 (3H, t, $CH_3$), 0.58-0.28 (4H, m, 4×$CH_{cycloprop}$).

8-(Cyclopropyl-methyl-sulfamoyl)-4-oxo-4,5-dihydro-3H-pyrrolo[2,3-c]quinoline-1-propyl carboxylate (125)

This compound is prepared according to synthesis 111, from 196 mg (0.6 mmol) of 8-chlorosulfonyl-4-oxo-4,5-dihydro-3H-pyrrolo[2,3-c]quinoline-1-carboxylic acid, 485 µL (4.8 mmol) of triethylamine and 62 mg (0.9 mmol) of N-methyl-cyclopropylamine hydrochloride to give, after esterification according to general method C (using di-n-propylsulfate as the dialkylsulfate) and purification by chromatography on silica (eluent dichloromethane/methanol 97/3) then trituration in diethyl ether, 100 mg (41% in two stages) of 8-(cyclopropyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 404.12

$^1$H-NMR: $\delta_H$ ppm 400 MHz, DMSO 13.23 (1H, bs, NH), 12.31 (1H, bs, NH), 9.85 (1H, s, $CH_{arom}$), 8.07 (1H, s, $CH_{arom}$), 7.80 (1H, dd, $CH_{arom}$), 7.60 (1H, d, $CH_{arom}$), 4.25 (2H, t, $OCH_2$), 2.70 (3H, s, $NCH_3$), 1.84-1.83 (1H, m, $CH_{cycloprop}$) 1.83-1.78 (2H, m, $CH_2$), 1.78-1.73 (2H, m, $CH_2$), 1.00 (3H, t, $CH_3$), 0.80-0.77 (4H, m, 4×$CH_{cycloprop}$).

In a sealed tube, a solution of 1.14 g (20 mmol) of cyclopropylamine in 5 mL of ethylformate is heated at 60° C. for 5 hours. The solvents are evaporated and the residue is added in portions to a solution of 1.07 g (28 mmol) of lithium aluminium hydride in 100 mL of anhydrous tetrahydrofuran. The reaction mixture is stirred at room temperature for 18 hours. Methanol is added and the reaction mixture is filtered on celite. 10 mL (20 mmol) of a 2M solution of hydrochloric acid in diethyl ether is added to the filtrate. The solvents are evaporated to give 1.5 g (74%) of N-methylcyclopropylamine hydrochloride in the form of an oil.

8-[(2-Cyano-ethyl)-methyl-sulfamoyl]-4-oxo-4,5-dihydro-3H-pyrrolo[2,3-c]quinoline-1-propyl carboxylate (126)

This compound is prepared according to synthesis 111, from 163 mg (0.5 mmol) of 8-chlorosulfonyl-4-oxo-4,5-dihydro-3H-pyrrolo[2,3-c]quinoline-1-carboxylic acid and 29 mg (0.5 mmol) of 3-methylamino-propionitrile to give, after esterification according to general method C (using di-n-propylsulfate as the dialkylsulfate) and purification by chromatography on silica (eluent dichloromethane/methanol 97/3) then trituration in diethyl ether, 30 mg (14% in two stages) of 8-[(2-cyano-ethyl)-methyl-sulfamoyl]-4-oxo-4,5-dihydro-3H-pyrrolo[2,3-c]quinoline-1-propyl carboxylate in the form of a white solid.

LCMS (IE, m/z): (M+1) 416.95

$^1$H-NMR: $\delta_H$ ppm 400 MHz, DMSO 13.13 (1H, bs, NH), 9.82 (1H, s, $CH_{arom}$), 8.08 (1H, s, $CH_{arom}$), 7.82 (1H, dd, $CH_{arom}$), 7.58 (1H, d, $CH_{arom}$), 4.26 (2H, t, $OCH_2$), 3.31-3.28 (2H, m, $CH_2$), 2.83-2.81 (2H, m, $NCH_2$), 2.75 (3H, s, $NCH_3$), 1.77-1.75 (2H, dd, $CH_2$), 1.00 (3H, t, $CH_3$).

8-[(2-Cyano-ethyl)-cyclopropyl-sulfamoyl]-4-oxo-4,5-dihydro-3H-pyrrolo[2,3-c]quinoline-1-ethyl carboxylate (127)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 118 µL (1.05 mmol) of 3-cyclopropylamino-propionitrile to give, after esterification according to general method C (using diethylsulfate as the dialkylsulfate) and purification by chromatography on silica (eluent dichloromethane/methanol 97/3), 60 mg (14% in two stages) of 8-[(2-cyano-ethyl)-cyclopropyl-sulfamoyl]-4-oxo-4,5-dihydro-3H-pyrrolo[2,3-c]quinoline-1-ethyl carboxylate in the form of a white solid.

LCMS (IE, m/z): (M+1) 429.13

$^1$H-NMR: $\delta_H$ ppm 400 MHz, DMSO 13.23 (1H, bs, NH), 12.13 (1H, bs, NH), 9.88 (1H, d, $CH_{arom}$), 8.07 (1H, s, $CH_{arom}$), 7.85 (1H, dd, $CH_{arom}$), 7.59 (1H, d, $CH_{arom}$), 4.33 (2H, q, $CH_2$), 3.41 (2H, t, $CH_2$), 2.84 (2H, t, $CH_2$), 2.08-2.01 (1H, m, $CH_{ali}$), 1.35 (3H, t, $CH_3$), 0.90-0.82 (2H, m, 2×$CH_{ali}$), 0.77-0.70 (2H, m, 2×$CH_{ali}$).

8-(Cyanomethyl-methyl-sulfamoyl)-4-oxo-4,5-dihydro-3H-pyrrolo[2,3-c]quinoline-1-propyl carboxylate (128)

This compound is prepared according to synthesis 111, from 294 mg (0.9 mmol) of 8-chlorosulfonyl-4-oxo-4,5-dihydro-3H-pyrrolo[2,3-c]quinoline-1-carboxylic acid, 273 µL (2.7 mmol) of triethylamine and 143 mg (1.35 mmol) of methylaminoacetonitrile to give, after esterification according to general method C (using di-n-propylsulfate as the dialkylsulfate) and purification by chromatography on silica (eluent dichloromethane/methanol 99/1 to 95/5), 137 mg (38% in two stages) of 8-(cyanomethyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 403.10

$^1$H-NMR: $\delta_H$ ppm 400 MHz, DMSO 13.24 (1H, bs, NH), 12.12 (1H, s, NH), 9.86 (1H, d, $CH_{arom}$), 8.07 (1H, s, $CH_{arom}$), 7.82 (1H, dd, $CH_{arom}$), 7.59 (1H, d, $CH_{arom}$), 4.40 (2H, s, $CH_2$), 4.24 (2H, t, $CH_2$), 2.84 (3H, s, $CH_3$), 1.80-1.71 (2H, m, $CH_2$), 0.99 (3H, t, $CH_3$).

8-[1,3]Dioxolan-2-ylmethyl-methyl-sulfamoyl)-4-oxo-4,5-dihydro-3H-pyrrolo[2,3-c]quinoline-1-propyl carboxylate (129)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid, 117 mg (1 mmol) of [1,3]dioxolan-2-ylmethyl-methyl-amine to give, after esterification according to general method C (using di-n-propylsulfate as the dialkylsulfate) and purification by chromatography on silica (eluent dichloromethane/methanol 97/3), 100 mg (21% in two stages) of 8-([1,3]dioxolan-2-ylmethyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 449.95

$^1$H-NMR: $\delta_H$ ppm 400 MHz, DMSO 12.09 (1H, bs, NH), 9.81 (1H, s, $CH_{arom}$), 8.07 (1H, x, $CH_{arom}$), 7.80 (1H, dd, $CH_{arom}$), 7.87 (1H, d, $CH_{arom}$), 4.99 (1H, t, CH), 4.45 (2H, t, $OCH_2$), 3.89-3.78 (4H, m, $OCH_2CH_2O$), 3.13 (2H, d, $CH_2$), 2.80 (3H, s, $NCH_3$), 1.78-1.73 (2H, m, $CH_2$), 0.98 (3H, t, $CH_3$).

8-[(1-Benzhydryl-azetidin-3-yl)-methyl-sulfamoyl]-4-oxo-4,5-dihydro-3H-pyrrolo[2,3-c]quinoline-1-propyl carboxylate (130)

This compound is prepared according to synthesis 111, from 196 mg (0.6 mmol) of 8-chlorosulfonyl-4-oxo-4,5-dihydro-3H-pyrrolo[2,3-c]quinoline-1-carboxylic acid, 334 µL (2.4 mmol) of triethylamine and 50 mg (0.72 mmol) of (1-benzhydryl-azetidin-3-yl)-methylamine hydrochloride (prepared according to the method described by Okada Tetsuo et al., Chem. Pharm. Bull., 1993, 41(1), 126-31) to give, after esterification according to general method C (using di-n-propylsulfate as the dialkylsulfate) and purification by chromatography on silica (eluent dichloromethane/methanol 97/3), 60 mg (17% in two stages) of 8-[(1-benzhydryl-azetidin-3-yl)-methyl-sulfamoyl]-4-oxo-4,5-dihydro-3H-pyrrolo[2,3-c]quinoline-1-propyl carboxylate in the form of a white solid.

LCMS (IE, m/z): (M+1) 627.53

$^1$H-NMR: $\delta_H$ ppm 400 MHz, DMSO 13.24 (1H, bs, NH), 12.08 (1H, bs, NH), 9.76 (1H, s, $CH_{arom}$), 8.08 (1H, s, $CH_{arom}$), 7.73 (1H, dd, $CH_{arom}$), 7.56 (1H, d, $CH_{arom}$), 7.38 (4H, dd, $CH_{arom}$), 7.26-7.22 (4H, m, $CH_{arom}$), 7.18-7.16 (2H, m, 2×$CH_{arom}$), 4.42 (1H, s, CH), 4.23 (2H, t, $OCH_2$), 3.74 (1H, quin, CH), 3.35 (2H, t, $NCH_2$), 2.90 (2H, t, $NCH_2$), 2.59 (3H, s, $NCH_3$), 1.80-1.75 (2H, m, $CH_{arom}$), 1.05-1.01 (3H, m, $CH_3$).

8-[Methyl-(tetrahydro-thiopyran-4-yl)-sulfamoyl]-4-oxo-4,5-dihydro-3H-pyrrolo[2,3-c]quinoline-1-propyl carboxylate (131)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid, 558 µL (4 mmol) of triethylamine and 168 mg (1 mmol) of methyl-(tetrahydro-thiopyran-4-yl)-amine hydrochloride to give, after esterification according to general method C (using di-n-propylsulfate as the dialkylsulfate) and purification by chromatography on silica (eluent dichloromethane/methanol 97/3) then trituration in diethyl ether, 140 mg (30% in two stages) of 8-[methyl-(tetrahydro-thiopyran-4-yl)-sulfamoyl]-4-oxo-4,5-dihydro-3H-pyrrolo[2,3-c]quinoline-1-propyl carboxylate in the form of a white solid.

LCMS (IE, t/z): (M+1) 464.13

$^1$H-NMR: $\delta_H$ ppm 400 MHz, DMSO 12.09 (1H, bs, NH), 9.86 (1H, s, $CH_{arom}$), 8.26 (1H, s, $CH_{arom}$), 7.80 (1H, dd, $CH_{arom}$), 7.52 (1H, d, $CH_{arom}$), 4.26 (2H, t, $OCH_2$), 3.80 (1H, quin, CH), 2.71 (3H, s, $NCH_3$), 2.50-2.52 (4H, m, 2×$CH_2$), 1.77 (2H, q, $CH_2$), 1.68-1.62 (1H, m, 2×$CH_2$), 1.00 (3H, t, $CH_3$).

4 mL (13.2 mmol) of titanium isopropoxide and 1.16 g (10 mmol) of tetrahydro-thiopyran-4-one are added to 3.7 mL (30 mmol) of a 33% solution of methylamine in ethanol. The solution is stirred for 5 hours at room temperature then 378 mg (10 mmol) of sodium borohydride is added. Stirring is continued for a further 2 hours then 2 mL of water is added. The reaction mixture is filtered then the solvents are evaporated. The residue is taken up in diethyl ether then a 2M solution of hydrochloric acid in diethyl ether is added. The solid is filtered and washed with diethyl ether to give 920 mg (55%) of N-methyl-(tetrahydro-thiopyran-4-yl)-amine hydrochloride in the form of a brown solid.

8-[(1,1-Dioxo-hexahydro-1,6-thiopyran-4-yl)-methyl-sulfamoyl]-4-oxo-4,5-dihydro-3H-pyrrolo[2,3-c]quinoline-1-propyl carboxylate (132)

307 mg (0.5 mmol) of Oxone is added to a solution of 46 mg (0.1 mmol) of 8-[methyl-(tetrahydro-thiopyran-4-yl)-sulfamoyl]-4-oxo-4,5-dihydro-3H-pyrrolo[2,3-c]quinoline-1-propyl carboxylate dissolved in methanol (2 mL). The solution is stirred at room temperature for 48 hours. The solvents are evaporated then the residue is taken up in water. The solid is filtered then purified by chromatography on silica (eluent dichloromethane/methanol 97/3) then triturated in methanol to give 36 mg (72%) of 8-[(1,1-dioxo-hexahydro-1,6-thiopyran-4-yl)-methyl-sulfamoyl]-4-oxo-4,5-dihydro-3H-pyrrolo[2,3-c]quinoline-1-propyl carboxylate in the form of a white solid.

LCMS (IE, m/z): (M+1) 496.03
$^1$H-NMR: $\delta_H$ ppm 400 MHz, DMSO
13.23 (1H, bs, NH), 12.09 (1H, bs, NH), 9.82 (1H, s, $CH_{arom}$), 8.08 (1H, s, $CH_{arom}$), 7.84 (1H, d, $CH_{arom}$), 7.55 (1H, d, $CH_{arom}$), 4.29-4.18 (3H, m, $CH_2$ and CH), 3.02 (2H, d, $CH_2$), 2.73 (3H, s, $NCH_3$), 2.05 (2H, d, $CH_2$), 1.73-1.67 (4H, m, 2×$CH_2$), 1.00 (3H, t, $CH_3$).

8-[Methyl-(tetrahydro-pyran-4-yl)-sulfamoyl]-4-oxo-4,5-dihydro-3H-pyrrolo[2,3-c]quinoline-1-propyl carboxylate (133)

This compound is prepared according to synthesis 111, from 163 mg (0.5 mmol) of 8-chlorosulfonyl-4-oxo-4,5-dihydro-3H-pyrrolo[2,3-c]quinoline-1-carboxylic acid, 278 µL (2 mmol) of triethylamine and 76 mg (0.54 mmol) of methyl-(tetrahydro-pyran-4-yl)-amine hydrochloride to give, after esterification according to general method C (using di-n-propylsulfate as the dialkylsulfate) and purification by chromatography on silica (eluent dichloromethane/methanol 97/3) then trituration in diethyl ether, 40 mg (18% in two stages) of 8-[methyl-(tetrahydro-pyran-4-yl)-sulfamoyl]-4-oxo-4,5-dihydro-3H-pyrrolo[2,3-c]quinoline-1-propyl carboxylate in the form of a white solid.

LCMS (IE, m/z): (M+1) 448.39
$^1$H-NMR: $\delta_H$ ppm 400 MHz, DMSO
13.22 (1H, bs, NH), 12.07 (1H, bs, NH), 9.85 (1H, s, $CH_{arom}$), 8.07 (1H, s, $CH_{arom}$), 7.81 (1H, dd, $CH_{arom}$), 7.54 (1H, d, $CH_{arom}$), 4.26 (2H, t, $CH_2$), 4.12-4.00 (1H, m, CH), 3.78 (2H, dd, $CH_2$), 3.32-3.30 (2H, m, $CH_2$), 2.71 (3H, s, $NCH_3$), 1.82-1.76 (2H, m, $CH_2$), 1.75-1.55 (2H, m, $CH_2$), 1.59 (2H, dd, $CH_2$), 1.01 (3H, t, $CH_3$). 4 mL (13.2 mmol) of titanium isopropoxide and 1 g (10 mmol) of tetrahydro-pyran-4-one are added to 3.7 mL (30 mmol) of a 33% solution of methylamine in ethanol. The solution is stirred for 5 hours at room temperature then 378 mg (10 mmol) of sodium borohydride is added. Stirring is continued for a further 2 hours then 2 mL of water is added. The reaction mixture is filtered then the solvents are evaporated. The residue is taken up in diethyl ether then a 2M solution of hydrochloric acid in diethyl ether is added. The solid is filtered and washed with diethyl ether to give 400 mg (26%) of N-methyl-(tetrahydro-pyran-4-yl)-amine hydrochloride in the form of a brown solid.

8-(Methyl-prop-2-ynyl-sulfamoyl)-4-oxo-4,5-dihydro-3H-pyrrolo[2,3-c]quinoline-1-propyl carboxylate (134)

This compound is prepared according to synthesis 111, from 196 mg (0.6 mmol) of 8-chlorosulfonyl-4-oxo-4,5-dihydro-3H-pyrrolo[2,3-c]quinoline-1-carboxylic acid, 242 µL (2.4 mmol) of triethylamine and 45 mg (0.66 mmol) of N-methyl-prop-2-ynyl-amine to give, after esterification according to general method C (using di-n-propylsulfate as the dialkylsulfate) and purification by chromatography on silica (eluent dichloromethane/methanol 97/3) then trituration in diethyl ether, 80 mg (33% in two stages) of 8-(methyl-prop-2-ynyl-sulfamoyl)-4-oxo-4,5-dihydro-3H-pyrrolo[2,3-c]quinoline-1-propyl carboxylate in the form of a white solid.

LCMS (IE, m/z): (M+1) 401.96
$^1$H-NMR: $\delta_H$ ppm 400 MHz, DMSO 13.22 (1H, bs, NH), 12.08 (1H, bs, NH), 9.82 (1H, s, $CH_{arom}$), 8.07 (1H, s, $CH_{arom}$), 7.79 (1H, dd, $CH_{arom}$), 7.56 (1H, d, $CH_{arom}$), 4.25 (2H, t, $OCH_2$), 4.01 (2H, s, $NCH_2$), 3.07 (1H, s, CH), 2.77 (3H, s, $NCH_3$), 1.80-1.75 (2H, m, $CH_2$), 1.00 (3H, t, $CH_3$).

8-[Methyl-(2-methylsulfanyl-ethyl)-sulfamoyl]-4-oxo-4,5-dihydro-3H-pyrrolo[2,3-c]quinoline-1-propyl carboxylate (135)

This compound is prepared according to synthesis 111, from 196 mg (0.6 mmol) of 8-chlorosulfonyl-4-oxo-4,5-dihydro-3H-pyrrolo[2,3-c]quinoline-1-carboxylic acid, 242 µL (2.4 mmol) of triethylamine and 102 mg (0.72 mmol) of N-methyl-(2-methylsulfanyl-ethyl)-amine hydrochloride to give, after esterification according to general method C (using di-n-propylsulfate as the dialkylsulfate) and purification by chromatography on silica (eluent dichloromethane/methanol 97/3) then trituration in diethyl ether, 80 mg (30% in two stages) of 8-[methyl-(2-methylsulfanyl-ethyl)-sulfamoyl]-4-oxo-4,5-dihydro-3H-pyrrolo[2,3-c]quinoline-1-propyl carboxylate in the form of a white solid.

LCMS (IE, m/z): (M+1) 438.10
$^1$H-NMR: $\delta_H$ ppm 400 MHz, DMSO
13.22 (1H, bs, NH), 12.08 (1H, bs, NH), 9.81 (1H, s, $CH_{arom}$), 8.07 (1H, s, $CH_{arom}$), 7.79 (1H, dd, $CH_{arom}$), 7.57 (1H, d, $CH_{arom}$), 4.24 (2H, t, $OCH_2$), 3.20 (2H, t, $CH_2$), 2.74 (3H, s, $NCH_3$), 2.63 (2H, t, $CH_2$), 2.08 (3H, s, $SCH_3$), 1.77-1.72 (2H, m, $CH_2$), 1.00 (3H, t, $CH_3$).

In a sealed tube, a solution of 1 g (11 mmol) of 2-methylsulfanyl-ethylamine in 20 mL of ethylformate is heated at 60° C. for 5 hours. The solvents are evaporated and the residue is added in portions to a solution of 478 mg (12.6 mmol) of lithium aluminium hydride in 100 mL of anhydrous tetrahydrofuran. The reaction mixture is stirred at room temperature for 18 hours. Methanol is added and the reaction mixture is filtered on celite. 10 mL (20 mmol) of a 2M solution of hydrochloric acid in diethyl ether is added to the filtrate. The solid is evaporated and washed with diethyl ether to give 600 mg (50%) of N-methyl-(2-methylsulfanyl-ethyl)-amine hydrochloride in the form of a brown solid.

8-[(2-Dimethylamino-ethyl)-methyl-sulfamoyl]-4-oxo-4,5-dihydro-3H-pyrrolo[2,3-c]quinoline-1-propyl carboxylate (136)

292 µL (2.09 mmol) of triethylamine and 213 µL (1.68 mmol) of N,N,N'-trimethyl-ethane-1,2-diamine are added to 456 mg (1.4 mmol) of 8-chlorosulfonyl-4-oxo-4,5-dihydro-3H-pyrrolo[2,3-c]quinoline-1-carboxylic acid suspended in 4 mL of anhydrous dichloromethane and 1 mL of anhydrous dimethylformamide. The reaction mixture is stirred for 20 hours at room temperature. The solvents are evaporated then the residue is taken up in anhydrous dimethylformamide (6 mL) before adding 322 µL (2.31 mmol) of triethylamine and 215 µL (1.31 mmol) of di-n-propylsulfate. The reaction is monitored by LC/MS over a period of three days with addition of 107 µL (0.77 mmol) and 63 µL (0.39 mmol) of di-n-propylsulfate so as to consume all of the intermediate carboxylic acid. Ammonia (1 mL) is added and the solvents are evaporated. The residue is purified by chromatography on silica (eluent dichloromethane/methanol/ammonia 200/16/3) to give 37% (6% in two stages) of 8-[(2-dimethylamino-ethyl)-methyl-sulfamoyl]-4-oxo-4,5-dihydro-3H-pyrrolo[2,3c]-quinoline-1-propyl carboxylate in the form of a white solid.

LC/MS (IE, m/z): (M+1) 435.29

$^1$H-NMR: $\delta_H$ ppm 400 MHz, DMSO 13.21 (1H, bs, NH), 12.05 (1H, bs, NH), 9.80 (1H, s, $CH_{arom}$), 8.06 (1H, s, $CH_{arom}$), 7.77 (1H, dd, $CH_{arom}$), 7.56 (1H, d, $CH_{arom}$), 4.24 (2H, t, $CH_2$), 3.08 (2H, t, $CH_2$), 2.72 (3H, s, $CH_3$), 2.38 (2H, t, $CH_2$), 2.13 (6H, s, 2×$CH_3$), 1.79-1.70 (2H, m, $CH_2$), 0.99 (3H, 1, $CH_3$).

8-[Methyl-(2-pyrrolidin-1-yl-ethyl)-sulfamoyl]-4-oxo-4,5-dihydro-3H-pyrrolo[2,3-c]quinoline-1-propyl carboxylate (137)

This compound is prepared according to synthesis 136, from 196 mg (0.6 mmol) of 8-chlorosulfonyl-4-oxo-4,5-dihydro-3H-pyrrolo[2,3-c]quinoline-1-carboxylic acid, 485 µL (8 mmol) of triethylamine and 128 mg (0.78 mmol) of N-methyl-(2-pyrrolidin-1-yl-ethyl)-amine hydrochloride to give, after esterification according to general method C (using di-n-propylsulfate as the dialkylsulfate) and purification by chromatography on silica (eluent dichloromethane/methanol/triethylamine 97/3/1) then trituration in diethyl ether, 50 mg (18% in two stages) of 8-[methyl-(2-pyrrolidin-1-yl-ethyl)-sulfamoyl]-4-oxo-4,5-dihydro-3H-pyrrolo[2,3-c]quinoline-1-propyl carboxylate in the form of a yellow solid.

LCMS (IE, m/z): (M+1) 461.30

$^1$H-NMR: $\delta_H$ ppm 400 MHz, DMSO 13.23 (1H, bs, NH), 12.08 (1H, bs, NH), 9.80 (1H, s, $CH_{arom}$), 8.07 (1H, s, $CH_{arom}$), 7.78 (1H, dd, $CH_{arom}$), 7.58 (1H, d, $CH_{arom}$), 4.24 (2H, t, $OCH_2$), 3.40-3.32 (2H, m, $CH_2$), 3.12 (2H, t, $CH_2$), 2.53-2.52 (2H, m, $CH_2$), 2.73 (3H, s, $NCH_3$), 2.44-2.43 (2H, m, $CH_2$), 1.77-1.72 (2H, m, $CH_2$), 1.23-1.20 (3H, m, $CH_3$), 1.19-0.98 (4H, m, 2×CH).

In a sealed tube, a solution of 1.14 g (10 mmol) of 2-pyrrolidin-1-yl-ethylamine in 5 mL of ethylformate is heated at 60° C. for 5 hours. The solvents are evaporated and the residue is added in portions to a solution of 520 mg (13.7 mmol) of lithium aluminium hydride in 100 mL of anhydrous tetrahydrofuran. The reaction mixture is stirred at room temperature for 18 hours. Methanol is added and the reaction mixture is filtered on celite then 10 mL (20 mmol) of a 2M solution of hydrochloric acid in diethyl ether is added. The solid is evaporated and washed with diethyl ether to give 980 mg (65%) of N-methyl-2-pyrrolidin-1-yl-ethylamine hydrochloride in the form of a brown solid.

8-[(2-Diethylamino-ethyl)-methyl-sulfamoyl]-4-oxo-4,5-dihydro-3H-pyrrolo[2,3-c]quinoline-1-propyl carboxylate (138)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 156 mg (1.2 mmol) of N,N-diethyl-N'-methyl-ethane-1,2-diamine to give, after esterification according to general method C (using di-n-propylsulfate as the dialkylsulfate) and purification by chromatography on silica (eluent dichloromethane/methanol/ammonia 200/20/0 then 200/20/3) then trituration in acetonitrile, 29 mg (6% in two stages) of 8-[(2-diethylamino-ethyl)-methyl-sulfamoyl]-4-oxo-4,5-dihydro-3H-pyrrolo[2,3-c]quinoline-1-propyl carboxylate in the form of a white solid.

LCMS (IE, m/z): (M+1) 463.35

$^1$H-NMR: $\delta_H$ ppm 400 MHz, DMSO 13.22 (1H, bs, NH), 12.06 (1H, s, NH), 9.80 (1H, s, $CH_{arom}$), 8.06 (1H, s, $CH_{arom}$), 7.77 (1H, dd, $CH_{arom}$), 7.56 (1H, d, $CH_{arom}$), 4.24 (2H, t, $CH_2$), 3.06 (2H, dd, $CH_2$), 2.73 (3H, s, $CH_3$), 2.57-2.51 (2H, m, $CH_2$), 2.44 (4H, q, 2×$CH_2$), 1.80-1.71 (2H, m, CH), 0.99 (3H, t, $CH_3$), 0.90 (6H, 1, 2×$CH_3$).

8-[Methyl-(2-methylamino-ethyl)-sulfamoyl]-4-oxo-4,5-dihydro-3H-pyrrolo[2,3-c]quinoline-1-propyl carboxylate hydrochloride (139)

2 mL (4 mmol) of a 2M solution of hydrochloric acid in diethyl ether is added to a solution of 50 mg (0.1 mmol) of 8-{[2-(tert-butoxycarbonyl-methyl-amino)-ethyl]-methyl-sulfamoyl}-4-oxo-4,5-dihydro-3H-pyrrolo[2,3-c]quinoline-1-propyl carboxylate dissolved in 5 mL of anhydrous tetrahydrofuran. The solution is stirred at room temperature for 3 days then the solid that forms is filtered, and triturated in diisopropyl ether to give 26 mg (60%) of 8-[methyl-(2-methylamino-ethyl)-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 421.26

$^1$H-NMR: $\delta_H$ ppm 400 MHz, DMSO 13.26 (1H, bs, NH), 12.15 (1H, s, NH), 9.82 (1H, s, $CH_{arom}$), 8.78 (2H, bs, NH.HCl), 8.07 (1H, d, $CH_{arom}$), 7.79 (1H, dd, $CH_{arom}$), 7.62 (1H, d, $CH_{arom}$), 4.24 (2H, t, $CH_2$), 3.28-3.22 (2H, m, $CH_2$), 3.17-3.09 (2H, m, $CH_2$), 2.75 (3H, s, $CH_3$), 2.59 (3H, t, $CH_3$), 1.80-1.70 (2H; m, $CH_2$), 0.99 (3H, t, $CH_3$).

8-{[2-(tert-Butoxycarbonyl-methyl-amino)-ethyl]-methyl-sulfamoyl}-4-oxo-4,5-dihydro-3H-pyrrolo[2,3-c]quinoline-1-propyl carboxylate (140)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 226 mg (1.2 mmol) of N-tert-butoxycarbonyl-N,N'-dimethyl-ethane-1,2-diamine (prepared according to the method described by Kleemann, Heinz-Werner et al., J. Med. Chem., 1992, 35(3), 559-67) to give, after esterification according to general method C (using di-n-propylsulfate as the dialkylsulfate) and purification by trituration in a 1/1 dichloromethane/ethyl acetate mixture, 264 mg (50% in two stages) of 8-{[2-(tert-butoxycarbonyl-methyl-amino)-ethyl]-methyl-sulfamoyl}-4-oxo-4,5-dihydro-3H-pyrrolo[2,3-c]quinoline-1-propyl carboxylate in the form of a white solid.

LCMS (IE, m/z): (M+J) 521.18

$^1$H-NMR: $\delta_H$ ppm 400 MHz, DMSO 13.21 (1H, bs, NH), 12.07 (1H, s, NH), 9.79 (1H, s, $CH_{arom}$), 8.06 (1H, s, $CH_{arom}$), 7.75 (1H, dd, $CH_{arom}$), 7.57 (1H, d, $CH_{arom}$), 4.23 (2H, t, $CH_2$), 3.37-3.31 (2H, m, $CH_2$), 3.16-3.08 (2H, m, $CH_2$), 2.80 (3H, s, $CH_3$), 2.72 (3H, s, $CH_3$), 1.79-1.70 (2H, m, $CH_2$), 1.39 (9H, s, 3×$CH_3$), 0.99 (3H, t, $CH_3$).

8-[Cyclopropyl-(2-methyl-2-methylamino-propyl)-sulfamoyl]-4-oxo-4,5-dihydro-3H-pyrrolo[2,3-c]quinoline-1-propyl carboxylate hydrochloride (141)

This compound is prepared according to synthesis 139, from 47 mg (0.1 mmol) of 8-{[2-(tert-butoxycarbonyl-methyl-amino)-2-methyl-propyl]-cyclopropyl-sulfamoyl}-4-oxo-4,5-dihydro-3H-pyrrolo[2,3-c]quinoline-1-propyl carboxylate and 3 mL (6 mmol)) of a 2M solution of hydrochloric acid in diethyl ether to give, after filtration, 32 mg (62%) of 8-[cyclopropyl-(2-methyl-2-methylamino-propyl)-sulfamoyl]-4-oxo-4,5-dihydro-3H-pyrrolo[2,3-c] quinoline-1-propyl carboxylate hydrochloride in the form of a white solid.

LC/MS (IE, m/z): (M+1) 475.00

$^1$H-NMR: $\delta_H$ ppm 400 MHz, DMSO 13.26 (1H, bs, NH), 12.14 (1H, bs, NH), 9.88 (1H, s, $CH_{arom}$), 8.63 (2H, bs, NH.HCl), 8.07 (1H, s, $CH_{arom}$), 7.85 (1H, dd, $CH_{arom}$), 7.60 (1H, d, $CH_{arom}$), 4.23 (2H, t, $CH_2$), 3.46 (2H, s, $CH_2$), 2.58 (3H, s, $CH_3$), 2.37-2.30 (1H, m, CH), 1.80-1.71 (2H, m, $CH_2$), 1.34 (6H, s, 2×$CH_3$), 1.0 (3H, t, $CH_3$), 0.79-0.64 (4H, m, 4×$CH_{cycloprop}$).

8-{[2-(tert-Butoxycarbonyl-methyl-amino)-2-methyl-propyl]-cyclopropyl-sulfamoyl}-4-oxo-4,5-dihydro-3H-pyrrolo[2,3-c]quinoline-1-propyl carboxylate is prepared according to synthesis 111, from 360 mg (1.1 mmol) of 8-chlorosulfonyl-4-oxo-4,5-dihydro-3H-pyrrolo[2,3-c]quinoline-1-carboxylic acid and 290 mg (1.2 mmol) of N-tert-butoxycarbonyl-N'-cyclopropyl-N-methyl-2-methyl-propane-1,2-diamine to give, after esterification according to general method C (using di-n-propylsulfate as the dialkylsulfate) and purification by chromatography on silica (eluent cyclohexane/ethyl acetate 7/3 then 1/1), 50 mg (8% in two stages) of 8-{[2-(tert-butoxycarbonyl-methyl-amino)-2-methyl-propyl]-cyclopropyl-sulfamoyl}-4-oxo-4,5-dihydro-3H-pyrrolo[2,3-c]quinoline-1-propyl carboxylate in the form of a white solid.

3.6 mL (12 mmol) of titanium isopropoxide and 1.85 g (9.2 mmol) of 2-(tert-butoxycarbonyl-methyl-amino)-2-methyl-propionaldehyde (prepared according to a method similar to that described by Kato, Shiro et al., J. Chem. Soc. Perkin Trans. 1, 1997, 21, 3219-26) are added to a solution of 1.57 g (27.6 mmol) of cyclopropylamine in 10 mL of anhydrous methanol. The solution is stirred for 5 hours at room temperature then 454 mg (12 mmol) of sodium borohydride is added. Stirring is continued for a further 2 hours then 2 mL of water is added. The reaction mixture is filtered then the solvents are evaporated. The residue is purified by chromatography on silica (eluent dichloromethane/methanol 98/2) to give 1.18 g (53%) of N-tert-butoxycarbonyl-N'-cyclopropyl-N-methyl-2-methyl-propane-1,2-diamine in the form of a colourless oil.

8-[Cyclopropyl-(2-isopropylamino-ethyl)-sulfamoyl]-4-oxo-4,5-dihydro-3H-pyrrolo[2,3-c]quinoline-1-propyl carboxylate hydrochloride (142)

This compound is prepared according to synthesis 139, from 195 mg (0.34 mmol) of 8-{[2-(tert-butoxycarbonyl-isopropyl-amino)-ethyl]-cyclopropyl-sulfamoyl}-4-oxo-4,5-dihydro-3H-pyrrolo[2,3-c]quinoline-1-propyl carboxylate and 6.8 mL (13.6 mmol) of a 2M solution of hydrochloric acid in diethyl ether to give, after filtration, 160 mg (92%) of 8-[cyclopropyl-(2-isopropylamino-ethyl)-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 475

$^1$H-NMR: $\delta_H$ ppm 400 MHz, DMSO 13.26 (1H, bs, NH), 12.15 (1H, s, NH), 9.89 (1H, s, $CH_{arom}$), 8.67 (2H, bs, NH.HCl), 8.07 (1H, ds, $CH_{arom}$), 7.84 (1H, dd, $CH_{arom}$), 7.62 (1H, d, $CH_{arom}$), 4.24 (2H, t, $CH_2$), 3.43-3.25 (3H, m, CH and $CH_2$), 3.17-3.09 (2H, m, $CH_2$), 2.14-2.09 (1H, m, $CH_{cycloprop}$), 1.78-1.70 (2H, m, $CH_2$), 1.23 (6H, d, 2×$CH_3$), 0.99 (3H, t, $CH_3$), 0.90-0.86 (2H, m, 2× $CH_{cycloprop}$), 0.78-0.72 (2H, m, 2×$CH_{cycloprop}$).

8-{[2-(tert-Butoxycarbonyl-isopropyl-amino)-ethyl]-cyclopropyl-sulfamoyl}-4-oxo-4,5-dihydro-3H-pyrrolo[2,3-c] quinoline-1-propyl carboxylate is prepared according to synthesis 111, from 326 mg (1 mmol) of 8-chlorosulfonyl-4-oxo-4,5-dihydro-3H-pyrrolo[2,3-c]quinoline-1-carboxylic acid and 288 mg (1.2 mmol) of N-tert-butoxycarbonyl-N'-cyclopropyl-N-isopropyl-ethane-1,2-diamine to give, after esterification according to general method C (using di-n-propylsulfate as the dialkylsulfate) and purification by chromatography on silica (eluent cyclohexane/ethyl acetate 1/1 then 1/3), 201 mg (35% in two stages) of 8-{[2-(tert-butoxycarbonyl-isopropyl-amino)-ethyl]-cyclopropyl-sulfamoyl}-4-oxo-4,5-dihydro-3H-pyrrolo[2,3-c]quinoline-1-propyl carboxylate in the form of a white solid.

3.9 mL (13 mmol) of titanium isopropoxide and 2 g (10 mmol) of (tert-butoxycarbonyl-isopropyl-amino)-acetaldehyde (prepared according to the method described by Kato, Shiro et al., J. Chem. Soc. Perkin Trans. 1, 1997, 21, 3219-26) are added to a solution of 1.71 g (30 mmol) of cyclopropylamine in 15 mL of anhydrous methanol. The solution is stirred for 5 hours at room temperature then 454 mg (12 mmol) of sodium borohydride is added. Stirring is continued for a further 2 hours then 2 mL of water is added. The reaction mixture is filtered then the solvents are evaporated. The residue is purified by chromatography on silica (eluent dichloromethane/methanol 98/2 then 95/5) to give 852 mg (35%) of N-tert-butoxycarbonyl-N-cyclopropyl-N'-isopropyl-ethane-1,2-diamine in the form of a colourless oil.

8-[Cyclopropyl-(1H-imidazol-4-ylmethyl)-sulfamoyl]-4-oxo-4,5-dihydro-3H-pyrrolo[2,3-c]quinoline-1-propyl carboxylate hydrochloride (143)

This compound is prepared according to synthesis 114, from 353 mg (0.67 mmol) of 8-[cyclopropyl-(1H-imidazol-4-ylmethyl)-sulfamoyl]-4-oxo-4,5-dihydro-3H-pyrrolo[2,3-c]quinoline-1-carboxylic acid, 934 μL (6.7 mmol) of triethylamine and 440 μL (2.68 mmol) of di-n-propylsulfate. The free base is purified by chromatography on silica (eluent chloroform/methanol/ammonia 220/25/4) then the hydrochloride is formed by adding a 2M solution of hydrochloric acid in ether to the free compound dissolved in anhydrous tetrahydrofuran to give 16 mg (26% in two stages) of 8-[cyclopropyl-(1H-imidazol-4-ylmethyl)-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 470.29

$^1$H-NMR: $\delta_H$ ppm 400 MHz, DMSO 14.35 (2H, bs, NH and HCl), 13.25 (1H, bs, NH), 12.15 (1H, bs, NH), 9.87 (1H, d, $CH_{arom}$), 8.99 (1H, s, $CH_{arom}$), 8.08 (1H, d, $CH_{arom}$), 7.82 (1H, dd, $CH_{arom}$), 7.60 (1H, d, $CH_{arom}$), 7.53 (1H, s, $CH_{arom}$), 4.40 (2H, s, $CH_2$), 4.24 (2H, t, $CH_2$), 2.09-2.02 (1H, m, $CH_{arom}$), 1.75 (2H, sex, $CH_2$), 0.99 (3H, t, $CH_3$), 0.74-0.64 (4H, m, 4×$CH_{ali}$).

8-[Cyclopropyl-(1H-imidazol-4-ylmethyl)-sulfamoyl]-4-oxo-4,5-dihydro-3H-pyrrolo[2,3-c]quinoline-1-carboxylic acid is prepared according to synthesis 178, from 284 mg (0.87 mmol) of 8-chlorosulfonyl-4-oxo-4,5-dihydro-3H-pyrrolo[2,3-c]quinoline-1-carboxylic acid, 605 μL (4.35 mmol) of triethylamine and 309 mg (1.3 mmol) of cyclopropyl-(1-tert-butoxycarbonyl-1H-imidazol-4-ylmethyl)-amine to give, after purification by precipitation and trituration in water, 350 mg (76%) of 8-[cyclopropyl-(1H-imidazol-4-yl-methyl)-sulfamoyl]-4-oxo-4,5-dihydro-3H -pyrrolo[2,3-c]quinoline-1-carboxylic acid in the form of a beige solid.

438 μL (6.3 mmol) of cyclopropylamine, 527 mg (8.4 mmol) of sodium cyanoborohydride and 1.52 mL (42 mmol) of acetic acid are added to a solution of 824 mg (4.2 mmol) of 1-tert-butoxycarbonyl-1H-imidazole-4 (5)-carbaldehyde in 20 mL of anhydrous methanol. The solution is stirred at room temperature for 24 hours then a saturated aqueous solution of sodium hydrogencarbonate is added to adjust the pH to 7. The compound is extracted with ethyl acetate. The organic phases are dried over magnesium sulfate, filtered then evaporated and the residue is purified by chromatography on silica (eluent dichloromethane/methanol 95/5) to give 398 mg (40%) of cyclopropyl-(1-tert-butoxycarbonyl-1H-imidazol-4-ylmethyl)-amine in the form of a viscous oil.

2.6 g (11.9 mmol) of di-tert-butyl bicarbonate and 610 mg (5 mmol) of 4-dimethylaminopyridine are added to a solution of 961 mg (10 mmol) of 1H-imidazole-4-carboxaldehyde dissolved in 40 mL of acetonitrile. The solution is stirred at room temperature for 7 hours then a saturated aqueous solution of ammonium chloride is added to adjust the pH to 5. The product is extracted with ethyl acetate and the organic phases are dried over magnesium sulfate, filtered and evaporated. The residue is purified by chromatography on silica (eluent dichloromethane/methanol 88/12) to give 1.68 g (85%) of 1-tert-butoxycarbonyl-1H-imidazole-4 (5)-carbaldehyde.

(S)-8-(Cyclopropyl-pyrrolidin-2-ylmethyl-sulfamoyl)-4-oxo-4,5-dihydro-3H-pyrrolo[2,3-c]quinoline-1-propyl carboxylate hydrochloride (144)

This compound is prepared according to synthesis 139, from 97 mg (0.17 mmol) of (S)-8-[(1-tert-butoxycarbony-pyrrolidin-2-ylmethyl)-cyclopropyl-sulfamoyl]-4-oxo-4,5-dihydro-3H-pyrrolo[2,3-c]quinoline-1-propyl carboxylate and 3.4 mL (6.8 mmol) of a 2M solution of hydrochloric acid in diethyl ether to give, after filtration, 46 mg (53%) of (S)-8-(cyclopropyl-pyrrolidin-2-ylmethyl-sulfamoyl)-4-oxo-4,5-dihydro-3H-pyrrolo[2,3-c]quinoline-1-propyl carboxylate hydrochloride in the form of a white solid.

LCMS (IE, m/z): (M+1) 473.2
$^1$H-NMR: H ppm 400 MHz, DMSO
13.26 (1H, bs, NH), 12.15 (1H, s, NH), 9.88 (1H, d, $CH_{arom}$), 9.27 (1H, bs, NH.HCl), 8.51 (1H, bs, NH.HCl), 8.07 (1H, d, $CH_{arom}$), 7.84 (1H, dd, $CH_{arom}$), 7.62 (1H, d, $CH_{arom}$), 4.24 (2H, t, $CH_2$), 3.89-3.78 (1H, m, CH), 3.38-3.18 (4H, m, $4 \times CH_{ali}$), 2.15-2.02 (2H, m, 2×CH), 1.99-1.86 (2H, m, 2×CH), 1.80-1.70 (2H, m, $CH_2$), 1.68-1.58 (1H, m, CH), 0.99 (3H, t, $CH_3$), 0.91-0.86 (2H, m, $2 \times CH_{cycloprop}$), 0.75-0.72 (2H, m, $2 \times CH_{cycloprop}$).

(S)-8-[(1-tert-butoxycarbony-pyrrolidin-2-ylmethyl)-cyclopropyl-sulfamoyl]-4-oxo-4,5-dihydro-3H-pyrrolo[2,3-c]quinoline-1-propyl carboxylate is prepared according to synthesis 111, from 326 mg (1 mmol) of 8-chlorosulfonyl-4-oxo-4,5-dihydro-3H-pyrrolo[2,3-c]quinoline-1-carboxylic acid and 288 mg (1.2 mmol) of (S)-1-tert-butoxycarbonyl-2-cyclopropylaminomethyl-pyrrolidine to give, after esterification according to general method C (using di-n-propylsulfate as the dialkylsulfate) and purification by chromatography on silica (eluent dichloromethane/methanol 99/1 then 95/5), 99 mg (17% in two stages) of (S)-8-[(1-tert-butoxycarbonyl-pyrrolidin-2-ylmethyl)-cyclopropyl-sulfamoyl]-4-oxo-4,5-dihydro-3H-pyrrolo[2,3-c]quinoline-1-propyl carboxylate in the form of a white solid.

3.78 mL (13 mmol) of titanium isopropoxide and 2 g (10 mmol) of (S)-1-tert-butoxycarbonyl-pyrrolidine-2-carbaldehyde are added to a solution of 1.7 mL (30 mmol) of cyclopropylamine in 10 mL of anhydrous methanol. The solution is stirred for 5 hours at room temperature then 378 mg (10 mmol) of sodium borohydride is added. Stirring is continued for a further 2 hours then 2 mL of water is added. The reaction mixture is filtered then the solvents are evaporated. Water is added and the compound is extracted with diethyl ether. The organic phases are dried over magnesium sulfate, filtered and evaporated to give 2.34 g (97%) of (S)—N-cyclopropyl-1-tert-butoxycarbonyl-pyrrolidin-2-ylmethyl-amine in the form of a colourless oil.

(S)-8-[Cyclopropyl-(1-methyl-pyrrolidin-2-ylmethyl)sulfamoyl]-4-oxo-4,5-dihydro-3H-pyrrolo[2,3-c]quinoline-1-propyl carboxylate (145)

This compound is prepared according to synthesis 119, from 76 mg (0.15 mmol) of (S)-8-(cyclopropyl-pyrrolidin-2-ylmethyl-sulfamoyl)-4-oxo-4,5-dihydro-3H-pyrrolo[2,3-c]quinoline-1-propyl carboxylate hydrochloride, 104 µL (0.75 mmol) of triethylamine and 28 µL (0.3 mmol)) of dimethylsulfate to give, after precipitation in water and trituration in diisopropyl ether, 48 mg (65%) of (S)-8-[cyclopropyl-(1-methyl-pyrrolidin-2-ylmethyl)-sulfamoyl]-4-oxo-4,5-dihydro-3H-pyrrolo[2,3-c]quinoline-1-propyl carboxylate in the form of a white solid.

LCMS (IE, m/z: (M+1) 487.35
$^1$H-NMR: $\delta_H$ ppm 400 MHz, DMSO
12.00 (1H, bs, NH), 9.86 (1H, bs, $CH_{arom}$), 8.07 (1H, s, $CH_{arom}$), 7.79 (1H, bs, $CH_{arom}$), 7.56 (1H, bs, $CH_{arom}$), 4.31-4.15 (2H, m, $CH_2$), 3.30-2.60 (4H, m, $CH_2$ and 2×CH), 2.26 (3H, s, $CH_3$), 2.10-1.60 (8H, m, 6×CH and $CH_2$), 0.99 (3H, t, $CH_3$), 1.00-0.64 (4H, m, $4 \times CH_{cycloprop}$).

(R)-8-[Cyclopropyl-(1-methyl-pyrrolidin-2-ylmethyl)-sulfamoyl]-4-oxo-4,5-dihydro-3H-pyrrolo[2, 3-c]quinoline-1-propyl carboxylate (146)

This compound is prepared according to synthesis 119, from 51 mg (0.1 mmol) of (R)-8-(cyclopropyl-pyrrolidin-2-ylmethyl-sulfamoyl)-4-oxo-4,5-dihydro-3H-pyrrolo[2,3-c]quinoline-1-propyl carboxylate, 67 µL (0.5 mmol) of triethylamine and 14 µL (0.15 mmol)) of dimethylsulfate to give, after precipitation in water and trituration in diisopropyl ether, 29 mg (60%) of (R)-8-[cyclopropyl-(1-methyl-pyrrolidin-2-ylmethyl)-sulfamoyl]-4-oxo-4,5-dihydro-3H-pyrrolo[2,1-c]quinoline-1-propyl carboxylate in the form of a white solid.

LC/MS (IE, m/z): (M+1) 487.36
$^1$H-NMR: $\delta_H$ ppm 400 MHz, DMSO
11.06 (1H, bs, NH), 9.86 (1H, s, $CH_{arom}$), 8.06 (1H, s, $CH_{arom}$), 7.81 (1H, d, $CH_{arom}$), 7.58 (1H, d, $CH_{arom}$), 4.24 (2H, t, $CH_2$), 3.03-2.90 (2H, m, 2×CH), 2.27 (3H, s, $NCH_3$), 2.12-2.02 (2H, m, 2×CH), 1.85-1.60 (7H, m, 7×CH), 0.99 (3H, t, $CH_3$), 0.85 (2H, m, $CH_2$), 0.73 (2H, m, $CH_2$).

(R)-8-[(1-tert-Butoxycarbony-pyrrolidin-2-ylmethyl)-cyclopropyl-sulfamoyl]-4-oxo-4,5-dihydro-3H-pyrrolo[2,3-c]quinoline-1-propyl carboxylate (147)

This compound is prepared according to synthesis 111, from 360 mg (1.1 mmol) of 8-chlorosulfonyl-4-oxo-4,5-dihydro-3H-pyrrolo[2,3-c]quinoline-1-carboxylic acid and 292 mg (1.21 mmol) of (R)-1-tert-butoxycarbonyl-2-cyclopropylaminomethyl-pyrrolidine to give, after esterification according to general method C (using di-n-propylsulfate as the dialkylsulfate) and purification by chromatography on silica (eluent cyclohexane/ethyl acetate 1/1 then 1/4), 226 mg (36% in two stages) of (R)-8-[(1-tert-butoxycarbonyl-pyrrolidin-2-ylmethyl)-cyclopropyl-sulfamoyl]-4-oxo-4,5-dihydro-3H-pyrrolo[2,3-c]quinoline-1-propyl carboxylate in the form of a white solid.

LC/MS (IE, m/z): (M+1) 573.40
$^1$H-NMR: g ppm 400 MHz, $CDCl_3$ 11.43 (1H, bs, NH), 10.73 (1H, bs, NH), 10.05 (1H, d, $CH_{arom}$), 8.00 (1H, d, $CH_{arom}$), 7.90-7.84 (1H, m, $CH_{arom}$), 7.49-7.43 (1H, m, $CH_{arom}$), 4.25 (2H, t, $CH_2$), 3.47-3.34 (4H, m, 2×$CH_2$), 3.11 (1H, dd, CH), 2.28-2.24 (1H, m, CH), 2.13-2.05 (2H, m, 2×CH), 1.90-1.87 (2H, m, 2×CH), 1.77 (2H, q, $CH_2$), 1.42 (9H, s, 3×$CH_3$), 1.00 (3H, t, $CH_3$), 0.83-0.70 (4H, m, 4×$CH_{cycloprop}$)

1.9 mL (6 mmol) of titanium isopropoxide and 1 g (10 mmol) of (R)-1-tert-butoxycarbonyl-pyrrolidine-2-carbaldehyde are added to a solution of 1 mL (30 mmol) of cyclopropylamine in 5 mL of anhydrous methanol. The solution is stirred for 5 hours at room temperature then 246 mg (605 mmol) of sodium borohydride is added. Stirring is continued for a further 2 hours then 2 mL of water is added. The reaction mixture is filtered then the solvents are evaporated. Water is added and the compound is extracted with diethyl ether. The organic phases are dried over magnesium sulfate, filtered and evaporated to give 1.17 g (97%) of (R)-1-tert-butoxycarbonyl-2-cyclopropylaminomethyl-pyrrolidine in the form of a colourless oil.

(R)-8-(Cyclopropyl-pyrrolidin-2-ylmethyl-sulfamoyl)-4-oxo-4,5-dihydro-3H-pyrrolo[2,3-c]quinoline-1-propyl carboxylate hydrochloride (148)

This compound is prepared according to synthesis 139, from 220 mg (0.38 mmol) of (R)-8-[(1-tert-butoxycarbonyl-pyrrolidin-2-ylmethyl)-cyclopropyl-sulfamoyl]-4-oxo-4,5-dihydro-3H-pyrrolo[2,3-c]quinoline-1-propyl carboxylate and 11.5 mL (23 mmol) of a 2M solution of hydrochloric acid in diethyl ether to give, after filtration, 126 mg (64%) of (R)-8-(cyclopropyl-pyrrolidin-2-ylmethyl-sulfamoyl)-4-oxo-4,5-dihydro-3H-pyrrolo[2,3-c]quinoline-1-propyl carboxylate hydrochloride in the form of a white solid.

LC/MS (IE, m/z): (M+1) 473.34

$^1$H-NMR: $\delta_H$ ppm 400 MHz, DMSO 13.26 (1H, bs, NH), 12.16 (1H, bs, NH), 9.90 (1H, s, $CH_{arom}$), 9.34 (1H, bs, NH.HCl), 8.59 (1H, bs, NH.HCl), 8.08 (1H, d, $CH_{arom}$), 7.86 (1H, d, $CH_{arom}$), 7.63 (1H, d, $CH_{arom}$), 4.24 (2H, t, $CH_2$), 3.86-3.80 (1H, m, $CH_{ali}$), 3.50-3.31 (2H, m, 2×$CH_{ali}$), 3.31-3.13 (2H, m, 2×$CH_{ali}$), 2.13-2.03 (2H, m, 2×$CH_{ali}$), 1.99-1.87 (2H, m, 2×$CH_{ali}$), 1.82-1.67 (2H, m, $CH_2$), 1.69-1.60 (1H, m, $CH_{ali}$) 0.99 (3H, t, $CH_3$), 0.93-0.83 (2H, m, 2×$CH_{cycloprop}$), 0.77-0.68 (2H, m, 2×$CH_{cycloprop}$),

(S)-8-(Isopropyl-pyrrolidin-2-ylmethyl-sulfamoyl)-4-oxo-4,5-dihydro-3H-pyrrolo[2,3-c]quinoline-1-propyl carboxylate hydrochloride (149)

This compound is prepared according to synthesis 139, from 103 mg (0.18 mmol) of (S)-8-[1-tert-butoxycarbonyl-isopropyl-pyrrolidin-2-ylmethyl-sulfamoyl]-4-oxo-4,5-dihydro-3H-pyrrolo[2,3-c]quinoline-1-propyl carboxylate and 4.5 mL (9 mmol) of a 2M solution of hydrochloric acid in diethyl ether to give, after filtration, 60 mg (65%) of (S)-8-(isopropyl-pyrrolidin-2-ylmethyl-sulfamoyl)-4-oxo-4,5-dihydro-3H-pyrrolo[2,3-c]quinoline-1-propyl carboxylate hydrochloride in the form of a white solid.

LCMS (IE, m/z): (M+1) 475.2

$^1$H-NMR: $\delta_H$ ppm 400 MHz, DMSO 13.26 (1H, bs, NH), 12.12 (1H, s, NH), 9.88 (1H, d, $CH_{arom}$), 9.18 (1H, bs, NH.HCl), 8.53 (1H, bs, NH.HCl), 8.07 (1H, s, $CH_{arom}$), 7.87 (1H, dd, $CH_{arom}$), 7.58 (1H, d, $CH_{arom}$), 4.25 (2H, t, $CH_2$), 4.09-4.00 (1H, m, $CH_{ali}$), 3.85-3.75 (1H, m, $CH_{ali}$), 3.48-3.17 (4H, m, 4×$CH_{ali}$), 2.19-2.09 (1H, m, $CH_{ali}$), 2.05-1.86 (2H, m, 2×$CH_{ali}$), 1.82-1.65 (3H, m, $CH_2$ and $CH_{ali}$), 1.05-0.91 (9H, m, 3×$CH_3$).

(S)-8-[1-tert-butoxycarbonyl-isopropyl-pyrrolidin-2-ylmethyl-sulfamoyl]-4-oxo-4,5-dihydro-3H-pyrrolo[2,3-c]quinoline-1-propyl carboxylate is prepared according to synthesis 111, from 326 mg (1 mmol) of 8-chlorosulfonyl-4-oxo-4,5-dihydro-3H-pyrrolo[2,3-c]quinoline-1-carboxylic acid and 290 mg (1.2 mmol) of (S)-1-tert-butoxycarbonyl-2-isopropylaminomethyl-pyrrolidine to give, after esterification according to general method C (using di-n-propylsulfate as the dialkylsulfate) and purification by chromatography on silica (eluent cyclohexane/ethyl acetate 1/1 then 1/3), 106 mg (18% in two stages) of (S)-8-[1-tert-butoxycarbonyl-isopropyl-pyrrolidin-2-ylmethyl-sulfamoyl]-4-oxo-4,5-dihydro-3H-pyrrolo[2,3-c]quinoline-1-propyl carboxylate in the form of a white solid.

1.9 mL (6 mmol) of titanium isopropoxide and 1 g (5 mmol) of (S)-1-tert-butoxycarbonyl-pyrrolidine-2-carbaldehyde are added to a solution of 886 mg (15 mmol) of isopropylamine in 10 mL of anhydrous methanol. The solution is stirred for 5 hours at room temperature then 227 mg (6 mmol) of sodium borohydride is added. Stirring is continued for a further 2 hours then 2 mL of water is added. The reaction mixture is filtered then the solvents are evaporated. Water is added and the compound is extracted with diethyl ether. The organic phases are dried over magnesium sulfate, filtered and evaporated to give 1.05 g (86%) of (S)-1-tert-butoxycarbonyl-2-isopropylaminomethyl-pyrrolidine in the form of a colourless oil.

(S)-4-Oxo-8-(prop-2-ynyl-pyrrolidin-2-ylmethyl-sulfamoyl)-4,5-dihydro-3H-pyrrolo[2,3-c]quinoline-1-propyl carboxylate hydrochloride (150)

This compound is prepared according to synthesis 139, from 188 mg (0.33 mmol) of (S)-8-[1-tert-butoxycarbonyl-prop-2-ynil-pyrrolidin-2-ylmethyl-sulfamoyl]-4-oxo-4,5-dihydro-3H-pyrrolo[2,3-c]quinoline-1-propyl carboxylate and 8.3 mL (16.6 mmol) of a 2M solution of hydrochloric acid in diethyl ether to give, after filtration, 110 mg (65%) of (S)-4-oxo-8-(prop-2-ynil-pyrrolidin-2-ylmethyl-sulfamoyl)-4,5-dihydro-3H-pyrrolo[2,3-c]quinoline-1-propyl carboxylate hydrochloride in the form of a white solid.

LCMS (IE, m/z): (M+1) 471.3

$^1$H-NMR: $\delta_H$ ppm 400 MHz, DMSO 13.26 (1H, bs, NH), 12.13 (1H, s, NH), 9.89 (1H, d, $CH_{arom}$), 9.23 (1H, bs, NH.HCl), 8.54 (1H, bs, NH.HCl), 8.08 (1H, s, $CH_{arom}$), 7.84 (1H, dd, $CH_{arom}$), 7.57 (1H, d, $CH_{arom}$), 4.30-4.20 (4H, m, 2×$CH_2$), 3.91-3.80 (1H, m, $CH_{ali}$), 3.54-3.42 (1H, m, $CH_{ali}$), 3.41-3.33 (1H, m, $CH_{ali}$), 3.27-3.15 (1H, m, $CH_{ali}$), 3.00 (1H, t, $CH_{alkyne}$), 2.12-1.88 (3H, m, 3×$CH_{ali}$), 1.81-1.66 (3H, m, $CH_{ali}$ and $CH_2$), 1.00 (3H, t, $CH_3$).

(S)-8-[1-tert-butoxycarbonyl-prop-2-ynil-pyrrolidin-2-ylmethyl-sulfamoyl]-4-oxo-4,5-dihydro-3H-pyrrolo[2,3-c]quinoline-1-propyl carboxylate is prepared according to synthesis 111, from 326 mg (1 mmol) of 8-chlorosulfonyl-4-oxo-4,5-dihydro-3H-pyrrolo[2,3-c]quinoline-1-carboxylic acid and 288 mg (1.2 mmol) of (S)-1-tert-butoxycarbonyl-prop-2-ynilaminomethyl-pyrrolidine to give, after esterification according to general method C (using di-n-propylsulfate as the dialkylsulfate) and purification by chromatography on silica (eluent cyclohexane/ethyl acetate 1/1 then 1/3), 192 mg (33% in two stages) of (S)-8-[1-tert-butoxycarbonyl-prop-2-ynyl-pyrrolidin-2-ylmethyl-sulfamoyl]-4-oxo-4,5-dihydro-3H-pyrrolo[2,3-c]quinoline-1-propyl carboxylate in the form of a white solid.

1.9 mL (6 mmol) of titanium isopropoxide and 1 g (5 mmol) of (S)-1-tert-butoxycarbonyl-pyrrolidine-2-carbaldehyde are added to a solution of 826 mg (15 mmol) of propargylamine in 10 mL of anhydrous methanol. The solution is stirred for 5 hours at room temperature then 227 mg (6 mmol) of sodium borohydride is added. Stirring is continued for a further 2 hours then 2 mL of water is added. The reaction mixture is filtered then the solvents are evaporated. Water is added and the compound is extracted with diethyl ether. The organic phases are dried over magnesium sulfate, filtered and evaporated to give 1.2 g (quantitative) of (S)-1-tert-butoxycarbonyl-prop-2-ynilaminomethyl-pyrrolidine in the form of a colourless oil.

(S)-8-[(1-Methyl-pyrrolidin-2-ylmethyl)-prop-2-ynyl-sulfamoyl]-4-oxo-4,5-dihydro-3H-pyrrolo[2,3-c]quinoline-1-propyl carboxylate (151)

This compound is prepared according to synthesis 119, from 51 mg (0.1 mmol) of (S)-4-oxo-8-(prop-2-ynyl-pyrrolidin-2-ylmethyl-sulfamoyl)-4,5-dihydro-3H-pyrrolo[2,3-c]quinoline-1-propyl carboxylate hydrochloride, 67 µL (0.5 mmol) of triethylamine and 14 µL (0.15 mmol) of dimethylsulfate to give, after precipitation in water and trituration in diisopropyl ether, 34 mg (70%) of (S)-8-[(1-methyl-pyrrolidin-2-ylmethyl)-prop-2-ynyl-sulfamoyl]-4-oxo-4,5-dihydro-3H-pyrrolo[2,3-c]quinoline-1-propyl carboxylate in the form of a white solid.

LCMS (IE, m/z): (M+1) 485.3

$^1$H-NMR: $\delta_H$ ppm 400 MHz, DMSO 12.00 (1H, s, NH), 9.84 (1H, d, $CH_{arom}$), 8.05 (1H, s, $CH_{arom}$), 7.78 (1H, dd, $CH_{arom}$), 753 (1H, d, $CH_{arom}$), 4.29-4.11 (4H, m, 2×$CH_2$), 3.20-288 (4H, m, 4×$CH_{ali}$), 2.75 (1H, t, $CH_{alkyne}$), 2.25 (3H, s, $NCH_3$), 2.15-2.05 (H, m, $CH_{ali}$), 1.92-1.55 (6H, m, 6×$CH_{ali}$), 0.99 (3H, t, $CH_3$).

(S)-8-[(2-tert-Butoxycarbonylamino-propyl)-cyclopropyl-sulfamoyl]-4-oxo-4,5-dihydro-3H-pyrrolo[2,3-c]quinoline 1-propyl carboxylate (152)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid, 1.11 mL (8 mmol) of triethylamine and 321 mg (1.5 mmol) of (S)—N'-tert-butoxycarbonyl-N-cyclopropyl-propane-1,2-diamine hydrochloride to give, after esterification according to general method C (using di-n-propylsulfate as the dialkylsulfate) and purification by chromatography on silica (eluent dichloromethane/methanol 97/3) then trituration in diethyl ether, 15 mg (21% in two stages) of (S)-8-[(2-tert-butoxycarbonylamino-propyl)-cyclopropyl-sulfamoyl]-4-oxo-4,5-dihydro-3H-pyrrolo[2,3-c]quinoline-1-propyl carboxylate in the form of a white solid.

LCMS (IE, m/z): (M+1) 547.19

$^1$H-NMR: $\delta_H$ ppm 400 MHz, $CDCl_3$ 11.57 (1H, bs, NH), 10.91 (1H, bs, NH), 10.01 (1H, s, $CH_{arom}$), 8.01 (1H, s, $CH_{arom}$), 7.87 (1H, d, $CH_{arom}$), 7.46 (1H, d, $CH_{arom}$), 4.97 (1H, bs, NH), 4.26 (2H, t, $OCH_2$), 4.06 (1H, s, CH), 3.47 (1H, s, $NCH_2$), 3.17 (1H, s, $NCH_2$), 2.18 (1H, s, CH), 1.79 (2H, dd, $CH_2$), 1.42 (9H, s, 3×$CH_3$), 1.21 (3H, d, $CH_3$), 1.03 (3H, t, $CH_3$), 0.98 (2H, bs, 2×$CH_{cycloprop}$) 0.74 (2H, bs, 2×$CH_{cycloprop}$).

4.3 mL (14.3 mmol) of titanium isopropoxide and 1.9 g (5 mmol) of (S)-2-(tert-butoxycarbonylamino)-propionaldehyde (prepared according to the method described by Itaya, Taisuke et al., Tetrahedron Lett., 1986, 52(27), 6349-52) are added to a solution of 1.88 g (33 mmol) of cyclopropylamine in 10 mL of anhydrous methanol. The solution is stirred for 5 hours at room temperature then 227 mg (6 mmol) of sodium borohydride is added. Stirring is continued for a further 2 hours then 2 mL of water is added. The reaction mixture is filtered then the solvents are evaporated. The residue is purified by chromatography on silica (eluent dichloromethane/methanol 98/2) to give 400 mg (17%) of (S)—N'-tert-butoxycarbonyl-N-cyclopropyl-propane-1,2-diamine in the form of a colourless oil.

(S)-8-[(2-Amino-propyl)-cyclopropyl-sulfamoyl]-4-oxo-4,5-dihydro-3H-pyrrolo[2,3-c]quinoline-1-propyl carboxylate hydrochloride (153)

This compound is prepared according to synthesis 139, from 44 mg (0.08 mmol) of (S)-8-[(2-tert-butoxycarbonylamino-propyl)-cyclopropyl-sulfamoyl]-4-oxo-4,5-dihydro-3H-pyrrolo[2,3-c]quinoline-1-propyl carboxylate and 2 mL (4 mmol) of a 2M solution of hydrochloric acid in diethyl ether to give, after filtration, 35 mg (78%) of (S)-8-[(2-amino-propyl)-cyclopropyl-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 447.28

$^1$H-NMR: $\delta_H$ ppm 400 MHz, DMSO 13.32 (1H, bs, NH), 12.22 (1H, bs, NH), 9.93 (1H, s, $CH_{arom}$), 8.12 (1H, s, $CH_{arom}$), 8.04 (2H, bs, $NH_2$), 7.88 (1H, d, $CH_{arom}$), 7.67 (1H, d, $CH_{arom}$), 4.27 (2H, t, $OCH_2$), 3.32-3.12 (3H, m, 3×$CH_{ali}$), 2.01 (1H, bs, CH), 1.85-1.75 (2H, m, $CH_2$), 1.23 (3H, d, $CH_3$), 1.05-1.00 (3H, m, $CH_3$), 0.93-0.74 (4H, m, 4×$CH_{cycloprop}$).

(R)-8-[(2-tert-Butoxycarbonylamino-propyl)-cyclopropyl-sulfamoyl]-4-oxo-4,5-dihydro-3H-pyrrolo[2,3-c]quinoline-1-propyl carboxylate (154)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid, 1.11 mL (8 mmol) of triethylamine and 321 mg (1.5 mmol) of (R)—N'-tert-butoxycarbonyl-N-cyclopropyl-propane-1,2-diamine hydrochloride to give, after esterification according to general method C (using di-n-propylsulfate as the dialkylsulfate) and purification by chromatography on silica (eluent dichloromethane/methanol 97/3) then trituration in diethyl ether, 165 mg (30% in two stages) of (R)-8-[(2-tert-butoxycarbonylamino-propyl)-cyclopropyl-sulfamoyl]-4-oxo-4,5-dihydro-3H-pyrrolo[2,3-c]quinoline-1-propyl carboxylate in the form of a white solid.

LCMS (IE, m/z): (M+1) 547.19

$^1$H-NMR: $\delta_H$ ppm 400 MHz, $CDCl_3$ 11.57 (1H, bs, NH), 10.91 (1H, bs, NH), 10.01 (1H, s, $CH_{arom}$), 8.01 (1H, s, $CH_{arom}$), 7.87 (1H, d, $CH_{arom}$), 7.46 (1H, d, $CH_{arom}$), 4.97 (1H, bs, NH), 4.26 (2H, t, $OCH_2$), 4.06 (1H, s, CH), 3.47 (1H, s, $CH_2$), 3.17 (1H, s, $CH_2$), 2.18 (1H, s, CH), 1.79 (2H, dd, $CH_2$), 1.42 (9H, s, 3×$CH_3$), 1.21 (3H, d, $CH_3$), 1.03 (3H, t, $CH_3$), 0.98 (2H, bs, 2×$CH_{cycloprop}$) 0.74 (2H, bs, 2×$CH_{cycloprop}$).

4.3 mL (14.3 mmol) of titanium isopropoxide and 1.9 g (5 mmol) of (R)-2-(tert-butoxycarbonylamino)-propionaldehyde (prepared according to the method described by Itaya, Taisuke et al., Tetrahedron Lett., 1986, 52(27), 6349-52) are added to a solution of 1.88 g (33 mmol) of cyclopropylamine in 10 mL of anhydrous methanol. The solution is stirred for 5 hours at room temperature then 227 mg (6 mmol) of sodium borohydride is added. Stirring is continued for a further 2 hours then 2 mL of water is added. The reaction mixture is filtered then the solvents are evaporated. The residue is purified by chromatography on silica (eluent dichloromethane/ methanol 98/2) to give 350 mg (14%) of (R)—N'-tert-butoxycarbonyl, N-cyclopropyl-propane-1,2-diamine in the form of a colourless oil.

(R)-8-[(2-Amino-propyl)-cyclopropyl-sulfamoyl]-4-oxo-4,5-dihydro-3H-pyrrolo[2,3-c]quinoline-1-propyl carboxylate hydrochloride (155)

This compound is prepared according to synthesis 139, from 44 mg (0.08 mmol) (R)-8-[(2-tert-butoxycarbonylamino-propyl)-cyclopropyl-sulfamoyl]-4-oxo-4,5-dihydro-3H-pyrrolo[2,3-c]quinoline-1-propyl carboxylate and 2 mL (4 mmol) of a 2M solution of hydrochloric acid in diethyl ether to give, after filtration, 36 mg (81%) of (R)-8-[(2-amino-propyl)-cyclopropyl-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 447.23

$^1$H-NMR: $\delta_H$ ppm 400 MHz, DMSO 13.32 (1H, bs, NH), 12.22 (1H, bs, NH), 9.93 (1H, s, $CH_{arom}$), 8.12 (1H, s, $CH_{arom}$), 8.04 (2H, bs, $NH_2$), 7.88 (1H, d, $CH_{arom}$), 7.67 (1H, d, $CH_{arom}$), 4.27 (2H, t, $OCH_2$), 3.32-3.12 (3H, m, 3×$CH_{ali}$), 2.01 (1H, bs, CH), 1.85-1.75 (2H, m, $CH_2$), 1.23 (3H, d, $CH_3$), 1.05-1.00 (3H, m, $CH_3$), 0.93-0.74 (4H, m, 4×$CH_{cycloprop}$).

8-[(2-Methylamino-ethyl)-prop-2-ynyl-sulfamoyl]-4-oxo-4,5-dihydro-3H-pyrrolo[2,3-c]quinoline-1-propyl carboxylate hydrochloride (156)

This compound is prepared according to synthesis 139, from 54 mg (0.1 mmol) of 8-{[2-(tert-butoxycarbonyl-methyl-amino)-ethyl]-prop-2-ynyl-sulfamoyl}-4-oxo-4,5-dihydro-3H-pyrrolo[2,3-c]quinoline-1-propyl carboxylate and 2.5 mL (5 mmol) of a 2M solution of hydrochloric acid in diethyl ether to give, after filtration, 42 mg (87%) of 8-[(2-methylamino-ethyl)-prop-2-ynyl-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 445.23

$^1$H-NMR: $\delta_H$ ppm 400 MHz, DMSO 13.22 (1H, bs, NH), 12.13 (1H, bs, NH), 9.89 (1H, s, $CH_{arom}$), 0.64 (2H, bs, $NH_2$), 8.07 (1H, s, $CH_{arom}$), 7.83 (1H, dd, $CH_{arom}$), 7.57 (1H, d, $CH_{arom}$), 4.26-4.22 (4H, m, $NCH_2$, $OCH_2$), 3.45 (2H, bs, $CH_2$), 3.20-3.18 (2H, m, CH), 3.03 (1H, s, $CH_{alkyne}$), 2.62 (3H, s, $NCH_3$), 1.79-1.73 (2H, m, $CH_2$), 1.00 (3H, t, $CH_3$).

8-{[2-(tert-Butoxycarbonyl-methyl-amino)-ethyl]-prop-2-ynyl-sulfamoyl}-4-oxo-4,5-dihydro-3H-pyrrolo[2,3-c]quinoline-1-propyl carboxylate (157)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid, 1.11 mL (8 mmol) of triethylamine and 318 mg (1.5 mmol) of N-tert-butoxycarbonyl-N-methyl-N'-prop-2-ynyl-ethane-1,2-diamine to give, after esterification according to general method C (using di-n-propylsulfate as the dialkylsulfate) and purification by chromatography on silica (eluent cyclohexane/ethyl acetate 1/1 then 1/9), 69 mg (12% in two stages) of 8-{[2-(tert-butoxycarbonyl-methyl-amino)-ethyl]-prop-2-ynyl-sulfamoyl}-4-oxo-4,5-dihydro-3H-pyrrolo[2,3-c]quinoline-1-propyl carboxylate in the form of a white solid.

LCMS (IE, m/z): (M+1−Boc) 445.26

$^1$H-NMR: $\delta_H$ ppm 400 MHz, CDCl$_3$ 11.18 (1H, bs, NH), 10.41 (1H, bs, NH), 10.11 (1H, s, $CH_{arom}$), 8.03 (1H, s, $CH_{arom}$), 7.88 (1H, dd, $CH_{arom}$), 7.45 (1H, bs, $CH_{arom}$), 4.32-4.22 (4H, m, 2×$CH_2$), 3.51 (2H, bs, $CH_2$), 2.96 (3H, s, $NCH_3$), 1.97-1.91 (1H, m, $CH_{alkyne}$), 1.81 (2H, dd, $CH_2$), 1.46 (9H, t, 3×$CH_3$), 1.04 (3H, t, $CH_3$).

2.7 mL (9.1 mmol) of titanium isopropoxide and 1.2 g (7 mmol) of (tert-butoxycarbonyl-methyl-amino)-acetaldehyde (prepared according to the method described by Kato, Shiro et al., J. Chem. Soc. Perkin Trans. 1, 1997, 21, 3219-26) are added to a solution of 1.16 g (21 mmol) of propargylamine in 50 mL of anhydrous tetrahydrofuran. The solution is stirred for 5 hours at room temperature then 5 mL of anhydrous methanol and 317 mg (8.4 mmol) of sodium borohydride is added. Stirring is continued for a further 2 hours then 2 mL of water is added. The reaction mixture is filtered then the solvents are evaporated. The residue is purified by chromatography on silica (eluent dichloromethane/methanol 98/2) to give 550 mg (37%) of N-tert-butoxycarbonyl-N-methyl-N'-prop-2-ynyl-ethane-1,2-diamine in the form of a colourless oil.

8-[(2-isopropylamino-ethyl)-prop-2-ynyl-sulfamoyl]-4-oxo-4,5-dihydro-3H-pyrrolo[2,3-c]quinoline-1-propyl carboxylate hydrochloride (158)

This compound is prepared according to synthesis 139, from 57 mg (0.1 mmol) of 8-{[2-(tert-butoxycarbonyl-isopropyl-amino)-ethyl]-prop-2-ynyl-sulfamoyl}-4-oxo-4,5-dihydro-3H-pyrrolo[2,3-c]quinoline-1-propyl carboxylate and 2.5 mL (5 mmol) of a 2M solution of hydrochloric acid in diethyl ether to give, after filtration, 42 mg (82%) of 8-[(2-isopropylamino-ethyl)-prop-2-ynyl-sulfamoyl]-4-oxo-4,5-dihydro-3H-pyrrolo[2,3-c]quinoline-1-propyl carboxylate hydrochloride in the form of a white solid.

LCMS (IE, m/z): (M+1) 473.25

$^1$H-NMR: $\delta_H$ ppm 400 MHz, DMSO 13.27 (1H, bs, NH), 12.15 (1H, bs, NH), 9.91 (1H, s, $CH_{arom}$), 8.49 (2H, bs, $NH_2$), 8.12 (1H, s, $CH_{arom}$), 7.86 (1H, d, $CH_{arom}$), 7.57 (1H, d, $CH_{arom}$), 4.28-4.24 (4H, m, 2×$CH_2$), 3.59-3.48 (2H, m, $NCH_2$), 3.42-3.36 (1H, m, CH), 3.23-3.14 (2H, bs, $CH_2$), 3.09 (1H, s, $CH_{alkyne}$) 1.82-1.75 (2H, m, $CH_2$), 1.27 (6H, d, 2×$CH_3$), 1.00 (3H, t, $CH_3$).

8-{[2-(tert-Butoxycarbonyl-isopropyl-amino)-ethyl]-prop-2-ynyl-sulfamoyl}-4-oxo-4,5-dihydro-3H-pyrrolo[2,3-c]quinoline-1-propyl carboxylate (159)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid, 1.11 ml, (8 mmol) of triethylamine and 360 mg (1.5 mmol) of N-tert-butoxycarbonyl-N-isopropyl-N'-prop-2-ynyl-ethane-1,2-diamine to give, after esterification according to general method C (using di-n-propylsulfate as the dialkylsulfate) and purification by chromatography on silica (eluent cyclohexane/ethyl acetate 1/1 then 1/9) then trituration in diethyl ether, 260 mg (45% in two stages) of 8-{[2-(tert-butoxycarbonyl-methyl-amino)-ethyl]-prop-2-ynyl-sulfamoyl}-4-oxo-4,5-dihydro-3H-pyrrolo[2,3-c]quinoline-1-propyl carboxylate in the form of a white solid.

LCMS (IE, m/z): (M+1) 573.38

$^1$H-NMR: $\delta_H$ ppm 400 MHz, CDCl$_3$ 11.36 (1H, bs, NH), 10.65 (1H, bs, NH), 10.10 (1H, s, $CH_{arom}$), 8.03 (1H, s, $CH_{arom}$), 7.88 (1H, d, $CH_{arom}$), 7.45 (1H, bs, $CH_{arom}$), 4.29-4.22 (4H, m, 2×$CH_2$), 3.45-3.36 (4H, m, 2×$CH_2$), 1.97 (1H, s, $CH_{alkyne}$), 1.82-1.75 (2H, m, $CH_2$), 1.67-1.62 (1H, m, $CH_{ali}$), 1.46 (9H, s, 3×$CH_3$) 1.20 (6H, d, 2×$CH_3$), 1.00 (3H, t, $CH_3$).

3.9 mL (13 mmol) of titanium isopropoxide and 2 g (10 mmol) of (tert-butoxycarbonyl-isopropyl-amino)-acetaldehyde (prepared according to the method described by Kato, Shiro et al., *J. Chem. Soc. Perkin Trans.* 1, 1997, 21, 3219-26) are added to a solution of 1.65 g (30 mmol) of propargylamine in 50 mL of anhydrous tetrahydrofuran. The solution is stirred for 5 hours at room temperature then 5 mL of anhydrous methanol and 317 mg (8.4 mmol) of sodium borohydride are added. Stirring is continued for a further 2 hours then 2 mL of water is added. The reaction mixture is filtered then the solvents are evaporated. The residue is purified by chromatography on silica (eluent dichloromethane/methanol 98/2) to give 1.2 g (50%) of N-tert-butoxycarbonyl-N-isopropyl-N'-prop-2-ynyl-ethane-1,2-diamine in the form of a colourless oil.

(S)-8-(Ethyl-pyrrolidin-3-yl-sulfamoyl)-4-oxo-4,5-dihydro-3H-pyrrolo[2,3-c]quinoline-1-propyl carboxylate hydrochloride (160)

This compound is prepared according to synthesis 139, from 82 mg (0.15 mmol) of (S)-8-[(1-tert-butoxycarbonyl-ethyl-pyrrolidin-3-yl)-sulfamoyl]-4-oxo-4,5-dihydro-3H-pyrrolo[2,3-c]quinoline-1-propyl carboxylate and 7 mL (14 mmol) of a 2M solution of hydrochloric acid in diethyl ether to give, after filtration, 15 mg (20%) of (S)-8-(ethyl-pyrrolidin-3-yl-sulfamoyl)-4-oxo-4,5-dihydro-3H-pyrrolo[2,3-c]quinoline-1-propyl carboxylate hydrochloride in the form of a white solid.

LCMS (IE, m/z): (M+1) 447.30

$^1$H-NMR: $\delta_H$ ppm 400 MHz, DMSO 13.29 (1H, bs, NH), 12.16 (1H, bs, NH), 9.86 (1H, d, $CH_{arom}$), 9.00-8.85 (1H, m, NH. HCl), 8.78-8.64 (1H, m, NH.HCl), 8.09 (1H, d, $CH_{arom}$), 7.85 (1H, dd, $CH_{arom}$), 7.57 (1H, d, $CH_{arom}$) 4.61-4.51 (1H, m, $CH_{ali}$), 4.25 (2H, t, $CH_2$), 3.63-3.57 (1H, m, $CH_{ali}$), 3.29-3.16 (3H, m, 3×$CH_{ali}$), 3.06-2.95 (1H, m, $CH_{ali}$), 2.85-2.75 (1H, m, $CH_{arom}$), 2.05-1.96 (H, m, $CH_{ali}$), 1.82-1.69 (3H, m, $CH_{ali}$ and CH), 1.20 (3H, t, $CH_3$), 1.00 (3H, t, $CH_3$).

(S)-8-[(1-tert-butoxycarbony-ethyl-pyrrolidin-3-yl)-sulfamoyl]-4-oxo-4,5-dihydro-3H-pyrrolo[2,3-c]quinoline-1-propyl carboxylate is prepared according to synthesis 111, from 500 mg (1.53 mmol) of 8-chlorosulfonyl-4-oxo-4,5-dihydro-3H-pyrrolo[2,3-c]quinoline-1-carboxylic acid, 640 mL (4.6 mmol) of triethylamine and 655 mg (3 mmol) of (S)-1-tert-butoxycarbonyl-3-ethylamino-pyrrolidine to give, after esterification according to general method C (using di-n-propylsulfate as the dialkylsulfate) and purification by chromatography on silica (eluent cyclohexane/ethyl acetate 1/1 then 1/3), 85 mg (10% in two stages) of (S)-8-[(1-tert-butoxycarbonyl-ethyl-pyrrolidin-3-yl)-sulfamoyl]-4-oxo-4,5-dihydro-3H-pyrrolo[2,3-c]quinoline-1-propyl carboxylate in the form of a white solid.

367 μL (6.5 mmol) of acetaldehyde, 817 mg (13 mmol) of sodium cyanoborohydride and 3.75 mL (65 mmol) of acetic acid are added to a solution of 1.47 mL (8.4 mmol) of (S)-3-amino-1-tert-butoxycarbonylpyrrolidine in 30 mL of anhydrous methanol. The solution is stirred at room temperature for 24 hours then a saturated aqueous solution of sodium hydrogencarbonate is added to adjust the pH to 7. The compound is extracted with ethyl acetate. The organic phases are dried over magnesium sulfate, filtered then evaporated and the residue is purified by chromatography on silica (eluent dichloromethane/methanol 94/6) to give 970 mg (70%) of (S)-1-tert-butoxycarbonyl-3-ethylamino-pyrrolidine in the form of a yellow oil.

(S)-8-[Ethyl-(1-methyl-pyrrolidin-3-yl)-sulfamoyl]-4-oxo-4,5-dihydro-3H-pyrrolo[2,3-c]quinoline-1-propyl carboxylate (161)

This compound is prepared according to synthesis 119, from 77 mg (0.16 mmol) of (S)-8-(ethyl-pyrrolidin-3-yl-sulfamoyl)-4-oxo-4,5-dihydro-3H-pyrrolo[2,3-c]quinoline-1-propyl carboxylate hydrochloride, 134 μL (0.96 mmol) of triethylamine and 30 μL (0.32 mmol)) of dimethylsulfate to give, after purification by chromatography on silica (eluent dichloromethane/methanol 9/1), 17 mg (23%) of (S)-8-[ethyl-(1-methyl-pyrrolidin-3-yl)-sulfamoyl]-4-oxo-4,5-dihydro-3H-pyrrolo[2,3-c]quinoline-1-propyl carboxylate in the form of a white solid.

LCMS (IE, m/z): (M+1) 461.34

$^1$H-NMR: $\delta_H$ ppm 400 MHz, DMSO 13.22 (1H, bs, NH), 12.08 (1H, bs, NH), 9.82 (1H, d, $CH_{arom}$), 8.07 (1H, d, $CH_{arom}$), 7.80 (1H, dd, $CH_{arom}$), 7.54 (1H, d, $CH_{arom}$), 4.55-4.44 (1H, m, $CH_{ali}$), 4.25 (2H, t, $CH_2$), 3.36-3.21 (2H, m, 2×$CH_{arom}$), 2.81-2.61 (1H, m, $CH_{ali}$), 2.52-2.38 (1H, m, $CH_{ali}$), 2.25 (3H, s, $CH_3$), 2.09-1.95 (1H, m, $CH_{ali}$), 1.90-1.76 (2H, m, $CH_2$), 1.63-1.50 (1H, m, $CH_{ali}$), 1.39-1.24 (4H, m, $CH_{ali}$ and $CH_3$), 1.06 (3H, it, $CH_3$), 0.97-0.87 (1H, m, $CH_{ali}$).

4-Oxo-8-(pyrrolidine-1-sulfonyl)-4,5-dihydro-3H-pyrrolo[2,3-c]quinoline-1-ethyl carboxylate (162)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 86 μL (1.05 mmol) of pyrrolidine to give, after esterification according to general method C (using diethylsulfate as the dialkylsulfate) and purification by chromatography on silica (eluent dichloromethane/methanol 97/3), 150 mg (38% in two stages) of 4-oxo-8-(pyrrolidine-1-sulfonyl)-4,5-dihydro-3H-pyrrolo[2,3-c]quinoline-1-ethyl carboxylate in the form of a white solid.

LCMS (IE, m/z): (M+1) 390.14

$^1$H-NMR: $\delta_H$ ppm 400 MHz, DMSO 13.20 (1H, bs, NH), 12.08 (1H, bs, NH), 9.80 (1H, d, $CH_{arom}$), 8.06 (1H, s, $CH_{arom}$), 7.80 (1H, dd, $CH_{arom}$), 7.57 (1H, d, $CH_{arom}$), 4.33 (2H, q, $CH_2$), 3.23-3.15 (4H, m, 4×$CH_{arom}$), 1.67-1.58 (4H, m, 4×$CH_{arom}$), 1.35 (3H, t, $CH_3$).

(S)-4-Oxo-8-(2-pyrrolidin-1-ylmethyl-pyrrolidine-1-sulfonyl)-4,5-dihydro-3H-pyrrolo[2,3-c]quinoline-1-ethyl carboxylate (163)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 162 mg (1.05 mmol) of (S)-2-pyyrolidin-1-ylmethylpyrrolidine to give, after esterification according to general method C (using diethylsulfate as the dialkylsulfate) and purification by chromatography on silica (eluent chloroform/methanol/ammonia 250/25/4), 56 mg (12% in two stages) of (S)-4-oxo-8-(2-pyrrolidin-1-ylmethyl-pyrrolidine-1-sulfonyl)-4,5-dihydro-3H-pyrrolo[2,3-c]quinoline-1-ethyl carboxylate in the form of a white solid.

LCMS (IE, m/z): (M+1) 473.10

$^1$H-NMR: $\delta_H$ ppm 400 MHz, DMSO 13.21 (1H, bs, NH), 12.08 (1H, bs, NH), 9.87 (1H, d, $CH_{arom}$), 8.06 (1H, s, $CH_{arom}$), 7.81 (1H, dd, $CH_{arom}$), 7.56 (1H, d, $CH_{arom}$), 4.32 (2H, q, $CH_2$), 3.85-3.78 (1H, m, CH$_{arom}$), 3.11-3.03 (1H, m, CH$_{ali}$), 2.65-2.39 (7H, m, 7×CH$_{ali}$), 1.78-1.58 (6H, m, 6×CH$_{ali}$), 1.45-1.33 (2H, m, 2×CH$_{ali}$), 1.34 (3H, t, CH$_3$).

(S)-8-(3-tert-Butoxycarbonylamino-pyrrolidine-1-sulfonyl)-4-oxo-4,5-dihydro-3H-pyrrolo[2,3-c]quinoline-1-propyl carboxylate (164)

This compound was prepared according to general method of esterification C from 5.45 g (11.44 mmol) of (S)-8-(3-tert-butoxycarbonylamino-pyrrolidine-1-sulfonyl)-4-oxo-4,5-dihydro-3H-pyrrolo[2,3-c]quinoline-1-carboxylic acid, 7.99 mL (45 mmol) of triethylamine and 2.07 mL (12.58 mmol) of di-n-propylsulfate. Stirring of the solution at 60° C. for 4 hours gives, after purification by chromatography on silica (eluent ethyl acetate) then recrystallization from propanol/ether diisopropyl mixture, 2.94 g (49%) of (S)-8-(3-tert-butoxycarbonylamino-pyrrolidine-1-sulfonyl)-4-oxo-4,5-dihydro-3H-pyrrolo[2,3-c]quinoline-1-propyl carboxylate in the form of a white solid.

LC/MS (IE, m/z): (M+1) 519.35

$^1$H-NMR: δ$_H$ ppm 400 MHz, DMSO 13.24 (1H, bs, NH), 12.13 (1H, bs, NH), 9.82 (1H, s, CH$_{arom}$), 8.08 (1H, s, CH$_{arom}$), 7.78 (1H, d, CH$_{arom}$), 7.58 (1H, d, CH$_{arom}$), 6.94 (1H, d, BocNH), 4.25 (2H, t, CH$_2$), 3.83-3.75 (1H, m, CH$_{pyrrol}$), 3.38-3.30 (2H, m, 2×CH$_{pyrrol}$), 3.24-3.17 (1H, m, CH$_{pyrrol}$), 3.00-2.94 (1H, m, CH$_{pyrrol}$) 1.91-1.82 (1H, m, CH$_{pyrrol}$) 1.75 (2H, m, CH$_2$), 1.65-1.57 (1H, m, CH$_{pyrrol}$), 1.28 (9H, s, 3×CH$_3$), 0.99 (3H, t, CH$_3$).

(S)-8-(3-tert-Butoxycarbonylamino-pyrrolidine-1-sulfonyl)-4-oxo-4,5-dihydro-3H-pyrrolo[2,3-c]quinoline-1-carboxylic acid (165)

This compound is prepared according to synthesis 178, from 5.88 g (118 mmol) of 8-chlorosulfonyl-4-oxo-4,5-dihydro-3H-pyrrolo[2,3-c]quinoline-1-carboxylic acid, 12.54 mL (90 mmol) of triethylamine and 3.69 g (19.8 mmol) of (S)—N-tert-butoxycarbonyl-N'-pyrrolidin-3-yl-amine to give, after purification by precipitation and trituration in water, 6.18 g (72%) of (S)-8-(3-tert-butoxycarbonylamino-pyrrolidine-1-sulfonyl)-4-oxo-4,5-dihydro-3H-pyrrolo[2,3-c]quinoline-1-carboxylic acid in the form of a beige solid.

LC/MS (IE, m/z): (M+1) 477.31

$^1$H-NMR: δ$_H$ ppm 400 MHz, DMSO 12.64 (1H, bs, CO$_2$H), 12.06 (1H, bs, NH), 9.97 (1H, s, CH$_{arom}$), 7.99 (1H, s, CH$_{arom}$), 7.76 (1H, d, CH$_{arom}$), 7.55 (1H, d, CH$_{arom}$), 694 (1H, bs, BocNH), 3.89-3.75 (1H, m, CH$_{pyrrol}$), 3.30-3.18 (3H, m, 3×CH$_{pyrrol}$), 3.03-2.93 (1H, m, CH$_{pyrrol}$) 1.93-1.82 (1H, m, CH$_{pyrrol}$), 1.68-1.57 (1H, m, CH$_{pyrrol}$), 1.30 (9H, s, 3×CH$_3$).

(S)-8-(3-amino-cyclopentanesulfonyl)-4-oxo-4,5-dihydro-3H-pyrrolo[2,3-c]quinoline-1-propyl carboxylate hydrochloride (166)

This compound is prepared according to synthesis 139, from 93 mg (0.18 mmol) of (S)-8-(3-tert-butoxycarbonylamino-pyrrolidine-1-sulfonyl)-4-oxo-4,5-dihydro-3H-pyrrolo[2,3-c]quinoline-1-propyl carboxylate and 4.5 mL (9 mmol) of a 2M solution of hydrochloric acid in diethyl ether to give, after filtration, 58 mg (71%) of (S)-8-(3-amino-cyclopentanesulfonyl)-4-oxo-4,5-dihydro-3H-pyrrolo[2,3-c]quinoline-1-propyl carboxylate hydrochloride in the form of a white solid.

LC/MS (IE, m/z): (M+1) 419.29

$^1$H-NMR: δ$_H$ ppm 400 MHz, DMSO 13.25 (1H, bs, NH), 12.15 (1H, bs, NH), 9.84 (1H, s, CH$_{arom}$), 8.15 (2H, bs, NH.HCl), 8.09 (1H, s, CH$_{arom}$), 7.82 (1H, d, CH$_{arom}$), 7.62 (1H, d, CH$_{arom}$), 4.26 (2H, t, CH$_2$), 3.75-3.63 (1H, m, CH$_{pyyrol}$), 3.49-3.39 (1H, m, CH$_{pyyrol}$), 3.39-3.27 (1H, m, CH$_{pyyrol}$), 3.27-3.12 (2H, m, 2×CH$_{pyyrol}$), 2.10-2.00 (1H, m, CH$_{pyyrol}$), 1.81-1.74 (3H, m, CH$_{pyrrol}$ and CH), 1.05 (3H, t, CH$_3$).

(R)-8-(3-amino-cyclopentanesulfonyl)-4-oxo-4,5-dihydro-3H-pyrrolo[2,3-c]quinoline-1-propyl carboxylate hydrochloride (167)

This compound is prepared according to synthesis 139, from 72 mg (0.14 mmol) of (R)-8-(3-tert-butoxycarbonylamino-pyrrolidine-1-sulfonyl)-4-oxo-4,5-dihydro-3H-pyrrolo[2,3-c]quinoline-1-propyl carboxylate and 3.5 mL (7 mmol) of a 2M solution of hydrochloric acid in diethyl ether to give, after filtration, 34 mg (53%) of (R)-8-(3-amino-cyclopentanesulfonyl)-4-oxo-4,5-dihydro-3H-pyrrolo[2,3-c]quinoline-1-propyl carboxylate hydrochloride in the form of a white solid.

LC/MS (IE, m/z): (M+1) 419.29

$^1$H-NMR: δ$_H$ ppm 400 MHz, DMSO 13.25 (1H, bs, NH), 12.15 (1H, bs, NH), 9.84 (1H, s, CH$_{arom}$), 8.15 (2H, bs, NH.HCl), 8.09 (1H, s, CH$_{arom}$), 7.82 (1H, d, CH$_{arom}$), 7.62 (1H, d, CH$_{arom}$), 4.26 (2H, 1, CH$_2$), 3.75-3.63 (1H, m, CH$_{pyyrol}$), 3.49-3.39 (1H, m, CH$_{pyyrol}$), 3.39-3.27 (1H, m, CH$_{pyyrol}$), 3.27-3.12 (2H, m, 2×CH$_{pyyrol}$), 2.10-2.00 (1H, m, CH$_{pyyrol}$) 1.81-1.74 (3H, m, CH$_{pyrrol}$ and CH$_2$), 1.05 (3H, t, CH$_3$).

(R)-8-(3-tert-butoxycarbonylamino-pyrrolidine-1-sulfonyl)-4-oxo-4,5-dihydro-3H-pyrrolo[2,3-c]quinoline-1-propyl carboxylate is prepared according to synthesis 136, from 360 mg (1.1 mmol) of 8-chlorosulfonyl-4-oxo-4,5-dihydro-3H-pyrrolo[2,3-c]quinoline-1-carboxylic acid, 767 μL (5.5 mmol) of triethylamine and 138 mg (1.21 mmol) of (R)—N-tert-butoxycarbonyl-N'-pyrrolidin-3-yl amine to give, after esterification according to general method C (using di-n-propylsulfate as the dialkylsulfate) and purification by chromatography on silica (eluent cyclohexane/ethyl acetate 2/3 then ethyl acetate/methanol 98/2), 80 mg (14% in two stages) of (R)-8-(3-tert-butoxycarbonylamino-pyrrolidine-1-sulfonyl)-4-oxo-4,5-dihydro-3H-pyrrolo[2,3-c]quinoline-1-propyl carboxylate in the form of a brown solid.

8-(3-Methylamino-pyrrolidine-1-sulfonyl)-4-oxo-4,5-dihydro-3H-pyrrolo[2,3-c]quinoline-1-propyl carboxylate hydrochloride (168)

This compound is prepared according to synthesis 139, from 129 mg (0.25 mmol) of 8-[3-(tert-butoxycarbonyl-methyl-amino)-pyrrolidine-1-sulfonyl]-4-oxo-4,5-dihydro-3H-pyrrolo[2,3-c]quinoline-1-propyl carboxylate and 6.3 mL (12.6 mmol) of a 2M solution of hydrochloric acid in diethyl ether to give, after filtration, 92 mg (78%) of the 8-(3-methylamino-pyrrolidine-1-sulfonyl)-4-oxo-4,5-dihydro-3H-pyrrolo[2,3-c]quinoline-1-propyl carboxylate hydrochloride in the form of a cream-coloured solid.

LC/MS (IE, m/z): (M+1) 433.27

$^1$H-NMR: δ$_H$ ppm 400 MHz, DMSO 13.25 (1H, bs, NH), 12.15 (1H, bs, NH), 9.82 (1H, s, CH$_{arom}$), 9.13 (2H, bs, NH.HCl), 8.07 (1H, s, CH$_{arom}$), 7.82 (1H, d, CH$_{arom}$), 7.62 (1H, d, CH$_{arom}$), 4.29-4.18 (2H, m, CH$_2$), 3.67-3.56 (1H, m CH$_{pyrrol}$), 3.45-3.25 (3H, m, 3×CH$_{pyrrol}$), 3.19-3.10 (1H, m, CH$_{pyrrol}$), 2.50 (3H, s, NCH$_3$), 2.11-2.02 (1H, m, CH$_{pyrrol}$) 1.97-1.87 (1H, m, CH$_{pyrrol}$), 1.81-1.67 (2H, m, CH$_2$), 1.04-0.95 (3H, t, CH$_3$).

8-[3-(tert-Butoxycarbonyl-methyl-amino)-pyrrolidine-1-sulfonyl]-4-oxo-4,5-dihydro-3H-pyrrolo[2,3-c]quinoline-1-propyl carboxylate (169)

This compound was prepared according to general method of esterification C from 294 mg (0.6 mmol) of 8-[3-(tert-butoxycarbonyl-methyl-amino)-pyrrolidine-1-sulfonyl]-4-oxo-4,5-dihydro-3H-pyrrolo[2,3-c]quinoline-1-carboxylic acid, 836 μL (6 mmol) of triethylamine and 492 μL (3 mmol) of di-n-propylsulfate to give, after purification by chromatography on silica (eluent dichloromethane/methanol 98/2), 155 mg (50%) of 8-[3-(tert-butoxycarbonyl-methyl-amino)-pyrrolidine-1-sulfonyl]-4-oxo-4,5-dihydro-3H-pyrrolo[2,3-c]quinoline-1-propyl carboxylate in the form of a brown solid.

LC/MS (IE, m/z): (M+1) 533.41

$^1$H-NMR: δ$_H$ ppm 400 MHz, CDCl$_3$ 11.41 (1H, bs, NH), 10.71 (1H, bs, NH), 10.03 (1H, s, CH$_{arom}$), 8.02 (1H, s, CH$_{arom}$), 7.86 (1H, d, CH$_{arom}$), 7.47 (1H, d, CH$_{arom}$), 4.77-4.62 (1H, m, CH), 4.28 (2H, t, CH$_2$), 3.71-3.58 (1H, m, CH), 3.53-3.43 (1H, m, CH), 3.35-3.321 (2H, m, 2×CH), 2.74 (3H, s, NCH$_3$), 2.10-1.89 (2H, m, 2×CH), 1.85-1.74 (2H, m, CH$_2$), 1.40 (9H, s, 3×CH$_3$), 1.02 (3H, t, CH$_3$).

8-[3-(tert-Butoxycarbonyl-methyl-amino)-pyrrolidine-1-sulfonyl]-4-oxo-4,5-dihydro-3H-pyrrolo[2,3-c]quinoline-1-carboxylic acid (170)

This compound is prepared according to synthesis 178, from 326 mg (1 mmol) of 8-chlorosulfonyl-4-oxo-4,5-dihydro-3H-pyrrolo[2,3-c]quinoline-1-carboxylic acid, 697 μL (5 mmol) of triethylamine and 220 mg (1.1 mmol) of N-tert-butoxycarbonyl-N-methyl-N'-pyrrolidin-3-yl-amine to give, after purification by precipitation and trituration in water, 389 mg (79%) of 8-[3-(tert-butoxycarbonyl-methyl-amino)-pyrrolidine-1-sulfonyl]-4-oxo-4,5-dihydro-3H-pyrrolo[2,3-c]quinoline-1-carboxylic acid in the form of a brown solid.

LC/MS (IE, m/z): (M+1) 491.27

$^1$H-NMR: δ$_H$ ppm 400 MHz, CD$_3$OD 10.15 (1H, s, CH$_{arom}$), 8.10 (1H, s, CH$_{arom}$), 7.88 (1H, d, CH$_{arom}$), 7.59 (1H, d, CH$_{arom}$), 4.55-4.35 (1H, m, CH), 3.63-3.39 (2H, m, CH$_2$), 2.70 (3H, s, NCH$_3$), 2.05-1.86 (3H, m, 3×CH), 1.34 (9H, s, 3×CH$_3$).

(S)-8-(3-Dimethylamino-cyclopentanesulfonyl)-4-oxo-4,5-dihydro-3H-pyrrolo[2,3-c]quinoline-1-propyl carboxylate (171)

This compound is prepared according to synthesis 136, from 360 mg (1.1 mmol) of 8-chlorosulfonyl-4-oxo-4,5-dihydro-3H-pyrrolo[2,3-c]quinoline-1-carboxylic acid, 767 μL (5.5 mmol) of triethylamine and 138 mg (1.21 mmol) of (S)—N,N-dimethyl-N'-pyrrolidin-3-yl-amine to give, after esterification according to general method C (using di-n-propylsulfate as the dialkylsulfate) and purification by chromatography on silica (eluent dichloromethane/methanol/ammonia 200/16/2) then trituration in diethyl ether, 68 mg (13% in two stages) of (S)-8-(3-dimethylamino-cyclopentanesulfonyl)-4-oxo-4,5-dihydro-3H-pyrrolo[2,3-c]quinoline-1-propyl carboxylate in the form of a brown solid.

LC/MS (IE, m/z): (M+1) 447.34

$^1$H-NMR: δ$_H$ ppm 400 MHz, DMSO 13.26 (1H, bs, NH), 12.12 (1H, bs, NH), 9.84 (1H, s, CH$_{arom}$), 8.08 (1H, s, CH$_{arom}$), 7.83 (1H, d, CH$_{arom}$), 7.58 (1H, d, CH$_{arom}$), 4.24 (2H, t, CH$_2$), 3.54-3.45 (1H, m, CH$_{pyrrol}$), 3.19-3.08 (1H, m, CH$_{pyrrol}$), 2.98-2.86 (1H, m, CH$_{pyrrol}$), 2.01 (6H, s, 2×CH$_3$), 1.95-1.80 (1H, m, CH$_{pyrrol}$) 1.79-1.70 (2H, m, CH$_2$), 1.54-1.42 (1H, m, CH$_{pyrrol}$), 0.99 (3H, t, CH$_3$).

(R)-8-(3-Dimethylamino-cyclopentanesulfonyl)-4-oxo-4,5-dihydro-3H-pyrrolo[2,3-c]quinoline-1-propyl carboxylate (172)

This compound is prepared according to synthesis 136, from 360 mg (1.1 mmol) of 8-chlorosulfonyl-4-oxo-4,5-dihydro-3H-pyrrolo[2,3-c]quinoline-1-carboxylic acid, 767 μL (5.5 mmol) of triethylamine and 138 mg (1.21 mmol) of (R)—N,N-dimethyl-N'-pyrrolidin-3-yl-amine to give, after esterification according to general method C (using di-n-propylsulfate as the dialkylsulfate) and purification by chromatography on silica (eluent dichloromethane/methanol/ammonia 200/16/2) then trituration in diethyl ether, 119 mg (24% in two stages) of (R)-8-(3-dimethylamino-cyclopentanesulfonyl)-4-oxo-4,5-dihydro-3H-pyrrolo[2,3-c]quinoline-1-propyl carboxylate in the form of a brown solid.

LC/MS (IE, m/z): (M+1) 447.34

$^1$H-NMR: δ$_H$ ppm 400 MHz, DMSO 13.26 (1H, bs, NH), 12.12 (1H, bs, NH), 9.84 (If, s, CH$_{arom}$), 8.08 (1H, s, CH$_{arom}$), 7.83 (1H, d, CH$_{arom}$), 7.58 (1H, d, CH$_{arom}$), 4.24 (2H, t, CH$_2$), 3.54-3.45 (1H, m, CH$_{pyrrol}$), 3.19-3.08 (1H, m, CH$_{pyrrol}$), 2.98-2.86 (1H, m, CH$_{pyrrol}$), 2.01 (6H, s, 2×CH$_3$), 1.95-1.80 (1H, m, CH$_{pyrrol}$), 1.79-1.70 (2H, m, CH$_2$), 1.54-1.42 (1H, m, CH$_{pyrrol}$), 0.99 (3H, t, CH$_3$).

8-[(2-Hydroxy-ethyl)isopropyl-sulfamoyl]-4-oxo-4,5-dihydro-3H-pyrrolo[2,3-c]quinoline-1-propyl carboxylate (173)

This compound is prepared according to synthesis 136, from 457 mg (1.4 mmol) of 8-chlorosulfonyl-4-oxo-4,5-dihydro-3H-pyrrolo[2,3-c]quinoline-1-carboxylic acid, 585 μL (4.2 mmol) of triethylamine and 193 μL (1.68 mmol) of 2-isopropylamino-ethanol to give, after esterification according to general method C (using di-n-propylsulfate as the dialkylsulfate) and purification by chromatography on silica (eluent dichloromethane/methanol 96/4), 25 mg (4% in two stages) of 8-[(2-hydroxy-ethyl)-isopropyl-sulfamoyl]-4-oxo-4,5-dihydro-3H-pyrrolo[2,3-c]quinoline-1-propyl carboxylate in the form of a white solid.

LCMS (IE, m/z): (M+1) 436.30

$^1$H-NMR: δ$_H$ ppm 400 MHz, DMSO 13.17 (1H, bs, NH), 12.06 (1H, bs, NH), 9.82 (1H, d, CH$_{arom}$), 8.06 (1H, s, CH$_{arom}$), 7.80 (1H, dd, CH$_{arom}$), 7.54 (1H, d, CH$_{arom}$), 4.75 (1H, t, OH), 4.25 (2H, t, CH$_2$), 4.00 (1H, sept, CH), 3.55 (2H, q, CH$_2$), 3.13 (2H, t, CH$_2$), 1.76 (2H, sex, CH$_2$), 0.99 (3H, t, CH$_3$), 0.95 (6H, m, 2×CH$_3$).

8-[Cyclopropyl-(2-hydroxy-ethyl)-sulfamoyl]-4-oxo-4,5-dihydro-3H-pyrrolo[2,3-c]quinoline-1-propyl carboxylate (174)

This compound is prepared according to synthesis 136, from 490 mg (1.5 mmol) of 8-chlorosulfonyl-4-oxo-4,5-dihydro-3H-pyrrolo[2,3-c]quinoline-1-carboxylic acid, 627 μL (3 mmol) of triethylamine and 227 mg (2.25 mmol) of 2-cyclopropylamino-ethanol (prepared according to the method described by Morrow, D. F. et al., *J. Med Chem.*, 1973, 16(6), 736-9) to give, after esterification according to general method C (using di-n-propylsulfate as the dialkylsulfate) and purification by chromatography on silica (eluent dichloromethane/methanol 95/5), 116 mg (17% in two stages) of 8-[cyclopropyl-(2-hydroxy-ethyl)-sulfamoyl]-4-oxo-4,5-dihydro-3H-pyrrolo[2,3-c]quinoline-1-propyl carboxylate in the form of a white solid.

LCMS (IE, m/z): (M+1) 434.22

$^1$H-NMR: $\delta_H$ ppm 400 MHz, DMSO 13.19 (1H, bs, NH), 12.08 (1H, bs, NH), 9.86 (1H, d, $CH_{arom}$), 8.06 (1H, s, $CH_{arom}$), 7.82 (1H, dd, $CH_{arom}$), 7.58 (1H, d, $CH_{arom}$), 4.71 (1H, t, OH), 4.25 (2H, t, $CH_2$), 3.53 (2H, q, $CH_2$), 3.18 (2H, t, $CH_2$), 2.10-2.03 (1H, m, $CH_{ali}$), 1.80-1.68 (2H, m, $CH_2$), 0.99 (3H, t, $CH_3$), 0.86-0.77 (2H, m, 2×$CH_{ali}$), 0.73-0.64 (2H, m, 2×$CH_{arom}$).

8-[(2-Hydroxy-ethyl)-prop-2-ynyl-sulfamoyl]-4-oxo-4,5-dihydro-3H-pyrrolo[2,3-c]quinoline-1-propyl carboxylate (175)

This compound is prepared according to synthesis 136, from 490 mg (1.5 mmol) of 8-chlorosulfonyl-4-oxo-4,5-dihydro-3H-pyrrolo[2,3-c]quinoline-1-carboxylic acid and 223 mg (2.25 mmol) of 2-prop-2-ynylamino-ethanol (prepared according to the method described by Carretero, Juan Carlos; Adrio Javier, *Synthesis*, 2001, 12, 1888-96), to give, after esterification according to general method C (using di-n-propylsulfate as the dialkylsulfate) and purification by chromatography on silica (eluent dichloromethane/methanol 95/5), 80 mg (10% in two stages) of 8-[(2-hydroxy-ethyl)-prop-2-ynyl-sulfamoyl]-4-oxo-4,5-dihydro-3H-pyrrolo[2,3-c]quinoline-1-propyl carboxylate in the form of a white solid.

LCMS (IE, m/z): (M+1) 432.20

$^1$H-NMR: $\delta_H$ ppm 400 MHz, DMSO 13.20 (1H, bs, NH), 12.06 (1H, bs, NH), 9.84 (1H, d, $CH_{arom}$), 8.06 (1H, s, $CH_{arom}$), 7.80 (1H, dd, $CH_{arom}$), 7.53 (1H, d, $CH_{arom}$), 4.82 (1H, t, OH), 4.25 (2H, t, $CH_2$), 4.19-4.15 (2H, m, $CH_2$), 3.56 (2H, q, $CH_2$), 3.23 (2H, t, $CH_2$), 3.00-2.96 (1H, m, CH), 1.76 (2H, m, $CH_2$), 1.00 (3H, t, $CH_3$).

8-[bis-(2-Hydroxy-ethyl)-sulfamoyl]-4-oxo-4,5-dihydro-3H-pyrrolo[2,3-c]quinoline-1-propyl carboxylate (176)

This compound is prepared according to synthesis 136, from 490 mg (1.5 mmol) of 8-chlorosulfonyl-4-oxo-4,5-dihydro-3H-pyrrolo[2,3-c]quinoline-1-carboxylic acid and 236 mg (2.25 mmol) of 2-(2-hydroxy-ethylamino)-ethanol to give, after esterification according to general method C (using di-n-propylsulfate as the dialkylsulfate) and purification by preparative LC/MS, 5 mg (1% in two stages) of 8-[bis-(2-hydroxy-ethyl)-sulfamoyl]-4-oxo-4,5-dihydro-3H-pyrrolo[2,3-c]quinoline-1-propyl carboxylate in the form of a white solid.

LCMS (IE, m/z): (M+1) 438.25

$^1$H-NMR: $\delta_H$ ppm 400 MHz, DMSO 13.24 (1H, bs, NH), 12.09 (1H, bs, NH), 9.82 (1H, d, $CH_{arom}$), 8.07 (1H, s, $CH_{arom}$), 7.80 (1H, dd, $CH_{arom}$), 7.55 (1H, d, $CH_{arom}$), 4.83 (2H, t, 2×OH), 4.25 (2H; t, $CH_2$), 3.53 (4H; q, 2×$CH_2$), 3.19 (4H, t, $CH_2$) 1.75 (2H, m, $CH_2$), 0.99 (3H, t, $CH_3$).

8-(Carbamoylmethyl-methyl-sulfamoyl)-4-oxo-4,5-dihydro-3H-pyrrolo[2,3-c]quinoline-1-propyl carboxylate (177)

This compound was prepared according to general method of esterification C from 265 mg (0.7 mmol) of 8-(carbamoylmethyl-methyl-sulfamoyl)-4-oxo-4,5-dihydro-3H-pyrrolo[2,3-c]quinoline-1-carboxylic acid, 1.4 mL (1.93 mmol) of triethylamine and 690 μL (4.2 mmol) of di-n-propylsulfate to give, after purification by preparative LC, 35 mg (11%) of 8-(carbamoylmethyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 421.29

$^1$H-NMR: $\delta_H$ ppm 400 MHz, DMSO 13.21 (1H, bs, NH), 12.08 (1H, bs, NH), 9.80 (1H, d, $CH_{arom}$), 8.07 (1H, s, $CH_{arom}$), 7.78 (1H, dd, $CH_{arom}$), 7.57 (1H, d, $CH_{arom}$), 7.38 (1H, s, NH), 7.17 (1H, s, NH), 4.25 (2H, t, $CH_2$), 3.58 (2H, s, $CH_2$), 2.76 (3H, s, $CH_3$), 1.75 (2H, sext, $CH_2$), 0.99 (3H, t, $CH_3$).

8-(Carbamoylmethyl-methyl-sulfamoyl)-4-oxo-4,5-dihydro-3H-pyrrolo[2,3-c]quinoline-1-carboxylic acid (178)

584 μL (3 mmol) of triethylamine and 208 mg (1.68 mmol) of 2 methylamino-acetamide are added to 456 mg (1.4 mmol) of 8-chlorosulfonyl-4-oxo-4,5-dihydro-3H-pyrrolo[2,3-c]quinoline-1-carboxylic acid suspended in 4 mL of anhydrous dichloromethane and 1 mL of anhydrous dimethylformamide. The reaction mixture is stirred for 3 days at room temperature. The solvents are evaporated then the residue is taken up in methanol. The solid is filtered, rinsed with methanol then diisopropyl ether and dried under vacuum to give 279 mg (53%) of 8-(carbamoylmethyl-methyl-sulfamoyl)-4-oxo-4,5-dihydro-3H-pyrrolo[2,3-c]quinoline-1-carboxylic acid in the form of a white solid.

LC/MS (IE, m/z): (M+1) 379.01

$^1$H-NMR: $\delta_H$ ppm 400 MHz, DMSO 13.10 (1H, bs, NH), 12.56 (1H, bs, $CO_2H$), 12.04 (1H, s, NH), 9.92 (1H, s, $CH_{arom}$), 8.01 (1H; d, $CH_{arom}$), 7.77 (1H; dd, $CH_{arom}$), 7.55 (1H, d, $CH_{arom}$), 7.38 (1H, bs, NH), 7.18 (1H, bs, NH), 3.58 (2H, s, $CH_2$), 2.77 (3H, s, $CH_3$).

8-(3-Carbamoyl-piperidine-1-sulfonyl)-4-oxo-4,5-dihydro-3H-pyrrolo[2,3-c]quinoline-1-propyl carboxylate (179)

This compound was prepared according to general method of esterification C from 251 mg (0.6 mmol) of 8-(3-carbamoyl-piperidine-1-sulfonyl)-4-oxo-4,5-dihydro-3H-pyrrolo[2,3-c]quinoline-1-carboxylic acid, 1.67 mL (12 mmol) of triethylamine and 394 μL (2.4 mmol) of di-n-propylsulfate to give, after purification by preparative LC, 13 mg (5%) of 8-(3-carbamoyl-piperidine-1-sulfonyl)-4-oxo-4,5-dihydro-3H-pyrrolo[2,3-c]quinoline-1-propyl carboxylate in the form of a white solid.

LC/MS (IE, m/z): (M+1) 461.23

$^1$H-NMR: $\delta_H$ ppm 400 MHz, DMSO 13.20 (1H, bs, NH), 12.08 (1H, s, NH), 9.77 (1H, s, $CH_{arom}$), 8.06 (1H, s, $CH_{arom}$), 7.73 (1H, d, $CH_{arom}$), 7.59 (1H, d, $CH_{arom}$), 7.38 (1H, bs, $NH_2$), 6.88 (1H, bs, NH), 4.24 (2H, t, $CH_2$), 3.69-3.58 (2H, m, 2×$CH_{piper}$), 2.42-2.32 (1H, m, $CH_{piper}$), 2.23 (2H, dd, 2×$CH_{piper}$), 1.80-1.68 (4H, m, 2×$CH_{piper}$ and $CH_2$), 1.53-1.40 (1H, m, $CH_{piper}$), 1.27-1.16 (1H, m, $CH_{piper}$), 0.99 (3H, t, $CH_3$).

8-(3-Carbamoyl-piperidine-1-sulfonyl)-4-oxo-4,5-dihydro-3H-pyrrolo[2,3-c]quinoline-1-carboxylic acid (180)

This compound is prepared according to synthesis 178, from 360 mg (1.1 mmol) of 8-chlorosulfonyl-4-oxo-4,5-dihydro-3H-pyrrolo[2,3-c]quinoline-1-carboxylic acid and 154 mg (1.2 mmol) of piperidine-3-carboxamide to give, after purification by precipitation and trituration in methanol, 275 mg (66%) of 8-(3-carbamoyl-piperidine-1-sulfonyl)-4-oxo-4,5-dihydro-3H-pyrrolo[2,3-c]quinoline-1-carboxylic acid in the form of a cream-coloured solid.

LC/MS (IE, m/z): (M+1) 419.4

$^1$H-NMR: $\delta_H$ ppm 400 MHz, DMSO 13.07 (1H, bs, NH), 12.48 (1H, bs, $CO_2H$), 12.05 (1H, s, NH), 9.90 (1H, s, $CH_{arom}$), 8.01 (1H, s, $CH_{arom}$), 7.73 (1H, dd, $CH_{arom}$), 7.57 (1H, d, $CH_{arom}$), 7.39 (1H, bs, NH), 687 (1H, bs, NH), 3.69-3.58 (2H, m, $2\times CH_{piper}$), 2.42-2.32 (1H, m, $CH_{piper}$), 2.30-2.16 (2H, m, $2\times CH_{piper}$), 1.80-1.65 (2H, m, $2\times CH_{piper}$), 1.53-1.40 (1H, m, $CH_{piper}$), 1.29-1.16 (1H, m, $CH_{piper}$).

8-[(2-Benzyloxy-ethyl)-cyclopropyl-sulfamoyl]-4-oxo-4,5-dihydro-3H-pyrrolo[2,3-c]quinoline-1-propyl carboxylate (181)

This compound is prepared according to synthesis 111, from 398 mg (1.22 mmol) of 8-chlorosulfonyl-4-oxo-4,5-dihydro-3H-pyrrolo[2,3-c]quinoline-1-carboxylic acid and 333 mg (1.46 mmol) of (2-benzyloxy-ethyl)-cyclopropyl-amine to give, after esterification according to general method C (using di-n-propylsulfate as the dialkylsulfate) and purification by chromatography on silica (eluent dichloromethane/methanol 99/1), 193 mg (30% in two stages) of 8-[(2-benzyloxy-ethyl)-cyclopropyl-sulfamoyl]-4-oxo-4,5-dihydro-3H-pyrrolo[2,3-c]quinoline-1-propyl carboxylate in the form of a white solid.

LC/MS (IE, m/z): (M+1) 524.45

$^1$H-NMR: $\delta_H$ ppm 400 MHz, DMSO 13.21 (1H, bs, NH), 12.07 (1H, bs, NH), 9.87 (1H, d, $CH_{arom}$), 8.05 (1H, s, $CH_{arom}$), 7.81 (1H, dd, $CH_{arom}$), 7.55 (1H, d, $CH_{arom}$), 7.32-7.18 (5H, m, $5\times CH_{arom}$), 4.40 (2H, s, $CH_2$), 4.22 (2H, q, $CH_2$), 3.59 (2H, t, $CH_2$), 3.36 (2H, t, $CH_2$), 2.15-2.07 (1H, m, $CH_{cycloprop}$), 1.76-1.69 (2H, m, $CH_2$), 1.03 (3H, t, $CH_3$), 0.83-0.77 (2H, m, $2CH_{cycloprop}$) 0.72-0.67 (2H, m, $2\times CH_{cycloprop}$)

3.8 mL (13 mmol) of titanium isopropoxide and 1.5 g (10 mmol) of benzyloxy-acetaldehyde are added to a solution of 2.1 mL (30 mmol) of cyclopropylamine in 10 mL of anhydrous methanol. The solution is stirred for 5 hours at room temperature then 378 mg (10 mmol) of sodium borohydride is added. Stirring is continued for a further 2 hours then 2 mL of water is added. The reaction mixture is filtered then the solvents are evaporated. The residue is taken up in diethyl ether, then a 2M solution of hydrochloric acid in diethyl ether is added. The solid is filtered and washed with diethyl ether to give 1.94 g (85%) of (2-benzyloxy-ethyl)-cyclopropyl-amine hydrochloride in the form of a brown solid.

8-(Carboxymethyl-methyl-sulfamoyl)-4-oxo-4,5-dihydro-3H-pyrrolo[2,3-c]quinoline-1-propyl carboxylate (182)

Trifluoroacetic acid (1 mL) is added slowly to a solution of 95 mg (0.2 mmol) of 8-(tert-butoxycarbonylmethyl-methyl-sulfamoyl)-4-oxo-4,5-dihydro-3H-pyrrolo[2,3-c]quinoline-1-propyl carboxylate dissolved in 9 mL of dichloroethane. The solution is stirred at room temperature for 5 hours then the solvents are evaporated. The residue is taken up and triturated in acetonitrile then in diisopropyl ether to give 76 mg (90%) of 8-(carboxymethyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 422

$^1$H-NMR: $\delta_H$ ppm 400 MHz, DMSO 13.21 (1H, s, NH), 12.61 (1H, s, $CO_2H$), 12.06 (1H, s, NH), 9.80 (1H, d, $CH_{arom}$), 8.07 (1H, d, $CH_{arom}$), 7.77 (1H, dd, $CH_{arom}$), 7.55 (1H, d, $CH_{arom}$), 4.25 (2H, t, $CH_2$), 3.87 (2H, s, $NCH_2$), 2.80 (3H, s, $NCH_3$), 1.75 (2H, m, $CH_2$), 0.99 (3H, t, $CH_3$).

8-(tert-Butoxycarbonylmethyl-methyl-sulfamoyl)-4-oxo-4,5-dihydro-3H-pyrrolo[2,3-c]quinoline-1-propyl carboxylate (183)

This compound is prepared according to synthesis 111, from 326 mg (1 mmol) of 8-chlorosulfonyl-4-oxo-4,5-dihydro-3H-pyrrolo[2,3-c]quinoline-1-carboxylic acid and 272 mg (1.46 mmol) of sarcosine tert-butylate hydrochloride to give, after esterification according to general method C (using di-n-propylsulfate as the dialkylsulfate) and purification by chromatography on silica (eluent ethyl acetate/methanol 98/2 then 95/5), 104 mg (21% in two stages) of 8-(tert-butoxycarbonylmethyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 478

$^1$H-NMR: $\delta_H$ ppm 400 MHz, DMSO 13.21 (1H, s, NH), 12.06 (1H, s, NH), 9.79 (1H, d, $CH_{arom}$), 8.06 (1H, d, $CH_{arom}$), 7.77 (1H, dd, $CH_{arom}$), 7.54 (1H, d, $CH_{arom}$), 4.25 (2H, t, $CH_2$), 3.90 (2H, s, $NCH_2$), 2.83 (3H, s, $NCH_3$), 1.80-1.71 (2H, m, $CH_2$), 1.27 (9H, s, $3\times CH_3$), 0.99 (3H, t, $CH_3$).

8-[(2-Dimethylamino-ethyl)-methyl-sulfamoyl]-7-fluoro-4-oxo-4,5-dihydro-3H-pyrrolo[2,3-c]quinoline-1-propyl carboxylate (184)

This compound is prepared according to synthesis 136, from 345 mg (1 mmol) of 7-fluoro-8-chlorosulfonyl-4-oxo-4,5-dihydro-3H-pyrrolo[2,3-c]quinoline-1-carboxylic acid, 1 mL (10 mmol) of triethylamine and 153 mg (1.5 mmol) of N,N,N'-trimethyl-ethane-1,2-diamine to give, after esterification according to general method C (using di-n-propylsulfate as dialkylsulfate) and purification by chromatography on silica (eluent dichloromethane/methanol/ammonia 400/16/3 then 200/16/13) then trituration in diethyl ether, 30 mg (7% in two stages) of 8-[(2-dimethylamino-ethyl)-methyl-sulfamoyl]-7-fluoro-4-oxo-4,5-dihydro-3H-pyrrolo[2,3-c]quinoline-1-propyl carboxylate in the form of a white solid.

LCMS (IE, m/z): (M+1) 453.17

$^1$H-NMR: $\delta_H$ ppm 400 MHz, DMSO 13.30 (1H, bs, NH), 12.17 (1H, bs, NH), 9.88 (1H, s, $CH_{arom}$), 8.09 (1H, s, $CH_{arom}$), 7.35 (1H, d, $CH_{arom}$), 4.24 (2H, t, $OCH_2$), 3.81-3.62 (2H, m, $NCH_2$), 2.83 (3H, s, $NCH_3$), 1.76 (2H, d, $CH_2$), 1.00-0.86 (3H, m, $CH_3$).

In a sealed tube, 601 mg (1.8 mmol) of 7-fluoro-4-oxo-4,5-dihydro-3H-pyrrolo[2,3-c]quinoline-1-ethyl carboxylate cocrystallized with one equivalent of acetic acid is dissolved in 2.4 mL (36 mmol) of chlorosulfonic acid. The reaction mixture is placed on an oil bath heated beforehand to 85° C. for 2 hours, cooled on an ice bath then poured slowly onto crushed ice. The solid is filtered, rinsed with water, diisopropyl ether and pentane then dried under vacuum to give 580 mg (93%) of 8-chlorosulfonyl-7-fluoro-4-oxo-4,5-dihydro-3H-pyrrolo[2,3-c]quinoline-1-carboxylic acid in the form of a brown solid.

7-Fluoro-8-[(2-hydroxy-ethyl)-isopropyl-sulfamoyl]-4-oxo-4,5-dihydro-3H-pyrrolo[2,3-c]quinoline-1-propyl carboxylate (185)

This compound is prepared according to synthesis 136, from 172 mg (0.5 mmol) of 7-fluoro-8-chlorosulfonyl-4-oxo- 4,5-dihydro-3H-pyrrolo[2,3-c]quinoline-1-carboxylic acid, 0.5 mL (10 mmol) of triethylamine and 77 mg (0.75 mmol) of 2-isopropylamino-ethanol to give, after esterification according to general method C (using di-n-propylsulfate as the dialkylsulfate) and purification by chromatography on silica (eluent dichloromethane/methanol 97/3) then trituration in diethyl ether, 30 mg (13% in two stages) of 7-fluoro-8-[(2-hydroxy-ethyl)-isopropyl-sulfamoyl]-4-oxo-4,5-dihydro-3H-pyrrolo[2,3-c]quinoline-1-propyl carboxylate in the form of a white solid.

LCMS (IE, m/z): (M+1) 454.26

$^1$H-NMR: $\delta_H$ ppm 400 MHz, DMSO 13.22 (1H, bs, NH), 12.10 (1H, bs, NH), 9.89 (1H, d, $CH_{arom}$), 8.06 (1H, s, $CH_{arom}$), 7.32 (1H, d, $CH_{arom}$), 4.78 (1H, bs, OH), 4.26 (2H, t, $OCH_2$), 4.01-3.90 (1H, m, CH), 3.52 (2H, dd, $CH_2$), 3.25 (2H, dd, $NCH_2$), 1.82-1.74 (2H, m, $CH_2$), 1.05-0.95 (9H, m, $3 \times CH_3$).

8-Dimethylsulfamoyl-7-fluoro-4-oxo-4,5-dihydro-3H-pyrrolo[2,3-c]quinoline-1-propyl carboxylate (186)

This compound is prepared according to synthesis 111, from 172 mg (0.5 mmol) of 7-fluoro-8-chlorosulfonyl-4-oxo-4,5-dihydro-3H-pyrrolo[2,3-c]quinoline-1-carboxylic acid, 697 µL (5 mmol) of triethylamine and 61 mg (0.75 mmol) of dimethylamine hydrochloride to give, after esterification according to general method C (using di-n-propylsulfate as the dialkylsulfate) and purification by chromatography on silica (eluent dichloromethane/methanol 97/3), 59 mg (30% in two stages) of 8-dimethylsulfamoyl-7-fluoro-4-oxo-4,5-dihydro-3H-pyrrolo[2,3-c]quinoline-1-propyl carboxylate in the form of a white solid.

LCMS (IE, m/z): (M+1) 396.06

$^1$H-NMR: $\delta_H$ ppm 400 MHz, DMSO 13.23 (1H, bs, NH), 12.11 (1H, bs, NH), 9.83 (1H, d, $CH_{arom}$), 8.06 (1H, s, $CH_{arom}$), 7.33 (1H, d, $CH_{arom}$), 4.24 (2H, t, $OCH_2$), 2.75 (6H, s, $2 \times CH_3$), 1.74 (2H, dd, $CH_2$), 0.9 (3H, t, $CH_3$).

8-(Cyclopropyl-methyl-sulfamoyl)-7-fluoro-4-oxo-4,5-dihydro-3H-pyrrolo[2,3-c]quinoline-1-propyl carboxylate (187)

This compound is prepared according to synthesis 111, from 172 mg (0.5 mmol) of 7-fluoro-8-chlorosulfonyl-4-oxo-4,5-dihydro-3H-pyrrolo[2,3-c]quinoline-1-carboxylic acid, 697 µL (5 mmol) of triethylamine and 80 mg (0.75 mmol) of cyclopropyl-methyl-amine hydrochloride to give, after esterification according to general method C (using di-n-propylsulfate as the dialkylsulfate) and purification by chromatography on silica (eluent dichloromethane/methanol 97/3), 90 mg (43% in two stages) of 8-(cyclopropyl-methyl-sulfamoyl)-7-fluoro-4-oxo-4,5-dihydro-3H-pyrrolo[2,3-c]quinoline-1-propyl carboxylate in the form of a white solid.

LCMS (IE, m/z): (M+1) 422.18

$^1$H-NMR: $\delta_H$ ppm 400 MHz, DMSO 13.22 (1H, bs, NH), 12.12 (1H, bs, NH), 9.88 (1H, d, $CH_{arom}$), 8.06 (1H, s, $CH_{arom}$), 7.32 (1H, d, $CH_{arom}$), 4.25 (2H, t, $OCH_2$), 2.79 (3H, s, $NCH_3$), 2.11-2.05 (1H, m, $CH_{cycloprop}$), 1.76 (2H, dd, CH), 0.90 (3H, t, $CH_3$), 0.76-0.66 (4H, m, $4 \times CH_{cycloprop}$).

7-Chloro-8-(cyclopropyl-methyl-sulfamoyl)-4-oxo-4,5-dihydro-3H-pyrrolo[2,3-c]quinoline-1-propyl carboxylate (188)

This compound is prepared according to synthesis 111, from 86 mg of a 2/1 mixture of 7-chloro-8-chlorosulfonyl-4-oxo-4,5-dihydro-3H-pyrrolo[2,3-c]quinoline-1-carboxylic acid and 7-chloro-6-chlorosulfonyl-4-oxo-4,5-dihydro-3H-pyrrolo[2,3-c]quinoline-1-carboxylic acid, 77 µl (0.55 mmol) of triethylamine and 30 mg (0.28 mmol) of cyclopropyl-methyl-amine hydrochloride to give, after esterification according to general method C (using di-n-propylsulfate as the dialkylsulfate) and purification by preparative LC, 4 mg (2% in three stages) of 7-chloro-8-(cyclopropyl-methyl-sulfamoyl)-4-oxo-4,5-dihydro-3H-pyrrolo[2,3-c]quinoline-1-propyl carboxylate in the form of a white solid.

LCMS (IE, m/z): (M+1) 434.28

$^1$H-NMR: $\delta_H$ ppm 400 MHz, CDCl$_3$ 10.30 (1H, bs, NH), 10.04 (1H, s, $CH_{arom}$), 9.35 (1H, bs, NH), 8.01 (1H, d, $CH_{arom}$), 6.78 (1H, s, $CH_{arom}$), 4.36 (2H, t, $CH_2$), 4.01 (3H, s, $CH_3$), 2.99 (3H, s, $CH_3$), 2.35-2.27 (1H, m, $CH_{arom}$), 1.82 (2H, sext, $CH_2$), 1.03 (3H, t, $CH_3$), 0.93-0.81 (2H, m, $2 \times CH_{ali}$), 0.71-0.63 (2H, m, $2 \times CH_{ali}$).

In a sealed tube, 100 mg (0.35 mmol) of 7-chloro-4-oxo-4,5-dihydro-3H-pyrrolo[2,3-c]quinoline-1-ethyl carboxylate cocrystallized with one equivalent of acetic acid is dissolved in 465 µL (7 mmol) of chlorosulfonic acid. The reaction mixture is placed on an oil bath heated beforehand to 50° C. for 2 hours, cooled on an ice bath then poured slowly onto crushed ice. The solid is filtered, rinsed with water, diisopropyl ether and pentane then dried under vacuum to give 86 mg of a 2/1 mixture of 7-chloro-8-chlorosulfonyl-4-oxo-4,5-dihydro-3H-pyrrolo[2,3-c]quinoline-1-carboxylic acid and 7-chloro-6-chlorosulfonyl-4-oxo-4,5-dihydro-3H-pyrrolo[2,3-c]quinoline-1-carboxylic acid in the form of a brown solid.

7-Chloro-8-dimethylsulfamoyl-4-oxo-4,5-dihydro-3H-pyrrolo[2,3-c]quinoline-1-propyl carboxylate (189)

This compound is prepared according to synthesis 111, from 542 mg (1.5 mmol) of 7-chloro-8-chlorosulfonyl-4-oxo-4,5-dihydro-3H-pyrrolo[2,3-c]quinoline-1-carboxylic acid, 627 µL (4.5 mmol) of triethylamine and 146 mg (1.8 mmol) of dimethylamine hydrochloride to give, after esterification according to general method C (using di-n-propylsulfate as the dialkylsulfate) and purification by precipitation in water then trituration in methanol and diisopropyl ether, 83 mg (13% in two stages) of 7-chloro-8-dimethylsulfamoyl-4-oxo-4,5-dihydro-3H-pyrrolo[2,3-c]quinoline-1-propyl carboxylate in the form of a brown solid.

LC/MS (IE, m/z): (M+1) 412.01

$^1$H-NMR: $\delta_H$ ppm 400 MHz, DMSO 13.27 (1H, bs, NH), 12.10 (1H, bs, NH), 9.93 (1H, s, $CH_{ali}$), 8.09 (1H, s, $CH_{arom}$), 7.61 (1H, s, $CH_{arom}$), 4.24 (2H, q, $CH_2$), 2.87 (6H, s, $2 \times CH_3$), 1.85-1.64 (2H, m, $CH_2$), 0.99 (3H, t, $CH_3$).

In a sealed tube, 1.16 g (4 mmol) of 7-chloro-4-oxo-4,5-dihydro-3H-pyrrolo[2,3-c]quinoline-1-ethyl carboxylate is dissolved in 5.3 mL (80 mmol) of chlorosulfonic acid. The reaction mixture is placed on an oil bath heated beforehand to 90° C. for 6 hours, cooled on an ice bath then poured slowly onto crushed ice. The solid is filtered, rinsed with water, diisopropyl ether and pentane then dried under vacuum to give 1.3 g (90%) of 7-chloro-8-chlorosulfonyl-4-oxo-4,5-dihydro-3H-pyrrolo[2,3-c]quinoline-1-carboxylic acid in the form of a brown solid.

(S)-8-(3-amino-cyclopentanesulfonyl)-7-chloro-4-oxo-4,5-dihydro-3H-pyrrolo[2,3-c]quinoline-1-propyl carboxylate hydrochloride (190)

This compound is prepared according to synthesis 139, from 136 mg (0.24 mmol) of (S)-8-(3-tert-butoxycarbonylamino-cyclopentanesulfonyl)-7-chloro-4-oxo-4,5-dihydro-3H-pyrrolo[2,3-c]quinoline-1-propyl carboxylate and 9.8 mL (19.6 mmol) of a 2M solution of hydrochloric acid in diethyl ether to give, after filtration, 80 mg (66%) of (S)-8-(3-amino-cyclopentanesulfonyl)-7-chloro-4-oxo-4,5-dihydro-3H-pyrrolo[2,3-c]quinoline-1-propyl carboxylate hydrochloride in the form of a white solid.

LCMS (IE, m/z): (M+1) 453
$^1$H-NMR: $\delta_H$ ppm 400 MHz, DMSO
13.34 (1H, bs, NH), 12.17 (1H, bs, NH)—, Hs, $CH_{arom}$), 8.34-8.20 (3H, m, $NH_2$.HCl), 8.10 (1H, d, $CH_{arom}$), 7.65 (1H, s, $CH_{arom}$), 4.24 (2H, t, $CH_2$), 3.89-3.80 (1H, m, $CH_{ali}$), 3.68-3.53 (2H, m, $2 \times CH_{ali}$), 3.44-3.33 (2H, m, $2 \times CH_{ali}$), 2.32-2.20 (1H, m, $CH_{ali}$), 2.01-1.90 (1H, m, $CH_{ali}$), 1.75 (2H, sext, $CH_2$), 0.99 (3H, t, $CH_3$).

(S)-8-(3-tert-butoxycarbonylamino-cyclopentanesulfonyl)-7-chloro-4-oxo-4,5-dihydro-3H-pyrrolo[2,3-c]quinoline-1-propyl carboxylate is prepared according to synthesis 111, from 505 mg (1.4 mmol) of 8-chlorosulfonyl-4-oxo-4,5-dihydro-3H-pyrrolo[2,3-c]quinoline-1-carboxylic acid, 582 μL (4.2 mmol) of triethylamine and 391 mg (2.1 mmol) of (S)—N-tert-butoxycarbonyl-N'-pyrrolidin-3-yl-amine to give, after esterification according to general method C (using di-n-propylsulfate as the dialkylsulfate) and purification by chromatography on silica (eluent dichloromethane/ethyl acetate 6/4), 136 mg (10% in two stages) of (S)-8-(3-tert-butoxycarbonylamino-cyclopentanesulfonyl)-7-chloro-4-oxo-4,5-dihydro-3H-pyrrolo[2,3-c]quinoline-1-propyl carboxylate in the form of a white solid.

4-Oxo-8-(piperidin-1-ylsulfamoyl)-4,5-dihydro-3H-pyrrolo[2,3-c]quinoline-1-methyl carboxylate (191)

This compound is prepared according to synthesis 111, from 490 mg (1.5 mmol) of 8-chlorosulfonyl-4-oxo-4,5-dihydro-3H-pyrrolo[2,3-c]quinoline-1-carboxylic acid and 178 μL (1.65 mmol) of 1-aminopiperidine to give, after esterification according to general method B and purification by trituration in water, 125 mg (20% in two stages) of 4-oxo-8-(piperidin-1-ylsulfamoyl)-4,5-dihydro-3H-pyrrolo[2,3-c]quinoline-1-methyl carboxylate in the form of a light brown solid.

LC/MS (IE, m/z): (M+1) 404.99
$^1$H-NMR: $\delta_H$ ppm 400 MHz, DMSO
13.19 (1H, bs, NH), 12.06 (1H, bs, NH), 9.90 (1H, s, $CH_{arom}$), 8.57 (1H, s, $CH_{arom}$), 8.07 (1H, s, $CH_{arom}$), 7.84 (1H, dd, $CH_{arom}$), 7.53 (1H, d, $CH_{arom}$), 3.87 (3H, s, $CH_3$), 2.46-2.40 (4H, m, $4 \times CH_{piper}$), 1.39-1.31 (4H, m, $2 \times CH_{piper}$), 1.20-1.15 (2H, m, $CH_{piper}$).

8-(Hexahydro-cyclopenta[c]pyrrol-2-ylsulfamoyl)-4-oxo-4,5-dihydro-3H-pyrrolo[2,3-c]quinoline-1-methyl carboxylate (192)

This compound is prepared according to synthesis 111, from 490 mg (1.5 mmol) of 8-chlorosulfonyl-4-oxo-4,5-dihydro-3H-pyrrolo[2,3-c]quinoline-1-carboxylic acid, 627 μL (4.5 mmol) of triethylamine and 269 mg (1.65 mmol) of 2-amino-hexahydro-cyclopenta[c]pyrrole hydrochloride to give, after esterification according to general method B and purification by trituration in water, 67 mg (10% in two stages) of 8-(hexahydro-cyclopenta[c]pyrrol-2-ylsulfamoyl)-4-oxo-4,5-dihydro-3H-pyrrolo[2,3-c]quinoline-1-methyl carboxylate in the form of a light brown solid.

LC/MS (IE, m/z): (M+1) 431.04
$^1$H-NMR: $\delta_H$ ppm 400 MHz, DMSO
13.17 (1H, bs, NH), 12.06 (1H, bs, NH), 9.87 (1H, d, $CH_{arom}$), 8.42 (1H, s, $CH_{arom}$), 8.07 (1H, s, $CH_{arom}$), 7.80 (1H, dd, $CH_{arom}$), 7.53 (1H, d, $CH_{arom}$), 3.86 (3H, s, $CH_3$), 2.63-2.53 (2H, m, $2 \times CH_{ali}$), 2.28-2.17 (4H, m, $4 \times CH_{ali}$), 1.53-1.42 (3H, m, $3 \times CH_{ali}$), 1.28-1.19 (1H, m, $CH_{ali}$), 1.16-1.05 (2H, m, $2 \times CH_{ali}$).

8-(4-Methyl-piperazin-1-ylsulfamoyl)-4-oxo-4,5-dihydro-3H-pyrrolo[2,3-c]quinoline-1-methyl carboxylate (193)

This compound is prepared according to synthesis 111, from 490 mg (1.5 mmol) of 8-chlorosulfonyl-4-oxo-4,5-dihydro-3H-pyrrolo[2,3-c]quinoline-1-carboxylic acid and 199 μL (1.65 mmol) of 1-amino-4-methylpiperazine to give, after esterification according to general method B and purification by chromatography on silica (eluent dichloromethane/methanol 95/5), 33 mg (5% in two stages) of 8-(4-methyl-piperazin-1-ylsulfamoyl)-4-oxo-4,5-dihydro-3H-pyrrolo[2,3-c]quinoline-1-methyl carboxylate in the form of a white solid.

LC/MS (IE, m/z): (M+1) 419.97
$^1$H-NMR: $\delta_H$ ppm 400 MHz, DMSO
13.16 (1H, bs, NH), 12.06 (1H, bs, NH), 9.90 (1H, s, $CH_{arom}$), 8.66 (1H, s, $CH_{arom}$), 8.07 (1H, s, $CH_{arom}$), 7.83 (1H, dd, $CH_{arom}$), 7.52 (1H, d, $CH_{arom}$), 4.11-4.06 (1H, m, NH), 3.87 (3H, s, $CH_3$), 3.31 (4H, s, $2 \times CH_2$), 3.16 (3H, bs, $NCH_3$), 2.33-2.17 (2H, m, $2 \times CH_{piper}$), 2.12-2.04 (2H, m, $CH_{piper}$).

8-(2,6-Dichlorophenylmethanesulfonyl)-4-oxo-4,5-dihydro-3H-pyrrolo[2,3-c]quinoline-1-ethyl carboxylate (194)

180 mg (0.55 mmol) of 8-chlorosulfonyl-4-oxo-4,5-dihydro-3H-pyrrolo[2,3-c]quinoline-1-carboxylic acid is added to a solution of 139 mg (1.1 mmol) of sodium sulfite and 78 mg (0.55 mmol) of dibasic sodium phosphate dissolved in 2.5 mL of water. The solution is heated at 60° C. for 20 hours then a solution of 132 mg (0.55) of 2,6-dichlorobenzyl bromide in 2.5 mL of dimethylformamide is added. Stirring is continued at 60° C. for 4 hours then the solution is filtered. The solid is triturated in hot methanol then filtered again to give 88 mg (35%) of 8-(2,6-dichlorophenylmethanesulfonyl)-4-oxo-4,5-dihydro-3H-pyrrolo[2,3-c]quinoline-1-ethyl carboxylate in the form of a white solid.

LCMS (IE, m/z): (M+1) 450.87
$^1$H-NMR: $\delta_H$ ppm 400 MHz, DMSO
13.20 (1H, bs, NH), 12.34 (1H, bs, $CO_2H$), 12.09 (1H, s, NH), 9.94 (1H, d, $CH_{arom}$), 7.99 (1H, s, $CH_{arom}$), 7.73 (1H, dd, $CH_{arom}$), 7.54 (1H, d, $CH_{arom}$), 7.48-7.44 (2H, m, $2 \times CH_{arom}$), 7.37 (1H, dd, $CH_{arom}$), 4.86 (2H, s, $CH_2$).

4-Oxo-8-(pyridin-4-ylmethanesulfonyl)-4,5-dihydro-3H-pyrrolo[2,3-c]quinoline-1-ethyl carboxylate (195)

326 mg (1 mmol) of 8-chlorosulfonyl-4-oxo-4,5-dihydro-3H-pyrrolo[2,3-c]quinoline-1-carboxylic acid is added to a solution of 272 mg (2 mmol) of sodium sulfite and 142 mg (1 mmol) of dibasic sodium phosphate dissolved in 3 mL of water. The solution is heated at 60° C. for 20 hours then a solution of 150 mg (1.2 mmol) of 4-chloromethylpyridine in 3 mL of acetone is added. Stirring is continued at 60° C. for 24 hours then the solution is filtered. The residue is esterified by general method C with 520 μL (4 mmol) of diethylsulfate in the presence of 700 μL (5 mmol) of triethylamine to give, after purification by chromatography on silica (eluent dichloromethane/methanol 96/4), 11 mg (2%) of 4-oxo-8-(pyridin-4-ylmethanesulfonyl)-4,5-dihydro-3H-pyrrolo[2,3-c]quinoline-1-ethyl carboxylate in the form of a white solid.

LCMS (IE, m/z): (M+1) 412.25

$^1$H-NMR: $\delta_H$ ppm 400 MHz, DMSO 13.20 (1H, bs, NH), 12.09 (1H, s, NH), 9.68 (1H, d, $CH_{arom}$), 8.46 (2H, d, $2\times CH_{arom}$), 8.04 (1H, s, $CH_{arom}$), 7.67 (1H, dd, $CH_{arom}$), 7.51 (1H, d, $CH_{arom}$), 7.16 (2H, d, $2\times CH_{arom}$), 4.70 (2H, s, $CH_2$), 4.31 (2H, q, $CH_2$), 1.35 (3H, t, $CH_3$).

4-Oxo-8-(pyridin-2-ylmethanesulfonyl)-4,5-dihydro-3H-pyrrolo[2,3-c]quinoline-1-ethyl carboxylate (196)

This compound is prepared according to synthesis 195, from 326 mg (1 mmol) of 8-chlorosulfonyl-4-oxo-4,5-dihydro-3H-pyrrolo[2,3-c]quinoline-1-carboxylic acid and 130 mg (1.1 mmol) of 2-chloromethylpyridine to give, after esterification according to general method C (diethylsulfate used as dialkylsulfate) and purification by trituration in dichloromethane/methanol mixture 1/1, 40 mg (18% in two stages) of 4-oxo-8-(pyridin-2-ylmethanesulfonyl)-4,5-dihydro-3H-pyrrolo[2,3-c]quinoline-1-ethyl carboxylate in the form of a white solid.

LCMS (IE, m/z): (M+1) 412.18

$^1$H-NMR: $\delta_H$ ppm 400 MHz, DMSO 13.18 (1H, bs, NH), 12.10 (1H, s, NH), 9.66 (1H, d, $CH_{arom}$), 8.35 (1H, d, $CH_{arom}$), 8.05 (1H, s, $CH_{arom}$), 7.76 (1H, td, $CH_{arom}$), 7.62 (1H, dd, $CH_{arom}$), 7.49 (1H, d, $CH_{arom}$), 7.39 (1H, d, $CH_{arom}$), 7.32-7.27 (1H, m, $CH_{arom}$), 4.74 (2H, s, $CH_2$), 4.31 (2H, q, $CH_2$), 1.35 (3H, t, $CH_3$).

8-Cyclohexanesulfonyl-4-oxo-4,5-dihydro-3H-pyrrolo[2,3-c]quinoline-1-ethyl carboxylate (197)

A solution of 410 mg (0.66 mmol) of Oxone in 2 mL of water is added to a solution of 49 mg (0.13 mmol) of 8-cyclohexylsulfanyl-4-oxo-4,5-dihydro-3H-pyrrolo[2,3-c]quinoline-1-ethyl carboxylate in methanol (5 mL) and acetonitrile (1 mL). The solution is stirred at room temperature for 24 hours. The solvents are evaporated then the residue is taken up in water. The product is extracted with ethyl acetate and the organic phases are dried over magnesium sulfate, filtered and evaporated. The residue is triturated in diethyl ether to give 40 mg (74%) of 8-cyclohexanesulfonyl-4-oxo-4,5-dihydro-3H-pyrrolo[2,3-c]quinoline-1-ethyl carboxylate in the form of a white solid.

LCMS (IE, m/z): (M+1) 403.31

$^1$H-NMR: $\delta_H$ ppm 400 MHz, DMSO 13.21 (1H, bs, NH), 12.12 (1H, bs, NH), 9.81 (1H, d, $CH_{arom}$), 8.06 (1H, s, $CH_{arom}$), 7.80 (1H, dd, $CH_{arom}$), 7.59 (1H, d, $CH_{arom}$), 4.33 (2H, q, $CH_2$), 3.12-3.03 (1H, m, CH), 1.97-1.89 (2H, m, $2\times CH$), 1.77-1.69 (2H, m, $2\times CH$), 1.60-1.53 (1H, m, CH), 1.35 (3H, t, $CH_3$), 1.32-4.15, (4H, m, $4\times CH$), 1.12-0.99 (1H, m, CH).

4-Oxo-8-phenylmethanesulfinyl-4,5-dihydro-3H-pyrrolo[2,3-c]quinoline-1-ethyl carboxylate (198)

41 mg (0.24 mmol) of metachloroperbenzoic acid is added at 0° C. to a solution of 90 mg (0.24 mmol) of 8-benzylsulfanyl-4-oxo-4,5-dihydro-3H-pyrrolo[2,3-c]quinoline-1-ethyl carboxylate suspended in dichloromethane (8 mL) and dioxan (8 mL). The reaction mixture is stirred for 6 hours at 0-5° C. then an aqueous solution of potassium carbonate is added and the product is extracted with ethyl acetate. The organic phase is washed with an aqueous solution of sodium chloride, dried over magnesium sulfate, filtered and evaporated. The residue is purified by preparative LCMS to give 40 mg (42%) of 4-oxo-8-phenylmethanesulfinyl-4,5-dihydro-3H-pyrrolo[2,3-c]quinoline-1-ethyl carboxylate in the form of a white solid.

LCMS (IE, m/z): (M+1) 395.31

$^1$H-NMR: $\delta_H$ ppm 400 MHz, DMSO 13.12 (1H, bs, NH), 11.93 (1H, s, NH), 9.38 (1H, s, $CH_{arom}$), 8.02 (1H, s, $CH_{arom}$), 7.56 (1H, dd, $CH_{arom}$), 7.51 (1H, d, $CH_{arom}$), 7.26-7.24 (3H, m, $3\times CH_{arom}$), 7.14-7.09 (2H, m, $2\times CH_{arom}$), 4.30 (2H, q, $CH_2$), 4.20 (1H, d, $CH_{ali}$), 4.15 (1H, d, $CH_{ali}$), 1.35 (3H, t, $CH_3$).

8-Ethynyl-4-oxo-4,5-dihydro-3H-pyrrolo[2,3-c]quinoline-1-ethyl carboxylate (199)

1.2 ml (1.2 mmol) of a 1M solution of tetrabutylammonium fluoride in tetrahydrofuran is added to a solution of 398 mg (1.13 mmol) of 4-oxo-8-trimethylsilanylethynyl-4,5-dihydro-3H-pyrrolo[2,3-c]quinoline-1-ethyl carboxylate in 10 ml of tetrahydrofuran, then the mixture is stirred for 1 hour at room temperature. The solvent is evaporated and the product is extracted with ethyl acetate. The organic phase is washed with a 1M aqueous solution of hydrochloric acid, a saturated solution of sodium chloride, dried over magnesium sulfate, filtered and evaporated. The product is crystallized in a methanol/acetone mixture (4/1) to give 160 mg (50%) of 8-ethynyl-4-oxo-4,5-dihydro-3H-pyrrolo[2,3-c]quinoline-1-ethyl carboxylate in the form of a white solid.

LCMS (IE, m/z): (M+1) 281.17

$^1$H-NMR: $\delta_H$ ppm 400 MHz, DMSO 13.12 (1H, s, NH), 11.88 (1H, s, NH), 9.43 (1H, s, $CH_{arom}$), 8.02 (1H, s, $CH_{arom}$), 7.50 (1H, d, $CH_{arom}$), 7.39 (1H, d, $CH_{arom}$), 4.33 (2H, q, $CH_2$), 4.12 (1H, s, CH), 1.37 (3H, t, $CH_3$).

4-Oxo-8-trimethylsilanylethynyl-4,5-dihydro-3H-pyrrolo[2,3-c]quinoline-1-ethyl carboxylate (200)

224 mg (1.2 mmol) of copper iodide, 309 mg (3 mmol) of triethylamine and 165 mg (0.23 mmol) of dichlorobis(triphenylphosphine)-palladium (11) are added to a suspension of 898 mg (2.35 mmol) of 8-iodo-4-oxo-4,5-dihydro-3H-pyrrolo[2,3-c]quinoline-1-ethyl carboxylate in 30 ml of anhydrous dioxan then this mixture is degassed under argon. After 15 minutes, 346 mg (3.52 mmol) of ethynyl-trimethyl-silane is added and the reaction mixture is heated at 100° C. for 3 hours. The raw reaction product is filtered on celite, then the filtrate is evaporated to dryness and the residue is purified on silica (eluent ethyl acetate) to give 400 mg (48%) of 4-oxo-8-trimethylsilanylethynyl-4,5-dihydro-3H-pyrrolo[2,3-c]quinoline-1-ethyl carboxylate in the form of a yellow solid.

LCMS (IE, m/z): (M+1) 353.20

$^1$H-NMR: $\delta_H$ ppm 400 MHz, DMSO 13.13 (1H, s, NH), 11.91 (1H, s, NH), 9.37 (1H, s, $CH_{arom}$), 8.03 (1H, s, $CH_{arom}$), 7.47 (1H, d, $CH_{arom}$), 7.40 (1H, d, $CH_{arom}$), 4.32 (2H, q, $CH_2$), 1.36 (3H, t, $CH_3$), 0.25 (9H, s, $3\times CH_3$).

4-Oxo-8-phenylethynyl-4,5-dihydro-3H-pyrrolo[2,3-c]quinoline-1-ethyl carboxylate (201)

20 mg (0.11 mmol) of copper iodide, 28 mg (0.27 mmol) of triethylamine and 14 mg (0.02 mmol) of dichlorobis(triphenylphosphine)-palladium (II) are added to a suspension of 80 mg (0.21 mmol) of 8-iodo-4-oxo-4,5-dihydro-3H-pyrrolo [2,3-c]quinoline-1-ethyl carboxylate in 2.4 ml of anhydrous dioxan, then this mixture is degassed under argon. After 15 minutes, 32 mg (0.31 mmol) of phenylacetylene is added, then the mixture is heated at 100° C. for 3 hours. The raw reaction product is filtered on celite, the filtrate is evaporated to dryness and the residue is purified by chromatography on silica (eluent cyclohexane/ethyl acetate) to give 70 mg (93%) of 4-oxo-8-phenylethynyl-4,5-dihydro-3H-pyrrolo[2,3-c] quinoline-1-ethyl carboxylate in the form of a yellow solid.

LCMS (IE, t/z): (M+1) 357.26

$^1$H-NMR: $\delta_H$ ppm 400 MHz, DMSO 13.14 (1H, s, NH), 11.92 (1H, s, NH), 9.48 (1H, s, $CH_{arom}$), 8.04 (1H, s, $CH_{arom}$), 7.57-759 (3H, m, $CH_{arom}$), 7.43-7.45 (4H, m, $CH_{arom}$), 4.33 (2H, q, $CH_2$), 1.37 (3H, t, $CH_3$).

4-Oxo-8 pyridin-2-ylethynyl-4,5-dihydro-3H-pyrrolo [2,3-c]quinoline-1-ethyl carboxylate (202)

20 mg (0.11 mmol) of copper iodide, 28 mg (0.27 mmol) of triethylamine and 14 mg (0.02 mmol) of dichlorobis(triphenylphosphine)-palladium (II) are added to a suspension of 80 mg (0.21 mmol) of 8-iodo-4-oxo-4,5-dihydro-3H-pyrrolo [2,3-c]quinoline-1-ethyl carboxylate in 2.4 ml of anhydrous dioxan, then this mixture is degassed under argon. After 15 minutes, 32 mg (0.31 mmol) of 2-ethynyl-pyridine are added, then the mixture is heated at 100° C. for 3 hours. The raw reaction product is then filtered on celite, the filtrate is evaporated to dryness and the residue is purified by chromatography on silica (eluent ethyl acetate) to give 34 mg (46%) of 4-oxo-8-pyridin-2-ylethynyl-4,5-dihydro-3H-pyrrolo[2,3-c] quinoline-1-ethyl carboxylate in the form of a brown solid.

LCMS (IE, n/z): (M+1) 358.21

$^1$H-NMR: $\delta_H$ ppm 400 MHz, DMSO 13.15 (1H, s, NH), 11.94 (1H, s, NH), 9.56 (1H, s, $CH_{arom}$), 8.63 (1H, m, $CH_{arom}$), 805 (1H, s, $CH_{arom}$), 7.84-7.88 (1H, m, $CH_{arom}$), 7.62-7.67 (2H, m, $CH_{arom}$), 7.42-7.48 (2H, m, $CH_{arom}$), 4.34 (2H, q, $CH_2$), 1.37 (3H, t, $CH_3$).

8-(3-Dimethylamino-prop-1-ynyl)-4-oxo-4,5-dihydro-3H-pyrrolo[2,3-c]quinoline-1-ethyl carboxylate (203)

50 mg (0.26 mmol) of copper iodide, 69 mg (0.68 mmol) of triethylamine and 37 mg (0.05 mmol) of dichlorobis(triphenylphosphine)-palladium (11) are added to a suspension of 200 mg (0.52 mmol) of 8-iodo-4-oxo-4,5-dihydro-3H-pyrrolo[2,3-c]quinoline-1-ethyl carboxylate in 5 ml of anhydrous dioxan, then this mixture is degassed under argon. After 15 minutes, 65 mg (0.78 mmol) of dimethyl-prop-2-ynyl-amine are added, then the mixture is heated at 100° C. for 6 hours. The raw reaction product is then filtered on celite, the filtrate is evaporated to dryness and the residue is purified by chromatography on silica (ethyl acetate/methanol/ammonia) to give 64 mg (36%) of 8-(3-dimethylamino-prop-1-ynyl)-4-oxo-4,5-dihydro-3H-pyrrolo[2,3-c]quinoline-1-ethyl carboxylate in the form of a white solid.

LCMS (IE, m/z): (M+1) 338.27

$^1$H-NMR: $\delta_H$ ppm 400 MHz, DMSO 12.82 (1H, bs, NH), 11.58 (1H, s, NH), 9.14 (1H, s, $CH_{arom}$), 7.77 (1H, s, $CH_{arom}$), 7.21 (1H, d, $CH_{arom}$), 7.16 (1H, d, $CH_{arom}$), 4.09 (2H, q, CH), 3.24 (2H, s, $CH_2$), 2.04 (6H, s, 2×$CH_3$), 1.13 (3H, t, $CH_3$).

8-(3-Hydroxy-3-methyl-but-1-ynyl)-4-oxo-4,5-dihydro-3H-pyrrolo[2,3-c]quinoline-1-ethyl carboxylate (204)

50 mg (0.26 mmol) of copper iodide, 69 mg (0.68 mmol) of triethylamine and 37 mg (0.05 mmol) of dichlorobis(triphenylphosphine)-palladium (II) are added to a suspension of 200 mg (0.52 mmol) of 8-iodo-4-oxo-4,5-dihydro-3H-pyrrolo[2,3-c]quinoline-1-ethyl carboxylate in 5 ml of anhydrous dioxan, then this mixture is degassed under argon. After 15 minutes, 66 mg (0.78 mmol) of 2-methyl-but-3-yn-2-ol are added, then the mixture is heated at 100° C. for 1 hour. The raw reaction product is then filtered on celite, the filtrate is evaporated to dryness and the residue is purified by chromatography on silica (ethyl acetate), then the product is triturated in methanol to give 135 mg (76%) of 8-(3-hydroxy-3-methyl-but-1-ynyl)-4-oxo-4,5-dihydro-3H-pyrrolo[2,3-c]quinoline-1-ethyl carboxylate in the form of a white solid.

LCMS (IE, m/z): (M+1) 339.26

$^1$H-NMR: $\delta_H$ ppm 400 MHz, DMSO 13.07 (1H, s, NH), 11.82 (1H, s, NH), 9.32 (1H, s, $CH_{arom}$), 8.01 (1H, s, $CH_{arom}$), 7.36-7.48 (3H, m, 2×$CH_{arom}$ and OH), 4.32 (2H, q, $CH_2$), 1.49 (6H, s, 2×$CH_3$), 1.36 (3H, t, $CH_3$).

8-(3-Morpholin-4-yl-prop-1-ynyl)-4-oxo-4,5-dihydro-3H-pyrrolo[2,3-c]quinoline-1-ethyl carboxylate (205)

15 mg (0.17 mmol) of para-formaldehyde, 15 mg (0.17 mmol) of morpholine and 3 mg (0.02 mmol) of copper iodide are added to a suspension of 47 mg (0.17 mmol) of 8-ethynyl-4-oxo-4,5-dihydro-3H-pyrrolo[2,3-c]quinoline-1-ethyl carboxylate in 5 ml of anhydrous dioxan, then a drop of acetic acid is added and the mixture is heated at 85° C. for 48 hours. The raw reaction product is then filtered, the filtrate is evaporated and the residue is purified by preparative LCMS to give 4 mg (6%) of 8-(3-morpholin-4-yl-prop-1-ynyl)-4-oxo-4,5-dihydro-3H-pyrrolo[2,3-c]quinoline-1-ethyl carboxylate in the form of a white solid.

LCMS (IE, m/z): (M+1) 380.25

$^1$H-NMR: $\delta_H$ ppm 400 MHz, $CD_3OD$ 9.55 (1H, bs, $CH_{arom}$), 8.06 (1H, s, $CH_{arom}$), 7.49 (1H, dd, $CH_{arom}$), 7.38 (1H, d, $CH_{arom}$), 4.41 (2H, q, $CH_2$), 3.92-3.86 (2H, m, $CH_2$), 3.83-3.76 (2H, m, $CH_2$), 3.63 (2H, s, CH), 3.27-3.21 (2H, m, $CH_2$), 2.83-2.72 (2H, m, $CH_2$), 1.45 (3H, t, $CH_3$).

8-{3-[(2-Cyano-ethylmethyl-amino]-prop-1-ynyl}-4-oxo-4,5-dihydro-3H-pyrrolo[2,3-c]quinoline-1-ethyl carboxylate (206)

31 mg (0.35 mmol) of para-formaldehyde, 35 mg (0.42 mmol) of 3-(methyl-prop-2-ynyl-amino)-propionitrile and 7 mg (0.04 mmol) of copper iodide are added to a suspension of 98 mg (0.35 mmol) of 8-ethynyl-4-oxo-4,5-dihydro-3H-pyrrolo[2,3-c]quinoline-1-ethyl carboxylate in 3 ml of anhydrous dioxan, then the mixture is heated at 110° C. for 6 hours. The raw reaction product is then filtered, and the filtrate is evaporated. The residue is triturated with methanol, then the new filtrate is evaporated. The product is recrystallized from methanol to give 10 mg (8%) of 8-{3-[(2-cyano-ethyl)-methyl-amino]-prop-1-ynyl}-4-oxo-4,5-dihydro-3H-pyrrolo[2, 3-c]quinoline-1-ethyl carboxylate in the form of a white solid.

LCMS (IE, m/z): (M+1) 377.35

$^1$H-NMR: $\delta_H$ ppm 400 MHz, DMSO 13.06 (1H, bs, NH), 11.82 (1H, bs, NH), 9.37 (1H, s, $CH_{arom}$), 8.01 (1H, s, $CH_{arom}$), 7.51-7.35 (2H, m, 2×$CH_{arom}$), 4.33 (2H, q, $CH_2$), 3.64 (2H, s, $CH_2$), 3.30-3.26 (2H, m, $CH_2$), 2.72 (3H, s, $CH_3$), 2.38-2.31 (2H, m, $CH_2$), 1.35 (3H, t, $CH_3$).

4-Oxo-8-phenethyl-4,5-dihydro-3H-pyrrolo[2,3-c] quinoline-1-ethyl carboxylate (207)

10 mg of palladium on charcoal is added to a suspension of 14 mg (0.04 mmol) of 4-oxo-8-phenylethynyl-4,5-dihydro- 3H-pyrrolo[2,3-c]quinoline-1-ethyl carboxylate in 5 ml of ethanol and the mixture is placed under a hydrogen atmosphere for 24 hours. The raw reaction product is then filtered on celite, and the filtrate is evaporated. The residue is triturated with methanol to give 4 mg (28%) of 4-oxo-8-phenethyl-4,5-dihydro-3H-pyrrolo[2,3-c]quinoline-1-ethyl carboxylate in the form of a white solid.

LCMS (IE, m/z): (M+1) 361.36
¹H-NMR: $\delta_H$ ppm 400 MHz, DMSO
12.98 (1H, bs, NH), 11.62 (1H, bs, NH), 9.15 (1H, s, $CH_{arom}$), 8.00 (1H, s, $CH_{arom}$), 7.32-7.14 (7H, m, 7×$CH_{arom}$), 4.36 (2H, q, $CH_2$), 3.02-2.97 (4H, m, 2×$CH_2$), 1.42-1.37 (3H, t, $CH_3$).

8-(3-Hydroxy-3-methyl-butyl)-4-oxo-4,5-dihydro-3H-pyrrolo[2,3-c]quinoline-1-ethyl carboxylate (208)

A suspension of 47 mg (0.14 mmol) of 8-(3-hydroxy-3-methyl-but-1-ynyl)-4-oxo-4,5-dihydro-3H-pyrrolo[2,3-c]quinoline-1-ethyl carboxylate, 164 mg (2.6 mmol) of ammonium formate and 5 mg of palladium on charcoal in 10 ml of ethanol is refluxed for 8 hours. The solution is filtered on celite and then evaporated. Water is added and the product is extracted twice with ethyl acetate. The organic phases are dried over magnesium sulfate, filtered and evaporated to give 5 mg (10%) of 8-(3-hydroxy-3-methyl-butyl)-4-oxo-4,5-dihydro-3H-pyrrolo[2,3-c]quinoline-1-ethyl carboxylate in the form of a colourless oil.

LCMS (IE, m/z): (M+1) 343.29
¹H-NMR: $\delta_H$ ppm 400 MHz, $CD_3OD$
9.15 (1H, s, $CH_{arom}$), 7.93 (1H, s, $CH_{arom}$), 7.18-7.25 (2H, m, 2×$CH_{arom}$), 4.30 (2H, q, $CH_2$), 2.70-2.74 (2H, m, $CH_2$), 1.73-1.78 (2H, m, $CH_2$), 1.33 (3H, t, $CH_3$) 1.19 (6H, s, 2×$CH_3$).

8-Iodo-4-oxo-4,5-dihydro-3H-pyrrolo[2,3-c]quinoline-1-ethyl carboxylate (209)

Method D 1.49 g (4.7 mmol) of 4-oxo-4,5-dihydro-3H-pyrrolo[2,3-c]quinoline-1-ethyl carboxylate cocrystallized with one equivalent of acetic acid is added to a suspension of 1.61 g (5.17 mmol) of diiodine and 1.31 g (5.17 mmol) of silver sulfate in anhydrous ethanol (100 mL). The reaction mixture is stirred at room temperature for 6 hours then the solvents are evaporated under vacuum. The residue is taken up in water and the product is extracted copiously with a mixture of ethyl acetate/methanol 95/5. The organic phases are dried over magnesium sulfate, filtered on celite and evaporated under vacuum to give 1.4 g (78%) of 8-iodo-4-oxo-4,5-dihydro-3H-pyrrolo[2,3-c]quinoline-1-ethyl carboxylate in the form of a white solid.

Method E

Alternatively, 1.5 mL (1.5 mmol) of a 1M solution of iodine monochloride in dichloromethane is added to a solution of 316 mg (1 mmol) of 4-oxo-4,5-dihydro-3H-pyrrolo[2,3-c]quinoline-1-ethyl carboxylate cocrystallized with 1 equivalent of acetic acid and 652 mg (1 mmol) of indium triflate in anhydrous acetonitrile (20 mL). The solution is heated at 45° C. for 3 hours then stirred at room temperature for 20 hours. The solid is filtered, and triturated with acetonitrile and diisopropyl ether to give 368 mg (96%) of 8-iodo-4-oxo-4,5-dihydro-3H-pyrrolo[2,3-c]quinoline-1-ethyl carboxylate in the form of a white solid.

LCMS (IE, m/z): (M+1) 382.85
¹H-NMR: $\delta_H$ ppm 400 MHz, DMSO
13.10 (1H, bs, NH), 11.79 (1H, bs, NH), 9.65 (1H, s, $CH_{arom}$), 8.01 (1H, d, $CH_{arom}$), 7.69 (1H, d, $CH_{arom}$), 7.22 (1H, d, $CH_{arom}$), 4.33 (2H, dd, $OCH_2$), 1.37 (3H, t, $CH_3$).

8-Iodo-4-oxo-4,5-dihydro-3H-pyrrolo[2,3-c]quinoline-1-propyl carboxylate (210)

This compound is prepared according to synthesis 209 (method D), from 202 mg (0.75 mmol) of 4-oxo-4,5-dihydro-3H-pyrrolo[2,3-c]quinoline-1-propyl carboxylate, 190 mg (0.75 mmol) of diiodine and 257 mg (0.82 mmol) of silver sulfate to give, after recrystallization from a dichloromethane/pentane mixture, 190 mg (64%) of 8-iodo-4-oxo-4,5-dihydro-3H-pyrrolo[2,3-c]quinoline-1-propyl carboxylate in the form of a white solid.

LCMS (IE, m/z): (M+1) 396.80
¹H-NMR: $\delta_H$ ppm 400 MHz, DMSO
13.11 (1H, bs, NH), 11.78 (1H, bs, NH), 9.64 (1H, s, $CH_{arom}$), 8.01 (1H, d, $CH_{arom}$), 7.70 (1H d, $CH_{arom}$), 7.22 (1H, d, $CH_{arom}$), 4.24 (2H, t, $OCH_2$), 1.79-1.74 (2H m, $CH_2$), 1.01 (3H, t, $CH_3$).

4-Oxo-4,5-dihydro-3H-pyrrolo[2,3-c]quinoline-1-propyl carboxylate was prepared according to method of esterification C from 194 mg (0.85 mmol) of 4-oxo-4,5-dihydro-3H-pyrrolo[2,3-c]quinoline-1-carboxylic acid, 1.29 mL (12.75 mmol) of triethylamine and 698 µL (1.1 mmol) of di-n-propylsulfate to give, after precipitation in water, 200 mg (87%) of 4-oxo-4,5-dihydro-3H-pyrrolo[2,3-c]quinoline-1-propyl carboxylate in the form of a beige solid.

8-Iodo-4-oxo-4,5-dihydro-3H-pyrrolo[2,3-c]quinoline-1-cyclopentyl carboxylate (211)

This compound is prepared according to synthesis 209 (method D), from 251 mg (0.85 mmol) of 4-oxo-4,5-dihydro-3H-pyrrolo[2,3-c]quinoline-1-cyclopentyl carboxylate, 237 mg (0.93 mmol) of diiodine and 291 mg (0.93 mmol) of silver sulfate to give, after trituration in diethyl ether, 275 mg (76%) of 8-iodo-4-oxo-4,5-dihydro-3H-pyrrolo[2,3-c]quinoline-1-cyclopentyl carboxylate in the form of a pale yellow solid.

LCMS (IE, m/z): (M+1) 422.88
¹H-NMR: $\delta_H$ ppm 400 MHz, DMSO
13.14 (1H, bs, NH), 11.82 (1H, bs, NH), 9.68 (1H, s, $CH_{arom}$), 8.03 (1H, d, $CH_{arom}$), 7.74 (1H, d, $CH_{arom}$), 7.27 (1H, d, $CH_{arom}$), 5.40 (1H, bs, OCH), 1.99-1.67 (8H, m, $CH_2$).

4-Oxo-4,5-dihydro-3H-pyrrolo[2,3-c]quinoline-1-cyclopentyl carboxylate was prepared according to method of esterification C from 194 mg (0.85 mmol) of 4-oxo-4,5-dihydro-3H-pyrrolo[2,3-c]quinoline-1-carboxylic acid, 1.29 mL (12.75 mmol) of triethylamine and 1.99 g (8.5 mmol) of dicyclopentylsulfate to give, after precipitation in water, 250 mg (98%) of 4-oxo-4,5-dihydro-3H-pyrrolo[2,3-c]quinoline-1-cyclopentyl carboxylate in the form of a beige solid.

8-Iodo-4-oxo-4,5-dihydro-3H-pyrrolo[2,3-c]quinoline-1-isobutyl carboxylate (212)

This compound is prepared according to synthesis 209 (method D), from 165 mg (0.58 mmol) of 4-oxo-4,5-dihydro-3H-pyrrolo[2,3-c]quinoline-1-isobutyl carboxylate, 465 mg (1.83 mmol) of diiodine and 570 mg (1.83 mmol) of silver sulfate to give, after trituration in methanol, 160 mg (67%) of 8-iodo-4-oxo-4,5-dihydro-3H-pyrrolo[2,3-c]quinoline-1-isobutyl carboxylate in the form of a white solid.

LCMS (IE, m/z): (M+1) 410.89
¹H-NMR: $\delta_H$ ppm 400 MHz, DMSO 13.13 (1H, bs, NH), 11.79 (1H, bs, NH), 9.65 (1H, s, $CH_{arom}$), 8.01 (1H, d, $CH_{arom}$), 7.70 (1H, d, $CH_{arom}$), 7.23 (1H, d, $CH_{arom}$), 4.07 (2H, d, $OCH_2$), 2.03-2.10 (1H, m, CH), 1.01 (6H, 1, 2×$CH_3$).

4-Oxo-4,5-dihydro-3H-pyrrolo[2,3-c]quinoine-1-isobutyl carboxylate was prepared according to method of esterification C from 194 mg (0.85 mmol) of 4-oxo-4,5-dihydro-3H-pyrrolo[2,3-c]quinoline-1-carboxylic acid, 1.29 mL (12.75 mmol) of triethylamine and 892 mg (4.25 mmol) of diisobutylsulfate to give, after precipitation in water, 164 mg (68%) of 4-oxo-4,5-dihydro-3H-pyrrolo[2,3-c]quinoline-1-isobutyl carboxylate in the form of a beige solid.

7-Methoxy-4-oxo-4,5-dihydro-3H-pyrrolo[2,3-c]quinoline-1-ethyl carboxylate (213)

This compound was synthesized according to synthesis 1, from 0.5 g (3.06 mmol) of 6-methoxy-1,3-dihydro-indol-2-one (prepared according to George J. Quallich and P. M. Morissey, *Synthesis,* 1993, 51-53) to give, after recrystallization from acetic acid, 140 mg (13% in two stages) of 7-methoxy-4-oxo-4,5-dihydro-3H-pyrrolo[2,3-c]quinoline-1-ethyl carboxylate cocrystallized with one equivalent of acetic acid in the form of a beige solid.

LCMS (IE, m/z): (M+1) 287
$^1$H-NMR: $\delta_H$ ppm 400 MHz, DMSO
12.86 (1H, bs, NH), 11.53 (1H, s, NH), 9.14 (1H, d, $CH_{arom}$), 7.93 (1H, s, $CH_{arom}$), 695 (1H, d, $CH_{arom}$), 6.84 (1H, dd, $CH_{arom}$), 4.29 (2H, q, $CH_2$), 3.50 (3H, s, $CH_3$), 1.33 (3H, t, $CH_3$).

8-Iodo-7-methoxy-4-oxo-4,5-dihydro-3H-pyrrolo[2,3-c]quinoline-1-ethyl carboxylate (214)

This compound is prepared according to synthesis 209 (method E), from 50 mg (0.14 mmol) of 7-methoxy-4-oxo-4,5-dihydro-3H-pyrrolo[2,3-c]quinoline-1-ethyl carboxylate, 81 mg (0.14 mg) of indium triflate and 140 µL (0.14 mmol) of a 1M solution of iodine monochloride in dichloromethane to give, after filtration, and trituration in acetonitrile, 25 mg (43%) of 8-iodo-7-methoxy-4-oxo-4,5-dihydro-3H-pyrrolo[2,3-c]quinoline-1-ethyl carboxylate in the form of a white solid.

LCMS (IE, m/z): (M+1) 413.19
$^1$H-NMR: $\delta_H$ ppm 400 MHz, DMSO
12.97 (1H, bs, NH), 11.64 (1H, s, NH), 9.69 (1H, s, $CH_{arom}$), 7.95 (1H, s, $CH_{arom}$), 7.00 (1H, s, $CH_{arom}$), 4.31 (2H, q, $CH_2$), 3.86 (3H, s, $CH_3$), 1.35 (3H, t, $CH_3$).

7-Fluoro-4-oxo-4,5-dihydro-3H-pyrrolo[2,3-c]quinoline-1-ethyl carboxylate (215)

This compound was synthesized according to synthesis 1, from 5 g (33 mmol) of 6-fluoro-1,3-dihydro-indol-2-one to give, after trituration in diethyl ether, 5.6 g (50% in two stages) of 7-fluoro-4-oxo-4,5-dihydro-3H-pyrrolo[2,3-c]quinoline-1-ethyl carboxylate cocrystallized with one equivalent of acetic acid in the form of a brown solid.

LCMS (IE, m/z): (M+1) 275.10
$^1$H-NMR: $\delta_H$ ppm 400 MHz, DMSO
13.02 (1H, bs, NH), 11.77 (1H, bs, NH), 9.30 (1H, dd, $CH_{arom}$), 7.99 (1H, s, $CH_{arom}$), 7.17 (1H, d, $CH_{arom}$), 7.09 (1H, t, $CH_{arom}$), 4.30 (2H, dd, $OCH_2$), 1.34 (3H, t, $CH_3$).

7-Chloro-4-oxo-4,5-dihydro-3H-pyrrolo[2,3-c]quinoline-1-ethyl carboxylate (216)

This compound was synthesized according to synthesis 1, from 0.5 g (3.06 mmol) of 6-chloro-1,3-dihydro-indol-2-one to give, after recrystallization from ethanol, 3.68 g (21% in two stages) of 7-chloro-4-oxo-4,5-dihydro-3H-pyrrolo[2,3-c]quinoline-1-ethyl carboxylate in the form of a cream-coloured solid.

LC/MS (IE, m/z): (M+1) 291.01
$^1$H-NMR: $\delta_H$ ppm 400 MHz, DMSO
13.10 (1H, bs, NH), 11.79 (1H, bs, NH), 9.26 (1H, d, $CH_{arom}$), 8.01 (1H, s, $CH_{arom}$), 7.44 (1H, d, $CH_{arom}$), 7.27 (1H, dd, $CH_{arom}$), 4.30 (2H, q, $CH_2$), 1.34 (3H, t, $CH_3$).

8-(3-Dimethylamino-acryloyl)-4-oxo-4,5-dihydro-3H-pyrrolo[2,3-c]quinoline-1-ethyl carboxylate (217)

4.36 g (25 mmol) of C-tert-butoxy-N,N',N'-tetramethyl-methanediamine is added to a solution of 1.49 g (5 mmol) of 8-acetyl-4-oxo-4,5-dihydro-3H-pyrrolo[2,3-c]quinoline-1-ethyl carboxylate dissolved in 25 mL of anhydrous dioxan. The mixture is stirred for 1 hour at 90° C. then the solvent is evaporated. The residue is triturated with a mixture of ethyl acetate and diisopropyl ether to give a solid which is filtered and washed with diisopropyl ether then pentane. After drying, 1.66 g (94%) of 8-(3-dimethylamino-acryloyl)-4-oxo-4,5-dihydro-3H-pyrrolo[2,3-c]quinoline-1-ethyl carboxylate is obtained in the form of a dark green solid. The product can be used without further purification. Further purification of the green solid (50 mg) by chromatography on silica (eluent chloroform/methanol 95/5) gives the product in the form of a beige solid.

LCMS (IE, m/z): (M+1) 354
$^1$H-NMR: $\delta_H$ ppm 400 MHz, DMSO
13.04 (1H, s, NH), 11.83 (1H, s, NH), 9.87 (1H, d, $CH_{arom}$), 8.00 (1H, s, $CH_{arom}$), 7.92 (1H, dd, $CH_{arom}$), 7.72 (1H, dd, $CH_{arom}$), 7.41 (1H, d, $CH_{arom}$), 5.94 (1H, d, $CH_{arom}$), 4.33 (2H, q, $CH_2$), 3.16 (3H, sb, $CH_3$), 2.94 (3H, s, $CH_3$), 1.36 (3H, t, $CH_3$).

8-(2-Morpholin-4-yl-acetyl)-4-oxo-4,5-dihydro-3H-pyrrolo[2,3-c]quinoline-ethyl carboxylate (218)

A solution of 80 mg (0.24 mmol) of 8-(2-chloro-acetyl)-4-oxo-4,5-dihydro-3H-pyrrolo[2,3-c]quinoline-1-ethyl carboxylate in 420 µL (4.8 mmol) of morpholine is heated at 60° C. for 4 hours. Water is added and the solid is filtered and then purified by chromatography on silica (eluent dichloromethane/methanol 95/5) to give 24 mg (26%) of 8-(2-morpholin-4-yl-acetyl)-4-oxo-4,5-dihydro-3H-pyrrolo[2,3-c]quinoline-1-ethyl carboxylate in the form of a brown solid.

LCMS (IE, m/z): (M+1) 384.074
$^1$H-NMR: $\delta_H$ ppm 400 MHz, DMSO
13.04 (1H, s, NH), 11.99 (1H, s, NH), 10.02 (1H, d, $CH_{arom}$), 8.04 (1H, s, $CH_{arom}$), 8.00 (1H, dd, $CH_{arom}$), 7.47 (1H, d, $CH_{arom}$), 4.33 (2H, q, $CH_2$), 3.84 (2H, s, $CH_2$), 3.62-3.55 (4H, m, 2×$CH_2$), 2.60-2.53 (4H, m, 2×CH), 1.36 (3H, t, $CH_3$).

1.04 g (3 mmol) of benzyltrimethylammonium dichloroiodate is added to a suspension of 596 mg (2 mmol) of 8-acetyl-4-oxo-4,5-dihydro-3H-pyrrolo[2,3-c]quinoline-1-ethyl carboxylate in 10 mL of a 3/1 mixture of 1,2-dichloroethane/methanol. The mixture is stirred at 80° C. for 48 hours then the mixture is cooled to room temperature. The excess of reagent is destroyed by addition of an aqueous solution of disodium sulfite, then the solvent is evaporated. Water is added to the residue, then the mixture is stirred using an ultrasonic bath to obtain a fine suspension. The precipitate is collected by filtration then triturated in methanol, diisopropyl ether then pentane to give, after drying, 385 mg (58%) of 8-(2-chloro-acetyl)-4-oxo-4,5-dihydro-3H-pyrrolo[2,3-c]quinoline-1-ethyl carboxylate in the form of a beige solid.

(S)-8-(cyclopropyl-pyrrolidin-2-ylmethyl-carbamoyl), 3-oxo-4,5-dihydro-3H-pyrrolo[2,3-c]quinoline-1-ethyl carboxylate hydrochloride (219)

This compound is prepared according to synthesis 139, from 78 mg (0.15 mmol) of (S)-8-[(1-tert-butoxycarbonypyrrolidin-2-ylmethyl)-cyclopropyl-carbamoyl]-4-oxo-4,5-dihydro-3H-pyrrolo[2,3-c]quinoline-1-ethyl carboxylate and 4 mL (7.5 mmol) of a 2M solution of hydrochloric acid in diethyl ether to give, after filtration, 67 mg (97%) of (S)-8-(cyclopropyl-pyrrolidin-2-ylmethyl-carbamoyl)-4-oxo-4,5-dihydro-3H-pyrrolo[2,3-c]quinoline-1-ethyl carboxylate hydrochloride in the form of a beige solid.

LCMS (IE, m/z): (M+1) 423.34

$^1$H-NMR: $\delta_H$ ppm 400 MHz, DMSO 13.10 (1H, bs, NH), 11.89 (1H, s, NH), 9.57 (1H, bs, NH.HCl), 9.48 (1H, s, $CH_{arom}$), 8.69 (1H, bs, NH.HCl), 8.01 (1H, d, $CH_{arom}$), 7.75 (1H, dd, $CH_{arom}$), 7.42 (1H, d, $CH_{arom}$), 4.24 (2H, q, $CH_2$), 3.92-3.71 (3H, m, 3×$CH_{ali}$), 3.19-3.12 (3H, m, 3×$CH_{ali}$), 2.28-2.15 (1H, m, $CH_{ali}$), 2.03-1.87 (2H, m, 2×$CH_{ali}$), 1.79-1.64 (1H, m, $CH_{ali}$), 1.34 (3H, t, $CH_3$), 0.58-0.43 (4H, m, 4×$CH_{cycloprop}$).

232 μL of a 20% solution of potassium tert-butoxide in THF is added to a solution of 169 mg (0.35 mmol) of (S)-2-{[cyclopropyl-(3-ethoxycarbonylmethylene-2-oxo-2,3-dihydro-1/1-indole-5-carbonyl)-amino]-methyl}-pyrrolidine-1-tert-butyl carboxylate and 75 mg (0.38 mmol) of 1-isocyanomethanesulfonyl-4-methyl-benzene in 5 ml of anhydrous dioxan, then the reaction mixture is stirred for 1 hour at 90° C. The solvent is evaporated, then the product is extracted twice with ethyl acetate. The organic phases are washed with water, then with a saturated solution of sodium chloride and dried over magnesium sulfate. The product is purified by chromatography on silica (eluent ethyl acetate/methanol 9/1) to give 82 mg (45%) of (S)-8-[(1-tert-butoxycarbonyl-pyrrolidin-2-ylmethyl)-cyclopropyl-carbamoyl]-4-oxo-4,5-dihydro-3H-pyrrolo[2,3-c]quinoline-1-ethyl carboxylate in the form of a beige solid.

5 mg (0.05 mmol) of piperidine is added to a solution of 231 mg (0.58 mmol) of (S)-2-{[cyclopropyl-(2-oxo-2,3-dihydro-1H-indole-5-carbonyl)-amino]-methyl}-pyrrolidine-1-tert-butyl carboxylate, of 65 mg (0.64 mmol) of ethyl glyoxalate in 10 ml of ethanol, then the mixture is heated for 18 hours at 70° C. The solvent is evaporated, then the product is purified by chromatography on silica (eluent cyclohexane/ethyl acetate 25/75) to give 173 mg (62%) of (S)-2-{[cyclopropyl-(3-ethoxycarbonylmethylene-2-oxo-2,3-dihydro-1H-indole-5-carbonyl)-amino]-methyl}-pyrrolidine-1-tert-butyl carboxylate in the form of a yellow solid.

264 mg (1.1 mmol) of (S)-2-cyclopropylaminomethyl-pyrrolidine-1-tert-butyl carboxylate is added to a solution of 177 mg (1 mmol) of 2-oxo-2,3-dihydro-1H-indole-5-carboxylic acid (prepared according to the following procedure: Li Sun, Ngoc Tran, Congxin Liang, Flora Tang, Audie Rice, Randall Schreck, Kara Waltz, Laura K. Shawver, Gerald McMahon, and Cho Tang, *Journal of Medicinal Chemistry*, 1999, Vol. 42, 25, 5120), 417 mg (1.1 mmol) of O-(benzotriazol-1-yl)-N,N,N',N'-tetramethyluronium, 646 mg (5 mmol) of diisopropylethylamine and 27 mg (0.1 mmol) of 1-hydroxybenzotriazole in 2 ml of dimethylformamide, then the reaction mixture is stirred at room temperature for 30 minutes. The solvent is evaporated, then the product is extracted with ethyl acetate. The organic phases are dried over magnesium sulfate, filtered and evaporated. The residue is purified by chromatography on silica (ethyl acetate/methanol 95/5 then 9/1) to give 254 mg (64%) of (S)-2-{[cyclopropyl-(2-oxo-2,3-dihydro-1H-indole-5-carbonyl)-amino]-methyl}-pyrrolidine-1-tert-butyl carboxylate in the form of a beige solid.

4-Oxo-8-phenylsulfanyl-4,5-dihydro-3H-pyrrolo[2,3-c]quinoline-1-ethyl carboxylate (220)

In a sealed tube, a suspension of 152 mg (0.4 mmol) of 8-iodo-4-oxo-4,5-dihydro-3H-pyrrolo[2,3-c]quinoline-1-ethyl carboxylate (synthesis 209) and 110 mg (0.8 mmol) of potassium carbonate in dimethoxyethane (0.6 mL) is purged with an argon stream before adding 15 mg (0.08 mmol) of copper iodide and 86 mg (0.6 mmol) of thiophenol. The reaction mixture is heated at 90° C. for 5 to 6 days then filtered on celite and rinsed with dichloromethane, then methanol. The filtrate is evaporated and the residue obtained is purified by chromatography on silica (eluent dichloromethane/methanol 96/4 then 9/1) to give 42 mg (29%) of 4-oxo-8-phenylsulfanyl-4,5-dihydro-3H-pyrrolo[2,3-c]quinoline-1-ethyl carboxylate in the form of a white solid.

LCMS (IE, m/z): (M+1) 365.20

$^1$H-NMR: $\delta_H$ ppm 400 MHz, DMSO 13.10 (1H, bs, NH), 11.85 (1H, s, NH), 9.48 (1H, s, $CH_{arom}$), 8.01 (1H, s, $CH_{arom}$), 7.46 (2H, s, 2×$CH_{arom}$), 7.35-7.27 (2H, m, 2×$CH_{arom}$), 7.24-7.15 (3H, m, 3×$CH_{arom}$), 4.26 (2H, q, $CH_2$), 1.30 (3H, t, $CH_3$).

8-Cyclohexylsulfanyl-4-oxo-4,5-dihydro-3H-pyrrolo[2,3-c]quinoline-1-ethyl carboxylate (221)

This compound is prepared according to synthesis 220, from 152 mg (0.4 mmol) of 8-iodo-4-oxo-4,5-dihydro-3H-pyrrolo[2,3-c]quinoline-1-ethyl carboxylate and 150 μL (1.2 mmol) of cyclohexylthio to give, after purification by chromatography on silica (eluent dichloromethane/methanol 98/2), 105 mg (71%) of 8-cyclohexylsulfanyl-4-oxo-4,5-dihydro-3H-pyrrolo[2,3-c]quinoline-1-ethyl carboxylate in the form of a white solid.

LCMS (IE, m/z): (M+1) 371.33

$^1$H-NMR: $\delta_H$ ppm 400 MHz, DMSO 13.02 (1H, bs, NH), 11.72 (1H, bs, NH), 9.33 (1H, d, $CH_{arom}$), 7.99 (1H, d, $CH_{arom}$), 7.41 (1H, dd, $CH_{arom}$), 7.36 (1H, d, $CH_{arom}$), 4.33 (2H, q, $CH_2$), 3.20-3.12 (1H, m, $CH_{cyclo}$), 1.98-1.88 (2H, m, 2×$CH_{cyclo}$) 1.76-1.66 (2H, m, 2×$CH_{cyclo}$), 1.60-1.53 (1H, m, $CH_{cyclo}$), 1.35 (3H, t, $CH_3$), 1.35-1.15 (5H, m, 5×$CH_{cyclo}$).

8-Benzylsulfanyl-4-oxo-4,5-dihydro-3H-pyrrolo[2,3-c]quinoline-1-ethyl carboxylate (222)

This compound is prepared according to synthesis 220, from 152 mg (0.4 mmol) of 8-iodo-4-oxo-4,5-dihydro-3H-pyrrolo[2,3-c]quinoline-1-ethyl carboxylate and 34 μL (0.29 mmol) of phenylmethanethiol to give, after purification by chromatography on silica (eluent dichloromethane/methanol 96/4), 106 mg (70%) of 8-benzylsulfanyl-4-oxo-4,5-dihydro-3H-pyrrolo[2,3-c]quinoline-1-ethyl carboxylate in the form of a white solid.

LCMS (IE, m/z): (M+1) 379.11

$^1$H-NMR: $\delta_H$ ppm 400 MHz, DMSO 13.04 (1H, bs, NH), 11.71 (1H, s, NH), 9.31 (1H, s, $CH_{arom}$), 7.99 (1H, s, $CH_{arom}$), 7.41-7.30 (4H, m, 4×$CH_{arom}$), 7.26 (2H, t, 2×$CH_{arom}$), 7.20 (1H, d, $CH_{arom}$), 4.31 (2H, q, $CH_2$), 4.23 (2H, s, $CH_2$), 1.34 (3H, t, $CH_3$).

8-(4-Acetylaminophenylsulfanyl)-4-oxo-4,5-dihydro-3H-pyrrolo[2,3-c]quinoline-1-ethyl carboxylate (223)

This compound is prepared according to synthesis 220, from 152 mg (0.4 mmol) of 8-iodo-4-oxo-4,5-dihydro-3H-pyrrolo[2,3-c]quinoline-1-ethyl carboxylate and 100 mg (0.6 mmol) of 4-acetylaminobenzenethiol to give, after purification by chromatography on silica (eluent dichloromethane/methanol 96/4) then trituration in diethyl ether, 67 mg (40%) of 8-(4-acetylaminophenylsulfanyl)-4-oxo-4,5-dihydro-3H-pyrrolo[2,3-c]quinoline-1-ethyl carboxylate in the form of a white solid.

LCMS (IE, m/z): (M+1) 422.25

$^1$H-NMR: $\delta_H$ ppm 400 MHz, DMSO 13.06 (1H, bs, NH), 11.79 (1H, s, NH), 10.00 (1H, s, NH), 9.37 (1H, s, CH$_{arom}$), 7.99 (1H, s, CH$_{arom}$), 7.55 (2H, d, 2×CH$_{arom}$), 7.41 (1H, d, CH$_{arom}$), 7.34 (1H, dd, CH$_{arom}$), 7.23 (2H, m, 2×CH$_{arom}$), 4.26 (2H, q, CH$_2$), 2.02 (3H, s, CH$_3$), 1.31 (3H, t, CH$_3$).

8-(3-Aminophenylsulfanyl)-4-oxo-4,5-dihydro-3H-pyrrolo[2,3-c]quinoline-1-ethyl carboxylate (224)

This compound is prepared according to synthesis 220, from 305 mg (0.8 mmol) of 8-iodo-4-oxo-4,5-dihydro-3H-pyrrolo[2,3-c]quinoline-1-ethyl carboxylate and 127 µL (1.2 mmol) of 3-aminobenzenethiol to give, after purification by chromatography on silica (eluent dichloromethane/methanol 96/4) then trituration in methanol, 150 mg (49%) of 8-(3-aminophenylsulfanyl)-4-oxo-4,5-dihydro-3H-pyrrolo[2,3-c]quinoline-1-ethyl carboxylate in the form of a white solid.

LCMS (IE, m/z): (M+1) 380.15

$^1$H-NMR: $\delta_H$ ppm 400 MHz, DMSO 13.07 (H, bs, NH), 11.82 (1H, s, NH), 9.44 (1H, s, CH$_{arom}$), 8.00 (1H, s, CH$_{arom}$), 7.45-7.39 (2H, m, 2×CH$_{arom}$), 6.92 (1H, t, CH$_{arom}$), 6.39-6.31 (3H, m, 3×CH$_{arom}$), 5.13 (2H, s, NH), 4.28 (2H, q, CH), 1.32 (3H, t, CH$_3$).

8-(3-Acetylaminophenylsulfanyl)-4-oxo-4,5-dihydro-3H-pyrrolo[2,3-c]quinoline-1-ethyl carboxylate (225)

This compound is prepared according to synthesis 60, from 132 mg (0.32 mmol) of 8-(3-aminophenylsulfanyl)-4-oxo-4,5-dihydro-3H-pyrrolo[2,3-c]quinoline-1-ethyl carboxylate, 89 µL (0.64 mmol) of triethylamine and 25 µL (0.35 mmol) of acetyl chloride to give, after precipitation in water and recrystallization from methanol, 70 mg (62%) of 8-(3-acetylaminophenylsulfanyl)-4-oxo-4,5-dihydro-3H-pyrrolo[2,3-c]quinoline-1-ethyl carboxylate in the form of a beige solid.

LCMS (IE, t/z): (M+1) 422.21

$^1$H-NMR: $\delta_H$ ppm 400 MHz, DMSO 13.09 (1H, bs, NH), 11.86 (1H, s, NH), 9.89 (1H, s, NH), 9.47 (1H, s, CH$_{arom}$), 8.01 (1H, d, CH$_{arom}$), 7.48-7.38 (4H, m, 4×CH$_{arom}$), 7.21 (1H, t, CH$_{arom}$), 6.86-6.82 (1H, m, CH$_{arom}$), 4.27 (2H, q, CH$_2$), 1.97 (3H, s, CH$_3$), 1.31 (3H, t, CH$_3$).

8-(2-Amino-ethylsulfanyl)-4-oxo-4,5-dihydro-3H-pyrrolo[2,3-c]quinoline-1-ethyl carboxylate hydrochloride (226)

This compound is prepared according to synthesis 139, from 331 mg (0.8 mmol) of 8-(2-tert-butoxycarbonylamino-ethylsulfanyl)-4-oxo-4,5-dihydro-3H-pyrrolo[2,3-c]quinoline-1-ethyl carboxylate and 20 mL (40 mmol) of a 2M solution of hydrochloric acid in diethyl ether to give, after filtration, 194 mg (65%) of 8-(2-amino-ethylsulfanyl)-4-oxo-4,5-dihydro-3H-pyrrolo[2,3-c]quinoline-1-ethyl carboxylate hydrochloride in the form of a cream-coloured solid.

LCMS (IE, m/z): (M+1) 332.36

$^1$H-NMR: $\delta_H$ ppm 400 MHz, DMSO 13.08 (1H, bs, NH), 11.79 (1H, s, NH), 9.37 (1H, d, CH$_{arom}$), 8.05 (3H, bs, NH$_2$. HCl), 8.01 (1H, d, CH$_{arom}$), 7.52 (1H, dd, CH$_{arom}$), 7.42 (1H, d, CH$_{arom}$), 4.32 (2H, q, CH$_2$), 3.18 (2H, t, CH$_2$), 3.03-2.94 (2H, m, CH$_2$), 1.35 (3H, t, CH$_3$).

8-(2-tert-Butoxycarbonylamino-ethylsulfanyl)-4-oxo-4,5-dihydro-3H-pyrrolo[2,3-c]quinoline-1-ethyl carboxylate is prepared according to synthesis 220, from 305 mg (0.8 mmol) of 8-iodo-4-oxo-4,5-dihydro-3H-pyrrolo[2,3-c]quinoline-1-ethyl carboxylate and 202 µL (1.2 mmol) of 2-tert-butoxycarbonylamine-ethanethiol to give, after purification by chromatography on silica (eluent dichloromethane/methanol 96/4) then trituration in diethyl ether, 345 mg (quantitative) of 8-(2-tert-butoxycarbonylamino-ethylsulfanyl)-4-oxo-4,5-dihydro-3H-pyrrolo[2,3-c]quinoline-1-ethyl carboxylate in the form of a white solid.

4-Oxo-8-sulfo-4,5-dihydro-3H-pyrrolo[2,3-c]quinoline-1-ethyl carboxylate (227)

This compound was isolated during purification by preparative LC of 4-oxo-8-[(piperidin-4-ylmethyl)-sulfamoyl]-4,5-dihydro-3H-pyrrolo[2,3-c]quinoline-1-ethyl carboxylate trifluoroacetate ( ) to give 4 mg (1%) of 4-oxo-8-sulfo-4,5-dihydro-3H-pyrrolo[2,3-c]quinoline-1-ethyl carboxylate in the form of a beige solid.

LCMS (IE, m/z): (M+1) 336.92

$^1$H-NMR: $\delta_H$ ppm 400 MHz, DMSO 12.96 (1H, bs, NH), 11.70 (1H, bs, NH), 9.49 (1H, d, CH$_{arom}$), 7.97 (1H, d, CH$_{arom}$), 7.62 (1H, dd, CH$_{arom}$), 7.31 (1H, d, CH$_{arom}$), 4.32 (2H, q, CH$_2$), 1.37 (3H, 1, CH$_3$).

4-Oxo-8-phenyl-4,5-dihydro-3H-pyrrolo[2,3-c]quinoline-1-ethyl carboxylate (228)

17 mg (0.025 mmol) of dichlorobis(triphenylphosphine)-palladium (II), 45 mg (0.37 mmol) of phenylboronic acid and 0.6 mL (1.2 ml) of a 2M aqueous solution of potassium carbonate are added to a degassed solution of 100 mg (0.25 mmol) of 8-bromo-4-oxo-4,5-dihydro-3H-pyrrolo[2,3-c]quinoline-1-ethyl carboxylate dissolved in 5 mL of anhydrous dioxan. The reaction mixture is stirred at 110° C. for 20 hours. Water is added and the product is extracted with ethyl acetate. The organic phases are washed with a saturated aqueous solution of sodium chloride, dried over magnesium sulfate, filtered and evaporated. The residue is purified by chromatography on silica (eluent dichloromethane/methanol 98/2) then triturated in methanol to give 16 mg (19%) of 4-oxo-8-phenyl-4,5-dihydro-3H-pyrrolo[2,3-c]quinoline-1-ethyl carboxylate in the form of a white solid.

LCMS (IE, m/z): (M+1) 332.96

$^1$H-NMR: $\delta_H$ ppm 400 MHz, CDCl$_3$ 12.07 (1H, bs, NH), 10.76 (1H, bs, NH), 9.72 (1H, d, CH$_{arom}$), 8.07 (1H, d, CH$_{arom}$), 7.74 (2H, d, 2×CH$_{arom}$), 7.63 (1H, dd, CH$_{arom}$), 7.50-7.42 (3H, m, 3×CH$_{arom}$), 7.35 (1H; d, CH$_{arom}$), 4.36 (2H, q, CH$_2$), 1.35 (3H, t, CH$_3$).

8-(2-Chlorophenyl)-4-oxo-4,5-dihydro-3H-pyrrolo[2,3-c]quinoline-1-ethyl carboxylate (229)

68 mg (0.01 mmol) of dichlorobis(triphenylphosphine)-palladium (II), 92 mg (0.59 mmol) of 2-chlorophenylboronic acid and 1 mL (2 mmol) of a 2M aqueous solution of tribasic potassium triphosphate are added to a degassed solution of 200 mg (0.49 mmol) of 8-bromo-4-oxo-4,5-dihydro-3H-pyrrolo[2,3-c]quinoline-1-ethyl carboxylate dissolved in 10 mL of anhydrous dioxan. The reaction mixture is stirred at 110° C. for 20 hours. Water is added and the product is extracted with ethyl acetate. The organic phases are washed with a saturated aqueous solution of sodium chloride, dried over magnesium sulfate, filtered and evaporated. The residue is purified by chromatography on silica (eluent dichloromethane/methanol 98/2) to give 27 mg (15%) of 8-(2-chlorophenyl)-4-oxo-4,5-dihydro-3H-pyrrolo[2,3-c]quinoline-1-ethyl carboxylate in the form of a white solid.

LCMS (IE, m/z): (M+1) 366.86-368.80

$^1$H-NMR: $\delta_H$ ppm 400 MHz, DMSO 13.04 (1H, bs, NH), 11.80 (1H, bs, NH), 9.35 (1H, d, $CH_{arom}$), 8.00 (1H, d, $CH_{arom}$), 7.61-7.58 (1H, m, $CH_{arom}$), 7.49-7.39 (5H, m, 5×$CH_{arom}$), 4.25 (2H, q, $CH_2$), 1.28 (3H, t, $CH_3$).

8-(2-tert-Butoxycarbonylaminophenyl)-4-oxo-4,5-dihydro-3H-pyrrolo[2,3-c]quinoline-1-ethyl carboxylate (230)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 234 mg (0.74 mmol) of 4,4,5,5-tetramethyl-2-(2-tert-butoxyaminophenyl)-[1,3,2]dioxaborolane to give, after purification by chromatography on silica (eluent dichloromethane/methanol 96/4) then trituration in methanol, 111 mg (50%) of 8-(2-tert-butoxycarbonylaminophenyl)-4-oxo-4,5-dihydro-3H-pyrrolo[2,3-c]quinoline-1-ethyl carboxylate in the form of a slightly yellow solid.

LCMS (IE, m/z): (M+1) 448.06

$^1$H-NMR: $\delta_H$ ppm 400 MHz, DMSO 13.02 (1H, bs, NH), 11.73 (1H, bs, NH), 9.29 (1H, s, $CH_{arom}$), 8.13 (1H, s, NH), 8.00 (1H, d, $CH_{arom}$), 7.52-7.47 (1H, m, $CH_{arom}$), 7.46-7.40 (2H, m, 2×$CH_{arom}$), 7.37-7.31 (2H, m, 2×$CH_{arom}$), 7.29-7.24 (1H, m, $CH_{arom}$), 4.25 (2H, q, $CH_2$), 1.28 (3H, t, $CH_3$), 1.26 (9H, s, 3×$CH_3$).

8-(2-Aminophenyl)-4-oxo-4,5-dihydro-3H-pyrrolo[2,3-c]quinoline-1-ethyl carboxylate (231)

0.5 mL of trifluoroacetic acid is added to a solution of 100 mg (0.22 mmol) of 8-(2-tert-butoxycarbonylaminophenyl)-4-oxo-4,5-dihydro-3H-pyrrolo[2,3-c]quinoline-1-ethyl carboxylate dissolved in 2 mL of dichloroethane. The solution is stirred at room temperature for 30 minutes then the solvents are evaporated. The residue is triturated with diisopropyl ether then the solid is filtered and washed with dichloromethane. It is taken up in 2 mL of dichloromethane then triethylamine is added to release the amine. Water is added and the compound is extracted with dichloromethane. The organic phases are dried over magnesium sulfate, filtered and evaporated. The solid is triturated with water to give 35 mg (45%) of 8-(2-aminophenyl)-4-oxo-4,5-dihydro-3H-pyrrolo[2,3-c]quinoline-1-ethyl carboxylate in the form of a white solid.

LCMS (IE, m/z): (M+1) 348.05

$^1$H-NMR: $\delta_H$ ppm 400 MHz, DMSO 13.01 (1H, bs, NH), 11.76 (1H, bs, NH), 9.27 (1H, d, $CH_{arom}$), 7.99 (1H, s, $CH_{arom}$), 7.49 (1H, d, $CH_{arom}$), 7.43 (1H, dd, $CH_{arom}$), 7.08-7.02 (2H, m, 2×$CH_{arom}$), 6.77 (1H dd, $CH_{arom}$), 6.65 (1H, ddd, $CH_{arom}$), 4.78 (2H, bs, $NH_2$), 4.26 (2H, q, $CH_2$), 1.29 (3H, t, $CH_3$).

8-(2-Methanesulfonylaminophenyl)-4-oxo-4,5-dihydro-3-pyrrolo[2,3-c]quinoline-1-ethyl carboxylate (232)

24 µL (0.3 mmol) of methanesulfonyl chloride is added to a solution of 70 mg (0.2 mmol) of 8-(2-aminophenyl)-4-oxo-4,5-dihydro-3H-pyrrolo[2,3-c]quinoline-1-ethyl carboxylate dissolved in 0.3 mL of anhydrous pyridine. The solution is stirred at room temperature for 4 hours then water is added. The compound is extracted with ethyl acetate. The organic phases are washed with an aqueous solution of copper sulfate, dried over magnesium sulfate, filtered and evaporated to give 22 mg (25%) of 8-(2-methanesulfonylaminophenyl)-4-oxo-4,5-dihydro-3H-pyrrolo[2,3-c]quinoline-1-ethyl carboxylate in the form of a white solid.

LCMS (IE, m/z): (M+1) 426.01

$^1$H-NMR: $\delta_H$ ppm 400 MHz, DMSO 13.01 (1H, bs, NH), 11.77 (1H, bs, NH), 9.27 (1H, d, $CH_{arom}$), 8.81 (1H, bs, NH), 7.99 (1H, s, $CH_{arom}$), 7.54 (1H, dd, $CH_{arom}$), 7.49-7.44 (2H, m, 2×$CH_{arom}$), 7.43-7.31 (3H, m, 3×$CH_{arom}$), 4.25 (2H, q, $CH_2$), 2.79 (3H, s, $CH_3$), 1.28 (3H, t, $CH_3$).

8-(3-tert-Butoxycarbonylaminophenyl)-4-oxo-4,5-dihydro-3H-pyrrolo[2,3-c]quinoline-1-ethyl carboxylate (233)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 174 mg (0.74 mmol) of 3-tert-butoxyaminophenylboronic acid to give, after purification by chromatography on silica (eluent dichloromethane/methanol 95/5), 135 mg (61%) of 8-(3-tert-butoxycarbonylaminophenyl)-4-oxo-4,5-dihydro-3H-pyrrolo[2,3-c]quinoline-1-ethyl carboxylate in the form of a slightly yellow solid.

LCMS (IE, m/z): (M+1) 447.95

$^1$H-NMR: $\delta_H$ ppm 400 MHz, DMSO 13.04 (1H, bs, NH), 11.76 (1H, bs, NH), 9.55 (1H, d, $CH_{arom}$), 9.44 (1H, bs, NH), 8.01 (1H, d, $CH_{arom}$), 7.85 (1H, s, $CH_{arom}$), 7.62 (1H, dd, $CH_{arom}$), 7.49 (1H, d, $CH_{arom}$), 7.45-7.35 (2H, m, 2×$CH_{arom}$), 7.32-7.28 (1H, m, $CH_{arom}$), 4.33 (2H, q, $CH_2$), 1.50 (9H, s, 3×$CH_3$), 1.33 (3H, t, $CH_3$).

Trifluoroacetate of 8-(3-aminophenyl)-4-oxo-4,5-dihydro-3H-pyrrolo[2,3-c]quinoline-1-ethyl carboxylate (234)

0.5 mL of trifluoroacetic acid is added to a solution of 120 mg (0.22 mmol) of 8-(3-tert-butoxycarbonylaminophenyl)-4-oxo-4,5-dihydro-3H-pyrrolo[2,3-c]quinoline-1-ethyl carboxylate dissolved in 2 mL of dichloroethane. The solution is stirred at room temperature for 30 minutes then the solvents are evaporated. The residue is triturated with diisopropyl ether then the solid is filtered and washed with dichloromethane to give 86 mg (69%) of 8-(3-aminophenyl)-4-oxo-4,5-dihydro-3H-pyrrolo[2,3-c]quinoline-1-ethyl carboxylate trifluoroacetate in the form of a beige solid.

LCMS (IE, m/z): (M+1) 348.00

$^1$H-NMR: $\delta_H$ ppm 400 MHz, DMSO 13.05 (1H, bs, NH), 11.79 (1H, bs, NH), 9.58 (1H, s, $CH_{arom}$), 8.02 (1H, s, $CH_{arom}$), 7.65 (1H, d, $CH_{arom}$), 7.49 (1H, d, $CH_{arom}$), 7.38 (1H, t, $CH_{arom}$), 7.32-7.19 (2H, m, 2×$CH_{arom}$), 6.98-6.90 (1H, m, $CH_{arom}$), 4.32 (2H, q, CH), 1.34 (3H, t, $CH_3$).

8-(3-Methanesulfonylaminophenyl)-4-oxo-4,5-dihydro-3H-pyrrolo[2,3-c]quinoline-1-ethyl carboxylate (235)

This compound is prepared according to synthesis 232, from 70 mg (0.15 mmol) of 8-(3-aminophenyl)-4-oxo-4,5-dihydro-3H-pyrrolo[2,3-c]quinoline-1-ethyl carboxylate trifluoroacetate and 14 µL (0.18 mmol) of methanesulfonyl chloride to give, after purification by chromatography on silica (eluent ethyl acetate/cyclohexane 7/3), 29 mg (45%) of 8-(3-methanesulfonylaminophenyl)-4-oxo-4,5-dihydro-3H-pyrrolo[2,3-c]quinoline-1-ethyl carboxylate in the form of a white solid.

LCMS (IE, m/z): (M+1) 425.95
$^1$H-NMR: $\delta_H$ ppm 400 MHz, DMSO
13.04 (1H, bs, NH), 11.77 (1H, bs, NH), 9.91 (1H, bs, NH), 9.61 (1H, s, $CH_{arom}$), 8.02 (1H, s, $CH_{arom}$), 7.67 (1H, dd, $CH_{arom}$), 7.55 (1H, d, $CH_{arom}$), 7.50 (1H, d, $CH_{arom}$), 7.49-7.41 (2H, m, 2×$CH_{arom}$), 7.22-7.17 (1H, m, $CH_{arom}$), 4.32 (2H, q, $CH_2$), 3.09 (3H, s, $CH_3$), 1.33 (3H, t, $CH_3$).

8-(3-Acetylaminophenyl)-4-oxo-4,5-dihydro-3H-pyrrolo[2,3-c]quinoline-1-ethyl carboxylate (236)

This compound is prepared according to synthesis 229, from 150 mg (0.36 mmol) of 8-bromo-4-oxo-4,5-dihydro-3H-pyrrolo[2,3-c]quinoline-1-ethyl carboxylate and 98 mg (0.55 mmol) of 3-acetylaminophenylboronic acid to give, after purification by chromatography on silica (eluent dichloromethane/methanol 98/2), 23 mg (16%) of 8-(3-acetylaminophenyl)-4-oxo-4,5-dihydro-3H-pyrrolo[2,3-c]quinoline-1-ethyl carboxylate in the form of a white solid.

LCMS (IE, m/z): (M+1) 389.96
$^1$H-NMR: $\delta_H$ ppm 400 MHz, DMSO
13.04 (1H, bs, NH), 11.77 (1H, bs, NH), 10.04 (1H, bs, NH), 9.56 (1H, s, $CH_{arom}$), 8.02 (1H, s, $CH_{arom}$), 7.88 (1H, s, $CH_{arom}$), 7.61 (2H, t, 2×$CH_{arom}$), 7.50 (1H, d, $CH_{arom}$), 7.42 (1H, t, $CH_{arom}$), 7.35 (1H, d, $CH_{arom}$), 4.32 (2H, q, $CH_2$), 2.08 (3H, s, $CH_3$), 1.33 (3H, t, $CH_3$).

8-(3-Hydroxy-phenyl)-4-oxo-4,5-dihydro-3H-pyrrolo[2,3-c]quinoline-1-ethyl carboxylate (237)

This compound is prepared according to synthesis 229, from 150 mg (0.36 mmol) of 8-bromo-4-oxo-4,5-dihydro-3H-pyrrolo[2,3-c]quinoline-1-ethyl carboxylate and 76 mg (0.55 mmol) of 3-hydroxyphenylboronic acid to give, after purification by chromatography on silica (eluent dichloromethane/methanol 95/5), 10 mg (8%) of 8-(3-hydroxyphenyl)-4-oxo-4,5-dihydro-3H-pyrrolo[2,3-c]quinoline-1-ethyl carboxylate in the form of a yellow solid.

LCMS (IE, m/z): (M+1) 348.88
$^1$H-NMR: $\delta_H$ ppm 400 MHz, DMSO
12.95 (1H, bs, NH), 11.75 (1H, bs, NH), 9.58 (1H, d, $CH_{arom}$), 9.53 (1H, s, OH), 8.01 (1H, s, $CH_{arom}$), 7.67 (1H, dd, $CH_{arom}$), 7.47 (1H, d, $CH_{arom}$), 7.28 (1H, 1, $CH_{arom}$), 7.16-7.09 (2H, m, 2×$CH_{arom}$), 6.78-6.74 (1H, m, $CH_{arom}$), 4.33 (2H, q, $CH_2$), 1.34 (3H, t, $CH_3$).

8-(3-Methanesulfonyl-phenyl)-4-oxo-4,5-dihydro-3H-pyrrolo[2,3-c]quinoline-1-ethyl carboxylate (238)

This compound is prepared according to synthesis 229, from 140 mg (0.36 mmol) of 8-iodo-4-oxo-4,5-dihydro-3H-pyrrolo[2,3-c]quinoline-1-ethyl carboxylate and 105 mg (0.55 mmol) of 3-methanesulfonylphenylboronic acid to give, after purification by chromatography on silica (eluent dichloromethane/methanol 95/5) then trituration in methanol, 30 mg (20%) of 8-(3-methanesulfonyl-phenyl)-4-oxo-4,5-dihydro-3H-pyrrolo[2,3-c]quinoline-1-ethyl carboxylate in the form of a beige solid.

LCMS (IE, m/z): (M+1) 410.97
$^1$H-NMR: $\delta_H$ ppm 400 MHz, DMSO
13.08 (1H, bs, NH), 11.83 (1H, bs, NH), 9.69 (1H, s, $CH_{arom}$), 8.22 (1H, s, $CH_{arom}$), 8.09-8.01 (2H, m, 2×$CH_{arom}$), 7.92 (1H, d, $CH_{arom}$), 7.87-7.77 (2H, m, 2×$CH_{arom}$), 7.54 (1H, d, $CH_{arom}$), 4.33 (2H, q, $CH_2$), 3.31 (3H, s, $CH_3$), 1.33 (3H, t, $CH_3$).

8-(3-Cyano-phenyl)-4-oxo-4,5-dihydro-3H-pyrrolo[2,3-c]quinoline-1-ethyl carboxylate (239)

This compound is prepared according to synthesis 229, from 200 mg (0.52 mmol) of 8-iodo-4-oxo-4,5-dihydro-3H-pyrrolo[2,3-c]quinoline-1-ethyl carboxylate and 115 mg (0.78 mmol) of 3-cyanophenylboronic acid to give, after purification by chromatography on silica (eluent dichloromethane/methanol 98/2), 19 mg (10%) of 8-(3-cyano-phenyl)-4-oxo-4,5-dihydro-3H-pyrrolo[2,3-c]quinoline-1-ethyl carboxylate in the form of a pale yellow solid.

LCMS (IE, m/z): (M+1) 358.29
$^1$H-NMR: $\delta_H$ ppm 400 MHz, DMSO
13.08 (1H, bs, NH), 11.82 (1H, bs, NH), 9.67 (1H, s, $CH_{arom}$), 8.14 (1H, s, $CH_{arom}$), 8.08-8.01 (2H, m, 2×$CH_{arom}$), 7.83 (2H, d, 2×$CH_{arom}$), 7.73 (1H, t, $CH_{arom}$), 7.51 (1H, d, $CH_{arom}$), 4.33 (2H, q, $CH_2$), 1.33 (3H, t, $CH_3$).

8-(3-Hydroxymethyl-phenyl)-4-oxo-4,5-dihydro-3H-pyrrolo[2,3-c]quinoline-1-ethyl carboxylate (240)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 158 mg (0.73 mmol) of 3-bromomethylphenylboronic acid to give, after purification by chromatography on silica (eluent dichloromethane/methanol 96/4), 29 mg (14%) of 8-(3-hydroxymethyl-phenyl)-4-oxo-4,5-dihydro-3H-pyrrolo[2,3-c]quinoline-1-ethyl carboxylate in the form of a pale yellow solid.

LCMS (IE, m/z): (M+1) 363.03
$^1$H-NMR: $\delta_H$ ppm 400 MHz, DMSO
13.04 (1H, bs, NH), 11.76 (1H, bs, NH), 9.61 (1H, d, $CH_{arom}$), 8.01 (1H, s, $CH_{arom}$), 7.72 (1H, dd, $CH_{arom}$), 7.67 (1H, s, $CH_{arom}$), 7.59 (1H, d, $CH_{arom}$), 7.49 (1H, d, $CH_{arom}$), 7.46 (1H, t, $CH_{arom}$), 7.31 (1H, d, $CH_{arom}$), 5.25 (1H, t, OH), 4.59 (2H, d, $CH_2$), 4.33 (2H, q, CH), 1.34 (3H, 1, $CH_3$).

8-(3-Methylaminomethyl-phenyl)-4-oxo-4,5-dihydro-3H-pyrrolo[2,3-c]quinoline-1-ethyl carboxylate (241)

68 mg (0.1 mmol) of dichlorobis(triphenylphosphine)-palladium (11), 117 mg (0.78 mmol) of 3-formylphenylboronic acid and 1 mL (2 mmol) of a 2M aqueous solution of tribasic potassium triphosphate are added to a degassed solution of 200 mg (0.52 mmol) of 8-iodo-4-oxo-4,5-dihydro-3H-pyrrolo[2,3-c]quinoline-1-ethyl carboxylate dissolved in 10 mL of anhydrous dioxan. The reaction mixture is stirred at 110° C. for 20 hours. Water is added and the product is extracted with ethyl acetate. The organic phases are washed with a saturated aqueous solution of sodium chloride, dried over magnesium sulfate, filtered and evaporated. The residue is purified by chromatography on silica (eluent dichloromethane/methanol 95/5) to give 107 mg of an 8/2 mixture of 8-(3-formyl-phenyl)-4-oxo-4,5-dihydro-3H-pyrrolo[2,3-c]quinoline-1-ethyl carboxylate and 4-oxo-4,5-dihydro-3H-pyrrolo[2,3-c]quinoline-1-ethyl carboxylate. The mixture is taken up in 0.3 mL of anhydrous methanol before adding 220 µL of a 33% ethanolic solution of methylamine and 300 µL (1 mmol) of titanium isopropoxide. The solution is stirred for 5 hours at room temperature then 133 mg (3.5 mmol) of sodium borohydride is added. Stirring is continued for a further 24 hours then 2 mL of water is added. The reaction mixture is filtered then the solvents are evaporated. The residue is purified by chromatography on silica (eluent dichloromethane/methanol 9/1 then chloroform/methanol/ammonia 200/16/3) to give 10 mg (35%) of 8-(3-methylaminomethyl-phenyl)-4-oxo-4,5-dihydro-3H-pyrrolo[2,3-c]quinoline-1-ethyl carboxylate in the form of a white solid.

LCMS (IE, m/z): (M+1) 376.15

$^1$H-NMR: $\delta_H$ ppm 400 MHz, DMSO 11.75 (1H, bs, NH), 9.61 (1H, d, $CH_{arom}$), 8.01 (1H, s, $CH_{arom}$), 7.73 (1H, dd, $CH_{arom}$), 7.66 (1H, s, $CH_{arom}$), 7.58 (1H, d, $CH_{arom}$), 7.49 (1H, d, $CH_{arom}$), 7.44 (1H, t, $CH_{arom}$), 7.30 (OH, d, $CH_{arom}$), 4.33 (2H, q, $CH_2$), 3.72 (2H, s, $CH_2$), 2.31 (3H, s, $CH_3$), 1.34 (3H, t, $CH_3$).

8-(3-Dimethylaminomethyl-phenyl)-4-oxo-4,5-dihydro-3H-pyrrolo[2,3-c]quinoline-1-ethyl carboxylate (242)

In a sealed tube, 30 mg (0.14 mmol) of 3-bromomethylphenylboronic acid is dissolved in 100 µL of a 40% aqueous solution of dimethylamine and the solution is heated at 100° C. for 4 hours. The solvents are evaporated and the residue is taken up in 1.5 mL of anhydrous dioxan. The solution is degassed before adding 38 mg (0.14 mmol) of 8-bromo-4-oxo-4,5-dihydro-3H-pyrrolo[2,3-c]quinoline-1-ethyl carboxylate, 13 mg (0.028 mmol) of dichlorobis(triphenylphosphine)-palladium (11) and 200 µL (0.4 mmol) of a 2M aqueous solution of tribasic potassium triphosphate. The reaction mixture is stirred at II 0° C. for 20 hours. Water is added and the product is extracted with ethyl acetate. The organic phases are washed with a saturated aqueous solution of sodium chloride, dried over magnesium sulfate, filtered and evaporated. The residue is purified by chromatography on silica (eluent chloroform/methanol/ammonia 90/25/4) to give 5 mg (10%) of 8-(3-dimethylaminomethyl-phenyl)-4-oxo-4,5-dihydro-3H-pyrrolo[2,3-c]quinoline-1-ethyl carboxylate in the form of a beige solid.

LCMS (IE, t/z): (M+1) 390.16

$^1$H-NMR: $\delta_H$ ppm 400 MHz, DMSO 13.04 (1H, bs, NH), 11.76 (1H, bs, NH), 9.62 (1H, d, $CH_{arom}$), 8.02 (1H, s, $CH_{arom}$), 773 (1H, dd, $CH_{arom}$), 7.67 (1H, s, $CH_{arom}$), 7.64 (1H, d, $CH_{arom}$), 7.49 (2H, d, $2\times CH_{arom}$), 7.32 (1H, d, $CH_{arom}$), 4.33 (2H, q, $CH_2$), 3.65 (2H, s, CH), 2.31 (6H, s, $2\times CH_3$), 1.34 (3H, t, $CH_3$).

8-(4-tert-Butoxycarbonylaminophenyl)-4-oxo-4,5-dihydro-3H-pyrrolo[2,3-c]quinoline-1-ethyl carboxylate (243)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 174 mg (0.74 mmol) of 4-tert-butoxyaminophenylboronic acid to give, after purification by chromatography on silica (eluent dichloromethane/methanol 95/5), 131 mg (59%) of 8-(4-tert-butoxycarbonylaminophenyl)-4-oxo-4,5-dihydro-3H-pyrrolo[2,3-c]quinoline-1-ethyl carboxylate in the form of a slightly yellow solid.

LCMS (IE, m/z): (M+1) 447.92

$^1$H-NMR: $\delta_H$ ppm 400 MHz, DMSO 13.01 (1H, bs, NH), 11.71 (1H, bs, NH), 9.58 (1H, d, $CH_{arom}$), 9.43 (1H, bs, NH), 8.00 (1H, s, $CH_{arom}$), 7.69 (1H, dd, $CH_{arom}$), 7.62 (2H, d, $2\times CH_{arom}$), 7.57 (2H, d, $2\times CH_{arom}$), 7.46 (1H, d, $CH_{arom}$), 4.33 (2H, q, $CH_2$), 1.50 (9H, s, $3\times CH_3$), 1.34 (3H, t, $CH_3$).

8-(4-Aminophenyl)-4-oxo-4,5-dihydro-3H-pyrrolo[2,3-c]quinoline-1-ethyl carboxylate (244)

This compound is prepared according to synthesis 051816, from 110 mg (0.24 mmol) of 8-(4-tert-butoxycarbonylaminophenyl)-4-oxo-4,5-dihydro-3H-pyrrolo[2,3-c]quinoline-1-ethyl carboxylate to give, after trituration in diethyl ether, 35 mg (41%) of 8-(4-aminophenyl)-4-oxo-4,5-dihydro-3H-pyrrolo[2,3-c]quinoline-1-ethyl carboxylate in the form of a beige solid.

LCMS (IE, m/z): (M+1) 348.01

$^1$H-NMR: $\delta_H$ ppm 400 MHz, DMSO 12.97 (1H, bs, NH), 11.64 (1H, bs, NH), 9.47 (1H, s, $CH_{arom}$), 7.99 (1H, s, $CH_{arom}$), 7.61 (1H, d, $CH_{arom}$), 7.46-7.357 (3H, m, $3\times CH_{arom}$), 6.67 (2H, d, $2\times CH_{arom}$), 5.19 (2H, s, $NH_2$), 4.33 (2H, q, $CH_2$), 1.34 (3H, t, $CH_3$).

8-(4-Methanesulfonyl-phenyl)-4-oxo-4,5-dihydro-3H-pyrrolo[2,3-c]quinoline-1-ethyl carboxylate (245)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 110 mg (0.55 mmol) of 4-methanesulfonylphenylboronic acid to give, after purification by chromatography on silica (eluent dichloromethane/methanol 95/5), 49 mg (32%) of 8-(4-methanesulfonyl-phenyl)-4-oxo-4,5-dihydro-3H-pyrrolo[2,3-c]quinoline-1-ethyl carboxylate in the form of a white solid.

LCMS (IE, m/z): (M+1) 410.86

$^1$H-NMR: $\delta_H$ ppm 400 MHz, DMSO 13.09 (1H, bs, NH), 11.84 (1H, bs, NH), 9.73 (1H, d, $CH_{arom}$), 8.05 (2H, d, $2\times CH_{arom}$), 8.04 (1H, s, $CH_{arom}$), 7.97 (2H, d, $2\times CH_{arom}$), 7.83 (1H, dd, $CH_{arom}$), 7.54 (1H, d, $CH_{arom}$), 4.33 (2H, q, $CH_2$), 3.27 (3H, s, $CH_3$), 1.34 (3H, t, $CH_3$).

8-(4-Methoxy-phenyl)-4-oxo-4,5-dihydro-3H-pyrrolo[2,3-c]quinoline-1-ethyl carboxylate (246)

This compound is prepared according to synthesis 229, from 200 mg (0.49 mmol) of 8-iodo-4-oxo-4,5-dihydro-3H-pyrrolo[2,3-c]quinoline-1-ethyl carboxylate and 119 mg (0.78 mmol) of 4-methoxyphenylboronic acid to give, after purification by chromatography on silica (eluent dichloromethane/methanol 97/3), 51 mg (27%) of 8-(4-methoxyphenyl)-4-oxo-4,5-dihydro-3,1-pyrrolo[2,3-c]quinoline-1-ethyl carboxylate in the form of a white solid.

LCMS (IE, m/z): (M+1) 363.21

$^1$H-NMR: $\delta_H$ ppm 400 MHz, DMSO 13.01 (1H, bs, NH), 11.71 (1H, bs, NH), 9.58 (1H, d, $CH_{arom}$), 8.01 (1H, s, $CH_{arom}$), 769 (1H, dd, $CH_{arom}$), 7.66 (2H, d, $2\times CH_{arom}$), 7.46 (1H, d, CH . . . ), 7.08 (2H, d, $2\times CH_{arom}$), 4.32 (2H, q, $CH_2$), 3.81 (3H, s, $CH_3$), 1.34 (3H, t, $CH_3$).

8-(4-Cyano-phenyl)-4-oxo-4,5-dihydro-3H-pyrrolo[2,3-c]quinoline-1-ethyl carboxylate (247)

This compound is prepared according to synthesis 229, from 200 mg (0.49 mmol) of 8-iodo-4-oxo-4,5-dihydro-3H- pyrrolo[2,3-c]quinoline-1-ethyl carboxylate and 115 mg (0.78 mmol) of 4-cyanophenylboronic acid to give, after purification by chromatography on silica (eluent dichloromethane/methanol 98/2) then recrystallization from methanol, 11 mg (6%) of 8-(4-cyano-phenyl)-4-oxo-4,5-dihydro-3H-pyrrolo[2,3-c]quinoline-1-ethyl carboxylate in the form of a pale yellow solid.

LCMS (IE, m/z): (M+1) 358.17

$^1$H-NMR: $\delta_H$ ppm 400 MHz, DMSO 13.09 (1H, bs, NH), 11.85 (1H, bs, NH), 9.75 (1H, d, $CH_{arom}$), 8.04 (1H s, $CH_{arom}$), 7.98 (2H, d, 2×$CH_{arom}$), 7.93 (2H, d, 2×$CH_{arom}$), 7.85 (1H, dd, $CH_{arom}$), 7.53 (1H, d, $CH_{arom}$), 4.33 (2H, q, $CH_2$), 1.34 (3H, t, $CH_3$).

8-(2,3-Dihydro-benzo[1,4]dioxin-6-yl)-4-oxo-4,5-dihydro-3H-pyrrolo[2,3-c]quinoline-1-ethyl carboxylate (248)

This compound is prepared according to synthesis 229, from 200 mg (0.52 mmol) of 8-iodo-4-oxo-4,5-dihydro-3H-pyrrolo[2,3-c]quinoline-1-ethyl carboxylate and 141 mg (0.78 mmol) of 2,3-dihydro-benzo[1,4]dioxin-6-ylboronic acid to give, after purification by chromatography on silica (eluent dichloromethane/methanol 98/2) then recrystallization from methanol, 70 mg (34%) of 8-(2,3-dihydro-benzo[1,4]dioxin-6-yl)-4-oxo-4,5-dihydro-3H-pyrrolo[2,3-c]quinoline-1-ethyl carboxylate in the form of a beige solid.

LCMS (IE, m/z): (M+1) 391.22

$^1$H-NMR: $\delta_H$ ppm 400 MHz, DMSO 13.01 (1H, bs, NH), 11.71 (1H, bs, NH), 9.56 (1H, d, $CH_{arom}$), 8.00 (1H s, $CH_{arom}$), 7.64 (1H, dd, $CH_{arom}$), 7.44 (1H, d, $CH_{arom}$), 7.22-7.18 (2H, m, 2×$CH_{arom}$), 6.98 (1H, d, $CH_{arom}$), 4.33 (2H, q, CH), 4.29 (4H, s, 2×$CH_2$), 1.34 (3H, t, $CH_3$).

8-Naphthalen-1-yl-4-oxo-4,5-dihydro-3H-pyrrolo[2,3-c]quinoline-1-ethyl carboxylate (249)

68 mg (0.1 mmol) of dichlorobis(triphenylphosphine)-palladium (11), 149 mg (0.59 mmol) of bis(pinacolo)diborane and 273 µL (1.96 mmol) of triethylamine are added to a degassed solution of 200 mg (0.49 mmol) of 8-bromo-4-oxo-4,5-dihydro-3H-pyrrolo[2,3-c]quinoline-1-ethyl carboxylate dissolved in 4 mL of anhydrous dioxan. The reaction mixture is stirred at 110° C. for 4 days. Water is added and the product is extracted with ethyl acetate. The organic phases are washed with a saturated aqueous solution of sodium chloride, dried over magnesium sulfate, filtered and evaporated. The residue is taken up in 5 mL of anhydrous dioxan. The solution is degassed with a stream of nitrogen before adding 81 µL (0.59 mmol) of 1-bromonaphthalene, 69 mg (0.1 mmol) of dichlorobis(triphenylphosphine)-palladium (II) and 1 mL (2 mmol) of a 2M aqueous solution of tribasic potassium triphosphate. The reaction mixture is stirred at 110° C. for 20 hours. Water is added and the product is extracted with ethyl acetate. The organic phases are washed with a saturated aqueous solution of sodium chloride, dried over magnesium sulfate, filtered and evaporated. The residue is purified by chromatography on silica (eluent dichloromethane/methanol 98/2) to give 27 mg (3% in two stages) of 8-naphthalen-1-yl-4-oxo-4,5-dihydro-3H-pyrrolo[2,3-c]quinoline-1-ethyl carboxylate in the form of a beige solid.

LCMS (IE, m/z): (M+1) 383.18

$^1$H-NMR: $\delta_H$ ppm 400 MHz, $CD_3OD$ 9.57 (1H, s, $CH_{arom}$), 8.07 (1H, s, $CH_{arom}$), 7.96 (2H, d, 2×$CH_{arom}$), 7.92 (1H, d, $CH_{arom}$), 7.60-7.43 (6H, m, 6×$CH_{arom}$), 4.26 (2H, q, $CH_2$), 1.28 (3H, t, $CH_3$).

4-Oxo-8-quinolin-8-yl-4,5-dihydro-3H-pyrrolo[2,3-c]quinoline-1-ethyl carboxylate (250)

This compound is prepared according to synthesis 229, from 180 mg (0.47 mmol) of 8-iodo-4-oxo-4,5-dihydro-3H-pyrrolo[2,3-c]quinoline-1-ethyl carboxylate and 244 mg (1.41 mmol) of 8-quinolinylboronic acid to give, after purification by chromatography on silica (eluent dichloromethane/methanol 98/2) then trituration in a mixture of dichloromethane, ethyl acetate and methanol 1/1/1, 2 mg (3%) of 4-oxo-8-quinolin-8-yl-4,5-dihydro-3H-pyrrolo[2,3-c]quinoline-1-ethyl carboxylate in the form of a white solid.

LCMS (IE, m/z): (M+1) 384.27

$^1$H-NMR: $\delta_H$ ppm 400 MHz, DMSO 13.00 (1H, bs, NH), 11.76 (1H, s, NH), 9.42 (1H, d, $CH_{arom}$), 8.90-8.88 (1H, m, $CH_{arom}$), 8.45 (1H, dd, $CH_{arom}$), 8.02 (1H, dd, $CH_{arom}$), 7.99 (1H, s, $CH_{arom}$), 7.82 (1H, dd, $CH_{arom}$), 7.75-7.70 (2H, m, 2×$CH_{arom}$), 7.58 (1H, d, $CH_{arom}$), 7.50 (1H, d, $CH_{arom}$), 4.20 (2H, q, $CH_2$), 1.22 (3H, t, $CH_3$).

8-(2-Amino-5-methanesulfonyl-phenyl)-4-oxo-4,5-dihydro-3H-pyrrolo[2,3-c]quinoline-1-ethyl carboxylate (251)

This compound is prepared according to synthesis 249, from 200 mg (0.49 mmol) of 8-bromo-4-oxo-4,5-dihydro-3H-pyrrolo[2,3-c]quinoline-1-ethyl carboxylate, 149 mg (0.59 mmol) of bis(pinacolo)diborane and 175 mg (0.59 mmol) of 2-iodo-4-methanesulfonyl-phenylamine (prepared according to the method described by Lachance Nicolas, Chan Wing Yan, *J. Heterocycl. Chem.*, 2003, 10(2), 289-96) to give, after purification by chromatography on silica (eluent dichloromethane/methanol 98/2 then 96/4), 26 mg (12%) of 8-(2-amino-5-methanesulfonyl-phenyl)-4-oxo-4,5-dihydro-3H-pyrrolo[2,3-c]quinoline-1-ethyl carboxylate in the form of a beige solid.

LCMS (IE, m/z): (M+1) 426.05

$^1$H-NMR: $\delta_H$ ppm 400 MHz, DMSO 13.02 (1H, bs, NH), 11.79 (1H, bs, NH), 9.31 (1H, d, $CH_{arom}$), 8.00 (1H, s, $CH_{arom}$), 7.56 (1H, dd, $CH_{arom}$), 7.51 (1H, d, $CH_{arom}$), 7.47 (1H, d, $CH_{arom}$), 7.44 (1H, dd, $CH_{arom}$), 6.88 (1H, d, $CH_{arom}$), 5.81 (2H, bs, $NH_2$), 4.26 (2H, q, $CH_2$), 1.29 (3H, t, $CH_3$).

8-(1H-Indol-5-yl)-4-oxo-4,5-dihydro-3H-pyrrolo[2,3-c]quinoline-1-ethyl carboxylate (252)

1 mL of trifluoroacetic acid is added to a solution of 70 mg (0.15 mmol) 8-(1-tert-butoxycarbonyl-1H-indol-5-yl)-4-oxo-4,5-dihydro-3H-pyrrolo[2,3-c]quinoline-1-ethyl carboxylate dissolved in 4 mL of dichloroethane. The solution is stirred for 2 hours at room temperature then the precipitate that forms is filtered and washed with diethyl ether to give 26 mg (45%) of 8-(1H-indol-5-yl)-4-oxo-4,5-dihydro-3H-pyrrolo[2,3-c]quinoline-1-ethyl carboxylate in the form of a brown solid.

LCMS (IE, m/z): (M+1) 372.2

$^1$H-NMR: $\delta_H$ ppm 400 MHz, DMSO 13.02 (1H, bs, NH), 11.73 (1H, s, NH), 11.16 (1H, s, NH), 9.61 (1H, s, $CH_{arom}$), 8.01 (1H, d, $CH_{arom}$), 7.86 (1H, s, $CH_{arom}$), 7.74 (1H, dd, $CH_{arom}$), 7.55-7.40 (3H, m, 3×$CH_{arom}$), 7.38 (1H, d, $CH_{arom}$), 6.50 (1H, s, $CH_{arom}$), 4.32 (2H, q, $CH_2$), 1.33 (3H, t, $CH_3$).

8-(1-tert-Butoxycarbonyl-1H-indol-5-yl)-4-oxo-4,5-dihydro-3H-pyrrolo[2,3-c]quinoline-1-ethyl carboxylate (253)

This compound is prepared according to synthesis 229, from 191 mg (0.5 mmol) of 8-iodo-4-oxo-4,5-dihydro-3H- pyrrolo[2,3-c]quinoline-1-ethyl carboxylate and 343 mg (1 mmol) of 1-tert-butoxycarbonyl-5-(4,4,5,5-tetramethyl-[1,3,2]dioxaborolan-2-yl)-indole to give, after purification by chromatography on silica (eluent ethyl acetate/methanol 95/5), 97 mg (41%) of 8-(1-tert-butoxycarbonyl-1H-indol-5-yl)-4-oxo-4,5-dihydro-3H-pyrrolo[2,3-c]quinoline-1-ethyl carboxylate in the form of a slightly pale yellow solid.

LCMS (IE, m/z): (M+1) 472.3

$^1$H-NMR: $\delta_H$ ppm 400 MHz, DMSO 13.07 (1H, bs, NH), 11.79 (1H, s, NH), 9.65 (1H, s, $CH_{arom}$), 8.14 (1H, d, $CH_{arom}$), 8.03 (1H, s, $CH_{arom}$), 7.93 (1H, s, $CH_{arom}$), 7.76-7.48 (4H, m, 4×$CH_{arom}$), 6.80 (1H, d, $CH_{arom}$), 4.32 (2H, q, $CH_2$), 1.66 (9H, s, 3×$CH_3$), 1.33 (3H, t, $CH_3$).

8-(3-Methanesulfonyl-phenyl)-4-oxo-4,5-dihydro-3H-pyrrolo[2,3-c]quinoline-1-propyl carboxylate (254)

This compound is prepared according to synthesis 229, from 147 mg (0.37 mmol) of 8-iodo-4-oxo-4,5-dihydro-3H-pyrrolo[2,3-c]quinoline-1-propyl carboxylate and 148 mg (0.74 mmol) of 3-methanesulfonylphenylboronic acid to give, after purification by chromatography on silica (eluent dichloromethane/methanol 96/4) then trituration in methanol, 70 mg (45%) of 8-(3-methanesulfonyl-phenyl)-4-oxo-4,5-dihydro-3H-pyrrolo[2,3-c]quinoline-1-propyl carboxylate in the form of a slightly yellow solid.

LCMS (IE, m/z): (M+1) 425.15

$^1$H-NMR: $\delta_H$ ppm 400 MHz, DMSO 13.10 (1H, bs, NH), 11.83 (1H, bs, NH), 9.69 (1H, s, $CH_{arom}$), 8.21 (1H, s, $CH_{arom}$), 807-8.03 (2H, m, 2×$CH_{arom}$), 7.94-7.91 (1H, m, $CH_{arom}$), 7.86-7.79 (2H, m, 2×$CH_{arom}$), 7.54 (1H, d, $CH_{arom}$), 4.26 (2H, t, $OCH_2$), 3.31 (3H, s, $CH_3$), 1.78-1.72 (2H, m, $CH_2$), 0.98 (3H, t, $CH_3$).

8-(3-Methanesulfonyl-phenyl)-4-oxo-4,5-dihydro-3H-pyrrolo[2,3-c]quinoline-1-isobutyl carboxylate (255)

This compound is prepared according to synthesis 229, from 152 mg (0.37 mmol) of 8-iodo-4-oxo-4,5-dihydro-3H-pyrrolo[2,3-c]quinoline-1-isobutyl carboxylate and 148 mg (0.74 mmol) of 3-methanesulfonylphenylboronic acid to give, after purification by chromatography on silica (eluent dichloromethane/methanol 96/4) then trituration in methanol, 45 mg (28%) of 8-(3-methanesulfonyl-phenyl)-4-oxo-4,5-dihydro-3H-pyrrolo[2,3-c]quinoline-1-isobutyl carboxylate in the form of a slightly yellow solid.

LCMS (IE, m/z): (M+1) 439.18

$^1$H-NMR: $\delta_H$ ppm 400 MHz, DMSO 13.12 (1H, bs, NH), 11.83 (1H, bs, NH), 9.70 (1H, s, $CH_{arom}$), 8.22 (1H, s, $CH_{arom}$), 8.05-8.03 (2H, m, 2×$CH_{arom}$), 7.93-7.91 (1H, m, $CH_{arom}$), 7.86-7.80 (2H, m, 2×$CH_{arom}$), 7.55 (1H, d, $CH_{arom}$), 4.09 (2H, t, $OCH_2$), 3.31 (3H, s, $CH_3$), 2.12-2.00 (1H, m, CH), 0.98 (6H, d, 2×$CH_3$).

8-(3-Methanesulfonyl-phenyl)-4-oxo-4,5-dihydro-3H-pyrrolo[2,3-c]quinoline-1-cyclopentyl carboxylate (256)

This compound is prepared according to synthesis 229, from 224 mg (0.53 mmol) of 8-iodo-4-oxo-4,5-dihydro-3H-pyrrolo[2,3-c]quinoline-1-cyclopentyl carboxylate and 212 mg (1.06 mmol) of 3-methanesulfonylphenylboronic acid to give, after purification by chromatography on silica (eluent dichloromethane/methanol 96/4) then trituration in methanol, 95 mg (40%) of 8-(3-methanesulfonyl-phenyl)-4-oxo-4,5-dihydro-3H-pyrrolo[2,3-c]quinoline-1-cyclopentyl carboxylate in the form of a slightly yellow solid.

LCMS (IE, m/z): (M+1) 451.17

$^1$H-NMR: $\delta_H$ ppm 400 MHz, DMSO 13.06 (1H, bs, NH), 11.80 (1H, bs, NH), 9.68 (1H, s, $CH_{arom}$), 8.20 (1H, s, $CH_{arom}$), 8.05-783 (3H, m, 3×$CH_{arom}$), 7.82-7.78 (2H, m, 2×$CH_{arom}$), 7.53 (1H, d, $CH_{arom}$), 5.35 (1H, bs, OCH), 3.31 (3H, s, $CH_3$), 1.92-1.59 (8H, m, 9×$CH_{pyrrol}$ and $CH_3$).

7-Chloro-8-(3-methanesulfonyl-phenyl)-4-oxo-4,5-dihydro-3H-pyrrolo[2,3-c]quinoline-1-ethyl carboxylate (257)

This compound is prepared according to synthesis 229, from 196 mg (0.47 mmol) of 7-chloro-8-iodo-4-oxo-4,5-dihydro-3H-pyrrolo[2,3-c]quinoline-1-ethyl carboxylate to give, after purification by chromatography on silica (eluent dichloromethane/methanol 96/4) then trituration in methanol, 60 mg (29%) of 7-chloro-8-(3-methanesulfonyl-phenyl)-4-oxo-4,5-dihydro-3H-pyrrolo[2,3-c]quinoline-1-ethyl carboxylate in the form of a beige solid.

LCMS (IE, m/z): (M+1) 445.07-447.05

$^1$H-NMR: $\delta_H$ ppm 400 MHz, DMSO 13.16 (1H, bs, NH), 11.89 (1H, s, NH), 9.40 (1H, s, $CH_{arom}$), 8.05-7.98 (3H, m, 3×$CH_{arom}$), 7.88-7.78 (2H, m, 2×$CH_{arom}$), 7.61 (1H, s, $CH_{arom}$), 4.24 (2H, q, CH), 3.29 (3H, s, $CH_3$), 1.26 (311, t, $CH_3$).

4-Oxo-8-pyridin-3-yl-4,5-dihydro-3H-pyrrolo[2,3-c]quinoline-1-ethyl carboxylate (258)

63 mg (0.001 mmol) of dichlorobis(triphenylphosphine)-palladium (II), 197 mg (1.34 mmol) of 3-diethylboranyl-pyridine and 7 mL of a saturated aqueous solution of sodium hydrogencarbonate are added to a degassed solution of 300 mg (0.73 mmol) of 8-bromo-4-oxo-4,5-dihydro-3H-pyrrolo[2,3-c]quinoline-1-ethyl carboxylate dissolved in 15 mL of anhydrous dioxan. The reaction mixture is stirred at 110° C. for 20 hours. The solid that forms is filtered to give 210 mg of a mixture of 4-oxo-8-pyridin-3-yl-4,5-dihydro-3H-pyrrolo[2,3-c]quinoline-1-ethyl carboxylate and 4-oxo-8-pyridin-3-yl-4,5-dihydro-3H-pyrrolo[2,3-c]quinoline-1-carboxylic acid. This mixture is esterified according to general method of esterification A (using ethanol as the alcohol) to give, after purification by chromatography on silica (eluent dichloromethane/methanol 85/15 then chloroform/methanol/ammonia 65/25/4), 37 mg (15%) of 4-oxo-8-pyridin-3-yl-4,5-dihydro-3H-pyrrolo[2,3-c]quinoline-1-ethyl carboxylate in the form of a beige solid.

LCMS (IE, m/z): (M+1) 334.10

$^1$H-NMR: $\delta_H$ ppm 400 MHz, DMSO 13.10 (1H, bs, NH), 11.84 (1H, bs, NH), 9.70 (1H, s, $CH_{arom}$), 8.97 (1H, s, $CH_{arom}$), 8.58 (1H, s, $CH_{arom}$), 8.11 (1H, d, $CH_{arom}$), 8.04 (1H, d, $CH_{arom}$), 7.82 (III, d, $CH_{arom}$), 7.59-7.50 (2H, m, 2×$CH_{arom}$), 4.33 (2H, q, $CH_2$), 1.33 (3H, t, $CH_3$).

8-(6-Chloro-pyridin-3-yl)-4-oxo-4,5-dihydro-3H-pyrrolo[2,3-c]quinoline-1-ethyl carboxylate (259)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 117 mg (0.49 mmol) of 2-chloro-5-(4,4,5,5-tetramethyl-[1,3,2]dioxaborolan-2-yl)-pyridine to give, after purification by chromatography on silica (eluent ethyl acetate) then trituration in acetonitrile, 14 mg (8%) of 8-(6-chloro-pyridin-3-yl)-4-oxo-4,5-dihydro-3H-pyrrolo[2,3-c]quinoline-1-ethyl carboxylate in the form of a white solid.

LCMS (IE, m/z): (M+1) 368.00-369.96
$^1$H-NMR: 9H ppm 400 MHz, DMSO
13.09 (1H, bs, NH), 11.83 (1H, bs, NH), 9.68 (1H, d, $CH_{arom}$), 8.77 (1H, d, $CH_{arom}$), 8.17 (1H, dd, $CH_{arom}$), 8.03 (1H, s, $CH_{arom}$), 7.82 (1H, dd, $CH_{arom}$), 7.67 (1H, d, $CH_{arom}$), 7.53 (1H, d, $CH_{arom}$), 4.33 (2H, q, $CH_2$), 1.34 (3H, t, $CH_3$).

8-(6-Methoxy-pyridin-3-yl)-4-oxo-4,5-dihydro-3H-pyrrolo[2,3-c]quinoline-1-ethyl carboxylate (260)

This compound is prepared according to synthesis 229, from 200 mg (0.49 mmol) of 8-bromo-4-oxo-4,5-dihydro-3H-pyrrolo[2,3-c]quinoline-1-ethyl carboxylate and 112 mg (0.73 mmol) of 6-methoxy-pyridin-3-ylboronic acid to give, after purification by chromatography on silica (eluent dichloromethane/methanol 95/5 then 90/10), 86 mg (48%) of 8-(6-methoxy-pyridin-3-yl)-4-oxo-4,5-dihydro-3H-pyrrolo[2,3-c]quinoline-1-ethyl carboxylate in the form of a white solid.

LCMS (IE, t/z): (M+1) 363.96
$^1$H-NMR: $\delta_H$ ppm 400 MHz, DMSO
13.04 (1H, bs, NH), 11.75 (1H, bs, NH), 9.61 (1H, d, $CH_{arom}$), 8.53 (1H, d, $CH_{arom}$), 8.04 (1H, dd, $CH_{arom}$), 8.02 (1H, s, $CH_{arom}$), 7.73 (1H, dd, $CH_{arom}$), 7.49 (1H, d, $CH_{arom}$), 6.97 (1H, d, $CH_{arom}$), 4.33 (2H, q, $CH_2$), 3.91 (3H, s, $CH_3$), 1.34 (3H, t, $CH_3$).

8-(2-Amino-pyrimidin-4-yl)-4-oxo-4,5-dihydro-3H-pyrrolo[2,3-c]quinoline-1-ethyl carboxylate (261)

83 mg (0.87 mmol) of guanidine hydrochloride is added to a suspension of 204 mg (0.58 mmol) of 8-(3-dimethylamino-acryloyl)-4-oxo-4,5-dihydro-3H-pyrrolo[2,3-c]quinoline-1-ethyl carboxylate in 2.3 mL of anhydrous dimethylacetamide. The mixture is stirred at 130° C. for 4 days then the solvent is evaporated. The residue is triturated with methanol to give a solid which is collected by filtration then washed with methanol and then diisopropyl ether. After drying, 114 mg (56%) of 8-(2-amino-pyrimidin-4-yl)-4-oxo-4,5-dihydro-3H-pyrrolo[2,3-c]quinoline-1-ethyl carboxylate is obtained in the form of a brown solid.

LCMS (IE, m/z): (M+1) 350.23
$^1$H-NMR: $\delta_H$ ppm 400 MHz, DMSO
11.64 (1H, s, NH), 9.96 (1H, s, $CH_{arom}$), 8.32 (1H, d, $CH_{arom}$), 8.11 (1H, dd, $CH_{arom}$), 7.98 (1H, s, $CH_{arom}$), 7.45 (1H, d, $CH_{arom}$), 7.09 (1H, d, $CH_{arom}$), 6.58 (2H, bs, $NH_2$), 4.33 (2H, q $CH_2$), 1.34 (3H, t, $CH_3$).

8-(2-Dimethylamino-pyrimidin-4-yl)-4-oxo-4,5-dihydro-3H-pyrrolo[2,3-c]quinoline-1-ethyl carboxylate (262)

80.5 mg (0.44 mmol) of N,N-dimethylguanidine sulfate is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 5 days then the solvent is evaporated. The product is purified by preparative LCMS to give, after drying, 10 mg (9%) of 8-(2-dimethylamino-pyrimidin-4-yl)-4-oxo-4,5-dihydro-3H-pyrrolo[2,3-c]quinoline-1-ethyl carboxylate in the form of a brown solid.

LCMS (IE, m/z): (M+1) 378.15
$^1$H-NMR: $\delta_H$ ppm 400 MHz, DMSO
13.06 (1H, s, NH), 11.86 (1H, s, NH), 10.16 (1H, s, $CH_{arom}$), 8.43 (1H, d, $CH_{arom}$), 8.21 (1H, d, $CH_{arom}$), 8.02 (1H, s, $CH_{arom}$), 7.50 (1H, d, $CH_{arom}$), 7.13 (1H, d, $CH_{arom}$), 4.33 (2H, q, $CH_2$), 3.25 (6H, s, 2×$CH_3$), 1.34 (3H, t, $CH_3$).

8-(2-Methylamino-pyrimidin-4-yl)-4-oxo-4,5-dihydro-3H-pyrrolo[2,3-c]quinoline-1-ethyl carboxylate formate (263)

48 mg (0.44 mmol) of N-methylguanidine hydrochloride is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 4 days then the solvent is evaporated. The product is purified by preparative L-CMS to give, after drying, 31 mg (26%) of 8-(2-methylamino-pyrimidin-4-yl)-4-oxo-4,5-dihydro-3H-pyrrolo[2,3-c]quinoline-1-ethyl carboxylate in the form of a brown solid, mono salt of formic acid.

LCMS (IE, m/z): (M+1) 364.1
$^1$H-NMR: $\delta_H$ ppm 400 MHz, DMSO
13.07 (1H, s, NH), 11.88 (1H, s, NH), 10.06 (1H, s, $CH_{arom}$), 8.38 (1H, bs, $CH_{arom}$), 8.20 (1H, dl, $CH_{arom}$), 8.16 (1H, s, $HCO_2H$), 8.03 (1H, s, $CH_{arom}$), 7.50 (1H, d, $CH_{arom}$), 7.11 (1H, d, $CH_{arom}$), 7.04 (1H, q, NH), 4.34 (2H, qb, $CH_2$), 2.94 (3H, bs, $CH_3$), 1.35 (3H, t, $CH_3$).

8-(2-Ethylamino-pyrimidin-4-yl)-4-oxo-4,5-dihydro-3H-pyrrolo[2,3-c]quinoline-1-ethyl carboxylate (264)

60 mg (0.44 mmol) of N-ethylguanidine hemi-sulfate is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 5 days then 121 μL (0.44 mmol) of a 21% solution of sodium ethylate in ethanol is added to speed up the reaction. It is left overnight at 130° C., then the solvent is evaporated. The product is purified by preparative LCMS to give, after drying, 15 mg (13%) of 8-(2-ethylamino-pyrimidin-4-yl)-4-oxo-4,5-dihydro-3H-pyrrolo[2,3-c]quinoline-1-ethyl carboxylate in the form of a brown solid.

LCMS (IE, m/z): (M+1) 378.38
$^1$H-NMR: $\delta_H$ ppm 400 MHz, DMSO
13.05 (1H, s, NH), 11.88 (1H, s, NH), 10.07 (1H, s, $CH_{arom}$), 8.37 (1H, bs, $CH_{arom}$), 8.18 (1H, d, $CH_{arom}$), 8.03 (1H, s, $CH_{arom}$), 7.50 (1H, d, $CH_{arom}$), 7.14-7.09 (2H, m, NH and $CH_{arom}$), 4.35 (2H, qb, $CH_2$), 3.45 (2H, m, CH), 1.36 (3H, t, $CH_3$), 1.19 (3H, 1, $CH_3$).

4-Oxo-8-[2-(4-pyridin-2-yl-piperazin-1-yl)-pyrimidin-4-yl]-4,5-dihydro-3H-pyrrolo[2,3-c]quinoline-1-ethyl carboxylate (265)

145 mg (0.44 mmol) of 4-pyridin-2-ylpiperazine-1-carboximidamide hydroiodide is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 4 days, then the solvent is evaporated. The product is purified by preparative LCMS to give, after drying, 25 mg (17%) of 4-oxo-8-[2-(4-pyridin-2-yl-piperazin-1-yl)-pyrimidin-4-yl]-4,5-dihydro-3H-pyrrolo[2,3-c]quinoline-1-ethyl carboxylate in the form of a brown solid.

LCMS (IE, m/z): (M+1) 496.2
$^1$H-NMR: $\delta_H$ ppm 400 MHz, DMSO 13.08 (1H, s, NH), 11.88 (1H, s, NH), 10.26 (1H, s, CH$_{arom}$), 8.50 (1H, d, CH$_{arom}$), 8.22 (1H, d, CH$_{arom}$), 8.16 (1H, bs, CH$_{arom}$), 8.04 (1H, s, CH$_{arom}$), 7.61-7.55 (1H, m, CH$_{arom}$), 7.52 (1H, d, CH$_{arom}$), 7.22 (1H, d, CH$_{arom}$), 690 (1H, d, CH$_{arom}$), 6.68 (1H, d, CH$_{arom}$), 4.39 (2H, q, CH$_2$), 4.04 (4H, bs, 2×CH$_2$), 3.65 (4H, bs, 2×CH$_2$), 1.39 (3H, t, CH$_3$).

4-Oxo-8-(2-phenylamino-pyrimidin-4-yl)-4,5-dihydro-3H-pyrrolo[2,3-c]quinoline-1-ethyl carboxylate (266)

51 mg (0.38 mmol) of phenylguanidine carbonate is added to a suspension of 88 mg (0.25 mmol) of 8-(3-dimethylamino-acryloyl)-4-oxo-4,5-dihydro-3H-pyrrolo[2,3-c]quinoline-1-ethyl carboxylate in 2 mL of anhydrous dimethylacetamide. The mixture is stirred at 130° C. for 2 days then the solvent is evaporated. The residue is triturated with acetonitrile to give a solid which is collected by filtration then washed with acetonitrile then diisopropyl ether. After drying, 47 mg (44%) of 4-oxo-8-(2-phenylamino-pyrimidin-4-yl)-4,5-dihydro-3H-pyrrolo[2,3-c]quinoline-1-ethyl carboxylate is obtained in the form of a brown solid.

LCMS (IE, m/z): (M+1) 426.07
$^1$H-NMR: δ$_H$ ppm 400 MHz, DMSO
13.11 (1H, bs, NH), 11.94 (1H, s, NH), 10.05 (1H, s, NH), 9.63 (1H, s, CH$_{arom}$), 8.59 (1H, d, CH$_{arom}$), 8.23 (1H, dd, CH$_{arom}$), 8.05 (1H, s, CH$_{arom}$), 7.90 (2H, d, 2×CH$_{arom}$), 7.55 (1H, d, CH$_{arom}$), 7.37-7.29 (3H, m, 3×CH$_{arom}$), 6.96 (1H, t, CH$_{arom}$), 4.33 (2H, q, CH$_2$), 1.34 (3H, t, CH$_3$).

8-[2-(1H-Benzoimidazol-2-ylamino)-pyrimidin-4-yl]-4-oxo-4,5-dihydro-3H-pyrrolo[2,3-c]quinoline-1-ethyl carboxylate (267)

76 mg (0.44 mmol) of 2-guanidinobenzimidazole is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 4 days then the solvent is evaporated. The solid is triturated in methanol then collected by filtration. The solid is washed with hot dioxan then with hot methanol to give, after drying, 21 mg (15%) of 8-[2-(1H-benzoimidazol-2-ylamino)-pyrimidin-4-yl]-4-oxo-4,5-dihydro-3H-pyrrolo[2,3-c]quinoline-1-ethyl carboxylate in the form of a brown solid.

LCMS (IE, m/z): (M+1) 466.17
$^1$H-NMR: δ$_H$ ppm 400 MHz, DMSO
13.16 (1H, s, NH), 12.15-11.85 (2H, m, 2×NH), 11.21 (1H, s, NH), 10.16 (1H, s, CH$_{arom}$), 8.76 (1H, d, CH$_{arom}$), 8.28 (1H, d, CH$_{arom}$), 8.08 (1H, s, CH$_{arom}$), 7.64-7.52 (2H, m, 2×CH$_{arom}$), 7.44 (2H, bs, 2×CH$_{arom}$), 7.07 (2H, bs, 2×CH$_{arom}$), 4.26 (2H, q, CH$_2$), 1.31 (3H, t, CH$_3$).

8-[2-(4-Acetyl-piperazin-1-yl)-pyrimidin-4-yl]-4-oxo-4,5-dihydro-3H-pyrrolo[2,3-c]quinoline-1-ethyl carboxylate (268)

130 mg (0.44 mmol) of 4-acetyl-piperazine-1-carboxamidine hydroiodide is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 4 days then the solvent is evaporated. The product is purified by preparative LCMS to give, after drying, 32 mg (24%) of 8-[2-(4-acetyl-piperazin-1-yl)-pyrimidin-4-yl]-4-oxo-4,5-dihydro-3H-pyrrolo[2,3-c]quinoline-1-ethyl carboxylate in the form of a brown solid.

LCMS (IE, m/z): (M+1) 461.2
$^1$H-NMR: δ$_H$ ppm 400 MHz, DMSO
13.08 (1H, s, NH), 11.88 (1H, s, NH), 10.26 (1H, s, CH$_{arom}$), 8.48 (1H, d, CH$_{arom}$), 8.20 (1H, d, CH$_{arom}$), 8.04 (1H, s, CH$_{arom}$), 7.51 (1H, d, CH$_{arom}$), 7.23 (1H, d, CH$_{arom}$), 4.35 (2H, q, CH$_2$), 3.93 (4H, dl, 2×CH$_2$), 3.59 (4H, bs, 2×CH$_2$), 2.08 (3H, s, CH$_3$), 1.37 (3H, t, CH$_3$).

8-{2-[(2-Dimethylamino-ethyl)-methyl-amino]-pyrimidin-4-yl}-4-oxo-4,5-dihydro-3H-pyrrolo[2,3-c]quinoline-1-ethyl carboxylate formate (269)

119 mg (0.44 mmol) of N-[2-(dimethylamino)ethyl]-N-methylguanidine hydriodide is added to a suspension of 102 mg (0.29 mmol) of 8-(3-dimethylamino-acryloyl)-4-oxo-4,5-dihydro-3H-pyrrolo[2,3-c]quinoline-1-ethyl carboxylate in 2.5 mL of anhydrous dimethylacetamide. The mixture is stirred at 130° C. for 5 days then the solvent is evaporated. The product is purified by preparative LCMS to give, after drying, 22 mg (16%) of 8-(2-methylamino-pyrimidin-4-yl)-4-oxo-4,5-dihydro-3H-pyrrolo[2,3-c]quinoline-1-ethyl carboxylate in the form of a brown solid, mono salt of formic acid.

LCMS (IE, m/z): (M+1) 435.2
$^1$H-NMR: δ$_H$ ppm 400 MHz, DMSO
13.07 (1H, s, NH), 11.88 (1H, s, NH), 10.16 (1H, s, CH$_{arom}$), 8.44 (1H, d, CH$_{arom}$), 8.22-8.17 (2H, m, HCO$_2$H and CH$_{arom}$), 8.03 (1H, s, CH$_{arom}$), 7.50 (1H, d, CH$_{arom}$), 7.14 (1H, d, CH$_{arom}$), 4.34 (2H, q, CH$_2$), 3.87 (2H, bs, CH$_2$), 3.24 (2H, bs, CH$_2$), 2.54 (3H, s, CH$_3$), 2.25 (6H, s, 2×CH$_3$), 1.36 (3H, t, CH$_3$).

8-(2-Amino-thiazol-4-yl)-4-oxo-4,5-dihydro-3H-pyrrolo[2,3-c]quinoline-1-ethyl carboxylate (270)

17 mg (1.5 mmol) of thiourea is added to a suspension of 57 mg (0.15 mmol) of 8-(2-bromo-acetyl)-4-oxo-4,5-dihydro-3H-pyrrolo[2,3-c]quinoline-1-ethyl carboxylate in 3 mL of ethanol. The mixture is stirred at 90° C. for 3 hours then the mixture is cooled to room temperature. Triethylamine (2 mmol) is added then the solvent is evaporated and the product is purified by chromatography on silica (chloroform/methanol/triethylamine 8/2/1). After drying, 9 mg (17%) of 8-(2-amino-thiazol-4-yl)-4-oxo-4,5-dihydro-3H-pyrrolo[2,3-c]quinoline-1-ethyl carboxylate is obtained in the form of a beige solid.

LCMS (IE, m/z): (M+1) 355.1
$^1$H-NMR: δ$_H$ ppm 400 MHz, DMSO
12.99 (1H, bs, NH), 11.70 (1H, bs, NH), 9.62 (1H, d, CH$_{arom}$), 7.98 (1H, d, CH$_{arom}$), 7.80 (1H, dd, CH$_{arom}$), 7.38 (1H, d, CH$_{arom}$), 7.05 (2H, bs, NH$_2$), 6.78 (1H, s, CH$_{arom}$), 4.33 (2H, q, CH$_2$), 1.33 (3H, t, CH$_3$).

383 mg (2.4 mmol) of bromine is added to a solution of 596 mg (2 mmol) of 8-acetyl-4-oxo-4,5-dihydro-3H-pyrrolo[2,3-c]quinoline-1-ethyl carboxylate in 10 mL of anhydrous dioxan. The mixture is stirred at 70° C. for 2 hours then the mixture is cooled to room temperature. The precipitate is collected by filtration then triturated in diisopropyl ether then pentane to give, after drying, 610 mg (81%) of 8-(2-bromo-acetyl)-4-oxo-4,5-dihydro-3H-pyrrolo[2,3-c]quinoline-1-ethyl carboxylate in the form of a brown solid.

4-Oxo-8-(2-phenylamino-thiazol-4-yl)-4,5-dihydro-3H-pyrrolo[2,3-c]quinoline-1-ethyl carboxylate (271)

34 mg (1.5 mmol) of N-phenylthiourea is added to a suspension of 57 mg (0.15 mmol) of 8-(2-bromo-acetyl)-4-oxo- 4,5-dihydro-3H-pyrrolo[2,3-c]quinoline-1-ethyl carboxylate in 3 mL of ethanol. The mixture is stirred at 90° C. for 48 hours then the mixture is cooled to room temperature. Triethylamine (2 mmol) is added, then the solvent is evaporated and the product is purified by chromatography on silica (chloroform/methanol/triethylamine 8/2/1). After drying, 11 mg (17%) of 4-oxo-8-(2-phenylamino-thiazol-4-yl)-4,5-dihydro-3H-pyrrolo[2,3-c]quinoline-1-ethyl carboxylate is obtained in the form of a beige solid.

LCMS (IE, m/z): (M+1) 431.2

$^1$H-NMR: $\delta_H$ ppm 400 MHz, DMSO 12.99 (1H, s, NH), 11.67 (1H, s, NH), 9.15 (1H, d, $CH_{arom}$), 7.95 (1H, s, $CH_{arom}$), 7.28 (2H, m, 2×$CH_{arom}$), 7.23-7.15 (4H, m, 4×$CH_{arom}$), 7.02 (1H, dd, $CH_{arom}$), 6.27 (1H, s, $CH_{arom}$), 4.33 (2H, q, $CH_2$), 1.36 (3H, t, $CH_3$).

8-[2-(2-Chlorophenylamino)-thiazol-4-yl]-4,5-dihydro-3H-pyrrolo[2,3-c]quinoline-1-ethyl carboxylate (272)

74 mg (1.2 mmol) of (2-chlorophenyl)-thiourea is added to a suspension of 124 mg (0.33 mmol) of 8-(2-bromo-acetyl)-4-oxo-4,5-dihydro-3H-pyrrolo[2,3-c]quinoline-1-ethyl carboxylate in 3.5 mL of ethanol. The mixture is stirred at 90° C. for 6 hours then the mixture is cooled to room temperature. The solvent is evaporated, then the product is purified by preparative LCMS. After drying, 41 mg (27%) of 8-[2-(2-chlorophenylamino)-thiazol-4-yl]-4-oxo-4,5-dihydro-3H-pyrrolo[2,3-c]quinoline-1-ethyl carboxylate is obtained in the form of a beige solid.

LCMS (IE, m/z): (M+1) 465.20

$^1$H-NMR: $\delta_H$ ppm 400 MHz, DMSO 13.03 (1H, bs, NH), 11.75 (1H, s, NH), 9.78 (1H, s, $CH_{arom}$), 9.61 (1H, s, $CH_{arom}$), 7.98 (1H, bs, $CH_{arom}$), 7.76 (1H, d, $CH_{arom}$), 7.61 (2H, d, $CH_{arom}$), 7.40 (2H, d, $CH_{arom}$), 7.02 (1H, bs, $CH_{arom}$), 4.26 (2H, q, $CH_2$), 1.32 (3H, t, $CH_3$).

8-[2-(3,4-Dichlorophenylamino)-thiazol-4-yl]-4-oxo-4,5-dihydro-3H-pyrrolo[2,3-c]quinoline-1-ethyl carboxylate (273)

87 mg (1.2 mmol) of (3,4-dichlorophenyl)-thiourea is added to a suspension of 124 mg (0.33 mmol) of 8-(2-bromo-acetyl)-4-oxo-4,5-dihydro-3H-pyrrolo[2,3-c]quinoline-1-ethyl carboxylate in 3.5 mL of ethanol. The mixture is stirred at 90° C. for 6 hours then the mixture is cooled to room temperature. The solvent is evaporated, then the product is purified by preparative LCMS. After drying, 23 mg (14%) of 8-[2-(3,4-dichlorophenylamino)-thiazol-4-yl]-4-oxo-4,5-dihydro-3H-pyrrolo[2,3-c]quinoline-1-ethyl carboxylate is obtained in the form of a beige solid.

LCMS (IE, m/z): (M+1) 499.20

$^1$H-NMR: $\delta_H$ ppm 400 MHz, DMSO 13.02 (1H, bs, NH), 11.76 (1H, s, NH), 10.78 (1H, s, NH), 9.91-9.87 (1H, m, $CH_{arom}$), 8.18 (1H, dd, $CH_{arom}$), 8.04-8.00 (11H, m, $CH_{arom}$), 7.93-7.89 (2H, m, $CH_{arom}$), 7.59 (1H, d, $CH_{arom}$), 7.44 (1H, d, $CH_{arom}$), 7.26 (1H, bs, $CH_{arom}$), 4.38 (2H, q, $CH_2$), 1.36 (3H, t, $CH_3$).

8-[2-(2,6-Dichlorophenylamino)-thiazol-4-yl]-4-oxo-4,5-dihydro-3H-pyrrolo[2,3-c]quinoline-1-ethyl carboxylate (274)

87 mg (1.2 mmol) of (2,6-dichlorophenyl)-thiourea is added to a suspension of 124 mg (0.33 mmol) of 8-(2-bromo-acetyl)-4-oxo-4,5-dihydro-3H-pyrrolo[2,3-c]quinoline-1-ethyl carboxylate in 3.5 mL of ethanol. The mixture is stirred at 90° C. for 6 hours then the mixture is cooled to room temperature. The solvent is evaporated, then the product is purified by preparative LCMS. After drying, 43 mg (26%) of 8-[2-(2,6-dichlorophenylamino)-thiazol-4-yl]-4-oxo-4,5-dihydro-3H-pyrrolo[2,3-c]quinoline-1-ethyl carboxylate is obtained in the form of a beige solid.

LCMS (IE, m/z): (M+1) 499.22

$^1$H-NMR: $\delta_H$ ppm 400 MHz, DMSO 13.03 (1H, bs, NH), 11.76 (1H, s, NH), 10.58 (1H, s, $CH_{arom}$), 9.89 (1H, s, $CH_{arom}$), 8.17 (1H, d, $CH_{arom}$), 8.02 (1H, bs, $CH_{arom}$), 7.91 (1H, bs, $CH_{arom}$), 7.61 (2H, d, $CH_{arom}$), 7.44 (1H, d, $CH_{arom}$), 7.26 (1H, bs, $CH_{arom}$), 4.36 (2H, q, $CH_2$), 1.36 (3H, t, $CH_3$).

8-[2-(Cyclopropanecarbonyl-amino)-thiazol-4-yl]-4-oxo-4,5-dihydro-3H-pyrrolo[2,3-c]quinoline-1-ethyl carboxylate (275)

57 mg (1.2 mmol) of cyclopropanecarbonyl-thiourea is added to a suspension of 124 mg (0.33 mmol) of 8-(2-bromo-acetyl)-4-oxo-4,5-dihydro-3H-pyrrolo[2,3-c]quinoline-1-ethyl carboxylate in 3.5 mL of ethanol. The mixture is stirred at 90° C. for 6 hours then the mixture is cooled to room temperature. The solvent is evaporated, then the product is purified by preparative LCMS. After drying, 39 mg (28%) of 8-[2-(cyclopropanecarbonyl-amino)-thiazol-4-yl]-4-oxo-4,5-dihydro-3H-pyrrolo[2,3-c]quinoline-1-ethyl carboxylate is obtained in the form of a beige solid.

LCMS (IE, m/z): (M+1) 423.24

$^1$H-NMR: $\delta_H$ ppm 400 MHz, DMSO 11.82 (1H, s, NH), 9.75 (1H, s, $CH_{arom}$), 8.03 (1H, s, $CH_{arom}$), 7.92 (1H, d, $CH_{arom}$), 7.46 (1H, d, $CH_{arom}$), 7.34 (1H, s, $CH_{arom}$), 4.34 (2H, q, $CH_2$), 2.02 (1H, m, CH), 1.35 (3H, t, $CH_3$), 0.91 (4H, m, 4×$CH_{cyclopr}$).

4-Oxo-8-(2-phenylsulfanylmethyl-thiazol-4-yl)-4,5-dihydro-3H-pyrrolo[2,3-c]quinoline-1-ethyl carboxylate (276)

38 mg (1.5 mmol) of phenylsulfanylmethyl-thiourea is added to a suspension of 57 mg (0.15 mmol) of 8-(2-bromo-acetyl)-4-oxo-4,5-dihydro-3H-pyrrolo[2,3-c]quinoline-1-ethyl carboxylate in 3 mL of ethanol. The mixture is stirred at 90° C. for 3 hours then the mixture is cooled to room temperature. Triethylamine (2 mmol) is added then the solvent is evaporated and the product is purified by chromatography on silica (chloroform/methanol 98/2 then 95/5). After drying, 26 mg (38%) of 4-oxo-8-(2-phenylsulfanylmethyl-thiazol-4-yl)-4,5-dihydro-3H-pyrrolo[2,3-c]quinoline-1-ethyl carboxylate is obtained in the form of a beige solid.

LCMS (IE, m/z): (M+1) 462

$^1$H-NMR: $\delta_H$ ppm 400 MHz, DMSO 13.03 (1H, bs, NH), 11.77 (1H, bs, NH), 9.75 (1H, d, $CH_{arom}$), 8.00 (1H, d, $CH_{arom}$), 7.92 (1H, dd, $CH_{arom}$), 7.76 (1H, s, $CH_{arom}$), 7.54-7.47 (2H, m, 2×$CH_{arom}$), 7.42-7.35 (3H, m, 3×$CH_{arom}$), 7.22 (1H, t, $CH_{arom}$), 4.69 (2H, s, $SCH_2$), 4.33 (2H, q, $CH_2$), 1.36 (3H, t, $CH_3$).

4-Oxo-8-(2-piperidin-4-yl-thiazol-4-yl)-4,5-dihydro-3H-pyrrolo[2,3-c]quinoline-1-ethyl carboxylate (277)

55 mg (1.5 mmol) of 4-thiocarbamoyl-piperidine-1-tert-butyl carboxylate is added to a suspension of 57 mg (0.15 mmol) of 8-(2-bromo-acetyl)-4-oxo-4,5-dihydro-3H-pyrrolo[2,3-c]quinoline-1-ethyl carboxylate in 3 mL of ethanol. The mixture is stirred at 90° C. for 3 hours then the mixture is cooled to room temperature. Triethylamine (2 mmol) is added, then the solvent is evaporated and the product is purified by chromatography on silica (chloroform/methanol/triethylamine 8/2/1). After drying, 11 mg (17%) of 4-oxo-8-(2-piperidin-4-yl-thiazol-4-yl)-4,5-dihydro-3H-pyrrolo[2,3-c]quinoline-1-ethyl carboxylate is obtained in the form of a beige solid.

LCMS (IE, m/z): (M+1) 423.24

$^1$H-NMR: $\delta_H$ ppm 400 MHz, DMSO 11.76 (1H, bs, NH), 9.76 (1H, d, $CH_{arom}$), 8.00 (1H, s, $CH_{arom}$), 7.95 (1H, dd, $CH_{arom}$), 7.74 (1H, s, $CH_{arom}$), 7.44 (1H, d, $CH_{arom}$), 4.35 (2H, q, $CH_2$), 3.35-3.30 (1H, m, $CH_{piper}$), 3.16-3.10 (2H, m, 2×$CH_{piper}$), 2.80-2.72 (2H, m, 2×$CH_{piper}$), 2.13-2.06 (2H, m, 2×$CH_{piper}$), 1.77-1.68 (2H, m, 2×$CH_{piper}$), 1.36 (3H, t, $CH_3$).

8-(2-Methyl-thiazol-4-yl)-4-oxo-4,5-dihydro-3H-pyrrolo[2,3-c]quinoline-1-ethyl carboxylate (278)

17 mg (1.5 mmol) of thioacetamide is added to a suspension of 57 mg (0.15 mmol) of 8-(2-bromo-acetyl)-4-oxo-4,5-dihydro-3H-pyrrolo[2,3-c]quinoline-1-ethyl carboxylate in 3 mL of ethanol. The mixture is stirred at 90° C. for 3 hours then the mixture is cooled to room temperature. Triethylamine (2 mmol) is added, then the solvent is evaporated and the product is purified by chromatography on silica (chloroform/methanol 95/5). After drying, 18 mg (34%) of 8-(2-methyl-thiazol-4-yl)-4-oxo-4,5-dihydro-3H-pyrrolo[2,3-c]quinoline-1-ethyl carboxylate is obtained in the form of a beige solid.

LCMS (IE, m/z): (M+1) 354.09

$^1$H-NMR: $\delta_H$ ppm 400 MHz, DMSO 13.02 (1H, s, NH), 11.75 (1H, bs, NH), 9.76 (1H, d, $CH_{arom}$), 8.00 (1H, d, $CH_{arom}$), 795 (1H, dd, $CH_{arom}$), 7.69 (1H, s, $CH_{arom}$), 7.44 (1H, d, $CH_{arom}$), 4.35 (2H, q, $CH_2$), 2.74 (3H, s, $CH_3$), 1.37 (3H, t, $CH_3$).

4-Oxo-8-(2-phenyl-thiazol-4-yl)-4,5-dihydro-3H-pyrrolo[2,3-c]quinoline-1-ethyl carboxylate (279)

54 mg (1.2 mmol) of thiobenzamide is added to a suspension of 124 mg (0.33 mmol) of 8-(2-bromo-acetyl)-4-oxo-4,5-dihydro-3H-pyrrolo[2,3-c]quinoline-1-ethyl carboxylate in 3.5 mL of ethanol. The mixture is stirred at 90° C. for 6 hours then the mixture is cooled to room temperature. The solvent is evaporated, then the product is purified by preparative LCMS. After drying, 29 mg (21%) of 4-oxo-8-(2-phenyl-thiazol-4-yl)-4,5-dihydro-3H-pyrrolo[2,3-c]quinoline-1-ethyl carboxylate is obtained in the form of a beige solid.

LCMS (IE, m/z): (M+1) 416.20

$^1$H-NMR: $\delta_H$ ppm 400 MHz, DMSO 13.03 (1H, bs, NH), 11.79 (1H, s, NH), 9.92 (1H, s, $CH_{arom}$), 8.92-7.95 (4H, m, 4×$CH_{arom}$), 7.67-7.48 (5H, m, 5×$CH_{arom}$), 4.38 (2H, q, $CH_2$), 1.38 (3H, t, $CH_3$).

4-Oxo-8-[2-(N'-phenyl-hydrazino)-thiazol-4-yl]-4,5-dihydro-3H-pyrrolo[2,3-c]quinoline-1-ethyl carboxylate (280)

66 mg (1.2 mmol) of 1-phenylthiosemicarbazide is added to a suspension of 124 mg (0.33 mmol) of 8-(2-bromo-acetyl)-4-oxo-4,5-dihydro-3H-pyrrolo[2,3-c]quinoline-1-ethyl carboxylate in 3.5 mL of ethanol. The mixture is stirred at 90° C. for 6 hours then the mixture is cooled to room temperature. The solvent is evaporated, then the product is purified by preparative LCMS. After drying, 62 mg (42%) of 4-oxo-8-[2-(N'-phenyl-hydrazino)-thiazol-4-yl]-4,5-dihydro-3H-pyrrolo[2,3-c]quinoline-1-ethyl carboxylate is obtained in the form of a beige solid.

LCMS (IE, m/z): (M+1) 446.24

$^1$H-NMR: $\delta_H$ ppm 400 MHz, DMSO 12.70 (1H, bs, NH), 11.41 (1H, s, NH), 9.10 (1H, s, $CH_{arom}$), 7.69 (1H, bs, $CH_{arom}$), 7.04-6.95 (2H, m, 2×$CH_{arom}$), 7.73-6.45 (4H, m, 4×$CH_{arom}$), 7.20 (2H, d, 2×$CH_{arom}$), 5.01 (1H, bs, NH), 4.0 (2H, t, $CH_2$), 1.08 (3H, t, $CH_3$).

8-Isoxazol-5-yl-4-oxo-4,5-dihydro-3H-pyrrolo[2,3-c]quinoline-1-ethyl carboxylate (281)

25 mg (0.36 mmol) of hydroxylamine hydrochloride is added to a solution of 64 mg (0.18 mmol) of 8-(3-dimethylamino-acryloyl)-4-oxo-4,5-dihydro-3H-pyrrolo[2,3-c]quinoline-1-ethyl carboxylate in 2 mL of anhydrous dimethylformamide. The mixture is stirred at 130° C. for 3 hours then the product is precipitated by adding methanol. The solid is triturated in methanol then collected by filtration. The solid is washed with diisopropyl ether then pentane to give, after drying, 22 mg (38%) of 8-isoxazol-5-yl-4-oxo-4,5-dihydro-3H-pyrrolo[2,3-c]quinoline-1-ethyl carboxylate in the form of a beige solid.

LCMS (IE, m/z): (M+1) 324.04

$^1$H-NMR: $\delta_H$ ppm 400 MHz, DMSO 13.13 (1H, s, NH), 11.93 (1H, bs, NH), 9.84 (1H, d, $CH_{arom}$), 8.64 (1H, d, $CH_{arom}$), 8.05 (1H, s, $CH_{arom}$), 7.90 (1H, dd, $CH_{arom}$), 7.53 (1H, d, $CH_{arom}$), 6.87 (1H, d, $CH_{arom}$), 4.36 (2H, q, $CH_2$), 1.36 (3H, t, $CH_3$).

4-Oxo-8-(1H-pyrazol-3-yl)-4,5-dihydro-3H-pyrrolo[2,3-c]quinoline-1-ethyl carboxylate (282)

63 mg (1.25 mmol) of hydrazine hydrate is added to a suspension of 88 mg (0.25 mmol) of 8-(3-dimethylamino-acryloyl)-4-oxo-4,5-dihydro-3H-pyrrolo[2,3-c]quinoline-1-ethyl carboxylate in 2 mL of ethanol. The mixture is stirred at 80° C. for 3 hours then the mixture is cooled to room temperature. The precipitate is filtered then triturated in ethanol. The solid is washed with diisopropyl ether then pentane to give, after drying, 46 mg (57%) of 4-oxo-8-(1H-pyrazol-3-yl)-4,5-dihydro-3H-pyrrolo[2,3-c]quinoline-1-ethyl carboxylate in the form of a beige solid.

LCMS (IE, m/z): (M+1) 323.05

$^1$H-NMR: $\delta_H$ ppm 400 MHz, DMSO 12.82 (1H, s, NH), 11.70 (1H, bs, NH), 9.69 (1H, bs, $CH_{arom}$), 7.99 (1H, s, $CH_{arom}$), 785-7.40 (2H, m, 2×$CH_{arom}$), 7.42 (1H, d, $CH_{arom}$), 6.63 (1H, s, $CH_{arom}$), 4.34 (2H, q, $CH_2$), 1.36 (3H, 1, $CH_3$).

8-(1-Methyl-1H-pyrazol-3-yl)-4-oxo-4,5-dihydro-3H-pyrrolo[2,3-c]quinoline-1-ethyl carboxylate (283)

58 mg (1.25 mmol) of methylhydrazine is added to a suspension of 88 mg (0.25 mmol) of 8-(3-dimethylamino-acryloyl)-4-oxo-4,5-dihydro-3H-pyrrolo[2,3-c]quinoline-1-ethyl carboxylate in 2 mL of ethanol. The mixture is stirred at 80° C. for 3 hours then the mixture is cooled to room temperature. The precipitate is filtered, then triturated in ethanol. The solid is washed with diisopropyl ether then pentane to give, after drying, 27 mg (32%) of 8-(1-methyl-1H-pyrazol-3-yl)-4-oxo-4,5-dihydro-3H-pyrrolo[2,3-c]quinoline-1-ethyl carboxylate in the form of a beige solid.

LCMS (IE, m/z): (M+1) 337.05

$^1$H-NMR: $\delta_H$ ppm 400 MHz, DMSO 13.07 (1H, s, NH), 11.83 (1H, s, NH), 9.45 (1H, d, $CH_{arom}$), 8.02 (1H, s, $CH_{arom}$), 7.58-7.48 (3H, m, 3×$CH_{arom}$), 6.41 (1H, d, $CH_{arom}$), 4.30 (2H, q, $CH_2$), 3.92 (3H, s, $CH_3$), 1.31 (3H, t, $CH_3$).

EXAMPLE 2

Test for Measuring Inhibition of Ret Kinase Activity by the Recombinant RET Method The inhibition of the kinase activity of the compounds of the invention is assessed by measuring their IC50 on RET. This IC50 represents the concentration of compound required for inhibiting 50% of RET kinase activity and is calculated from the nonlinear regression curve that has the following equation:

$$Y = \text{Bottom} + \frac{(\text{Top} - \text{Bottom})}{1 + 10^{(\log IC50 - X)}}$$

where:
Y is the value of the luminescence
X is the logarithm of the concentration of the compound
Bottom is the minimum Y value
Top is the maximum Y value
LogIC50 is the value of X when Y is 50% from Top—Bottom.

The RET protein (Upstate #14-570MG batch PP030) is incubated in a buffer containing 40 mM MOPS/NaOH pH7.0 (Sigma M-8899), 1 mM EDTA (Amresco 0105-100G-APP), in the presence of 1.5 mg/ml of poly-EY4 substrate (Sigma #P-0275), 30 mM of magnesium acetate (Sigma 229768) and 20 μM of ATP. The quantity of RET required is 2 μg/ml.

The following buffer is used for dilution of RET: 20 mM MOPS/NaOH pH7.0, 1 mM EDTA, 5% glycerol, 0.01% Brij35 (Sigma B4184), 0.1% 2-mercaptoethanol, 1 mg/ml BSA (Sigma A3059-10G).

The compound to be tested is first added to the enzyme to give a reaction volume of 50 μl. The dilution of the compounds of the invention is distributed so as to obtain a scale of final concentrations between 10 nM and 30 μM.

After incubation of the reaction mixture for two hours at 30° C., the level of ATP that remains is assayed using the Kinase-Glo Luminescent Kinase Assay (Promega #V6712) according to the conditions recommended by the supplier. The luminescence induced is read in a plate reader (Envision-Perkin Elmer).

The tables given below show the values of IC50 for compounds of formulas II through IX, the substituents R, R2, R3, R4, R5, R7, R8, R12, R13, R14, R15, R16 and R17 being defined above. The values of IC50 are given by categories

| | |
|---|---|
| IC50 < 100 nM | Category A |
| 100 nM < IC50 < 1 μM | Category B |
| 1 μM < IC50 < 10 μM | Category C |
| 10 μM < IC50 < 100 μM | Category D |

TABLE 1

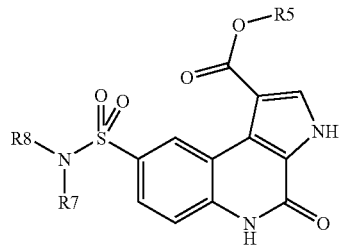

(II)

| Compound | Formula | Name | IC$_{50}$ |
|---|---|---|---|
| 2 | | 4-Oxo-8-phenylsulfamoyl-4,5-dihydro-3H-pyrrolo[2,3-c]quinoline-1-ethyl carboxylate | A |
| 3 | | 8-(Methyl-phenyl-sulfamoyl)-4-oxo-4,5-dihydro-3H-pyrrolo[2,3-c]quinoline-1-ethyl carboxylate | A |

TABLE 1-continued

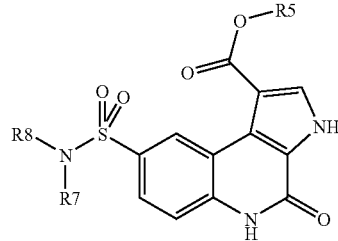

(II)

| Compound | Formula | Name | IC$_{50}$ |
|---|---|---|---|
| 4 | | 4-Oxo-8-o-tolylsulfamoyl-4,5-dihydro-3H-pyrrolo[2,3-c]quinoline-1-ethyl carboxylate | A |
| 5 | | 4-Oxo-8-m-tolylsulfamoyl-4,5-dihydro-3H-pyrrolo[2,3-c]quinoline-1-ethyl carboxylate | B |
| 6 | | 4-Oxo-8-p-tolylsulfamoyl-4,5-dihydro-3H-pyrrolo[2,3-c]quinoline-1-ethyl carboxylate | B |
| 7 | | 8-(2-Methoxy-phenylsulfamoyl)-4-oxo-4,5-dihydro-3H-pyrrolo[2,3-c]quinoline-1-ethyl carboxylate | B |
| 8 | | 8-(3-Methoxy-phenylsulfamoyl)-4-oxo-4,5-dihydro-3H-pyrrolo[2,3-c]quinoline-1-ethyl carboxylate | B |
| 9 | | 8-(4-Methoxy-phenylsulfamoyl)-4-oxo-4,5-dihydro-3H-pyrrolo[2,3-c]quinoline-1-ethyl carboxylate | B |

TABLE 1-continued

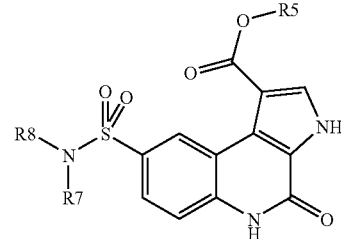

(II)

| Compound | Formula | Name | IC$_{50}$ |
|---|---|---|---|
| 10 | | 8-(3-Chlorophenylsulfamoyl)-4-oxo-4,5-dihydro-3H-pyrrolo[2,3-c]quinoline-1-ethyl carboxylate | B |
| 11 | | 8-(4-Chlorophenylsulfamoyl)-4-oxo-4,5-dihydro-3H-pyrrolo[2,3-c]quinoline-1-ethyl carboxylate | B |
| 12 | | 8-(4-Fluorophenylsulfamoyl)-4-oxo-4,5-dihydro-3H-pyrrolo[2,3-c]quinoline-1-ethyl carboxylate | A |
| 13 | | 8-[(4-Fluorophenyl)-methyl-sulfamoyl]-4-oxo-4,5-dihydro-3H-pyrrolo[2,3-c]quinoline-1-ethyl carboxylate | A |
| 103 | | 8-[(4-Fluorophenyl)-methyl-sulfamoyl]-4-oxo-4,5-dihydro-3H-pyrrolo[2,3-c]quinoline-1-carboxylic acid | D |
| 104 | | 8-[(4-Fluorophenyl)-methyl-sulfamoyl]-4-oxo-4,5-dihydro-3H-pyrrolo[2,3-c]quinoline-1-2-hydroxyethyl carboxylate | C |

TABLE 1-continued

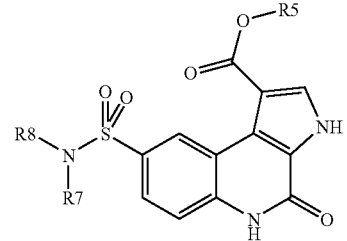
(II)

| Compound | Formula | Name | IC$_{50}$ |
|---|---|---|---|
| 105 | | 8-[(4-Fluorophenyl)-methyl-sulfamoyl]-4-oxo-4,5-dihydro-3H-pyrrolo[2,3-c]quinoline-1-2-aminoethyl carboxylate hydrochloride | D |
| 106 | | 8-[(4-Fluorophenyl)-methyl-sulfamoyl]-4-oxo-4,5-dihydro-3H-pyrrolo[2,3-c]quinoline-1-2-tert-butoxycarbonylaminoethyl carboxylate | D |
| 107 | | 8-[(4-fluorophenyl)-methyl-sulfamoyl]-4-oxo-4,5-dihydro-3H-pyrrolo[2,3-c]quinoline-1-3-aminopropyl carboxylate hydrochloride | D |
| 108 | | 8-[(4-Fluorophenyl)-methyl-sulfamoyl]-4-oxo-4,5-dihydro-3H-pyrrolo[2,3-c]quinoline-1-3-tert-butoxycarbonylamino-propyl carboxylate | D |
| 14 | | 8-(4-Ethoxycarbonyl-phenylsulfamoyl)-4-oxo-4,5-dihydro-3H-pyrrolo[2,3-c]quinoline-1-ethyl carboxylate | C |

TABLE 1-continued

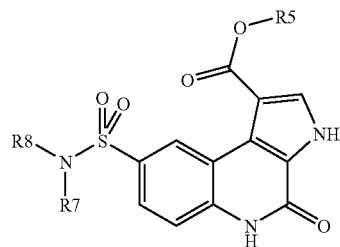

(II)

| Compound | Formula | Name | IC$_{50}$ |
|---|---|---|---|
| 15 | | 8-(3-Hydroxy-phenylsulfamoyl)-4-oxo-4,5-dihydro-3H-pyrrolo[2,3-c]quinoline-1-ethyl carboxylate | B |
| 16 | | 8-(3-Fluoro-2-methyl-phenylsulfamoyl)-4-oxo-4,5-dihydro-3H-pyrrolo[2,3-c]quinoline-1-ethyl carboxylate | A |
| 17 | | 8-(4-Fluoro-2-methyl-phenylsulfamoyl)-4-oxo-4,5-dihydro-3H-pyrrolo[2,3-c]quinoline-1-ethyl carboxylate | A |
| 18 | | 8-(3,4-Difluorophenylsulfamoyl)-4-oxo-4,5-dihydro-3H-pyrrolo[2,3-c]quinoline-1-ethyl carboxylate | A |
| 19 | | 8-(3,5-Difluorophenylsulfamoyl)-4-oxo-4,5-dihydro-3H-pyrrolo[2,3-c]quinoline-1-ethyl carboxylate | B |

TABLE 1-continued

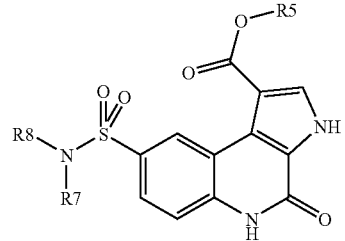
(II)

| Compound | Formula | Name | IC$_{50}$ |
|---|---|---|---|
| 20 | | 8-(4-Aminophenylsulfamoyl)-4-oxo-4,5-dihydro-3H-pyrrolo[2,3-c]quinoline-1-ethyl carboxylate | A |
| 21 | | 8-(2,3-Dihydro-indole-1-sulfonyl)-4-oxo-4,5-dihydro-3H-pyrrolo[2,3-c]quinoline-1-ethyl carboxylate | B |
| 22 | | 8-(4-Morpholin-4-yl-phenylsulfamoyl)-4-oxo-4,5-dihydro-3H-pyrrolo[2,3-c]quinoline-1-ethyl carboxylate | D |
| 23 | | 4-Oxo-8-(pyridin-3-ylsulfamoyl)-4,5-dihydro-3H-pyrrolo[2,3-c]quinoline-1-ethyl carboxylate | B |
| 24 | | 8-(Benzyl-methyl-sulfamoyl)-4-oxo-4,5-dihydro-3H-pyrrolo[2,3-c]quinoline-1-ethyl carboxylate | B |
| 25 | | 8-(Methyl-phenethyl-sulfamoyl)-4-oxo-4,5-dihydro-3H-pyrrolo[2,3-c]quinoline-1-ethyl carboxylate | C |

TABLE 1-continued (II)

| Compound | Formula | Name | IC$_{50}$ |
|---|---|---|---|
| 26 | | 8-Dimethylsulfamoyl-4-oxo-4,5-dihydro-3H-pyrrolo[2,3-c]quinoline-1-ethyl carboxylate | B |
| 109 | | N-Propyl-8-dimethylsulfamoyl-4-oxo-4,5-dihydro-3H-pyrrolo[2,3-c]quinoline-1-carboxamide | D |
| 110 | | N-Methyl-N-propyl-8-dimethylsulfamoyl-4-oxo-4,5-dihydro-3H-pyrrolo[2,3-c]quinoline-1-carboxamide | D |
| 27 | | 8-Methylsulfamoyl-4-oxo-4,5-dihydro-3H-pyrrolo[2,3-c]quinoline-1-ethyl carboxylate | B |
| 28 | | 8-(Morpholine-4-sulfonyl)-4-oxo-4,5-dihydro-3H-pyrrolo[2,3-c]quinoline-1-ethyl carboxylate | B |

TABLE 1-continued

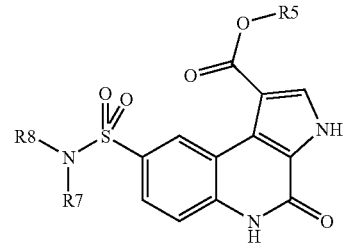

(II)

| Compound | Formula | Name | IC$_{50}$ |
|---|---|---|---|
| 29 | | 8-(2-Ethoxycarbonyl-ethylsulfamoyl)-4-oxo-4,5-dihydro-3H-pyrrolo[2,3-c]quinoline-1-ethyl carboxylate | C |
| 111 | | 8-Cyclohexylsulfamoyl-4-oxo-4,5-dihydro-3H-pyrrolo[2,3-c]quinoline-1-methyl carboxylate | C |
| 30 | | 8-Cyclohexylsulfamoyl-4-oxo-4,5-dihydro-3H-pyrrolo[2,3-c]quinoline-1-ethyl carboxylate | B |
| 31 | | 8-Cycloheptylsulfamoyl-4-oxo-4,5-dihydro-3H-pyrrolo[2,3-c]quinoline-1-ethyl carboxylate | B |
| 32 | | 8-(3-Dimethylamino-propylsulfamoyl)-4-oxo-4,5-dihydro-3H-pyrrolo[2,3-c]quinoline-1-ethyl carboxylate | B |
| 33 | | 8-(4-Amino-butylsulfamoyl)-4-oxo-4,5-dihydro-3H-pyrrolo[2,3-c]quinoline-1-ethyl carboxylate | B |

TABLE 1-continued

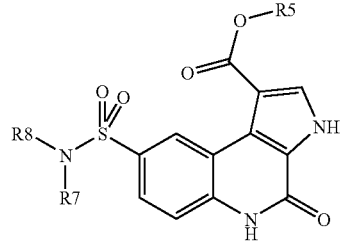
(II)

| Compound | Formula | Name | IC$_{50}$ |
|---|---|---|---|
| 34 | | 8-[(3-Chlorophenyl)-methyl-sulfamoyl)-4-oxo-4,5-dihydro-3H-pyrrolo[2,3-c]quinoline-1-ethyl carboxylate | B |
| 91 | | 4-Oxo-8-(piperidin-4-ylsulfamoyl)-4,5-dihydro-3H-pyrrolo[2,3-c]quinoline-1-ethyl carboxylate | B |
| 112 | | 4-Oxo-8-(piperidin-3-ylsulfamoyl)-4,5-dihydro-3H-pyrrolo[2,3-c]quinoline-1-methyl carboxylate | C |
| 113 | | 4-Oxo-8-(piperidin-4-ylsulfamoyl)-4,5-dihydro-3H-pyrrolo[2,3-c]quinoline-1-methyl carboxylate | B |
| 114 | | 4-Oxo-8-(piperidin-4-ylsulfamoyl)-4,5-dihydro-3H-pyrrolo[2,3-c]quinoline-1-propyl carboxylate | A |
| 115 | | 4-Oxo-8-(piperidin-4-ylsulfamoyl)-4,5-dihydro-3H-pyrrolo[2,3-c]quinoline-1-butyl carboxylate | A |

TABLE 1-continued

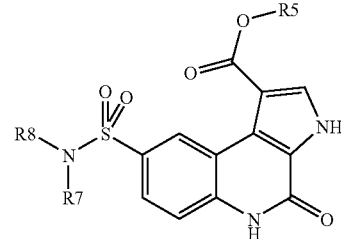
(II)

| Compound | Formula | Name | IC$_{50}$ |
|---|---|---|---|
| 116 | | 4-Oxo-8-(piperidin-4-ylsulfamoyl)-4,5-dihydro-3H-pyrrolo[2,3-c]quinoline-1-pentyl carboxylate | A |
| 117 | | 4-Oxo-8-(piperidin-4-ylsulfamoyl)-4,5-dihydro-3H-pyrrolo[2,3-c]quinoline-1-methylcyclohexyl carboxylate | B |
| 118 | | 4-Oxo-8-(piperidin-4-ylsulfamoyl)-4,5-dihydro-3H-pyrrolo[2,3-c]quinoline-1-methyltetrahydrofuran-3-yl carboxylate | B |
| 119 | | 8-(1-Methyl-piperidin-4-ylsulfamoyl)-4-oxo-4,5-dihydro-3H-pyrrolo[2,3-c]quinoline-1-cyclopentyl carboxylate | B |

TABLE 1-continued

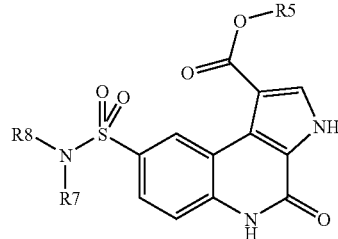

(II)

| Compound | Formula | Name | IC$_{50}$ |
|---|---|---|---|
| 120 | | 8-(Methyl-piperidin-4-yl-sulfamoyl)-4-oxo-4,5-dihydro-3H-pyrrolo[2,3-c]quinoline-1-propyl carboxylate | A |
| 121 | | 4-Oxo-8-[(piperidin-4-ylmethyl)-sulfamoyl]-4,5-dihydro-3H-pyrrolo[2,3-c]quinoline-1-ethyl carboxylate | C |
| 122 | | 8-(8-Aza-bicyclo[3.2.1]oct-3-ylsulfamoyl)-4-oxo-4,5-dihydro-3H-pyrrolo[2,3-c]quinoline-1-ethyl carboxylate | A |
| 92 | | 8-Cyclopentylsulfamoyl-4-oxo-4,5-dihydro-3H-pyrrolo[2,3-c]quinoline-1-methyl carboxylate | C |
| 93 | | 8-(Hexahydro-pyrrolo[3,4-c]pyrrole-2-sulfonyl)-4-oxo-4,5-dihydro-3H-pyrrolo[2,3-c]quinoline-1-ethyl carboxylate | B |
| 94 | | 8-(1-Azabicyclo[2.2.2]oct-3-ylsulfamoyl)-4-oxo-4,5-dihydro-3H-pyrrolo[2,3-c]quinoline-1-ethyl carboxylate | B |

TABLE 1-continued

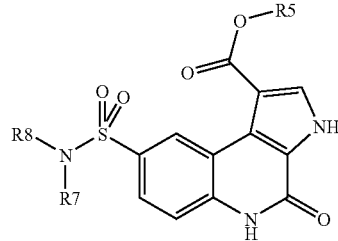

(II)

| Compound | Formula | Name | IC$_{50}$ |
|---|---|---|---|
| 95 | | 8-(4-Methyl-piperazine-1-sulfonyl)-4-oxo-4,5-dihydro-3H-pyrrolo[2,3-c]quinoline-1-ethyl carboxylate | C |
| 96 | | 4-Oxo-8-sulfamoyl-4,5-dihydro-3H-pyrrolo[2,3-c]quinoline-1-ethyl carboxylate | B |
| 97 | | 4-Oxo-8-[(pyrrolidin-3-methyl)-sulfamoyl]-4,5-dihydro-3H-pyrrolo[2,3-c]quinoline-1-ethyl carboxylate | B |
| 98 | | 4-Oxo-8-(4-hydroxy-phenylsulfamoyl)-4,5-dihydro-3H-pyrrolo[2,3-c]quinoline-1-ethyl carboxylate | A |
| 123 | | 8-Cyclopropylsulfamoyl-4-oxo-4,5-dihydro-3H-pyrrolo[2,3-c]quinoline-1-ethyl carboxylate | B |
| 124 | | 8-Cyclopropylsulfamoyl-4-oxo-4,5-dihydro-3H-pyrrolo[2,3-c]quinoline-1-propyl carboxylate | B |

TABLE 1-continued (II)

| Compound | Formula | Name | IC$_{50}$ |
|---|---|---|---|
| 125 | | 8-(Cyclopropyl-methyl-sulfamoyl)-4-oxo-4,5-dihydro-3H-pyrrolo[2,3-c]quinoline-1-propyl carboxylate | A |
| 126 | | 8-[(2-Cyano-ethyl)-methyl-sulfamoyl]-4-oxo-4,5-dihydro-3H-pyrrolo[2,3-c]quinoline-1-propyl carboxylate | B |
| 127 | | 8-[(2-Cyano-ethyl)-cyclopropyl-sulfamoyl]-4-oxo-4,5-dihydro-3H-pyrrolo[2,3-c]quinoline-1-ethyl carboxylate | A |
| 128 | | 8-(Cyanomethyl-methyl-sulfamoyl)-4-oxo-4,5-dihydro-3H-pyrrolo[2,3-c]quinoline-1-propyl carboxylate | B |
| 129 | | 8-([1,3]Dioxolan-2-ylmethyl-methyl-sulfamoyl)-4-oxo-4,5-dihydro-3H-pyrrolo[2,3-c]quinoline-1-propyl carboxylate | B |

TABLE 1-continued

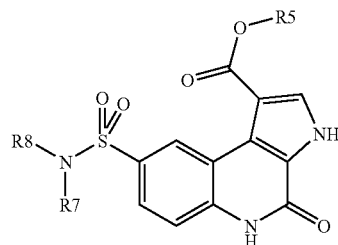

(II)

| Compound | Formula | Name | IC$_{50}$ |
|---|---|---|---|
| 130 | | 8-[(1-Benzhydryl-azetidin-3-yl)-methyl-sulfamoyl]-4-oxo-4,5-dihydro-3H-pyrrolo[2,3-c]quinoline-1-propyl carboxylate | B |
| 131 | | 8-[Methyl-(tetrahydro-thiopyran-4-yl)-sulfamoyl]-4-oxo-4,5-dihydro-3H-pyrrolo[2,3-c]quinoline-1-propyl carboxylate | B |
| 132 | | 8-[(1,1-Dioxo-hexahydro-1l6-thiopyran-4-yl)-methyl-sulfamoyl]-4-oxo-4,5-dihydro-3H-pyrrolo[2,3-c]quinoline-1-propyl carboxylate | C |
| 133 | | 8-[Methyl-(tetrahydro-pyran-4-yl)-sulfamoyl]-4-oxo-4,5-dihydro-3H-pyrrolo[2,3-c]quinoline-1-propyl carboxylate | A |

TABLE 1-continued

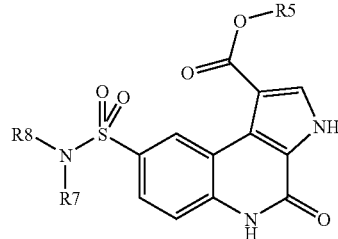

(II)

| Compound | Formula | Name | IC$_{50}$ |
|---|---|---|---|
| 134 | | 8-(Methyl-prop-2-ynyl-sulfamoyl)-4-oxo-4,5-dihydro-3H-pyrrolo[2,3-c]quinoline-1-propyl carboxylate | B |
| 135 | | 8-[Methyl-(2-methylsulfanyl-ethyl)-sulfamoyl]-4-oxo-4,5-dihydro-3H-pyrrolo[2,3-c]quinoline-1-propyl carboxylate | B |
| 136 | | 8-[(2-Dimethylamino-ethyl)-methyl-sulfamoyl]-4-oxo-4,5-dihydro-3H-pyrrolo[2,3-c]quinoline-1-propyl carboxylate | A |
| 137 | | 8-[Methyl-(2-pyrrolidin-1-yl-ethyl)-sulfamoyl]-4-oxo-4,5-dihydro-3H-pyrrolo[2,3-c]quinoline-1-propyl carboxylate | B |
| 138 | | 8-[(2-Diethylamino-ethyl)-methyl-sulfamoyl]-4-oxo-4,5-dihydro-3H-pyrrolo[2,3-c]quinoline-1-propyl carboxylate | B |

TABLE 1-continued

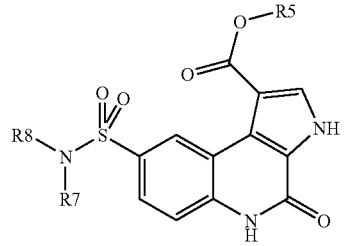

(II)

| Compound | Formula | Name | IC$_{50}$ |
|---|---|---|---|
| 139 | | 8-[Methyl-(2-methylamino-ethyl)-sulfamoyl]-4-oxo-4,5-dihydro-3H-pyrrolo[2,3-c]quinoline-1-propyl carboxylate hydrochloride | A |
| 140 | | 8-{[2-(tert-Butoxycarbonyl-methyl-amino)-ethyl]-methyl-sulfamoyl}-4-oxo-4,5-dihydro-3H-pyrrolo[2,3-c]quinoline-1-propyl carboxylate | C |
| 141 | | 8-[Cyclopropyl-(2-methyl-2-methylamino-propyl)-sulfamoyl]4-oxo-4,5-dihydro-3H-pyrrolo[2,3-c]quinoline-1-propyl carboxylate hydrochloride | B |
| 142 | | 8-[Cyclopropyl-(2-isopropylamino-ethyl)-sulfamoyl]-4-oxo-4,5-dihydro-3H-pyrrolo[2,3-c]quinoline-1-propyl carboxylate hydrochloride | B |

TABLE 1-continued

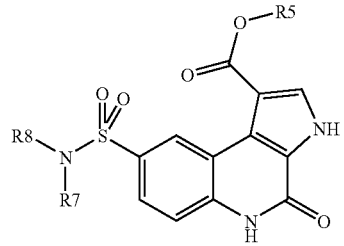

(II)

| Compound | Formula | Name | IC$_{50}$ |
|---|---|---|---|
| 143 | | 8-[Cyclopropyl-(1H-imidazol-4-ylmethyl)-sulfamoyl]-4-oxo-4,5-dihydro-3H-pyrrolo[2,3-c]quinoline-1-propyl carboxylate hydrochloride | B |
| 144 | | (S)-8-(Cyclopropyl-pyrrolidin-2-ylmethyl-sulfamoyl)-4-oxo-4,5-dihydro-3H-pyrrolo[2,3-c]quinoline-1-propyl carboxylate hydrochloride | A |
| 145 | | (S)-8-[Cyclopropyl-(1-methyl-pyrrolidin-2-ylmethyl)-sulfamoyl]-4-oxo-4,5-dihydro-3H-pyrrolo[2,3-c]quinoline-1-propyl carboxylate | B |
| 146 | | (R)-8-[Cyclopropyl-(1-methyl-pyrrolidin-2-ylmethyl)-sulfamoyl]-4-oxo-4,5-dihydro-3H-pyrrolo[2,3-c]quinoline-1-propyl carboxylate | B |

TABLE 1-continued

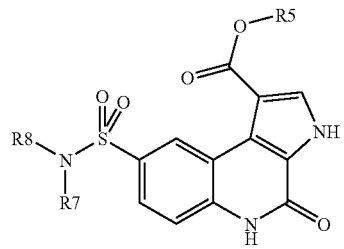

(II)

| Compound | Formula | Name | IC$_{50}$ |
|---|---|---|---|
| 147 | | (R)-8-[(1-tert-Butoxycarbonyl-pyrrolidin-2-ylmethyl)-cyclopropyl-sulfamoyl]-4-oxo-4,5-dihydro-3H-pyrrolo[2,3-c]quinoline-1-propyl carboxylate | C |
| 148 | | (R)-8-(Cyclopropyl-pyrrolidin-2-ylmethyl-sulfamoyl)-4-oxo-4,5-dihydro-3H-pyrrolo[2,3-c]quinoline-1-propyl carboxylate hydrochloride | B |
| 149 | | (S)-8-(Isopropyl-pyrrolidin-2-ylmethyl-sulfamoyl)-4-oxo-4,5-dihydro-3H-pyrrolo[2,3-c]quinoline-1-propyl carboxylate hydrochloride | A |
| 150 | | (S)-4-Oxo-8-(prop-2-ynyl-pyrrolidin-2-ylmethyl-sulfamoyl)-4,5-dihydro-3H-pyrrolo[2,3-c]quinoline-1-propyl carboxylate hydrochloride | A |

TABLE 1-continued

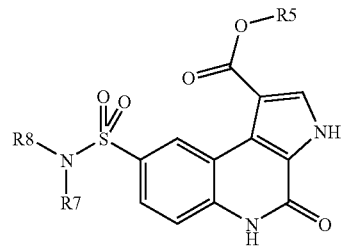
(II)

| Compound | Formula | Name | IC$_{50}$ |
|---|---|---|---|
| 151 | | (S)-8-[(1-Methyl-pyrrolidin-2-ylmethyl)-prop-2-ynyl-sulfamoyl]-4-oxo-4,5-dihydro-3H-pyrrolo[2,3-c]quinoline-1-propyl carboxylate | B |
| 152 | | (S)-8-[(2-tert-Butoxycarbonylamino-propyl)-cyclopropyl-sulfamoyl]-4-oxo-4,5-dihydro-3H-pyrrolo[2,3-c]quinoline-1-propyl carboxylate | B |
| 153 | | (S)-8-[(2-Amino-propyl)-cyclopropyl-sulfamoyl]-4-oxo-4,5-dihydro-3H-pyrrolo[2,3-c]quinoline-1-propyl carboxylate hydrochloride | A |
| 154 | | (R)-8-[(2-tert-Butoxycarbonylamino-propyl)-cyclopropyl-sulfamoyl]-4-oxo-4,5-dihydro-3H-pyrrolo[2,3-c]quinoline-1-propyl carboxylate | C |

TABLE 1-continued

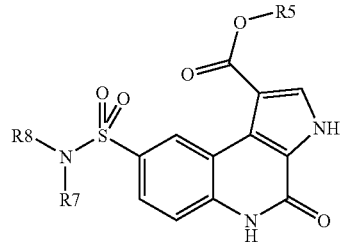

(II)

| Compound | Formula | Name | IC$_{50}$ |
|---|---|---|---|
| 155 | | (R)-8-[(2-Amino-propyl)-cyclopropyl-sulfamoyl]-4-oxo-4,5-dihydro-3H-pyrrolo[2,3-c]quinoline-1-propyl carboxylate hydrochloride | A |
| 156 | | 8-[(2-Methylamino-ethyl)-prop-2-ynyl-sulfamoyl]-4-oxo-4,5-dihydro-3H-pyrrolo[2,3-c]quinoline-1-propyl carboxylate hydrochloride | A |
| 157 | | 8-{[2-tert-Butoxycarbonyl-methyl-amino)-ethyl]-prop-2-ynyl-sulfamoyl}-4-oxo-4,5-dihydro-3H-pyrrolo[2,3-c]quinoline-1-propyl carboxylate | A |
| 158 | | 8-[(2-Isopropylamino-ethyl)-prop-2-ynyl-sulfamoyl]-4-oxo-4,5-dihydro-3H-pyrrolo[2,3-c]quinoline-1-propyl carboxylate hydrochloride | B |

TABLE 1-continued

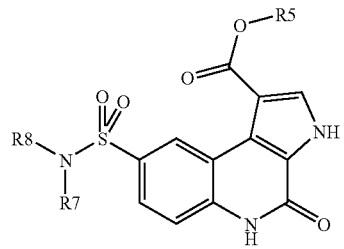

(II)

| Compound | Formula | Name | IC$_{50}$ |
|---|---|---|---|
| 159 | | 8-{[2-(tert-Butoxycarbonyl-isopropyl-amino)-ethyl]-prop-2-ynyl-sulfamoyl}-4-oxo-4,5-dihydro-3H-pyrrolo[2,3-c]quinoline-1-propyl-carboxylate | C |
| 160 | | 8-(Ethyl-pyrrolidin-3-yl-sulfamoyl)-4-oxo-4,5-dihydro-3H-pyrrolo[2,3-c]quinoline-1-propyl carboxylate hydrochloride | A |
| 161 | | 8-[Ethyl-(1-methyl-pyrrolidin-3-yl)-sulfamoyl]-4-oxo-4,5-dihydro-3H-pyrrolo[2,3-c]quinoline-1-propyl carboxylate | A |
| 162 | | 4-Oxo-8-(pyrrolidine-1-sulfonyl)-4,5-dihydro-3H-pyrrolo[2,3-c]quinoline-1-ethyl carboxylate | B |

TABLE 1-continued

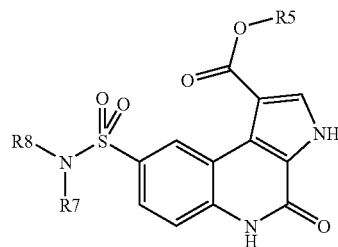

| Compound | Formula | Name | IC$_{50}$ |
|---|---|---|---|
| 163 | | 4-Oxo-8-(2-pyrrolidin-1-ylmethyl-pyrrolidine-1-sulfonyl)-4,5-dihydro-3H-pyrrolo[2,3-c]quinoline-1-ethyl carboxylate | B |
| 164 | | (S)-8-(3-tert-Butoxycarbonylamino-pyrrolidine-1-sulfonyl)-4-oxo-4,5-dihydro-3H-pyrrolo[2,3-c]quinoline-1-propyl carboxylate | C |
| 165 | | (S)-8-(3-tert-Butoxycarbonylamino-pyrrolidine-1-sulfonyl)-4-oxo-4,5-dihydro-3H-pyrrolo[2,3-c]quinoline-1-carboxylic acid | D |
| 166 | | (S)-8-(3-Amino-cyclopentanesulfonyl)-4-oxo-4,5-dihydro-3H-pyrrolo[2,3-c]quinoline-1-propyl carboxylate hydrochloride | A |
| 167 | | (R)-8-(3-Amino-cyclopentanesulfonyl)-4-oxo-4,5-dihydro-3H-pyrrolo[2,3-c]quinoline-1-propyl carboxylate hydrochloride | B |

TABLE 1-continued

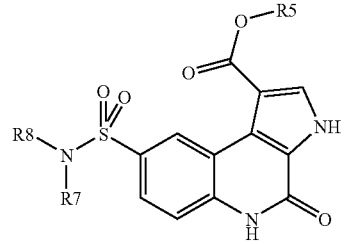

(II)

| Compound | Formula | Name | IC$_{50}$ |
|---|---|---|---|
| 168 | | 8-(3-Methylamino-pyrrolidine-1-sulfonyl)-4-oxo-4,5-dihydro-3H-pyrrolo[2,3-c]quinoline-1-propyl carboxylate hydrochloride | B |
| 169 | | 8-[3-tert-Butoxycarbonyl-methyl-amino)-pyrrolidine-1-sulfonyl]-4-oxo-4,5-dihydro-3H-pyrrolo[2,3-c]quinoline-1-propyl carboxylate | C |
| 170 | | 8-[3-tert-Butoxycarbonyl-methyl amino)-pyrrolidine-1-sulfonyl]-4-oxo-4,5-dihydro-3H-pyrrolo[2,3-c]quinoline-1-carboxylic acid | D |
| 171 | | (S)-8-(3-Dimethylamino-cyclopentanesulfonyl)-4-oxo-4,5-dihydro-3H-pyrrolo[2,3-c]quinoline-1-propyl carboxylate | B |
| 172 | | (R)-8-(3-Dimethylamino-cyclopentanesulfonyl)-4-oxo-4,5-dihydro-3H-pyrrolo[2,3-c]quinoline-1-propyl carboxylate | C |

TABLE 1-continued

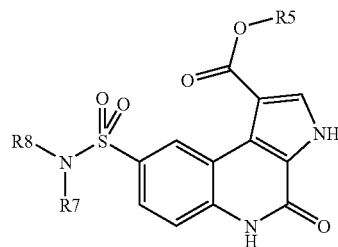

(II)

| Compound | Formula | Name | IC$_{50}$ |
|---|---|---|---|
| 173 | | 8-[(2-Hydroxy-ethyl)-isopropyl-sulfamoyl]-4-oxo-4,5-dihydro-3H-pyrrolo[2,3-c]quinoline-1-propyl carboxylate | A |
| 174 | | 8-[Cyclopropyl-(2-hydroxy-ethyl)-sulfamoyl]-4-oxo-4,5-dihydro-3H-pyrrolo[2,3-c]quinoline-1-propyl carboxylate | A |
| 175 | | 8-[(2-Hydroxy-ethyl)-prop-2-ynyl-sulfamoyl]-4-oxo-4,5-dihydro-3H-pyrrolo[2,3-c]quinoline-1-propyl carboxylate | B |
| 176 | | 8-[Bis-(2-hydroxy-ethyl)-sulfamoyl]-4-oxo-4,5-dihydro-3H-pyrrolo[2,3-c]quinoline-1-propyl carboxylate | B |

TABLE 1-continued

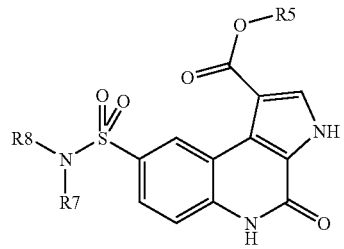

(II)

| Compound | Formula | Name | IC$_{50}$ |
|---|---|---|---|
| 177 | | 8-(Carbamoylmethyl-methyl-sulfamoyl)-4-oxo-4,5-dihydro-3H-pyrrolo[2,3-c]quinoline-1-propyl carboxylate | B |
| 178 | | 8-(Carbamoylmethyl-methyl-sulfamoyl)-4-oxo-4,5-dihydro-3H-pyrrolo[2,3-c]quinoline-1-carboxylic acid | C |
| 179 | | 8-(3-Carbamoyl-piperidine-1-sulfonyl)-4-oxo-4,5-dihydro-3H-pyrrolo[2,3-c]quinoline-1-propyl carboxylate | B |
| 180 | | 8-(3-Carbamoyl-piperidine-1-sulfonyl)-4-oxo-4,5-dihydro-3H-pyrrolo[2,3-c]quinoline-1-carboxylic acid | D |

TABLE 1-continued

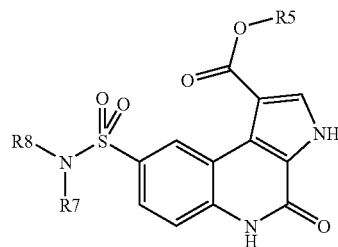

(II)

| Compound | Formula | Name | IC$_{50}$ |
|---|---|---|---|
| 181 | | 8-[(2-Benzyloxy-ethyl)-cyclopropyl-sulfamoyl]-4-oxo-4,5-dihydro-3H-pyrrolo[2,3-c]quinoline-1-propyl carboxylate | C |
| 182 | | 8-(Carboxymethyl-methyl-sulfamoyl)-4-oxo-4,5-dihydro-3H-pyrrolo[2,3-c]quinoline-1-propyl carboxylate | C |
| 183 | | 8-tert-Butoxycarbonylmethyl-methyl-sulfamoyl)-4-oxo-4,5-dihydro-3H-pyrrolo[2,3-c]quinoline-1-propyl carboxylate | C |
| 184 | | 8-[(2-Dimethylamino-ethyl)-methyl-sulfamoyl]-7-fluoro-4-oxo-4,5-dihydro-3H-pyrrolo[2,3-c]quinoline-1-propyl carboxylate | A |

TABLE 1-continued

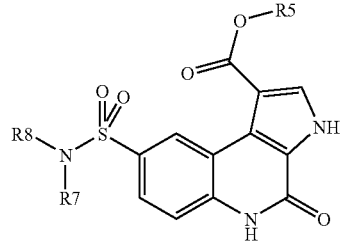

(II)

| Compound | Formula | Name | IC$_{50}$ |
|---|---|---|---|
| 185 | | 7-Fluoro-8-[(2-hydroxy-ethyl)-isopropyl-sulfamoyl]-4-oxo-4,5-dihydro-3H-pyrrolo[2,3-c]quinoline-1-propyl carboxylate | A |
| 186 | | 8-Dimethylsulfamoyl-7-fluoro-4-oxo-4,5-dihydro-3H-pyrrolo[2,3-c]quinoline-1-propyl carboxylate | B |
| 187 | | 8-(Cyclopropyl-methyl-sulfamoyl)-7-fluoro-4-oxo-4,5-dihydro-3H-pyrrolo[2,3-c]quinoline-1-propyl carboxylate | B |
| 188 | | 8-(Cyclopropyl-methyl-sulfamoyl)-7-methoxy-4-oxo-4,5-dihydro-3H-pyrrolo[2,3-c]quinoline-1-propyl carboxylate | C |
| 189 | | 7-Chloro-8-dimethylsulfamoyl-4-oxo-4,5-dihydro-3H-pyrrolo[2,3-c]quinoline-1-propyl carboxylate | B |

TABLE 1-continued

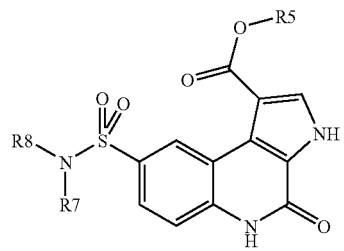

(II)

| Compound | Formula | Name | IC$_{50}$ |
|---|---|---|---|
| 190 | | (S)-8-(3-Amino-cyclopentanesulfonyl)-7-chloro-4-oxo-4,5-dihydro-3H-pyrrolo[2,3-c]quinoline-1-propyl carboxylate hydrochloride | B |
| 191 | | 4-Oxo-8-(piperidin-1-ylsulfamoyl)-4,5-dihydro-3H-pyrrolo[2,3-c]quinoline-1-methyl carboxylate | C |
| 192 | | 8-(Hexahydro-cyclopenta[c]pyrrol-2-ylsulfamoyl)-4-oxo-4,5-dihydro-3H-pyrrolo[2,3-c]quinoline-1-methyl carboxylate | C |
| 193 | | 8-(4-Methyl-piperazin-1-ylsulfamoyl)-4-oxo-4,5-dihydro-3H-pyrrolo[2,3-c]quinoline-1-methyl carboxylate | C |

TABLE II (III)

| Compound | Formula | Name | IC50 |
|---|---|---|---|
| 35 | | 4-Oxo-8-phenylmethanesulfonyl-4,5-dihydro-3H-pyrrolo[2,3-c]quinoline-1-ethyl carboxylate | A |
| 36 | | 8-(2,6-Dichlorophenylmethanesulfonyl)-4-oxo-4,5-dihydro-3H-pyrrolo[2,3-c]quinoline-1-ethyl carboxylate | B |
| 194 | | 8-(2,6-Dichlorophenylmethanesulfonyl)-4-oxo-4,5-dihydro-3H-pyrrolo[2,3-c]quinoline-1-ethyl carboxylate | C |
| 195 | | 4-Oxo-8-(pyridin-4-ylmethanesulfonyl)-4,5-dihydro-3H-pyrrolo[2,3-c]quinoline-1-ethyl carboxylate | B |
| 196 | | 4-Oxo-8-(pyridin-2-ylmethanesulfonyl)-4,5-dihydro-3H-pyrrolo[2,3-c]quinoline-1-ethyl carboxylate | B |
| 197 | | 8-Cyclohexanesulfonyl-4-oxo-4,5-dihydro-3H-pyrrolo[2,3-c]quinoline-1-ethyl carboxylate | B |

TABLE II-continued
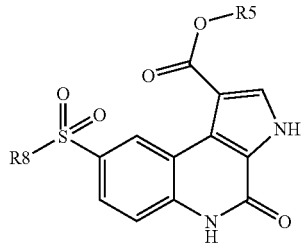
(III)
| Compound | Formula | Name | IC50 |
|---|---|---|---|
| 198 | EtO₂C ... | 4-Oxo-8-phenylmethanesulfinyl-4,5-dihydro-3H-pyrrolo[2,3-c]quinoline-1-ethyl carboxylate | B |
TABLE III
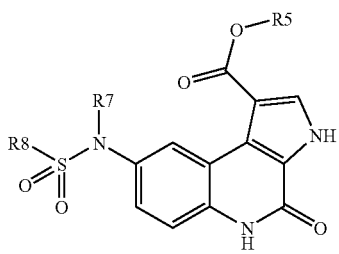
(IV)
| Compound | Formula | Name | IC50 |
|---|---|---|---|
| 37 | EtO₂C ... | 8-Benzenesulfonylamino-4-oxo-4,5-dihydro-3H-pyrrolo[2,3-c]quinoline-1-ethyl carboxylate | B |
| 38 | EtO₂C ... | 8-Methanesulfonylamino-4-oxo-4,5-dihydro-3H-pyrrolo[2,3-c]quinoline-1-ethyl carboxylate | B |

TABLE III-continued

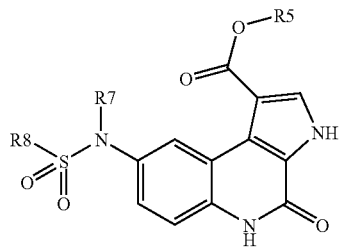

(IV)

| Compound | Formula | Name | IC50 |
|---|---|---|---|
| 39 | 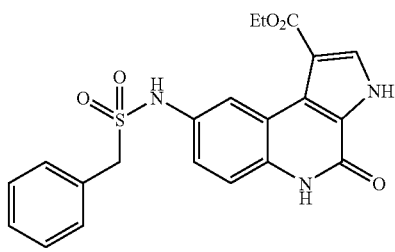 [SMILES: CCOC(=O)c1c[nH]c2c(=O)[nH]c3ccc(NS(=O)(=O)Cc4ccccc4)cc3c12] | 4-Oxo-8-phenylmethanesulfonylamino-4,5-dihydro-3H-pyrrolo[2,3-c]quinoline-1-ethyl carboxylate | B |
| 40 | 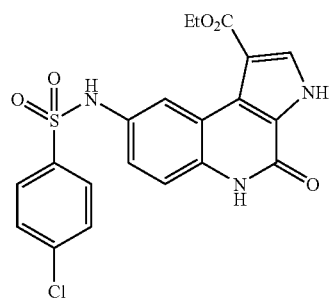 [SMILES: CCOC(=O)c1c[nH]c2c(=O)[nH]c3ccc(NS(=O)(=O)c4ccc(Cl)cc4)cc3c12] | 8-(4-Chloro-benzenesulfonylamino)-4-oxo-4,5-dihydro-3H-pyrrolo[2,3-c]quinoline-1-ethyl carboxylate | B |
| 41 | 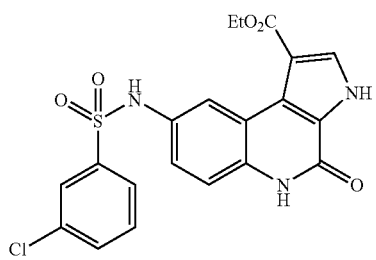 [SMILES: CCOC(=O)c1c[nH]c2c(=O)[nH]c3ccc(NS(=O)(=O)c4cccc(Cl)c4)cc3c12] | 8-(3-Chloro-benzenesulfonylamino)-4-oxo-4,5-dihydro-3H-pyrrolo[2,3-c]quinoline-1-ethyl carboxylate | B |
| 42 | 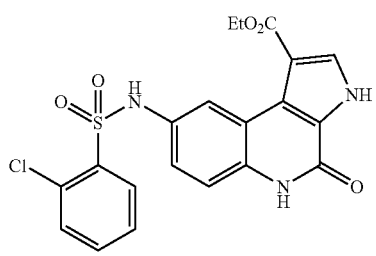 [SMILES: CCOC(=O)c1c[nH]c2c(=O)[nH]c3ccc(NS(=O)(=O)c4ccccc4Cl)cc3c12] | 8-(2-Chloro-benzenesulfonylamino)-4-oxo-4,5-dihydro-3H-pyrrolo[2,3-c]quinoline-1-ethyl carboxylate | D |

TABLE III-continued (IV)

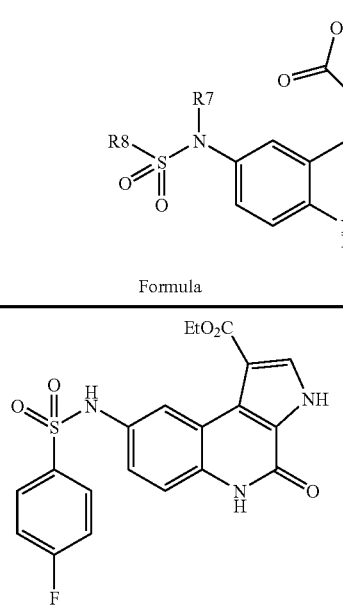

| Compound | Formula | Name | IC50 |
|---|---|---|---|
| 43 | 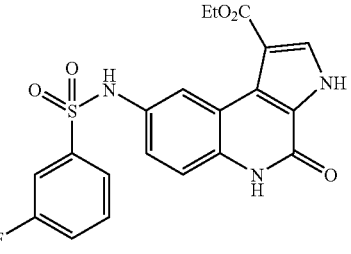 | 8-(4-Fluoro-benzenesulfonylamino)-4-oxo-4,5-dihydro-3H-pyrrolo[2,3-c]quinoline-1-ethyl carboxylate | B |
| 44 | 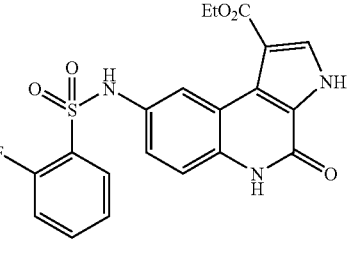 | 8-(3-Fluoro-benzenesulfonylamino)-4-oxo-4,5-dihydro-3H-pyrrolo[2,3-c]quinoline-1-ethyl carboxylate | B |
| 45 | 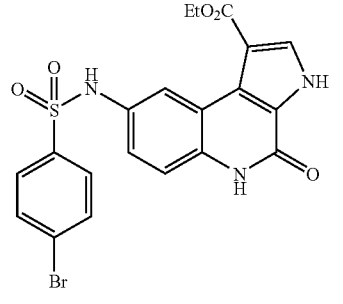 [SMILES: CCOC(=O)c1c[nH]c2c(=O)[nH]c3ccc(NS(=O)(=O)c4ccc(Br)cc4)cc3c12] | 8-(2-Fluoro-benzenesulfonylamino)-4-oxo-4,5-dihydro-3H-pyrrolo[2,3-c]quinoline-1-ethyl carboxylate | C |
| 46 | 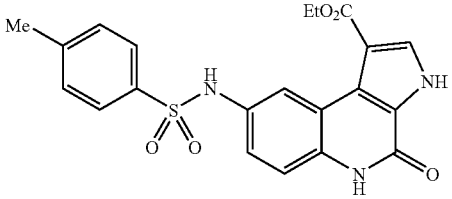 [SMILES: CCOC(=O)c1c[nH]c2c(=O)[nH]c3ccc(NS(=O)(=O)c4ccc(C)cc4)cc3c12] | 8-(4-Bromo-benzenesulfonylamino)-4-oxo-4,5-dihydro-3H-pyrrolo[2,3-c]quinoline-1-ethyl carboxylate | B |
| 47 | | 4-Oxo-8-(4-toluenesulfonylamino)-4,5-dihydro-3H-pyrrolo[2,3-c]quinoline-1-ethyl carboxylate | B |

TABLE III-continued (IV)

| Compound | Formula | Name | IC50 |
|---|---|---|---|
| 48 | | 4-Oxo-8-(3-toluenesulfonylamino)-4,5-dihydro-3H-pyrrolo[2,3-c]quinoline-1-ethyl carboxylate | D |
| 49 | | 8-(4-tert-Butyl-benzenesulfonylamino)-4-oxo-4,5-dihydro-3H-pyrrolo[2,3-c]quinoline-1-ethyl carboxylate | D |
| 50 | | 8-(4-Methoxy-benzenesulfonylamino)-4-oxo-4,5-dihydro-3H-pyrrolo[2,3-c]quinoline-1-ethyl carboxylate | C |
| 51 | | 8-(3-Methoxy-benzenesulfonylamino)-4-oxo-4,5-dihydro-3H-pyrrolo[2,3-c]quinoline-1-ethyl carboxylate | C |
| 52 | | 8-(4-Acetylamino-benzenesulfonylamino)-4-oxo-4,5-dihydro-3H-pyrrolo[2,3-c]quinoline-1-ethyl carboxylate | C |

TABLE III-continued (IV)

| Compound | Formula | Name | IC50 |
|---|---|---|---|
| 53 | | 8-(4-Nitro-benzenesulfonylamino)-4-oxo-4,5-dihydro-3H-pyrrolo[2,3-c]quinoline-1-ethyl carboxylate | B |
| 54 | | 8-(Naphthalene-2-sulfonylamino)-4-oxo-4,5-dihydro-3H-pyrrolo[2,3-c]quinoline-1-ethyl carboxylate | D |
| 55 | | 8-(4-Acetyl-benzenesulfonylamino)-4-oxo-4,5-dihydro-3H-pyrrolo[2,3-c]quinoline-1-ethyl carboxylate | C |
| 56 | | 4-Oxo-8-(thiophene-2-sulfonylamino)-4,5-dihydro-3H-pyrrolo[2,3-c]quinoline-1-ethyl carboxylate | B |
| 57 | | 8-(5-Chloro-thiophene-2-sulfonylamino)-4-oxo-4,5-dihydro-3H-pyrrolo[2,3-c]quinoline-1-ethyl carboxylate | B |
| 58 | | 8-(Benzenesulfonyl-methyl-amino)-4-oxo-4,5-dihydro-3H-pyrrolo[2,3-c]quinoline-1-ethyl carboxylate | B |

TABLE III-continued
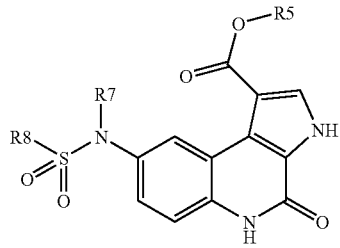
(IV)
| Compound | Formula | Name | IC50 |
|---|---|---|---|
| 59 | 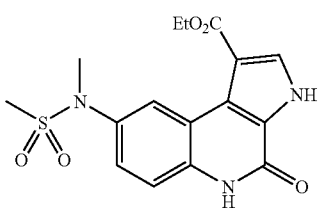 [SMILES: CCOC(=O)c1c[nH]c2c(=O)[nH]c3ccc(N(C)S(C)(=O)=O)cc3c12] | 8-(Methanesulfonyl-methyl-amino)-4-oxo-4,5-dihydro-3H-pyrrolo[2,3-c]quinoline-1-ethyl carboxylate | B |
TABLE IV
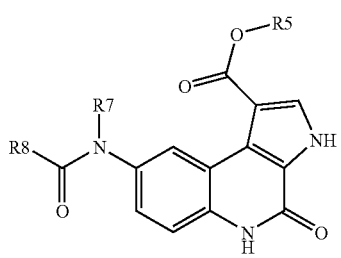
(V)
| Compound | Formula | Name | IC50 |
|---|---|---|---|
| 60 | 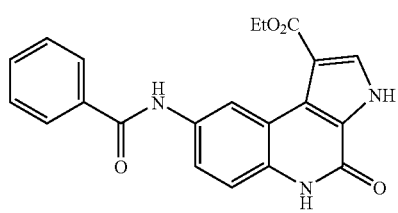 [SMILES: CCOC(=O)c1c[nH]c2c(=O)[nH]c3ccc(NC(=O)c4ccccc4)cc3c12] | 8-Benzoylamino-4-oxo-4,5-dihydro-3H-pyrrolo[2,3-c]quinoline-1-ethyl carboxylate | C |
| 61 | 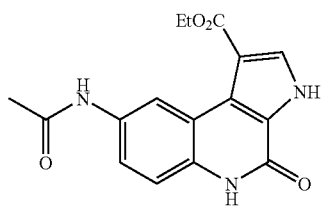 [SMILES: CCOC(=O)c1c[nH]c2c(=O)[nH]c3ccc(NC(C)=O)cc3c12] | 8-Acetylamino-4-oxo-4,5-dihydro-3H-pyrrolo[2,3-c]quinoline-1-ethyl carboxylate | C |

TABLE V (VI)

| Compound | Formula | Name | IC50 |
|---|---|---|---|
| 62 | EtO2C, NMe2 substituent | 8-Dimethylamino-4-oxo-4,5-dihydro-3H-pyrrolo[2,3-c]quinoline-1-ethyl carboxylate | C |
| 63 | EtO2C, NHMe substituent | 8-Methylamino-4-oxo-4,5-dihydro-3H-pyrrolo[2,3-c]quinoline-1-ethyl carboxylate | C |
| 64 | EtO2C, H2N substituent | 8-Amino-4-oxo-4,5-dihydro-3H-pyrrolo[2,3-c]quinoline-1-ethyl carboxylate | C |
| 66 | EtO2C, O2N substituent | 8-Nitro-4-oxo-4,5-dihydro-3H-pyrrolo[2,3-c]quinoline-1-ethyl carboxylate | C |
| 67 | EtO2C, NO2 substituent | 6-Nitro-4-oxo-4,5-dihydro-3H-pyrrolo[2,3-c]quinoline-1-ethyl carboxylate | D |
| 65 | EtO2C, EtO2C-vinyl substituent | 8-(2-Ethoxycarbonyl-vinyl)-4-oxo-4,5-dihydro-3H-pyrrolo[2,3-c]quinoline-1-ethyl carboxylate | C |

TABLE V-continued

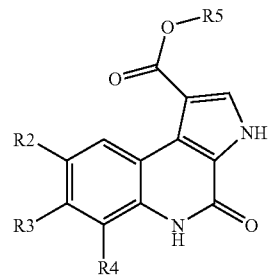

(VI)

| Compound | Formula | Name | IC50 |
|---|---|---|---|
| 68 | | 8-(2-Benzylcarbamoyl-vinyl)-4-oxo-4,5-dihydro-3H-pyrrolo[2,3-c]quinoline-1-ethyl carboxylate | C |
| 69 | | 8-[2-(2-Methoxycarbonyl-ethylcarbamoyl)-vinyl]-4-oxo-4,5-dihydro-3H-pyrrolo[2,3-c]quinoline-1-ethyl carboxylate | C |
| 70 | | 4-Oxo-8-styryl-4,5-dihydro-3H-pyrrolo[2,3-c]quinoline-1-ethyl carboxylate | C |
| 199 | | 8-Ethynyl-4-oxo-4,5-dihydro-3H-pyrrolo[2,3-c]quinoline-1-ethyl carboxylate | C |
| 200 | | 4-Oxo-8-trimethylsilanylethynyl-4,5-dihydro-3H-pyrrolo[2,3-c]quinoline-1-ethyl carboxylate | C |

TABLE V-continued (VI)

| Compound | Formula | Name | IC50 |
|---|---|---|---|
| 201 | | 4-Oxo-8-phenylethynyl-4,5-dihydro-3H-pyrrolo[2,3-c]quinoline-1-ethyl carboxylate | C |
| 202 | | 4-Oxo-8-pyridin-2-ylethynyl-4,5-dihydro-3H-pyrrolo[2,3-c]quinoline-1-ethyl carboxylate | C |
| 203 | | 8-(3-Dimethylamino-prop-1-ynyl)-4-oxo-4,5-dihydro-3H-pyrrolo[2,3-c]quinoline-1-ethyl carboxylate | B |
| 204 | | 8-(3-Hydroxy-3-methyl-but-1-ynyl)-4-oxo-4,5-dihydro-3H-pyrrolo[2,3-c]quinoline-1-ethyl carboxylate | B |
| 205 | | 8-(3-Morpholin-4-yl-prop-1-ynyl)-4-oxo-4,5-dihydro-3H-pyrrolo[2,3-c]quinoline-1-ethyl carboxylate | B |

TABLE V-continued

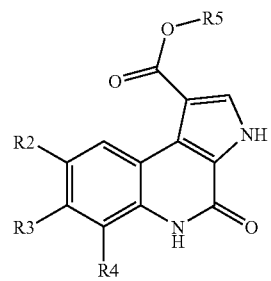

(VI)

| Compound | Formula | Name | IC50 |
|---|---|---|---|
| 206 | | 8-{3-[(2-Cyano-ethyl)-methyl-amino]-prop-1-ynyl}-4-oxo-4,5-dihydro-3H-pyrrolo[2,3-c]quinoline-1-ethyl carboxylate | B |
| 207 | | 4-Oxo-8-phenethyl-4,5-dihydro-3H-pyrrolo[2,3-c]quinoline-1-ethyl carboxylate | B |
| 208 | | 8-(3-Hydroxy-3-methyl-butyl)-4-oxo-4,5-dihydro-3H-pyrrolo[2,3-c]quinoline-1-ethyl carboxylate | B |
| 71 | | 8-Bromo-4-oxo-4,5-dihydro-3H-pyrrolo[2,3-c]quinoline-1-ethyl carboxylate | B |
| 209 | | 8-Iodo-4-oxo-4,5-dihydro-3H-pyrrolo[2,3-c]quinoline-1-ethyl carboxylate | B |

TABLE V-continued (VI)

| Compound | Formula | Name | IC50 |
|---|---|---|---|
| 210 | | 8-Iodo-4-oxo-4,5-dihydro-3H-pyrrolo[2,3-c]quinoline-1-propyl carboxylate | B |
| 211 | | 8-Iodo-4-oxo-4,5-dihydro-3H-pyrrolo[2,3-c]quinoline-1-cyclopentyl carboxylate | C |
| 212 | | 8-Iodo-4-oxo-4,5-dihydro-3H-pyrrolo[2,3-c]quinoline-1-isobutyl carboxylate | C |
| 72 | | 7,8-Dimethoxy-4-oxo-4,5-dihydro-3H-pyrrolo[2,3-c]quinoline-1-ethyl carboxylate | C |
| 213 | | 7-Methoxy-4-oxo-4,5-dihydro-3H-pyrrolo[2,3-c]quinoline-1-ethyl carboxylate | C |

TABLE V-continued

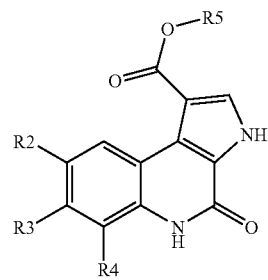

(VI)

| Compound | Formula | Name | IC50 |
|---|---|---|---|
| 214 | | 8-Iodo-7-methoxy-4-oxo-4,5-dihydro-3H-pyrrolo[2,3-c]quinoline-1-ethyl carboxylate | C |
| 99 | | 8-Fluoro-4-oxo-4,5-dihydro-3H-pyrrolo[2,3-c]quinoline-1-ethyl carboxylate | D |
| 100 | | 8-Fluoro-4-oxo-4,5-dihydro-3H-pyrrolo[2,3-c]quinoline-1-2-diethylaminoethyl carboxylate | D |
| 215 | | 7-Fluoro-4-oxo-4,5-dihydro-3H-pyrrolo[2,3-c]quinoline-1-ethyl carboxylate | C |
| 216 | | 7-Chloro-4-oxo-4,5-dihydro-3H-pyrrolo[2,3-c]quinoline-1-ethyl carboxylate | C |

TABLE V-continued (VI)

| Compound | Formula | Name | IC50 |
|---|---|---|---|
| 101 | EtO₂C, acetyl substituent | 8-Acetyl-4-oxo-4,5-dihydro-3H-pyrrolo[2,3-c]quinoline-1-ethyl carboxylate | C |
| 102 | EtO₂C, benzoyl substituent | 8-Benzoyl-4-oxo-4,5-dihydro-3H-pyrrolo[2,3-c]quinoline-1-ethyl carboxylate | C |
| 217 | EtO₂C, 3-dimethylamino-acryloyl substituent | 8-(3-Dimethylamino-acryloyl)-4-oxo-4,5-dihydro-3H-pyrrolo[2,3-c]quinoline-1-ethyl carboxylate | B |
| 218 | EtO₂C, morpholinyl-acetyl substituent | 8-(2-Morpholin-4-yl-acetyl)-4-oxo-4,5-dihydro-3H-pyrrolo[2,3-c]quinoline-1-ethyl carboxylate | C |
| 219 | EtO₂C, cyclopropyl-pyrrolidinylmethyl-carbamoyl substituent | (S)-8-(Cyclopropyl-pyrrolidin-2-ylmethyl-carbamoyl)-4-oxo-4,5-dihydro-3H-pyrrolo[2,3-c]quinoline-1-ethyl carboxylate hydrochloride | C |
| 220 | EtO₂C, phenylsulfanyl substituent | 4-Oxo-8-phenylsulfanyl-4,5-dihydro-3H-pyrrolo[2,3-c]quinoline-1-ethyl carboxylate | B |

TABLE V-continued (VI)

| Compound | Formula | Name | IC50 |
|---|---|---|---|
| 221 | | 8-Cyclohexylsulfanyl-4-oxo-4,5-dihydro-3H-pyrrolo[2,3-c]quinoline-1-ethyl carboxylate | B |
| 222 | | 8-Benzylsulfanyl-4-oxo-4,5-dihydro-3H-pyrrolo[2,3-c]quinoline-1-ethyl carboxylate | B |
| 223 | | 8-(4-Acetylaminophenylsulfanyl)-4-oxo-4,5-dihydro-3H-pyrrolo[2,3-c]quinoline-1-ethyl carboxylate | B |
| 224 | | 8-(3-Aminophenylsulfanyl)-4-oxo-4,5-dihydro-3H-pyrrolo[2,3-c]quinoline-1-ethyl carboxylate | B |
| 225 | | 8-(3-Acetylaminophenylsulfanyl)-4-oxo-4,5-dihydro-3H-pyrrolo[2,3-c]quinoline-1-ethyl carboxylate | B |

TABLE V-continued (VI)

| Compound | Formula | Name | IC50 |
|---|---|---|---|
| 226 | EtO₂C... (structure with ClH·H₂N-CH₂CH₂-S-) | 8-(2-Amino-ethylsulfanyl)-4-oxo-4,5-dihydro-3H-pyrrolo[2,3-c]quinoline-1-ethyl carboxylate hydrochloride | A |
| 227 | EtO₂C... (structure with HO-SO₂-) | 4-Oxo-8-sulfo-4,5-dihydro-3H-pyrrolo[2,3-c]quinoline-1-ethyl carboxylate | C |

TABLE VI (VII)

| Compound | Formula | Name | IC50 |
|---|---|---|---|
| 1 | EtO₂C | 4-Oxo-4,5-dihydro-3H-pyrrolo[2,3-c]quinoline-1-ethyl carboxylate | C |
| 73 | MeO₂C | 4-Oxo-4,5-dihydro-3H-pyrrolo[2,3-c]quinoline-1-methyl carboxylate | C |

TABLE VI-continued
(VII)
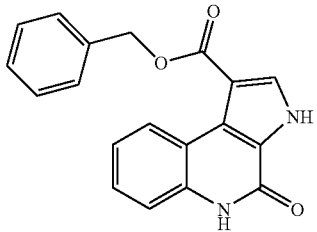 [SMILES: O=C(OCc1ccccc1)c1c[nH]c2c(=O)[nH]c3ccccc3c12]
| Compound | Formula | Name | IC50 |
|---|---|---|---|
| 74 | 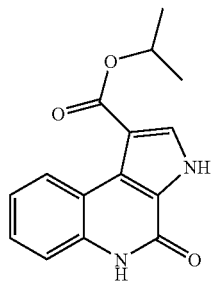 [SMILES: CC(C)OC(=O)c1c[nH]c2c(=O)[nH]c3ccccc3c12] | 4-Oxo-4,5-dihydro-3H-pyrrolo[2,3-c]quinoline-1-benzyl carboxylate | C |
| 78 |  | 4-Oxo-4,5-dihydro-3H-pyrrolo[2,3-c]quinoline-1-isopropyl carboxylate | C |
| 75 | 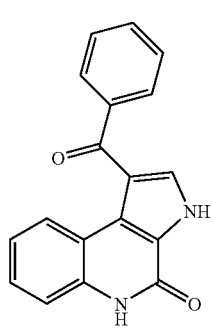 [SMILES: O=C(c1ccccc1)c1c[nH]c2c(=O)[nH]c3ccccc3c12] | 4-Oxo-4,5-dihydro-3H-pyrrolo[2,3-c]quinoline-1-carboxylic acid | D |
| 76 |  | 1-Benzoyl-3,5-dihydro-pyrrolo[2,3-c]quinolin-4-one | C |
| 77 | | 1-Acetyl-3,5-dihydro-pyrrolo[2,3-c]quinolin-4-one | D |

TABLE VI-continued

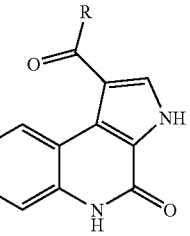
(VII)

| Compound | Formula | Name | IC50 |
|---|---|---|---|
| 79 | | N-(2-Dimethylamino-ethyl)-4-oxo-4,5-dihydro-3H-pyrrolo[2,3-c]quinoline-1-carboxamide | D |
| 80 | | N-(3-Dimethylamino-propyl)-4-oxo-4,5-dihydro-3H-pyrrolo[2,3-c]quinoline-1-carboxamide | D |
| 81 | | 3-[(4-Oxo-4,5-dihydro-3H-pyrrolo[2,3-c]quinoline-1-carbonyl)-amino]-methyl propanoate | D |
| 82 | | N-(Cyclohexylmethyl)-4-oxo-4,5-dihydro-3H-pyrrolo[2,3-c]quinoline-1-carboxamide | D |
| 83 | | N-(Benzyl)-4-oxo-4,5-dihydro-3H-pyrrolo[2,3-c]quinoline-1-carboxylamide | D |

TABLE VI-continued
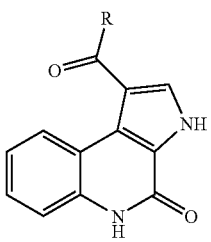
(VII)
| Compound | Formula | Name | IC50 |
|---|---|---|---|
| 84 | | N-[2-(1H-Indol-3-yl)-ethyl]-4-oxo-4,5-dihydro-3H-pyrrolo[2,3-c]quinoline-1-carboxamide | D |
| 85 | | N-(3-Hydroxy-propyl)-4-oxo-4,5-dihydro-3H-pyrrolo[2,3-c]quinoline-1-carboxamide | D |
| 86 | | N-(Pyridin-4-ylmethyl)-4-oxo-4,5-dihydro-3H-pyrrolo[2,3-c]quinoline-1-carboxamide | D |
| 87 | | N-(Phenyl)-4-oxo-4,5-dihydro-3H-pyrrolo[2,3-c]quinoline-1-carboxamide | D |

TABLE VI-continued
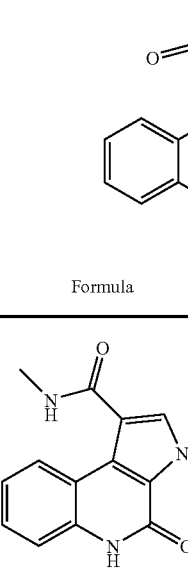
(VII)
| Compound | Formula | Name | IC50 |
|---|---|---|---|
| 88 | 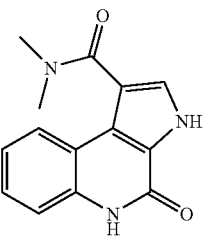 [SMILES: CN(C)C(=O)c1c[nH]c2c(=O)[nH]c3ccccc3c12] | N-(Methyl)-4-oxo-4,5-dihydro-3H-pyrrolo[2,3-c]quinoline-1-carboxamide | D |
| 89 | 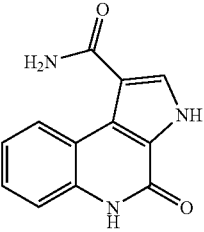 [SMILES: NC(=O)c1c[nH]c2c(=O)[nH]c3ccccc3c12] | N,N-(Dimethyl)-4-oxo-4,5-dihydro-3H-pyrrolo[2,3-c]quinoline-1-carboxamide | D |
| 90 | | 4-Oxo-4,5-dihydro-3H-pyrrolo[2,3-c]quinoline-1-carboxamide | D |

TABLE VII

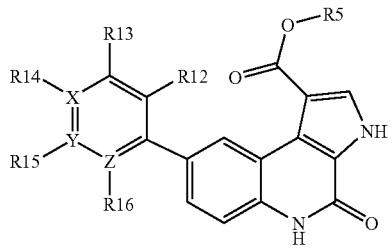

(VIII)

| Compound | Formula | Name | IC50 |
|---|---|---|---|
| 228 | | 4-Oxo-8-phenyl-4,5-dihydro-3H-pyrrolo[2,3-c]quinoline-1-ethyl carboxylate | C |
| 229 | | 8-(2-Chlorophenyl)-4-oxo-4,5-dihydro-3H-pyrrolo[2,3-c]quinoline-1-ethyl carboxylate | B |
| 230 | | 8-(2-tert-Butoxycarbonylaminophenyl)-4-oxo-4,5-dihydro-3H-pyrrolo[2,3-c]quinoline-1-ethyl carboxylate | D |
| 231 | | 8-(2-Aminophenyl)-4-oxo-4,5-dihydro-3H-pyrrolo[2,3-c]quinoline-1-ethyl carboxylate | B |
| 232 | | 8-(2-Methanesulfonylaminophenyl)-4-oxo-4,5-dihydro-3H-pyrrolo[2,3-c]quinoline-1-ethyl carboxylate | B |

TABLE VII-continued (VIII)

| Compound | Formula | Name | IC50 |
|---|---|---|---|
| 233 | | 8-(3-tert-Butoxycarbonylaminophenyl)-4-oxo-4,5-dihydro-3H-pyrrolo[2,3-c]quinoline-1-ethyl carboxylate | C |
| 234 | | 8-(3-Aminophenyl)-4-oxo-4,5-dihydro-3H-pyrrolo[2,3-c]quinoline-1-ethyl carboxylate | B |
| 235 | | 8-(3-Methanesulfonylaminophenyl)-4-oxo-4,5-dihydro-3H-pyrrolo[2,3-c]quinoline-1-ethyl carboxylate | B |
| 236 | | 8-(3-Acetylaminophenyl)-4-oxo-4,5-dihydro-3H-pyrrolo[2,3-c]quinoline-1-ethyl carboxylate | B |
| 237 | | 8-(3-Hydroxy-phenyl)-4-oxo-4,5-dihydro-3H-pyrrolo[2,3-c]quinoline-1-ethyl carboxylate | B |
| 238 | | 8-(3-Methanesulfonyl-phenyl)-4-oxo-4,5-dihydro-3H-pyrrolo[2,3-c]quinoline-1-ethyl carboxylate | B |

TABLE VII-continued (VIII)
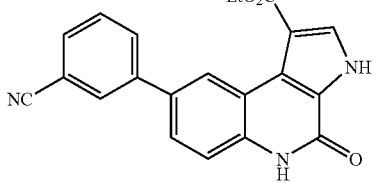

| Compound | Formula | Name | IC50 |
|---|---|---|---|
| 239 | 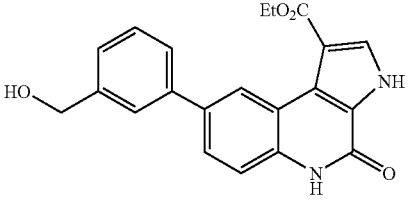 [SMILES: CCOC(=O)c1c[nH]c2c(=O)[nH]c3ccc(-c4cccc(CO)c4)cc3c12] | 8-(3-Cyano-phenyl)-4-oxo-4,5-dihydro-3H-pyrrolo[2,3-c]quinoline-1-ethyl carboxylate | B |
| 240 | 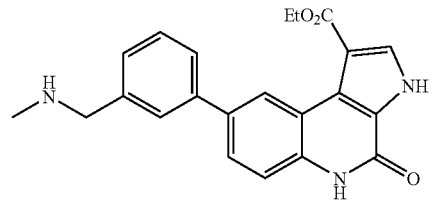 [SMILES: CCOC(=O)c1c[nH]c2c(=O)[nH]c3ccc(-c4cccc(CNC)c4)cc3c12] | 8-(3-Hydroxymethyl-phenyl)-4-oxo-4,5-dihydro-3H-pyrrolo[2,3-c]quinoline-1-ethyl carboxylate | B |
| 241 | 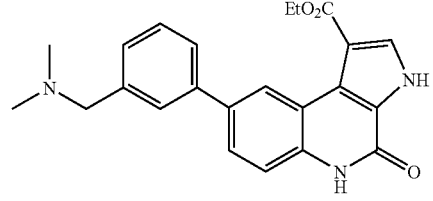 [SMILES: CCOC(=O)c1c[nH]c2c(=O)[nH]c3ccc(-c4cccc(CN(C)C)c4)cc3c12] | 8-(3-Methylaminomethyl-phenyl)-4-oxo-4,5-dihydro-3H-pyrrolo[2,3-c]quinoline-1-ethyl carboxylate | B |
| 242 | 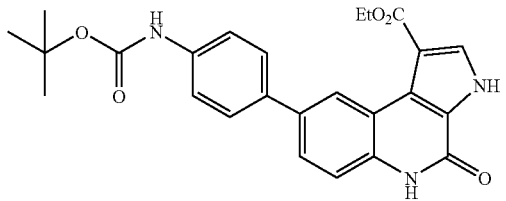 [SMILES: CCOC(=O)c1c[nH]c2c(=O)[nH]c3ccc(-c4ccc(NC(=O)OC(C)(C)C)cc4)cc3c12] | 8-(3-Dimethylaminomethyl-phenyl)-4-oxo-4,5-dihydro-3H-pyrrolo[2,3-c]quinoline-1-ethyl carboxylate | B |
| 243 | 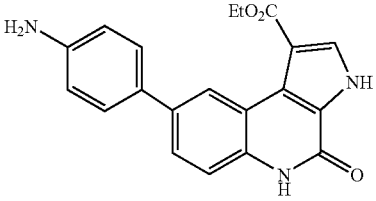 [SMILES: CCOC(=O)c1c[nH]c2c(=O)[nH]c3ccc(-c4ccc(N)cc4)cc3c12] | 8-(4-tert-Butoxycarbonylaminophenyl)-4-oxo-4,5-dihydro-3H-pyrrolo[2,3-c]quinoline-1-ethyl carboxylate | C |
| 244 |  | 8-(4-Aminophenyl)-4-oxo-4,5-dihydro-3H-pyrrolo[2,3-c]quinoline-1-ethyl carboxylate | B |

TABLE VII-continued (VIII)

| Compound | Formula | Name | IC50 |
|---|---|---|---|
| 245 | | 8-(4-Methanesulfonyl-phenyl)-4-oxo-4,5-dihydro-3H-pyrrolo[2,3-c]quinoline-1-ethyl carboxylate | C |
| 246 | | 8-(4-Methoxy-phenyl)-4-oxo-4,5-dihydro-3H-pyrrolo[2,3-c]quinoline-1-ethyl carboxylate | C |
| 247 | | 8-(4-Cyano-phenyl)-4-oxo-4,5-dihydro-3H-pyrrolo[2,3-c]quinoline-1-ethyl carboxylate | D |
| 248 | | 8-(2,3-Dihydro-benzo[1,4]dioxin-6-yl)-4-oxo-4,5-dihydro-3H-pyrrolo[2,3-c]quinoline-1-ethyl carboxylate | B |
| 249 | | 8-Naphthalen-1-yl-4-oxo-4,5-dihydro-3H-pyrrolo[2,3-c]quinoline-1-ethyl carboxylate | B |
| 250 | | 4-Oxo-8-quinolin-8-yl-4,5-dihydro-3H-pyrrolo[2,3-c]quinoline-1-ethyl carboxylate | C |

TABLE VII-continued (VIII)

| Compound | Formula | Name | IC50 |
|---|---|---|---|
| 251 | | 8-(2-Amino-5-methanesulfonyl-phenyl)-4-oxo-4,5-dihydro-3H-pyrrolo[2,3-c]quinoline-1-ethyl carboxylate | B |
| 252 | | 8-(1H-Indol-5-yl)-4-oxo-4,5-dihydro-3H-pyrrolo[2,3-c]quinoline-1-ethyl carboxylate | B |
| 253 | | 8-(1-tert-Butoxycarbonyl-1H-indol-5-yl)-4-oxo-4,5-dihydro-3H-pyrrolo[2,3-c]quinoline-1-ethyl carboxylate | C |
| 254 | | 8-(3-Methanesulfonyl-phenyl)-4-oxo-4,5-dihydro-3H-pyrrolo[2,3-c]quinoline-1-propyl carboxylate | B |
| 255 | | 8-(3-Methanesulfonyl-phenyl)-4-oxo-4,5-dihydro-3H-pyrrolo[2,3-c]quinoline-1-isobutyl carboxylate | C |

TABLE VII-continued (VIII)

| Compound | Formula | Name | IC50 |
|---|---|---|---|
| 256 | | 8-(3-Methanesulfonyl-phenyl)-4-oxo-4,5-dihydro-3H-pyrrolo[2,3-c]quinoline-1-cyclopentyl carboxylate | B |
| 257 | | 7-Chloro-8-(3-methanesulfonyl-phenyl)-4-oxo-4,5-dihydro-3H-pyrrolo[2,3-c]quinoline-1-ethyl carboxylate | B |
| 258 | | 4-Oxo-8-pyridin-3-yl-4,5-dihydro-3H-pyrrolo[2,3-c]quinoline-1-ethyl carboxylate | C |
| 259 | | 8-(6-Chloro-pyridin-3-yl)-4-oxo-4,5-dihydro-3H-pyrrolo[2,3-c]quinoline-1-ethyl carboxylate | C |
| 260 | | 8-(6-Methoxy-pyridin-3-yl)-4-oxo-4,5-dihydro-3H-pyrrolo[2,3-c]quinoline-1-ethyl carboxylate | C |

TABLE VII-continued (VIII)

| Compound | Formula | Name | IC50 |
|---|---|---|---|
| 261 | | 8-(2-Amino-pyrimidin-4-yl)-4-oxo-4,5-dihydro-3H-pyrrolo[2,3-c]quinoline-1-ethyl carboxylate | B |
| 262 | | 8-(2-Dimethylamino-pyrimidin-4-yl)-4-oxo-4,5-dihydro-3H-pyrrolo[2,3-c]quinoline-1-ethyl carboxylate | C |
| 263 | | 8-(2-Methylamino-pyrimidin-4-yl)-4-oxo-4,5-dihydro-3H-pyrrolo[2,3-c]quinoline-1-ethyl carboxylate formate | B |
| 264 | | 8-(2-Ethylamino-pyrimidin-4-yl)-4-oxo-4,5-dihydro-3H-pyrrolo[2,3-c]quinoline-1-ethyl carboxylate | B |
| 265 | | 4-Oxo-8-[2-(4-pyridin-2-yl-piperazin-1-yl)-pyrimidin-4-yl]-4,5-dihydro-3H-pyrrolo[2,3-c]quinoline-1-ethyl carboxylate | C |
| 266 | | 4-Oxo-8-(2-phenylamino-pyrimidin-4-yl)-4,5-dihydro-3H-pyrrolo[2,3-c]quinoline-1-ethyl carboxylate | C |

TABLE VII-continued
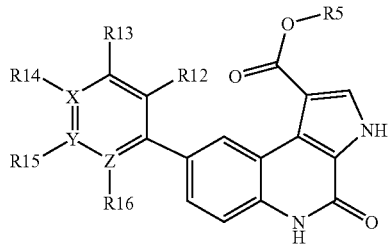
(VIII)
| Compound | Formula | Name | IC50 |
|---|---|---|---|
| 267 | | 8-[2-(1H-Benzoimidazol-2-ylamino)-pyrimidin-4-yl]-4-oxo-4,5-dihydro-3H-pyrrolo[2,3-c]quinoline-1-ethyl carboxylate | C |
| 268 | | 8-[2-(4-Acetyl-piperazin-1-yl)-pyrimidin-4-yl]-4-oxo-4,5-dihydro-3H-pyrrolo[2,3-c]quinoline-1-ethyl carboxylate | C |
| 269 | | 8-{2-[(2-Dimethylamino-ethyl)-methyl-amino]-pyrimidin-4-yl}-4-oxo-4,5-dihydro-3H-pyrrolo[2,3-c]quinoline-1-ethyl carboxylate formate | C |

TABLE VIII

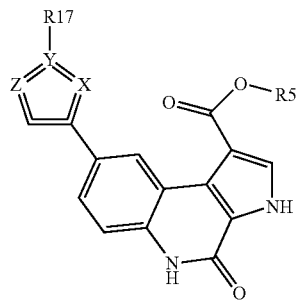

(IX)

| Compound | Formula | Name | IC50 |
|---|---|---|---|
| 270 | | 8-(2Amino-thiazol-4-yl)-4-oxo-4,5-dihydro-3H-pyrrolo[2,3-c]quinoline-1-ethyl carboxylate | B |
| 271 | | 8-[2-Phenylamino-thiazol-4-yl]-4-oxo-4,5-dihydro-3H-pyrrolo[2,3-c]quinoline-1-ethyl carboxylate | B |
| 272 | | 8-[2-(2-Chlorophenylamino)-thiazol-4-yl]-4-oxo-4,5-dihydro-3H-pyrrolo[2,3-c]quinoline-1-ethyl carboxylate | C |
| 273 | | 8-[2-(3,4-Dichlorophenylamino)-thiazol-4-yl]-4-oxo-4,5-dihydro-3H-pyrrolo[2,3-c]quinoline-1-ethyl carboxylate | C |

TABLE VIII-continued

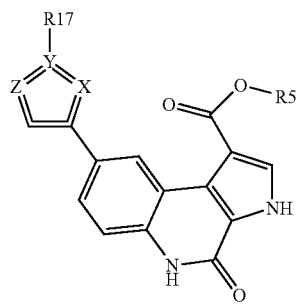

(IX)

| Compound | Formula | Name | IC50 |
|---|---|---|---|
| 274 | | 8-[2-(2,6-Dichlorophenylamino)-thiazol-4-yl]-4-oxo-4,5-dihydro-3H-pyrrolo[2,3-c]quinoline-1-ethyl carboxylate | D |
| 275 | | 8-[2-(Cyclopropanecarbonyl-amino)-thiazol-4-yl]-4-oxo-4,5-dihydro-3H-pyrrolo[2,3-c]quinoline-1-ethyl carboxylate | B |
| 276 | | 4-Oxo-8-(2-phenylsulfanylmethyl-thiazol-4-yl)-4,5-dihydro-3H-pyrrolo[2,3-c]quinoline-1-ethyl carboxylate | B |
| 277 | | 4-Oxo-8-(2-piperidin-4-yl-thiazol-4-yl)-4,5-dihydro-3H-pyrrolo[2,3-c]quinoline-1-ethyl carboxylate | B |

TABLE VIII-continued (IX)

| Compound | Formula | Name | IC50 |
|---|---|---|---|
| 278 | | 8-(2-Methyl-thiazol-4-yl)-4-oxo-4,5-dihydro-3H-pyrrolo[2,3-c]quinoline-1-ethyl carboxylate | C |
| 279 | | 4-Oxo-8-(2-phenyl-thiazol-4-yl)-4,5-dihydro-3H-pyrrolo[2,3-c]quinoline-1-ethyl carboxylate | C |
| 280 | | 4-Oxo-8-[2-(N'-phenyl-hydrazino)-thiazol-4-yl]-4,5-dihydro-3H-pyrrolo[2,3-c]quinoline-1-ethyl carboxylate | C |
| 281 | | 8-Isoxazol-5-yl-4-oxo-4,5-dihydro-3H-pyrrolo[2,3-c]quinoline-1-ethyl carboxylate | B |
| 282 | | 4-Oxo-8-(1H-pyrazol-3-yl)-4,5-dihydro-3H-pyrrolo[2,3-c]quinoline-1-ethyl carboxylate | B |

TABLE VIII-continued

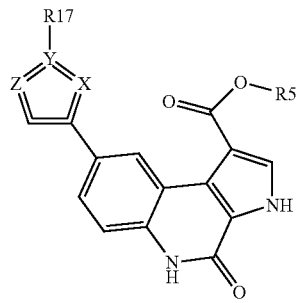

(IX)

| Compound | Formula | Name | IC50 |
|---|---|---|---|
| 283 | | 8-(1-Methyl-1H-pyrazol-3-yl)-4-oxo-4,5-dihydro-3H-pyrrolo[2,3-c]quinoline-1-ethyl carboxylate | B |

EXAMPLE 3

Test for Measuring Inhibition of the Kinase Activity of ALK, PIM-1, TrkA and TrkB The inhibition of the kinase activity of some compounds of the invention was also assessed from inhibition by measuring their IC50 on other kinases.

Test for Measuring Inhibition of Kinase PIM-1:

Protein PIM-1 (Upstate #14-573 batch 25864U) is incubated at a concentration of 0.625 µg/ml in a buffer containing 8 mM of MOPS/NaOH pH7, 0.2 mM EDTA, 5 mM MgAc (Sigma #229768), 0.01% Triton Tx100, in the presence of 70 µM of peptide substrate S6 Kinase/Rsk2 (Upstate #12-243), and 10 µM of ATP.

The dilution buffer for PIM-1 is as follows: 20 mM MOPS/NaOH pH7, 1 mM EDTA, 5% glycerol, 0.01% Brij35, 0.1% 2-mercapto, 1 mg/ml BSA The compound to be tested is first added to the enzyme to give a reaction volume of 50 µl. The dilution of the compounds of the invention is distributed so as to obtain a scale of final concentrations between 10 nM and 30 µM.

After incubation of the reaction mixture for forty minutes at 30° C., the level of ATP that remains is assayed using the Kinase-Glo Luminescent Kinase Assay (Promega #V6712) according to the conditions recommended by the supplier. The luminescence induced is read in a plate reader (Envision-Perkin Elmer).

Test for Measuring Inhibition of Kinase TrkA:

Protein TrkA (Upstate 14-571; batch #25634U) is incubated at a concentration of 4 µg/ml in a buffer containing 8 mM of MOPS/NaOH pH7, 0.2 mM EDTA, 40 mM MgAc (Sigma #229768), 1 mM DTT (Fluka #43816), NaOV 1 mM, 0.01% Triton Tx100, in the presence of 1 mg/ml of peptide substrate poly-EY (Upstate #P0275), and 30 µM of ATP.

The dilution buffer for TrkA is as follows: 20 mM MOPS/NaOH pH7, 1 mM EDTA, 5% glycerol, 0.01% Brij35, 0.1% 2-mercapto, 1 mg/ml BSA.

The compound to be tested is first added to the enzyme to give a reaction volume of 50 µl. The dilution of the compounds of the invention is distributed so as to obtain a scale of final concentrations between 10 nM and 30 µM.

After incubation of the reaction mixture for two hours at 30° C., the level of ATP that remains is assayed using the Kinase-Glo Luminescent Kinase Assay (Promega #V6712) according to the conditions recommended by the supplier. The luminescence induced is read in a plate reader (Envision-Perkin Elmer).

Test for Measuring Inhibition of Kinase TrkB:

Protein TrkB (Upstate 14-507; batch #25578U) is incubated at a concentration of 4 µg/ml in a buffer containing 8 mM of MOPS/NaOH pH7, 0.2 mM EDTA, 40 mM MgAc (Sigma #229768), 1 mM DTT (Fluka #43816), NaOV 1 mM, 25 mM 2-glycerolphosphate (Sigma #G9891), in the presence of 2.5 mg/ml of peptide substrate poly-EY (Upstate #P0275), and 40 µM of ATP.

The dilution buffer for TrkB is as follows: 20 mM MOPS/NaOH pH7, 1 mM EDTA, 5% glycerol, 0.01% Brij35, 0.1% 2-mercapto, 1 mg/ml BSA.

The compound to be tested is first added to the enzyme to give a reaction volume of 50 µl. The dilution of the compounds of the invention is distributed so as to obtain a scale of final concentrations between 10 nM and 30 µM.

After incubation of the reaction mixture for two hours at 30° C., the level of ATP that remains is assayed using the Kinase-Glo Luminescent Kinase Assay (Promega #V6712) according to the conditions recommended by the supplier. The luminescence induced is read in a plate reader (Envision-Perkin Elmer).

Test for Measuring Inhibition of Kinase ALK:

A ViewPlate plate (Packard #6005182) is incubated with the substrate PLCγl-GST (purified recombinant form) at 0.1 mg/ml in PBS buffer (100 µl/well) during one hour of stirring. Then, the plate is saturated by a blocking solution containing 5% of BSA (Sigma #B-7906) in PBS buffer.

After adding the inhibitor to the desired final concentration (usual range between 30 µM and 10 nM), reaction is effected by adding kinase ALK at 180 ng/ml in reaction buffer (Tris 13 mM pH7.5, MgCl2 6.5 mM, DTT 0.65 mM, β-glycerophosphate 39 mM, NaOV 0.65 mM) and 250 μM of ATP. Incubation is carried out for 30 minutes at 30° C. with agitation.

After washing three times in PBS buffer/Tween-20 0.1% with agitation, an anti-phosphotyrosine antibody coupled to HRP (UBI #16105) diluted to 1/1000 in PBS buffer containing BSA 5 mg/ml is incubated for one hour, with agitation. Then, after washing in PBS/Tween three more times, the wells are incubated for two minutes with 100 μl of SuperSignal ELISA mixture (Pierce #37070).

The signal is read in luminescent mode using a luminometer.

Table IX shown below presents some values of IC50 for compounds of type II to IX on kinases ALK, PIM-1, TrkA and TrkB. The values of IC50 are shown by the same categories as previously.

TABLE IX

| Compound | ALK | PIM-1 | TrkA | TrkB |
|---|---|---|---|---|
| 1 | | D | | |
| 2 | | | C | C |
| 3 | | D | C | D |
| 6 | | | D | D |
| 8 | | | D | D |
| 12 | B | | C | C |
| 32 | D | D | | |
| 33 | C | D | | |
| 34 | | C | | |
| 37 | | D | C | C |
| 43 | | | C | C |
| 44 | | | C | C |
| 45 | | | C | C |
| 49 | | | D | C |
| 56 | | | C | C |
| 58 | | | C | C |
| 63 | | D | | |
| 64 | | D | | |
| 66 | | C | | |
| 70 | | C | | |
| 71 | | C | | |
| 79 | | D | | |
| 91 | B | ; C | | |
| 93 | B | C | | |
| 94 | B | | | |
| 95 | | D | | |
| 97 | B | D | | |
| 111 | | | C | C |
| 112 | B | C | | |
| 113 | C | C | | |
| 114 | | C | D | D |
| 115 | | C | D | D |
| 116 | | C | | |
| 117 | | C | D | D |
| 118 | | D | | |
| 120 | | D | C | D |
| 121 | | C | | |
| 123 | C | | | |
| 127 | | D | C | C |
| 130 | B | | | |
| 141 | B | | | |
| 144 | B | | | |
| 145 | C | | | |
| 149 | B | | | |
| 150 | B | | | |
| 153 | B | | | |
| 155 | B | | | |
| 162 | | | C | C |
| 177 | B | | | |
| 209 | | B | | |
| 219 | C | | | |
| 221 | | C | | |
| 222 | | C | | |
| 227 | | C | C | C |
| 234 | | | C | C |
| 237 | | C | C | B |
| 240 | | C | C | C |
| 241 | | C | | |

TABLE IX-continued

| Compound | ALK | PIM-1 | TrkA | TrkB |
|---|---|---|---|---|
| 242 | | C | D | D |
| 244 | | B | | |
| 259 | | C | | |
| 261 | | D | | |
| 262 | | C | | |
| 263 | | C | | |
| 264 | | C | D | D |
| 266 | | | C | C |
| 267 | | | D | D |
| 268 | | C | | |
| 269 | | C | | |
| 270 | | D | | |
| 271 | B | D | C | C |
| 277 | | C | | |
| 282 | | D | D | D |

EXAMPLE 4

Test for Measuring Inhibition of the Activity of a Panel of Kinases by the Compounds Described in the Invention These kinases are produced by Upstate and screened according to the respective protocols indicated by the supplier (http://www.upstate.com/features/kp_protocols.asp).

Examples 1, 12, 166 and 238 were tested at a concentration of 20 μM, 10 μM, 1 μM and 1 μM respectively in the presence of 10 μM of ATP for examples 1 and 12 and at the concentrations of ATP shown in parentheses for examples 166 and 238. The results shown in Table VII correspond to percentage inhibition of the kinase tested in the presence of the compound, relative to a control effected without the compound.

The results are presented in Table X below.

TABLE X

| Kinase | Compound 1 % inhibition at 20 μMol | Compound 12 % inhibition at 10 μMol | Compound 166 % inhibition at 1 μMol | Compound 238 % inhibition at 1 μMol |
|---|---|---|---|---|
| Aurora-A (h) | 16 | 94 | 6 (15) | 24 (15) |
| c-RAF (h) | 17 | 79 | 0 (45) | 3 (45) |
| CDK2/cyclinE (h) | 97 | 12 | | |
| cKit (h) | 20 | 45 | 15 (200) | 4 (200) |
| cSRC (h) | 86 | 91 | 13 (200) | 7 (200) |
| EGFR (h) | 19 | 13 | 3 (10) | 3 (10) |
| FGFR1 (h) | | | 71 (200) | 51 (200) |
| FGFR2 (h) | 82 | 91 | | |
| Flt3 (h) | 91 | 51 | 0 (200) | 0 (200) |
| GSK3B (h) | | 22 | 0 (15) | 0 (15) |
| Hck (h) | | 91 | | |
| IGF-1R (h) | 42 | 0 | | |
| IKKβ (h) | 22 | 0 | 0 (10) | 0 (10) |
| JAK3 (h) | 58 | 50 | 0 (10) | 5 (10) |
| KDR (h) | 100 | 69 | 9 (90) | 21 (90) |
| MAPK2 (h) | 1 | 3 | 0 (155) | 0 (155) |
| Met (h) | 52 | | | |
| MLCK (h) | | | 75 (10) | 21 (10) |
| PDGFRβ (h) | 13 | 0 | 23 (120) | 0 (120) |
| PIM-1 (h) | 92 | | | |
| PKBγ (h) | 5 | 20 | 0 (200) | 2 (200) |
| RET (h) | 99 | | | |
| ROCK-II (h) | 8 | 17 | 3 (15) | 5 (15) |
| Rsk2 (h) | | | 60 (10) | 25 (10) |
| TrkA (h) | 97 | | | |
| TrkB (h) | | 98 | | |

EXAMPLE 5

Test for Measuring Inhibition of the Proliferation of a Panel of Cell Lines by the Compounds Described in the Invention The inhibition of the proliferation of cell lines by certain compounds of the invention was tested. Generally speaking, the proliferation of thyroid cell lines, and in particular cells derived from medullary thyroid cancers (MTC), is greatly inhibited by most of the compounds of the invention. In the example, the lines used were derived from cancers of the uterus, central nervous system, colon, stomach, head and neck, lung, breast, pancreas, and kidney, as well as from lymphoma, myeloma, pleura, or from melanoma.

The WST test for measuring cell proliferation and viability (Roche Applied Science) is based on cleavage of a tetrazolium salt by the mitochondrial dehydrogenases in viable cells.

After four days of incubation of the compounds with the cell line, 14 µl of WST-1 reagent is added to each well and the plates are incubated for four hours at 37° in humid atmosphere at 5% $CO_2$. The level of formazan formed is then determined by spectrophotometry at 450 nm whereas a reference is measured at 650 nm. A control with untreated cells is represented by six wells per plate and the group of treated cells is produced in triplicate for each of the concentrations measured.

The compounds are tested at five concentrations between 10 nM and 100 µM and two cytotoxic agents are used as controls: adriamycin and 5-fluorouracil.

The results obtained (Table XI for example 238) show inhibition of proliferation by compound 238, in particular lung cells, cells from the central nervous system, cells from the breast and to a lesser extent, cells from the uterus, pleura, melanoma, pancreas, kidney and lymphocytes. Another compound tested, compound 166, gives results similar to those obtained with example 238 on these lines, with slightly lower level of inhibition.

TABLE XI

Antiproliferative activity in vitro of compound 238 on cell lines

| line | tissue of origin | IC50 (µM) |
| --- | --- | --- |
| U251 | CMS | 33 |
| SKNAS | CMS | 12 |
| A172 | CMS | 13 |
| MDA-453 | Breast | 7 |
| MDA-468 | Breast | 38 |
| MDA-231 | Breast | 41 |
| SW756 | Cervix | 35 |
| SKUT1B | Uterus | 33 |
| 536L | Head/neck | 36 |
| A427 | Lung (NSCLC) | 36 |
| H69 | Lung (SCLC) | 0.5 |
| RAJI | Lymphoma | 34 |
| HT144 | Melanoma | 31 |
| CAPAN2 | Pancreas | 47 |
| 1752L | Pleuromesothelium | 35 |
| A498 | Kidney | 49 |

The invention claimed is:

1. A pyrroloquinoline derivative selected from the group consisting of the following compounds, and physiologically acceptable salts thereof:
   4-Oxo-8-phenylsulfamoyl-4,5-dihydro-3H-pyrrolo[2,3-c] quinoline-1-ethyl carboxylate
   8-(Methyl-phenyl-sulfamoyl)-4-oxo-4,5-dihydro-3H-pyrrolo[2,3-c]quinoline-1-ethyl carboxylate
   4-Oxo-8-o-tolylsulfamoyl-4,5-dihydro-3H-pyrrolo[2,3-c] quinoline-1-ethyl carboxylate
   4-Oxo-8-m-tolylsulfamoyl-4,5-dihydro-3H-pyrrolo[2,3-c]quinoline-1-ethyl carboxylate
   4-Oxo-8-p-tolylsulfamoyl-4,5-dihydro-3H-pyrrolo[2,3-c] quinoline-1-ethyl carboxylate
   8-(2-Methoxy-phenylsulfamoyl)-4-oxo-4,5-dihydro-3H-pyrrolo[2,3-c]quinoline-1-ethyl carboxylate
   8-(3-Methoxy-phenylsulfamoyl)-4-oxo-4,5-dihydro-3H-pyrrolo[2,3-c]quinoline-1-ethyl carboxylate
   8-(4-Methoxy-phenylsulfamoyl)-4-oxo-4,5-dihydro-3H-pyrrolo[2,3-c]quinoline-1-ethyl carboxylate
   8-(3-Chlorophenylsulfamoyl)-4-oxo-4,5-dihydro-3H-pyrrolo[2,3-c]quinoline-1-ethyl carboxylate
   8-(4-Chlorophenylsulfamoyl)-4-oxo-4,5-dihydro-3H-pyrrolo[2,3-c]quinoline-1-ethyl carboxylate
   8-(4-Fluorophenylsulfamoyl)-4-oxo-4,5-dihydro-3H-pyrrolo[2,3-c]quinoline-1-ethyl carboxylate
   8-[(4-Fluorophenyl)-methyl-sulfamoyl)-4-oxo-4,5-dihydro-3H-pyrrolo[2,3-c]quinoline-1-ethyl carboxylate
   8-[(4-Fluorophenyl)-methyl-sulfamoyl]-4-oxo-4,5-dihydro-3H-pyrrolo[2,3-c]quinoline-1-carboxylic acid
   8-[(4-Fluorophenyl)-methyl-sulfamoyl]-4-oxo-4,5-dihydro-3H-pyrrolo[2,3-c]quinoline-1-2-hydroxyethyl carboxylate
   8-[(4-Fluorophenyl)-methyl-sulfamoyl]-4-oxo-4,5-dihydro-3H-pyrrolo[2,3-c]quinoline-1-2-aminoethyl carboxylate hydrochloride
   8-[(4-Fluorophenyl)-methyl-sulfamoyl]-4-oxo-4,5-dihydro-3H-pyrrolo[2,3-c]quinoline-1-2-tert-butoxycarbonylaminomethyl carboxylate
   8-[(4-Fluorophenyl)-methyl-sulfamoyl]-4-oxo-4,5-dihydro-3H-pyrrolo[2,3-c]quinoline-1-3-aminopropyl carboxylate hydrochloride
   8-[(4-Fluorophenyl)-methyl-sulfamoyl]-4-oxo-4,5-dihydro-3H-pyrrolo[2,3-c]quinoline-1-3-tert-butoxycarbonylamino-propyl carboxylate
   8-(4-Ethoxycarbonyl-phenylsulfamoyl)-4-oxo-4,5-dihydro-3H-pyrrolo[2,3-c]quinoline-1-ethyl carboxylate
   8-(3-Hydroxy-phenylsulfamoyl)-4-oxo-4,5-dihydro-3H-pyrrolo[2,3-c]quinoline-1-ethyl carboxylate
   8-(3-Fluoro-2-methyl-phenylsulfamoyl)-4-oxo-4,5-dihydro-3H-pyrrolo[2,3-c]quinoline-1-ethyl carboxylate
   8-(4-Fluoro-2-methyl-phenylsulfamoyl)-4-oxo-4,5-dihydro-3H-pyrrolo[2,3-c]quinoline-1-ethyl carboxylate
   8-(3,4-Difluorophenylsulfamoyl)-4-oxo-4,5-dihydro-3H-pyrrolo[2,3-c]quinoline-1-ethyl carboxylate
   8-(3,5-Difluorophenylsulfamoyl)-4-oxo-4,5-dihydro-3H-pyrrolo[2,3-c]quinoline-1-ethyl carboxylate
   8-(4-Aminophenylsulfamoyl)-4-oxo-4,5-dihydro-3H-pyrrolo[2,3-c]quinoline-1-ethyl carboxylate
   8-(2,3-Dihydro-indole-1-sulfonyl)-4-oxo-4,5-dihydro-3H-pyrrolo[2,3-c]quinoline-1-ethyl carboxylate
   8-(4-Morpholin-4-yl-phenylsulfamoyl)-4-oxo-4,5-dihydro-3H-pyrrolo[2,3-c]quinoline-1-ethyl carboxylate
   4-Oxo-8-(pyridin-3-ylsulfamoyl)-4,5-dihydro-3H-pyrrolo[2,3-c]quinoline-1-ethyl carboxylate
   8-(Benzyl-methyl-sulfamoyl)-4-oxo-4,5-dihydro-3H-pyrrolo[2,3-c]quinoline-1-ethyl carboxylate
   8-(Methyl-phenethyl-sulfamoyl)-4-oxo-4,5-dihydro-3H-pyrrolo[2,3-c]quinoline-1-ethyl carboxylate
   8-Dimethylsulfamoyl-4-oxo-4,5-dihydro-3H-pyrrolo[2,3-c]quinoline-1-ethyl carboxylate
   N-Propyl-8-dimethylsulfamoyl-4-oxo-4,5-dihydro-3H-pyrrolo[2,3-c]quinoline-1-carboxamide
   N-Methyl-N-propyl-8-dimethylsulfamoyl-4-oxo-4,5-dihydro-3H-pyrrolo[2,3-c]quinoline-1-carboxamide 8-Methylsulfamoyl-4-oxo-4,5-dihydro-3H-pyrrolo[2,3-c]quinoline-1-ethyl carboxylate
8-(Morpholine-4-sulfonyl)-4-oxo-4,5-dihydro-3H-pyrrolo[2,3-c]quinoline-1-ethyl carboxylate
8-(2-Ethoxycarbonyl-ethylsulfamoyl)-4-oxo-4,5-dihydro-3H-pyrrolo[2,3-c]quinoline-1-ethyl carboxylate
8-Cyclohexylsulfamoyl-4-oxo-4,5-dihydro-3H-pyrrolo[2,3-c]quinoline-1-methyl carboxylate
8-Cyclohexylsulfamoyl-4-oxo-4,5-dihydro-3H-pyrrolo[2,3-c]quinoline-1-ethyl carboxylate
8-Cycloheptylsulfamoyl-4-oxo-4,5-dihydro-3H-pyrrolo[2,3-c]quinoline-1-ethyl carboxylate
8-(3-Dimethylamino-propylsulfamoyl)-4-oxo-4,5-dihydro-3H-pyrrolo[2,3-c]quinoline-1-ethyl carboxylate
8-(4-Amino-butylsulfamoyl)-4-oxo-4,5-dihydro-3H-pyrrolo[2,3-c]quinoline-1-ethyl carboxylate
8-[(3-Chlorophenyl)-methyl-sulfamoyl]-4-oxo-4,5-dihydro-3H-pyrrolo[2,3-c]quinoline-1-ethyl carboxylate
4-Oxo-8-(piperidin-4-ylsulfamoyl)-4,5-dihydro-3H-pyrrolo[2,3-c]quinoline-1-ethyl carboxylate
4-Oxo-8-(piperidin-3-ylsulfamoyl)-4,5-dihydro-3H-pyrrolo[2,3-c]quinoline-1-methyl carboxylate
4-Oxo-8-(piperidin-4-ylsulfamoyl)-4,5-dihydro-3H-pyrrolo[2,3-c]quinoline-1-methyl carboxylate
4-Oxo-8-(piperidin-4-ylsulfamoyl)-4,5-dihydro-3H-pyrrolo[2,3-c]quinoline-1-propyl carboxylate
4-Oxo-8-(piperidin-4-ylsulfamoyl)-4,5-dihydro-3H-pyrrolo[2,3-c]quinoline-1-butyl carboxylate
4-Oxo-8-(piperidin-4-ylsulfamoyl)-4,5-dihydro-3H-pyrrolo[2,3-c]quinoline-1-pentyl carboxylate
4-Oxo-8-(piperidin-4-ylsulfamoyl)-4,5-dihydro-3H-pyrrolo[2,3-c]quinoline-1-methylcyclohexyl carboxylate
4-Oxo-8-(piperidin-4-ylsulfamoyl)-4,5-dihydro-3H-pyrrolo[2,3-c]quinoline-1-methyltetrahydrofuran-3-yl carboxylate
8-(1-Methyl-piperidin-4-ylsulfamoyl)-4-oxo-4,5-dihydro-3H-pyrrolo[2,3-c]quinoline-1-cyclopentyl carboxylate
8-(Methyl-piperidin-4-yl-sulfamoyl)-4-oxo-4,5-dihydro-3H-pyrrolo[2,3-c]quinoline-1-propyl carboxylate
4-Oxo-8-[(piperidin-4-ylmethyl)-sulfamoyl]-4,5-dihydro-3H-pyrrolo[2,3-c]quinoline-1-ethyl carboxylate
8-(8-Aza-bicyclo[3.2.1]oct-3-ylsulfamoyl)-4-oxo-4,5-dihydro-3H-pyrrolo[2,3-c]quinoline-1-ethyl carboxylate
8-Cyclopentylsulfamoyl-4-oxo-4,5-dihydro-3H-pyrrolo[2,3-c]quinoline-1-methyl carboxylate
8-(Hexahydro-pyrrolo[3,4-c]pyrrole-2-sulfonyl)-4-oxo-4,5-dihydro-3H-pyrrolo[2,3-c]quinoline-1-ethyl carboxylate
8-(1-Azabicyclo[2.2.2]oct-3-ylsulfamoyl)-4-oxo-4,5-dihydro-3H-pyrrolo[2,3-c]quinoline-1-ethyl carboxylate
8-(4-Methyl-piperazine-1-sulfonyl)-4-oxo-4,5-dihydro-3H-pyrrolo[2,3-c]quinoline-1-ethyl carboxylate
4-Oxo-8-sulfamoyl-4,5-dihydro-3H-pyrrolo[2,3-c]quinoline-1-ethyl carboxylate
4-Oxo-8-[(pyrrolidin-3-methyl)-sulfamoyl]-4,5-dihydro-3H-pyrrolo[2,3-c]quinoline-1-ethyl carboxylate
4-Oxo-8-(4-Hydroxy-phenylsulfamoyl)-4,5-dihydro-3H-pyrrolo[2,3-c]quinoline-1-ethyl carboxylate
8-Cyclopropylsulfamoyl-4-oxo-4,5-dihydro-3H-pyrrolo[2,3-c]quinoline-1-ethyl carboxylate
8-Cyclopropylsulfamoyl-4-oxo-4,5-dihydro-3H-pyrrolo[2,3-c]quinoline-1-propyl carboxylate
8-(Cyclopropyl-methyl-sulfamoyl)-4-oxo-4,5-dihydro-3H-pyrrolo[2,3-c]quinoline-1-propyl carboxylate
8-[(2-Cyano-ethyl)-methyl-sulfamoyl]-4-oxo-4,5-dihydro-3H-pyrrolo[2,3-c]quinoline-1-propyl carboxylate
8-[(2-Cyano-ethyl)-cyclopropyl-sulfamoyl]-4-oxo-4,5-dihydro-3H-pyrrolo[2,3-c]quinoline-1-ethyl carboxylate
8-(Cyanomethyl-methyl-sulfamoyl)-4-oxo-4,5-dihydro-3H-pyrrolo[2,3-c]quinoline-1-propyl carboxylate
8-([1,3]Dioxolan-2-ylmethyl-methyl-sulfamoyl)-4-oxo-4,5-dihydro-3H-pyrrolo[2,3-c]quinoline-1-propyl carboxylate
8-[(1-Benzhydryl-azetidin-3-yl)-methyl-sulfamoyl]-4-oxo-4,5-dihydro-3H-pyrrolo[2,3-c]quinoline-1-propyl carboxylate
8-[Methyl-(tetrahydro-thiopyran-4-yl)-sulfamoyl]-4-oxo-4,5-dihydro-3H-pyrrolo[2,3-c]quinoline-1-propyl carboxylate
8-[(1,1-Dioxo-hexahydro-1l6-thiopyran-4-yl)-methyl-sulfamoyl]-4-oxo-4,5-dihydro-3H-pyrrolo[2,3-c]quinoline-1-propyl carboxylate
8-[Methyl-(tetrahydro-pyran-4-yl)-sulfamoyl]-4-oxo-4,5-dihydro-3H-pyrrolo[2,3-c]quinoline-1-propyl carboxylate
8-(Methyl-prop-2-ynyl-sulfamoyl)-4-oxo-4,5-dihydro-3H-pyrrolo[2,3-c]quinoline-1-propyl carboxylate
8-[Methyl-(2-methylsulfanyl-ethyl)-sulfamoyl]-4-oxo-4,5-dihydro-3H-pyrrolo[2,3-c]quinoline-1-propyl carboxylate
8-[(2-Dimethylamino-ethyl)-methyl-sulfamoyl]-4-oxo-4,5-dihydro-3H-pyrrolo[2,3-c]quinoline-1-propyl carboxylate
8-[Methyl-(2-pyrrolidin-1-yl-ethyl)-sulfamoyl]-4-oxo-4,5-dihydro-3H-pyrrolo[2,3-c]quinoline-1-propyl carboxylate
8-[(2-Diethylamino-ethyl)-methyl-sulfamoyl]-4-oxo-4,5-dihydro-3H-pyrrolo[2,3-c]quinoline-1-propyl carboxylate
8-[Methyl-(2-methylamino-ethyl)-sulfamoyl]-4-oxo-4,5-dihydro-3H-pyrrolo[2,3-c]quinoline-1-propyl carboxylate hydrochloride
8-{[2-(tert-Butoxycarbonyl-methyl-amino)-ethyl]-methyl-sulfamoyl}-4-oxo-4,5-dihydro-3H-pyrrolo[2,3-c]quinoline-1-propyl carboxylate
8-[Cyclopropyl-(2-methyl-2-methylamino-propyl)-sulfamoyl]-4-oxo-4,5-dihydro-3H-pyrrolo[2,3-c]quinoline-1-propyl carboxylate hydrochloride
8-[Cyclopropyl-(2-isopropylamino-ethyl)-sulfamoyl]-4-oxo-4,5-dihydro-3H-pyrrolo[2,3-c]quinoline-1-propyl carboxylate hydrochloride
8-[Cyclopropyl-(1H-imidazol-4-ylmethyl)-sulfamoyl]-4-oxo-4,5-dihydro-3H-pyrrolo[2,3-c]quinoline-1-propyl carboxylate hydrochloride
(S)-8-(Cyclopropyl-pyrrolidin-2-ylmethyl-sulfamoyl)-4-oxo-4,5-dihydro-3H-pyrrolo[2,3-c]quinoline-1-propyl carboxylate hydrochloride
(S)-8-[Cyclopropyl-(1-methyl-pyrrolidin-2-ylmethyl)-sulfamoyl]-4-oxo-4,5-dihydro-3H-pyrrolo[2,3-c]quinoline-1-propyl carboxylate
(R)-8-[Cyclopropyl-(1-methyl-pyrrolidin-2-ylmethyl)-sulfamoyl]-4-oxo-4,5-dihydro-3H-pyrrolo[2,3-c]quinoline-1-propyl carboxylate
(R)-8-[(1-tert-Butoxycarbonyl-pyrrolidin-2-ylmethyl)-cyclopropyl-sulfamoyl]-4-oxo-4,5-dihydro-3H-pyrrolo[2,3-c]quinoline-1-propyl carboxylate
(R)-8-(Cyclopropyl-pyrrolidin-2-ylmethyl-sulfamoyl)-4-oxo-4,5-dihydro-3H-pyrrolo[2,3-c]quinoline-1-propyl carboxylate hydrochloride
(S)-8-(Isopropyl-pyrrolidin-2-ylmethyl-sulfamoyl)-4-oxo-4,5-dihydro-3H-pyrrolo[2,3-c]quinoline-1-propyl carboxylate hydrochloride (S)-4-Oxo-8-(prop-2-ynyl-pyrrolidin-2-ylmethyl-sulfamoyl)-4,5-dihydro-3H-pyrrolo[2,3-c]quinoline-1-propyl carboxylate hydrochloride
(S)-8-[(1-Methyl-pyrrolidin-2-ylmethyl)-prop-2-ynyl-sulfamoyl]-4-oxo-4,5-dihydro-3H-pyrrolo[2,3-c]quinoline-1-propyl carboxylate
(S)-8-[(2-tert-Butoxycarbonylamino-propyl)-cyclopropyl-sulfamoyl]-4-oxo-4,5-dihydro-3H-pyrrolo[2,3-c]quinoline-1-propyl carboxylate
(S)-8-[(2-Amino-propyl)-cyclopropyl-sulfamoyl]-4-oxo-4,5-dihydro-3H-pyrrolo[2,3-c]quinoline-1-propyl carboxylate hydrochloride
(R)-8-[(2-tert-Butoxycarbonylamino-propyl)-cyclopropyl-sulfamoyl]-4-oxo-4,5-dihydro-3H-pyrrolo[2,3-c]quinoline-1-propyl carboxylate
(R)-8-[(2-Amino-propyl)-cyclopropyl-sulfamoyl]-4-oxo-4,5-dihydro-3H-pyrrolo[2,3-c]quinoline-1-propyl carboxylate hydrochloride
8-[(2-Methylamino-ethyl)-prop-2-ynyl-sulfamoyl]-4-oxo-4,5-dihydro-3H-pyrrolo[2,3-c]quinoline-1-propyl carboxylate hydrochloride
8-{[2-(tert-Butoxycarbonyl-methyl-amino)-ethyl]-prop-2-ynyl-sulfamoyl}-4-oxo-4,5-dihydro-3H-pyrrolo[2,3-c]quinoline-1-propyl carboxylate
8-[(2-Isopropylamino-ethyl)-prop-2-ynyl-sulfamoyl]-4-oxo-4,5-dihydro-3H-pyrrolo[2,3-c]quinoline-1-propyl carboxylate hydrochloride
8-{[2-(tert-Butoxycarbonyl-isopropyl-amino)-ethyl]-prop-2-ynyl-sulfamoyl}-4-oxo-4,5-dihydro-3H-pyrrolo[2,3-c]quinoline-1-propyl carboxylate
8-(Ethyl-pyrrolidin-3-yl-sulfamoyl)-4-oxo-4,5-dihydro-3H-pyrrolo[2,3-c]quinoline-1-propyl carboxylate hydrochloride
8-[Ethyl-(1-methyl-pyrrolidin-3-yl)-sulfamoyl]-4-oxo-4,5-dihydro-3H-pyrrolo[2,3-c]quinoline-1-propyl carboxylate
4-Oxo-8-(pyrrolidine-1-sulfonyl)-4,5-dihydro-3H-pyrrolo[2,3-c]quinoline-1-ethyl carboxylate
4-Oxo-8-(2-pyrrolidin-1-ylmethyl-pyrrolidine-1-sulfonyl)-4,5-dihydro-3H-pyrrolo[2,3-c]quinoline-1-ethyl carboxylate
(S)-8-(3-tert-Butoxycarbonylamino-pyrrolidine-1-sulfonyl)-4-oxo-4,5-dihydro-3H-pyrrolo[2,3-c]quinoline-1-propyl carboxylate
(S)-8-(3-tert-Butoxycarbonylamino-pyrrolidine-1-sulfonyl)-4-oxo-4,5-dihydro-3H-pyrrolo[2,3-c]quinoline-1-carboxylic acid
(S)-8-(3-Amino-cyclopentanesulfonyl)-4-oxo-4,5-dihydro-3H-pyrrolo[2,3-c]quinoline-1-propyl carboxylate hydrochloride
(R)-8-(3-Amino-cyclopentanesulfonyl)-4-oxo-4,5-dihydro-3H-pyrrolo[2,3-c]quinoline-1-propyl carboxylate hydrochloride
8-(3-Methylamino-pyrrolidine-1-sulfonyl)-4-oxo-4,5-dihydro-3H-pyrrolo[2,3-c]quinoline-1-propyl carboxylate hydrochloride
8-[3-(tert-Butoxycarbonyl-methyl-amino)-pyrrolidine-1-sulfonyl]-4-oxo-4,5-dihydro-3H-pyrrolo[2,3-c]quinoline-1-propyl carboxylate
8-[3-(tert-Butoxycarbonyl-methyl-amino)-pyrrolidine-1-sulfonyl]-4-oxo-4,5-dihydro-3H-1-pyrrolo[2,3-c]quinoline-1-carboxylic acid
(S)-8-(3-Dimethylamino-cyclopentanesulfonyl)-4-oxo-4,5-dihydro-3H-pyrrolo[2,3-c]quinoline-1-propyl carboxylate
(R)-8-(3-Dimethylamino-cyclopentanesulfonyl)-4-oxo-4,5-dihydro-3H-pyrrolo[2,3-c]quinoline-1-propyl carboxylate
8-[(2-Hydroxy-ethyl)-isopropyl-sulfamoyl]-4-oxo-4,5-dihydro-3H-pyrrolo[2,3-c]quinoline-1-propyl carboxylate
8-[Cyclopropyl-(2-hydroxy-ethyl)-sulfamoyl]-4-oxo-4,5-dihydro-3H-pyrrolo[2,3-c]quinoline-1-propyl carboxylate
8-[(2-Hydroxy-ethyl)-prop-2-ynyl-sulfamoyl]-4-oxo-4,5-dihydro-3H-pyrrolo[2,3-c]quinoline-1-propyl carboxylate
8-[Bis-(2-hydroxy-ethyl)-sulfamoyl]-4-oxo-4,5-dihydro-3H-pyrrolo[2,3-c]quinoline-1-propyl carboxylate
8-(Carbamoylmethyl-methyl-sulfamoyl)-4-oxo-4,5-dihydro-3H-pyrrolo[2,3-c]quinoline-1-propyl carboxylate
8-(Carbamoylmethyl-methyl-sulfamoyl)-4-oxo-4,5-dihydro-3H-pyrrolo[2,3-c]quinoline-1-carboxylic acid
8-(3-Carbamoyl-piperidine-1-sulfonyl)-4-oxo-4,5-dihydro-3H-pyrrolo[2,3-c]quinoline-1-propyl carboxylate
8-(3-Carbamoyl-piperidine-1-sulfonyl)-4-oxo-4,5-dihydro-3H-pyrrolo[2,3-c]quinoline-1-carboxylic acid
8-[(2-Benzyloxy-ethyl)-cyclopropyl-sulfamoyl]-4-oxo-4,5-dihydro-3H-pyrrolo[2,3-c]quinoline-1-propyl carboxylate
8-(Carboxymethyl-methyl-sulfamoyl)-4-oxo-4,5-dihydro-3H-pyrrolo[2,3-c]quinoline-1-propyl carboxylate
8-(tert-Butoxycarbonylmethyl-methyl-sulfamoyl)-4-oxo-4,5-dihydro-3H-pyrrolo[2,3-c]quinoline-1-propyl carboxylate
8-[(2-Dimethylamino-ethyl)-methyl-sulfamoyl]-7-fluoro-4-oxo-4,5-dihydro-3H-pyrrolo[2,3-c]quinoline-1-propyl carboxylate
7-Fluoro-8-[(2-hydroxy-ethyl)-isopropyl-sulfamoyl]-4-oxo-4,5-dihydro-3H-pyrrolo[2,3-c]quinoline-1-propyl carboxylate
8-Dimethylsulfamoyl-7-fluoro-4-oxo-4,5-dihydro-3H-pyrrolo[2,3-c]quinoline-1-propyl carboxylate
8-(Cyclopropyl-methyl-sulfamoyl)-7-fluoro-4-oxo-4,5-dihydro-3H-pyrrolo[2,3-c]quinoline-1-propyl carboxylate
8-(Cyclopropyl-methyl-sulfamoyl)-7-methoxy-4-oxo-4,5-dihydro-3H-pyrrolo[2,3-c]quinoline-1-propyl carboxylate
7-Chloro-8-dimethylsulfamoyl-4-oxo-4,5-dihydro-3H-pyrrolo[2,3-c]quinoline-1-propyl carboxylate
(S)-8-(3-Amino-cyclopentanesulfonyl)-7-chloro-4-oxo-4,5-dihydro-3H-pyrrolo[2,3-c]quinoline-1-propyl carboxylate hydrochloride
4-Oxo-8-(piperidin-1-ylsulfamoyl)-4,5-dihydro-3H-pyrrolo[2,3-c]quinoline-1-methyl carboxylate
8-(Hexahydro-cyclopenta[c]pyrrol-2-ylsulfamoyl)-4-oxo-4,5-dihydro-3H-pyrrolo[2,3-c]quinoline-1-methyl carboxylate and
8-(4-Methyl-piperazin-1-ylsulfamoyl)-4-oxo-4,5-dihydro-3H-pyrrolo[2,3-c]quinoline-1-methyl carboxylate.

2. A pyrroloquinoline derivative selected from the group consisting of the following compounds, and physiologically acceptable salts thereof:

4-Oxo-8-phenylmethanesulfonyl-4,5-dihydro-3H-pyrrolo[2,3-c]quinoline-1-ethyl carboxylate
8-(2,6-Dichlorophenylmethanesulfonyl)-4-oxo-4,5-dihydro-3H-pyrrolo[2,3-c]quinoline-1-ethyl carboxylate
8-(2,6-Dichlorophenylmethanesulfonyl)-4-oxo-4,5-dihydro-3H-pyrrolo[2,3-c]quinoline-1-ethyl carboxylic acid
4-Oxo-8-(pyridin-4-ylmethanesulfonyl)-4,5-dihydro-3H-pyrrolo[2,3-c]quinoline-1-ethyl carboxylate 4-Oxo-8-(pyridin-2-ylmethanesulfonyl)-4,5-dihydro-3H-pyrrolo[2,3-c]quinoline-1-ethyl carboxylate
8-Cyclohexanesulfonyl-4-oxo-4,5-dihydro-3H-pyrrolo[2,3-c]quinoline-1-ethyl carboxylate and
4-Oxo-8-phenylmethanesulfonyl-4,5-dihydro-3H-pyrrolo[2,3-c]quinoline-1-ethyl carboxylate.

3. A pyrroloquinoline derivative selected from the group consisting of the following compounds, and physiologically acceptable salts thereof:

8-Benzenesulfonylamino-4-oxo-4,5-dihydro-3H-pyrrolo[2,3-c]quinoline-1-ethyl carboxylate
8-Methanesulfonylamino-4-oxo-4,5-dihydro-3H-pyrrolo[2,3-c]quinoline-1-ethyl carboxylate
4-Oxo-8-phenylmethanesulfonylamino-4,5-dihydro-3H-pyrrolo[2,3-c]quinoline-1-ethyl carboxylate
8-(4-Chloro-benzenesulfonylamino)-4-oxo-4,5-dihydro-3H-pyrrolo[2,3-c]quinoline-1-ethyl carboxylate
8-(3-Chloro-benzenesulfonylamino)-4-oxo-4,5-dihydro-3H-pyrrolo[2,3-c]quinoline-1-ethyl carboxylate
8-(2-Chloro-benzenesulfonylamino)-4-oxo-4,5-dihydro-3H-pyrrolo[2,3-c]quinoline-1-ethyl carboxylate
8-(4-Fluoro-benzenesulfonylamino)-4-oxo-4,5-dihydro-3H-pyrrolo[2,3-c]quinoline-1-ethyl carboxylate
8-(3-Fluoro-benzenesulfonylamino)-4-oxo-4,5-dihydro-3H-pyrrolo[2,3-c]quinoline-1-ethyl carboxylate
8-(2-Fluoro-benzenesulfonylamino)-4-oxo-4,5-dihydro-3H-pyrrolo[2,3-c]quinoline-1-ethyl carboxylate
8-(4-Bromo-benzenesulfonylamino)-4-oxo-4,5-dihydro-3H-pyrrolo[2,3-c]quinoline-1-ethyl carboxylate
4-Oxo-8-(4-toluenesulfonylamino)-4,5-dihydro-3H-pyrrolo[2,3-c]quinoline-1-ethyl carboxylate
4-Oxo-8-(3-toluenesulfonylamino)-4,5-dihydro-3H-pyrrolo[2,3-c]quinoline-1-ethyl carboxylate
8-(4-tert-Butyl-benzenesulfonylamino)-4-oxo-4,5-dihydro-3H-pyrrolo[2,3-c]quinoline-1-ethyl carboxylate
8-(4-Methoxy-benzenesulfonylamino)-4-oxo-4,5-dihydro-3H-pyrrolo[2,3-c]quinoline-1-ethyl carboxylate
8-(3-Methoxy-benzenesulfonylamino)-4-oxo-4,5-dihydro-3H-pyrrolo[2,3-c]quinoline-1-ethyl carboxylate
8-(4-Acetylamino-benzenesulfonylamino)-4-oxo-4,5-dihydro-3H-pyrrolo[2,3-c]quinoline-1-ethyl carboxylate
8-(4-Nitro-benzenesulfonylamino)-4-oxo-4,5-dihydro-3H-pyrrolo[2,3-c]quinoline-1-ethyl carboxylate
8-(Naphthalene-2-sulfonylamino)-4-oxo-4,5-dihydro-3H-pyrrolo[2,3-c]quinoline-1-ethyl carboxylate
8-(4-Acetyl-benzenesulfonylamino)-4-oxo-4,5-dihydro-3H-pyrrolo[2,3-c]quinoline-1-ethyl carboxylate
4-Oxo-8-(thiophene-2-sulfonylamino)-4,5-dihydro-3H-pyrrolo[2,3-c]quinoline-1-ethyl carboxylate
8-(5-Chloro-thiophene-2-sulfonylamino)-4-oxo-4,5-dihydro-3H-pyrrolo[2,3-c]quinoline-1-ethyl carboxylate
8-(Benzenesulfonyl-methyl-amino)-4-oxo-4,5-dihydro-3H-pyrrolo[2,3-c]quinoline-1-ethyl carboxylate and
8-(Methanesulfonyl-methyl-amino)-4-oxo-4,5-dihydro-3H-pyrrolo[2,3-c]quinoline-ethyl carboxylate.

4. A pyrroloquinoline derivative selected from the group consisting of the following compounds, and physiologically acceptable salts thereof:

8-Benzoylamino-4-oxo-4,5-dihydro-3H-pyrrolo[2,3-c]quinoline-1-ethyl carboxylate and
8-Acetylamino-4-oxo-4,5-dihydro-3H-pyrrolo[2,3-c]quinoline-1-ethyl carboxylate.

5. A pyrroloquinoline derivative selected from the group consisting of the following compounds, and physiologically acceptable salts thereof:

8-Dimethylamino-4-oxo-4,5-dihydro-3H-pyrrolo[2,3-c]quinoline-1-ethyl carboxylate
8-Methylamino-4-oxo-4,5-dihydro-3H-pyrrolo[2,3-c]quinoline-1-ethyl carboxylate
8-Amino-4-oxo-4,5-dihydro-3H-pyrrolo[2,3-c]quinoline-1-ethyl carboxylate
8-Nitro-4-oxo-4,5-dihydro-3H-pyrrolo[2,3-c]quinoline-1-ethyl carboxylate
8-(2-Ethoxycarbonyl-vinyl)-4-oxo-4,5-dihydro-3H-pyrrolo[2,3-c]quinoline-1-ethyl carboxylate
8-(2-Benzylcarbamoyl-vinyl)-4-oxo-4,5-dihydro-3H-pyrrolo[2,3-c]quinoline-1-ethyl-carboxylate
8-[2-(2-Methoxycarbonyl-ethylcarbamoyl)-vinyl]-4-oxo-4,5-dihydro-3H-pyrrolo[2,3-c]quinoline-1-ethyl carboxylate
4-Oxo-8-styryl-4,5-dihydro-3H-pyrrolo[2,3-c]quinoline-1-ethyl carboxylate
8-Ethynyl-4-oxo-4,5-dihydro-3H-pyrrolo[2,3-c]quinoline-1-ethyl carboxylate
4-Oxo-8-trimethylsilanylethynyl-4,5-dihydro-3H-pyrrolo[2,3-c]quinoline-1-ethyl carboxylate
4-Oxo-8-phenylethynyl-4,5-dihydro-3H-pyrrolo[2,3-c]quinoline-1-ethyl carboxylate
4-Oxo-8-pyridin-2-ylethynyl-4,5-dihydro-3H-pyrrolo[2,3-c]quinoline-1-ethyl carboxylate
8-(3-Dimethylamino-prop-1-ynyl)-4-oxo-4,5-dihydro-3H-pyrrolo[2,3-c]quinoline-1-ethyl carboxylate
8-(3-Hydroxy-3-methyl-but-1-ynyl)-4-oxo-4,5-dihydro-3H-pyrrolo[2,3-c]quinoline-1-ethyl carboxylate
8-(3-Morpholin-4-yl-prop-1-ynyl)-4-oxo-4,5-dihydro-3H-pyrrolo[2,3-c]quinoline-1-ethyl carboxylate
8-{3-[(2-Cyano-ethyl)-methyl-amino]-prop-1-ynyl}-4-oxo-4,5-dihydro-3H-pyrrolo[2,3-c]quinoline-1-ethyl carboxylate
4-Oxo-8-phenethyl-4,5-dihydro-3H-pyrrolo[2,3-c]quinoline-1-ethyl carboxylate
8-(3-Hydroxy-3-methyl-butyl)-4-oxo-4,5-dihydro-3H-pyrrolo[2,3-c]quinoline-1-ethyl carboxylate
8-Bromo-4-oxo-4,5-dihydro-3H-pyrrolo[2,3-c]quinoline-1-ethyl carboxylate
8-Iodo-4-oxo-4,5-dihydro-3H-pyrrolo[2,3-c]quinoline-1-ethyl carboxylate
8-Iodo-4-oxo-4,5-dihydro-3H-pyrrolo[2,3-c]quinoline-1-propyl carboxylate
8-Iodo-4-oxo-4-5-dihydro-3H-pyrrolo[2,3-c]quinoline-1-cyclopentyl carboxylate
8-Iodo-4-oxo-4,5-dihydro-3H-pyrrolo[2,3-c]quinoline-1-isobutyl carboxylate
8-Fluoro-4-oxo-4,5-dihydro-3H-pyrrolo[2,3-c]quinoline-1-ethyl carboxylate
8-Fluoro-4-oxo-4,5-dihydro-3H-pyrrolo[2,3-c]quinoline-1-2-diethylaminoethyl carboxylate
8-Acetyl-4-oxo-4,5-dihydro-3H-pyrrolo[2,3-c]quinoline-1-ethyl carboxylate
8-Benzoyl-4-oxo-4,5-dihydro-3H-pyrrolo[2,3-c]quinoline-1-ethyl carboxylate
8-(3-Dimethylamino-acryloyl)-4-oxo-4,5-dihydro-3H-pyrrolo[2,3-c]quinoline-1-ethyl carboxylate
8-(2-Morpholin-4-yl-acetyl)-4-oxo-4,5-dihydro-3H-pyrrolo[2,3-c]quinoline-1-ethyl carboxylate
(S)-8-(Cyclopropyl-pyrrolidin-2-ylmethyl-carbamoyl)-4-oxo-4,5-dihydro-3H-pyrrolo[2,3-c]quinoline-1-ethyl carboxylate hydrochloride
4-Oxo-8-phenylsulfanyl-4,5-dihydro-3H-pyrrolo[2,3-c]quinoline-1-ethyl carboxylate
8-Cyclohexylsulfanyl-4-oxo-4,5-dihydro-3H-pyrrolo[2,3-c]quinoline-1-ethyl carboxylate
8-Benzylsulfanyl-4-oxo-4,5-dihydro-3H-pyrrolo[2,3-c]quinoline-1-ethyl carboxylate 8-(4-Acetylaminophenylsulfanyl)-4-oxo-4,5-dihydro-3H-pyrrolo[2,3-c]quinoline-1-ethyl carboxylate 8-(3-Aminophenylsulfanyl)-4-oxo-4,5-dihydro-3H-pyrrolo[2,3-c]quinoline-1-ethyl carboxylate 8-(3-Acetylaminophenylsulfanyl)-4-oxo-4,5-dihydro-3H-pyrrolo[2,3-c]quinoline-1-ethyl carboxylate 8-(2-Amino-ethylsulfanyl)-4-oxo-4,5-dihydro-3H-pyrrolo[2,3-c]quinoline-1-ethyl carboxylate hydrochloride and 4-Oxo-8-sulfo-4,5-dihydro-3H-pyrrolo[2,3-c]quinoline-1-ethyl carboxylate.

6. A pyrroloquinoline derivative compound, selected from the group consisting of the following compounds, and physiologically acceptable salts thereof:

4-Oxo-8-phenyl-4,5-dihydro-3H-pyrrolo[2,3-c]quinoline-1-ethyl carboxylate 8-(2-Chlorophenyl)-4-oxo-4,5-dihydro-3H-pyrrolo[2,3-c]quinoline-1-ethyl carboxylate 8-(2-tert-Butoxycarbonylaminophenyl)-4-oxo-4,5-dihydro-3H-pyrrolo[2,3-c]quinoline-1-ethyl carboxylate 8-(2-Aminophenyl)-4-oxo-4,5-dihydro-3H-pyrrolo[2,3-c]quinoline-1-ethyl carboxylate 8-(2-Methanesulfonylaminophenyl)-4-oxo-4,5-dihydro-3H-pyrrolo[2,3-c]quinoline-1-ethyl carboxylate 8-(3-tert-Butoxycarbonylaminophenyl)-4-oxo-4,5-dihydro-3H-pyrrolo[2,3-c]quinoline-1-ethyl carboxylate 8-(3-Aminophenyl)-4-oxo-4,5-dihydro-3H-pyrrolo[2,3-c]quinoline-1-ethyl carboxylate 8-(3-Methanesulfonylaminophenyl)-4-oxo-4,5-dihydro-3H-pyrrolo[2,3-c]quinoline-1-ethyl carboxylate 8-(3-Acetylaminophenyl)-4-oxo-4,5-dihydro-3H-pyrrolo[2,3-c]quinoline-1-ethyl carboxylate 8-(3-Hydroxy-phenyl)-4-oxo-4,5-dihydro-3H-pyrrolo[2,3-c]quinoline-1-ethyl carboxylate 8-(3-Methanesulfonyl-phenyl)-4-oxo-4,5-dihydro-3H-pyrrolo[2,3-c]quinoline-1-ethyl carboxylate 8-(3-Cyano-phenyl)-4-oxo-4,5-dihydro-3H-pyrrolo[2,3-c]quinoline-1-ethyl carboxylate 8-(3-Hydroxymethyl-phenyl)-4-oxo-4,5-dihydro-3H-pyrrolo[2,3-c]quinoline-1-ethyl carboxylate 8-(3-Methylaminomethyl-phenyl)-4-oxo-4,5-dihydro-3H-pyrrolo[2,3-c]quinoline-1-ethyl carboxylate 8-(3-Dimethylaminomethyl-phenyl)-4-oxo-4,5-dihydro-3H-pyrrolo[2,3-c]quinoline-1-ethyl carboxylate 8-(4-tert-Butoxycarbonylaminophenyl)-4-oxo-4,5-dihydro-3H-pyrrolo[2,3-c]quinoline-1-ethyl carboxylate 8-(4-Aminophenyl)-4-oxo-4,5-dihydro-3H-pyrrolo[2,3-c]quinoline-1-ethyl carboxylate 8-(4-Methanesulfonyl-phenyl)-4-oxo-4,5-dihydro-3H-pyrrolo[2,3-c]quinoline-1-ethyl carboxylate 8-(4-Methoxy-phenyl)-4-oxo-4,5-dihydro-3H-pyrrolo[2,3-c]quinoline-1-ethyl carboxylate 8-(4-Cyano-phenyl)-4-oxo-4,5-dihydro-3H-pyrrolo[2,3-c]quinoline-1-ethyl carboxylate 8-(2,3-Dihydro-benzo[1,4]dioxin-6-yl)-4-oxo-4,5-dihydro-3H-pyrrolo[2,3-c]quinoline-1-ethyl carboxylate 8-Naphthalen-1-yl-4-oxo-4,5-dihydro-3H-pyrrolo[2,3-c]quinoline-1-ethyl carboxylate 4-Oxo-8-quinolin-8-yl-4,5-dihydro-3H-pyrrolo[2,3-c]quinoline-1-ethyl carboxylate 8-(2-Amino-5-methanesulfonyl-phenyl)-4-oxo-4,5-dihydro-3H-pyrrolo[2,3-c]quinoline-1-ethyl carboxylate 8-(1H-Indol-5-yl)-4-oxo-4,5-dihydro-3H-pyrrolo[2,3-c]quinoline-1-ethyl carboxylate 8-(1-tert-Butoxycarbonyl-1H-indol-5-yl)-4-oxo-4,5-dihydro-3H-pyrrolo[2,3-c]quinoline-1-ethyl carboxylate 8-(3-Methanesulfonyl-phenyl)-4-oxo-4,5-dihydro-3H-pyrrolo[2,3-c]quinoline-1-propyl carboxylate 8-(3-Methanesulfonyl-phenyl)-4-oxo-4,5-dihydro-3H-pyrrolo[2,3-c]quinoline-1-isobutyl carboxylate 8-(3-Methanesulfonyl-phenyl)-4-oxo-4,5-dihydro-3H-pyrrolo[2,3-c]quinoline-1-cyclopentyl carboxylate 7-Chloro-8-(3-methanesulfonyl-phenyl)-4-oxo-4,5-dihydro-3H-pyrrolo[2,3-c]quinoline-1-ethyl carboxylate 4-Oxo-8-pyridin-3-yl-4,5-dihydro-3H-pyrrolo[2,3-c]quinoline-1-ethyl carboxylate 8-(6-Chloro-pyridin-3-yl)-4-oxo-4,5-dihydro-3H-pyrrolo[2,3-c]quinoline-1-ethyl carboxylate 8-(6-Methoxy-pyridin-3-yl)-4-oxo-4,5-dihydro-3H-pyrrolo[2,3-c]quinoline-1-ethyl carboxylate 8-(2-Amino-pyrimidin-4-yl)-4-oxo-4,5-dihydro-3H-pyrrolo[2,3-c]quinoline-1-ethyl carboxylate 8-(2-Dimethylamino-pyrimidin-4-yl)-4-oxo-4,5-dihydro-3H-pyrrolo[2,3-c]quinoline-1-ethyl carboxylate 8-(2-Methylamino-pyrimidin-4-yl)-4-oxo-4,5-dihydro-3H-pyrrolo[2,3-c]quinoline-1-ethyl carboxylate formate 8-(2-Ethylamino-pyrimidin-4-yl)-4-oxo-4,5-dihydro-3H-pyrrolo[2,3-c]quinoline-1-ethyl carboxylate 4-Oxo-8-[2-(4-pyridin-2-yl-piperazin-1-yl)-pyrimidin-4-yl]-4,5-dihydro-3H-pyrrolo[2,3-c]quinoline-1-ethyl carboxylate 4-Oxo-8-(2-phenylamino-pyrimidin-4-yl)-4,5-dihydro-3H-pyrrolo[2,3-c]quinoline-1-ethyl carboxylate 8-[2-(1H-Benzoimidazol-2-ylamino)-pyrimidin-4-yl]-4-oxo-4,5-dihydro-3H-pyrrolo[2,3-c]quinoline-1-ethyl carboxylate 8-[2-(4-Acetyl-piperazin-1-yl)-pyrimidin-4-yl]-4-oxo-4,5-dihydro-3H-pyrrolo[2,3-c]quinoline-1-ethyl carboxylate and 8-{2-[(2-Dimethylamino-ethyl)-methyl-amino]-pyrimidin-4-yl}-4-oxo-4,5-dihydro-3H-pyrrolo[2,3-c]quinoline-1-ethyl carboxylate formate.

7. A pyrroloquinoline derivative selected from the group consisting of the following compounds, and physiologically acceptable salts thereof:

8-(2-Amino-thiazol-4-yl)-4-oxo-4,5-dihydro-3H-pyrrolo[2,3-c]quinoline-1-ethyl carboxylate 8-[2-Phenylamino-thiazol-4-yl]-4-oxo-4,5-dihydro-3H-pyrrolo[2,3-c]quinoline-1-ethyl carboxylate 8-[2-(2-Chlorophenylamino)-thiazol-4-yl]-4-oxo-4,5-dihydro-3H-pyrrolo[2,3-c]quinoline-1-ethyl carboxylate 8-[2-(3,4-Dichlorophenylamino)-thiazol-4-yl]-4-oxo-4,5-dihydro-3H-pyrrolo[2,3-c]quinoline-1-ethyl-carboxylate 8-[2-(2,6-Dichlorophenylamino)-thiazol-4-yl]-4-oxo-4,5-dihydro-3H-pyrrolo[2,3-c]quinoline-1-ethyl carboxylate 8-[2-(Cyclopropanecarbonyl-amino)-thiazol-4-yl]-4-oxo-4,5-dihydro-3H-pyrrolo[2,3-c]quinoline-1-ethyl carboxylate 4-Oxo-8-(2-phenylsulfanylmethyl-thiazol-4-yl)-4,5-dihydro-3H-pyrrolo[2,3-c]quinoline-1-ethyl carboxylate 4-Oxo-8-(2-piperidin-4-yl-thiazol-4-yl)-4,5-dihydro-3H-pyrrolo[2,3-c]quinoline-1-ethyl carboxylate 8-(2-Methyl-thiazol-4-yl)-4-oxo-4,5-dihydro-3H-pyrrolo[2,3-c]quinoline-1-ethyl carboxylate 4-Oxo-8-(2-phenyl-thiazol-4-yl)-4,5-dihydro-3H-pyrrolo[2,3-c]quinoline-1-ethyl carboxylate 4-Oxo-8-[2-(N'-phenyl-hydrazino)-thiazol-4-yl]-4,5-dihydro-3H-pyrrolo[2,3-c]quinoline-1-ethyl carboxylate 8-Isoxazol-5-yl-4-oxo-4,5-dihydro-3H-pyrrolo[2,3-c]quinoline-1-ethyl carboxylate 4-Oxo-8-(1H-pyrazol-3-yl)-4,5-dihydro-3H-pyrrolo[2,3-c]quinoline-1-ethyl carboxylate and
8-(1-Methyl-1H-pyrazol-3-yl)-4-oxo-4,5-dihydro-3H-pyrrolo[2,3-c]quinoline-1-ethyl carboxylate.

8. A compound of formula VI

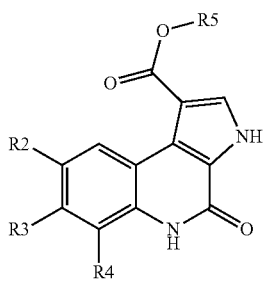

in which:
R3 and R4 each represents a hydrogen atom,
R2 represents a halogen or a group selected from the radicals alkenyl and -NO$_2$,
R5 represents an alkyl radical,
and physiologically acceptable salts thereof.

9. A compound of formula VI:

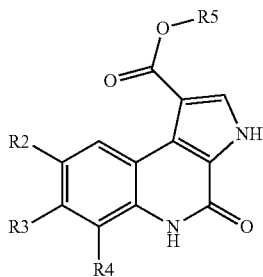

in which:
R2 represents —SO$_2$—NH—R8, —SO$_2$—R8, —NH—SO$_2$—R8, —NR7—CO—R8,
R3 and R4 represent a hydrogen atom,
R5 is selected from the groups methyl, ethyl, propyl, iso-propyl, butyl, iso-butyl, iso-pentyl, allyl, isoprenyl, propargyl, cyclopentyl, cyclohexyl, cyclopropylmethyl, cyclopentylmethyl, cyclohexylmethyl, tetrahydropyran-4-yl-methyl, tetrahydrofuran-3-yl-methyl, and/or
R7 is a hydrogen or is selected from the groups methyl, ethyl, propyl, iso-propyl, butyl, isobutyl, allyl, isoprenyl, propargyl, cyclopropyl, cyclopentyl, cyclohexyl, cyclopropylmethyl, cyclopentylmethyl, cyclohexylmethyl, tetrahydropyran-4-yl-methyl, tetrahydrofuran-3-yl-methyl, hydroxy-2-ethyl, and/or
R8 is selected from the groups methyl, hydroxy-2-ethyl, amino-2-ethyl, methylamino-2-ethyl, dimethylamino-2-ethyl, cyanomethyl, carbamoylmethyl, 2-cyanoethyl, cyclohexyl, cycoheptyl, cyclopropylmethyl, cycopentylmethyl, cyclohexylmethyl, piperidin-4-yl, piperidin-3-yl, piperidin-2-yl, piperidine-4-methyl, piperidine-3-methyl, piperidine-2-methyl, pyrrolidin-3-yl-methyl, pyrrolidin-2-yl-methyl, pyrrolidin-3-yl, azetidin-3-yl-methyl, tetrahydro-thiopyran-4-yl, tetrahydropyran-4-yl, imidazol-4-yl-methyl, phenyl, o-tolyl, m-tolyl, p-tolyl, 2-fluorophenyl, 3 fluorophenyl, 4-fluorophenyl, 2-chlorophenyl, 3-chlorophenyl, 4-chlorophenyl, 3-hydroxy-phenyl, 2-methoxy-phenyl, 3-methoxy-phenyl, 4-methoxy-phenyl, 4-aminopheryl, 4-nitrophenyl, 4-fluoro-2-methyl phenyl,3-fluoro-2-methyl-phenyl, 3,4-difluorophenyl, 3,5-difluorophenyl, 2,6-dichlorophenyl, pyridyl, thiophene, 5-chloro-thiophene or benzyl, and/or
R7 and R8 form, with the nitrogen to which they are attached, a 2,3-dihydro-indolyl, piperidinyl, piperazinyl, pyrrolidinyl or morpholinyl ring.

10. A pharmaceutical composition containing a compound as claimed in claim 1, 2, 3, 4, 5, 6, 7, 9, and 8 and a suitable pharmaceutical vehicle.

* * * * *